United States Patent [19]
DeVires et al.

[11] Patent Number: 5,474,062
[45] Date of Patent: Dec. 12, 1995

[54] MEDICAL VENTILATOR

[75] Inventors: Douglas F. DeVires, Redlands; Lindon A. Baker, Santa Ana, both of Calif.

[73] Assignee: Bird Products Corporation, Riverside, Calif.

[21] Appl. No.: 406,914

[22] Filed: Sep. 13, 1989

Related U.S. Application Data

[62] Division of Ser. No. 116,701, Nov. 4, 1987.
[51] Int. Cl.$^6$ ........................................... A62B 9/02
[52] U.S. Cl. .................. 128/205.24; 128/204.21; 128/204.27; 128/204.18
[58] Field of Search .................. 128/205.24, 204.23, 128/204.21, 204.18, 200.24, 204.22, 204.25, 205.11, 205.18, 205.23; 251/256

[56] References Cited

U.S. PATENT DOCUMENTS

| | | |
|---|---|---|
| 29,778 | 9/1878 | Stewart. |
| 2,503,563 | 4/1950 | Ray. |
| 2,536,691 | 1/1951 | Miller et al.. |
| 2,770,231 | 11/1956 | Falk. |
| 2,880,719 | 4/1959 | Andreasen. |
| 2,904,035 | 9/1959 | Andreasen. |
| 3,007,490 | 11/1961 | Passmore. |
| 3,015,963 | 1/1962 | Terry. |
| 3,374,410 | 3/1968 | Cronquist et al.. |
| 3,416,054 | 12/1968 | Galles. |
| 3,488,030 | 1/1970 | Hulme et al.. |
| 3,569,813 | 3/1971 | Clark et al.. |
| 3,579,279 | 5/1971 | Inaba et al.. |
| 3,586,953 | 6/1971 | Markhanen et al.. |
| 3,675,633 | 7/1972 | Nakajima et al.. |
| 3,813,592 | 5/1974 | Ryberg. |
| 3,820,539 | 6/1974 | Ollivier. |
| 3,839,662 | 10/1974 | N'Guyen Van. |
| 3,961,627 | 6/1976 | Ernst et al.. |
| 3,968,416 | 7/1976 | Leenhouts. |
| 4,024,447 | 5/1977 | Epstein. |
| 4,027,636 | 6/1977 | Yamamoto et al.. |
| 4,031,448 | 6/1977 | Adachi. |

(List continued on next page.)

FOREIGN PATENT DOCUMENTS

| | | |
|---|---|---|
| 2026326 | 2/1980 | United Kingdom. |
| 2126666 | 3/1984 | United Kingdom. |

OTHER PUBLICATIONS

Edited by B. C. Kuo, Step Motors and Control Systems, 1979, Chapter 4, entitled "Drive Circuitry for Step Motors", pp. 114–143.

(List continued on next page.)

*Primary Examiner*—Kyle L. Howell
*Assistant Examiner*—John P. Lacyk
*Attorney, Agent, or Firm*—Knobbe, Marten, Olson & Bear

[57] ABSTRACT

A medical ventilator having a valve which controls the flow of gas from a pressurized gas source to a patient for inhalation. Flow through the valve is choked and pressure upstream of the valve is held stable so that a known relationship exists between the position of the valve and the flow rate through the valve. An open loop control system causes the valve to open or close as needed to deliver a preselected tidal volume of gas to the patient on each breath. Since the flow rate is known, no feedback to the controller regarding actual flow conditions is required. The exact positioning of the valve and length of time that the valve is to be held open is predetermined by the controller before the breath is delivered, and is repeated for subsequent breaths. Preferably, the valve is driven by a stepping motor, and the controller comprises a microcomputer. The controller compensates for ramping of the stepping motor as the valve opens and closes in determining the positions of the valve required to deliver the preselected tidal volume. To ensure precise engagement between a valve member and a valve seat, the valve member is mounted on a flexible, linear wire. Additionally, a spirally-wound spring surrounds a stepping motor shaft and biases the shaft so as to close the valve in the event of a power loss.

19 Claims, 121 Drawing Sheets

U.S. PATENT DOCUMENTS

| | | |
|---|---|---|
| 4,036,221 | 7/1977 | Hillsman et al. . |
| 4,081,736 | 3/1978 | Leenhouts et al. . |
| 4,087,732 | 5/1978 | Pritchard . |
| 4,094,285 | 6/1978 | Oyama et al. . |
| 4,107,594 | 8/1978 | Jacobs . |
| 4,119,902 | 10/1978 | Newell . |
| 4,126,818 | 11/1978 | Taylor . |
| 4,126,821 | 11/1978 | Cannon . |
| 4,153,021 | 5/1979 | Hattori et al. . |
| 4,158,351 | 6/1979 | Ando et al. . |
| 4,176,687 | 12/1979 | Ensign . |
| 4,177,830 | 12/1979 | Munson . |
| 4,181,108 | 1/1980 | Bellicardi . |
| 4,199,132 | 4/1980 | deMey, II . |
| 4,204,536 | 5/1980 | Albarda . |
| 4,256,100 | 3/1981 | Levy et al. ............... 128/205.24 |
| 4,285,496 | 8/1981 | Coles . |
| 4,323,064 | 4/1982 | Hoenig et al. . |
| 4,326,513 | 4/1982 | Schulz et al. . |
| 4,333,453 | 6/1982 | Rodder . |
| 4,336,590 | 6/1982 | Jacq et al. . |
| 4,401,116 | 8/1983 | Fry et al. . |
| 4,448,192 | 5/1984 | Stawitcke et al. . |
| 4,457,339 | 7/1984 | Juan et al. . |
| 4,484,554 | 11/1984 | Nakajima et al. . |
| 4,527,557 | 7/1985 | De Vries et al. ............... 128/205.24 |
| 4,561,408 | 12/1985 | Jenkins . |
| 4,602,653 | 7/1986 | Ruiz-Vela et al. . |
| 4,617,637 | 10/1986 | Chu et al. . |
| 4,702,240 | 10/1987 | Chaoui . |

OTHER PUBLICATIONS

Editee by B. C. Kuo, Step Motors and Control Systems, 1979, Chapter 15, entitled "Microprocessor Control of Step Motores", pp. 391–402.

Gottlieb, Electric Motors & Control Techniques, 1982, pp. 183–198 and pp. 193–195.

Kenjo, Stepping Motors and Their Microprocessor Controls, 1984, pp. 121–165.

Siemans–Elema, "Service Manual" for the Servo Ventilator 900B, 1979, 56 pp.

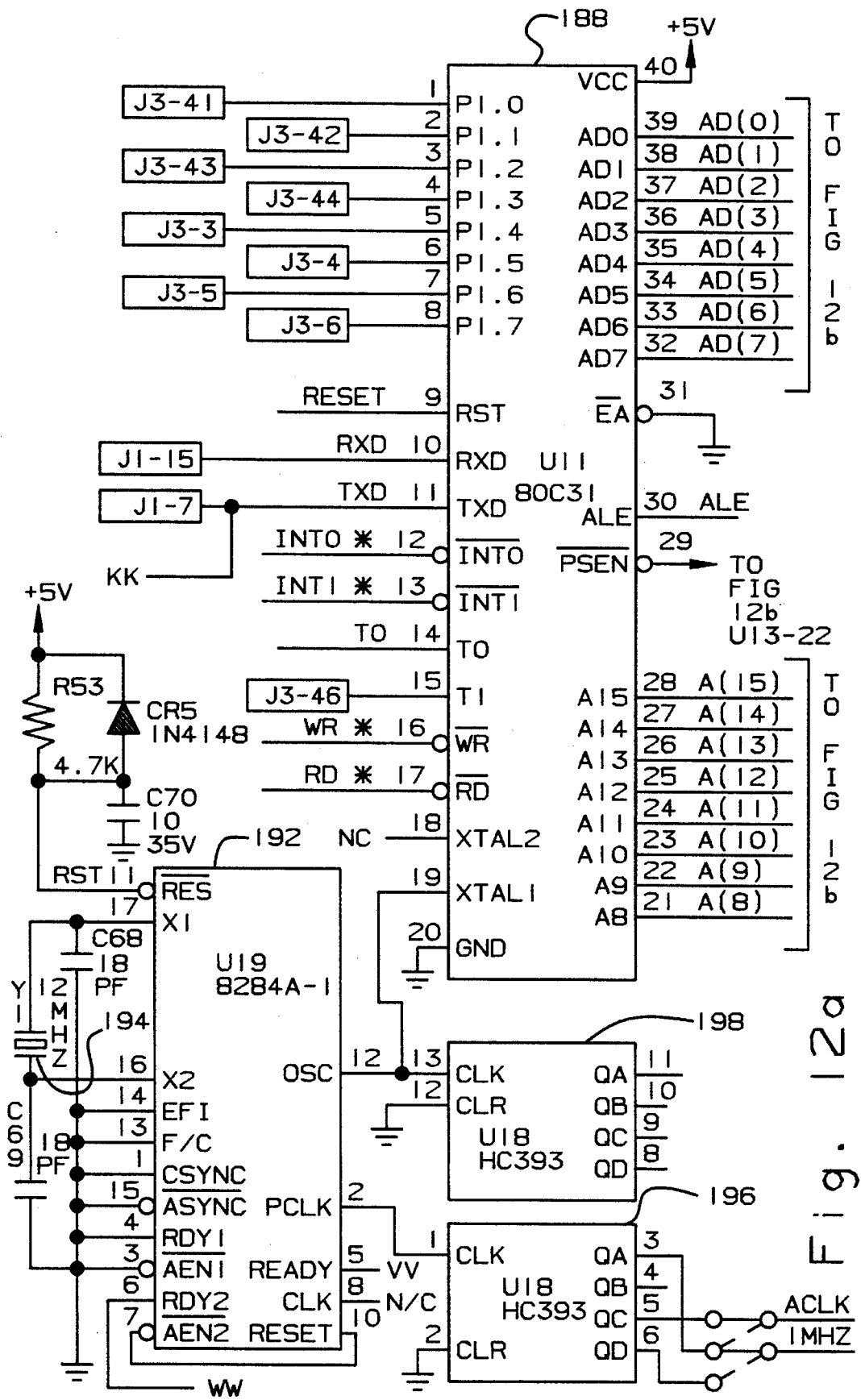

| MESSAGE | HEADER | DATA BYTES | | | |
|---|---|---|---|---|---|
| FLOW VALVE POSITION O | 13H | | | | |
| EXH VALVE POSITION O | 14H | | | | |
| STATUS REQUEST | 00H | | | | |
| OPEN SAFETY VALVE | 25H | | | | |
| CLOSE SAFETY VALVE | 26H | | | | |
| ITV ACCUMULATOR O | 0FH | | | | |
| FLOW VALVE POSITION | 03H OR 83H | 0 | 1 | | |
| EXH VALVE POSITION O | 04H | 0 | 1 | | |
| VENT INOP | EEH | 0 | | | |
| INSPIRATORY BREATH | AAH | 0 | 1 | 2 | 3 |
| | | 4 | 5 | 6 | 7 |
| | | 8 | 9 | A | B |
| | | C | D | E | F |
| EXPIRATORY BREATH | 55H | 0 | 1 | 2 | 3 |
| | | 4 | 5 | 6 | 7 |
| | | 8 | 9 | A | B |
| | | C | D | E | F |
| CONTROL PANEL | 5AH | 0 | 1 | 2 | 3 |
| | | 4 | 5 | 6 | 7 |
| | | 8 | 9 | A | B |
| | | C | D | E | F |
| SYSTEM STATUS | A5H | 0 | 1 | 2 | 3 |
| | | 4 | 5 | 6 | 7 |
| | | 8 | 9 | A | B |
| | | C | D | E | F |

Fig. 21a

| MESSAGE | HEADER | DATA BYTES | | | |
|---|---|---|---|---|---|
| FLOW VALVE DATA | 0BH | 0 | 1 | 2 | 3 |
|  |  | 4 |  |  |  |
| EXH VALVE DATA | 00H | 0 | 1 |  |  |
| FLOW VALVE BUSY | 1BH |  |  |  |  |
| EXH VALVE BUSY | 1CH |  |  |  |  |
| MCP READY | 0FH | 0 | 1 | 2 | 3 |
|  |  | 4 | 5 |  |  |
| FLOW VALVE HOME | 23H |  |  |  |  |
| EXH VALVE HOME | 24H |  |  |  |  |
| SAFETY VALVE CLOSED | 28H |  |  |  |  |
| SAFETY VALVE OPEN | 29H |  |  |  |  |
| DATA BYTE MISSING | DBH |  |  |  |  |
| HEADER BYTE MISSING | DCH |  |  |  |  |
| VENT INOP | EEH | 0 |  |  |  |

Fig. 21b

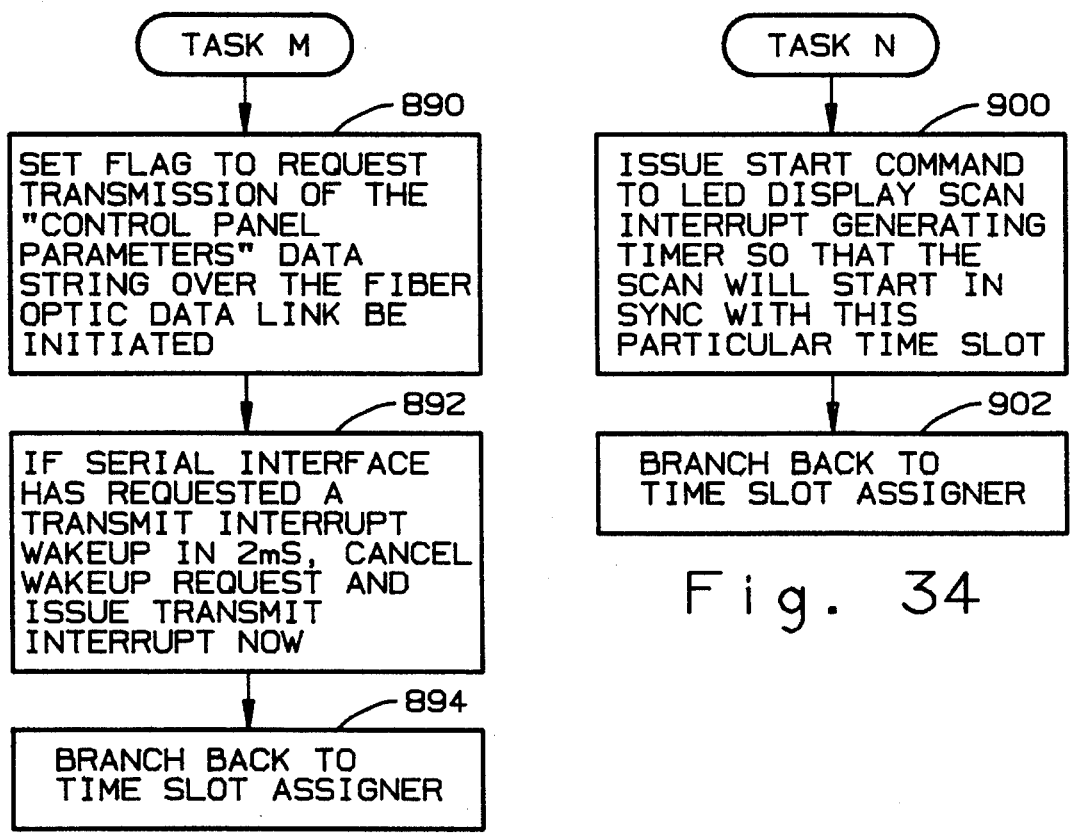
Fig. 33
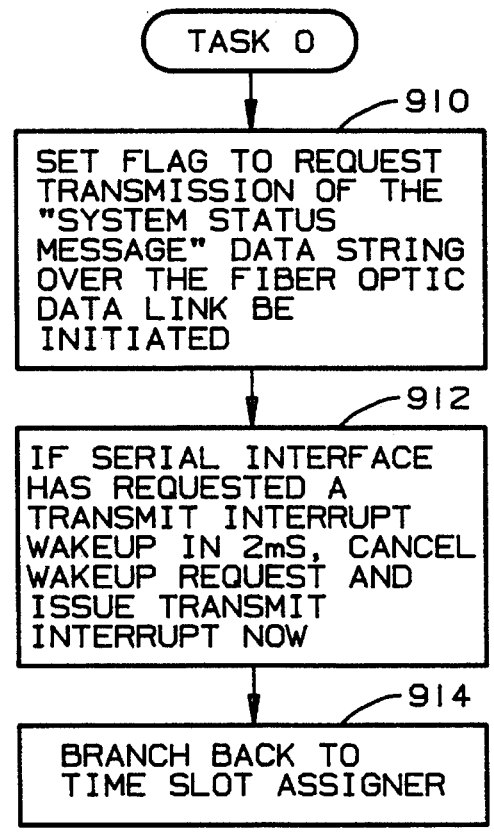
Fig. 34
Fig. 35

FROM FIG 40f

1112 —
TAPRACC = (TAPRACC+TAPTTEM) MOD TAPRMOD
C = INT[(TAPRACC+TAPRREM)/TAPRMOD]

1116 —
FDESTIN = FDESTIN-C-TAPRSTEP-TAPRTILT

1118 —
IF FDESTIN .LE. 0,
GOTO VOLDT7

1120 —
REQUEST MOTOR CONTROL
PROCESSOR TO MOVE FLOW
CONTROL VALVE TO FDSTIN
POSITION

1122 —
TAPRTILT = 0

1124 —
B = 1 ? → TO FIG 40f STEP 1102

↓ NO
TO FIG 40f STEP 1104

Fig. 40g

MEDICAL VENTILATOR

This application is a division of application Ser. No. 116,701, filed Nov. 4, 1987.

A microfiche appendix is included as part of this patent disclosure and is incorporated herein by reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

This invention relates generally to the field of medical ventilators, and more particularly to a ventilator having a valve which controls the flow of gases to a patient during artificial respiration and the means by which the valve is controlled.

Medical ventilators have been developed to provide artificial respiration to patients whose breathing ability is impaired. Typically, a ventilator will deliver a breath to the patient from a pressurized source of gas. Flow to the patient during inspiration is governed by a flow control valve. When the flow control valve opens, pressurized gas is introduced to the patient's lungs. After the flow control valve closes, ending the inspiration phase of the breath, the patient's respiratory gases are vented to the atmosphere through an exhalation valve, which opens after inspiration is completed and closes before the next inspiration phase begins.

Previous ventilators have been capable of operating in several modes so that the degree of support that the ventilator provides to the patient's natural breath patterns can be varied. At one extreme, the ventilator can provide fully controlled ventilation in which the ventilator has complete control over when the breath is delivered and the volume of gases received by the patient during each breath. In the fully controlled mode, all of the flow parameters are preset by an operator in accordance with the particular needs of the patient. The predetermined flow parameters include the tidal volume, or the volume of gas which is inhaled by the patient during each breath; the breath rate, which is the number of breaths per minute; the peak flow rate, which is the maximum flow rate of the gas delivered to the patient during inspiration; and the breath profile, which is the shape of the curve in a flow rate versus time graph. The most significant of these parameters is the tidal volume, since, depending on size and age of the patient, the tidal volume can vary significantly. Thus, the fully controlled ventilation mode is often called "volume controlled" ventilation.

At the other extreme, the ventilator can be programmed to permit "spontaneous" breathing by the patient. During the spontaneous breathing mode, the breath rate, the tidal volume and other flow parameters are not preselected. The inspiration and expiration phases of each breath are commenced in response to effort by the patient. In between the "volume controlled" and the "spontaneous breath" modes, various degrees of ventilator supported respiration are available.

One of the problems associated with previous ventilators has been that during the volume controlled mode, it is extremely difficult to precisely measure the volume of flow during inspiration so as to determine when the preselected tidal volume has been delivered, and thus at which point the flow control valve must be closed. Previous ventilators, such as that described in U.S. Pat. No. 4,527,557, have utilized a microcomputer controller which receives input regarding the desired flow parameters and compares these preselected parameters with actual flow conditions to control the opening and closing of the flow control valve.

In particular, a "closed loop" control system is utilized in the ventilator disclosed in U.S. Pat. No. 4,527,557 with feedback to the controller regarding the flow rate being generated by a flow transducer which is positioned downstream of the flow control valve. The actual flow rate as measured by the flow transducer is compared by the controller on a real-time basis with the preselected flow rate. If a discrepancy exists between these two values, the valve is opened or closed accordingly. During each breath, the microcomputer controller calculates the total volume of gas delivered by incrementally summing the product of the measured flow rate and the length of the incremental time interval. When the volume calculated by the controller equals the preselected tidal volume, the flow control valve is closed.

This system has several drawbacks, most notably being the unreliability of the flow transducer. Currently available flow transducers are expensive, delicate instruments which can provide accurate flow measurements only over a narrow range of flow conditions. Further, a lag time develops between a change in actual flow rate and the system's ability to correct or compensate for the change in flow. As a result, significant differences between the preselected tidal volume and the actual tidal volume delivered can occur.

Another problem with the system's closed loop servo, such as that disclosed in U.S. Pat. No. 4,527,557, is that the control system is complex and difficult to design so that the system is stable. On an unstable system, as the flow control valve is being opened to reach the desired peak flow rate position, flow would be choppy and irregular as the valve overshoots the desired flow rate, and the flow rate oscillates until the valve is able to settle.

Thus, a need exists for an inexpensive ventilator which can accurately and consistently deliver a breath having a preselected tidal volume.

SUMMARY OF THE INVENTION

The present invention is a ventilator which provides artificial respiration to a patient. The flow of gas to the patient during inspiration from a gas source is regulated by a flow control valve. Also provided are means for controlling the valve on an open loop basis, without requiring feedback to the control means regarding the position of the valve or the actual flow rate through the valve. Advantageously, the present open loop control system eliminates the need for a flow transducer, thus decreasing the cost of the ventilator and increasing its reliability.

Preferably, a known relationship exists between the position of the flow control valve and the rate of flow through the valve. In part, this is achieved by establishing a region of "choked" flow through the valve so that small changes in pressure downstream of the valve will not affect the flow rate through the valve. As a result, before a breath is delivered, the control means can determine the required positions of the valve and the length of time that the valve must be held open in order to deliver a desired tidal volume of gas to the patient.

Another aspect of the invention is that the length of the breath delivery period is adjusted to compensate for the volume of gas that is undelivered due to the initial, non-instantaneous increase in flow rate from the closed position of the valve, and due to the extra volume of gas that is delivered due to the non-instantaneous decrease in flow rate as the valve closes. In a preferred embodiment, the flow control valve is driven by a stepping motor, and the undelivered volume of gas and the extra volume of gas result from ramp-up and ramp-down of the stepping motor as the valve is driven to the open and closed positions. By compensating for ramping of the stepping motor, the actual tidal volume delivered can be accurately correlated to the preselected tidal volume.

The present invention further comprises means for generating a flow profile prior to the delivery of a breath. The flow profile is used as a pattern on which a plurality of substantially identical subsequent breaths are delivered to the patient. The flow profile is generated based on a preselected peak flow rate and a preselected tidal volume. Again, since the flow profile is used repeatedly, the ventilator delivers breaths of a consistent tidal volume.

In one preferred embodiment, the flow profile is translated into a sequence of steps to be carried out by the stepping motor which drives the flow control valve. A known relationship exists between each step of the stepping motor and the resulting change in flow rate. Consequently, the flow profile can be executed accurately by the valve, which enables the tidal volume delivered to the patient to be precisely controlled.

The present flow control valve has several additional unique features. The valve member, which preferably is a ball, is secured to a flexible, linear wire which allows radial movement of the ball to ensure proper seating of the ball on a valve seat. This feature enables secure sealing engagement between the ball and the valve seat despite misalignment or wear of either member. Also, the shaft of the motor which drives the valve is biased by a spring so that, in the event of a malfunction, the valve is automatically closed. This prevents high pressure air from being continuously forced into the patient's lungs in the event of a power loss which would otherwise leave the valve in an open position indefinitely.

BRIEF DESCRIPTION OF THE DRAWINGS

FIG. 21a illustrates the communication format for messages sent from the main processor to the motor control processor;

FIG. 21b illustrates the communication format used for messages sent from the motor control processor to the main processor;

FIG. 33 is a detailed flow chart of step 618 of FIG. 25;

FIG. 34 is a detailed flow chart of step 620 of FIG. 25;

FIG. 35 is a detailed flow chart of step 622 of FIG. 25;

DETAILED DESCRIPTION OF A PREFERRED EMBODIMENT

Figure 1:
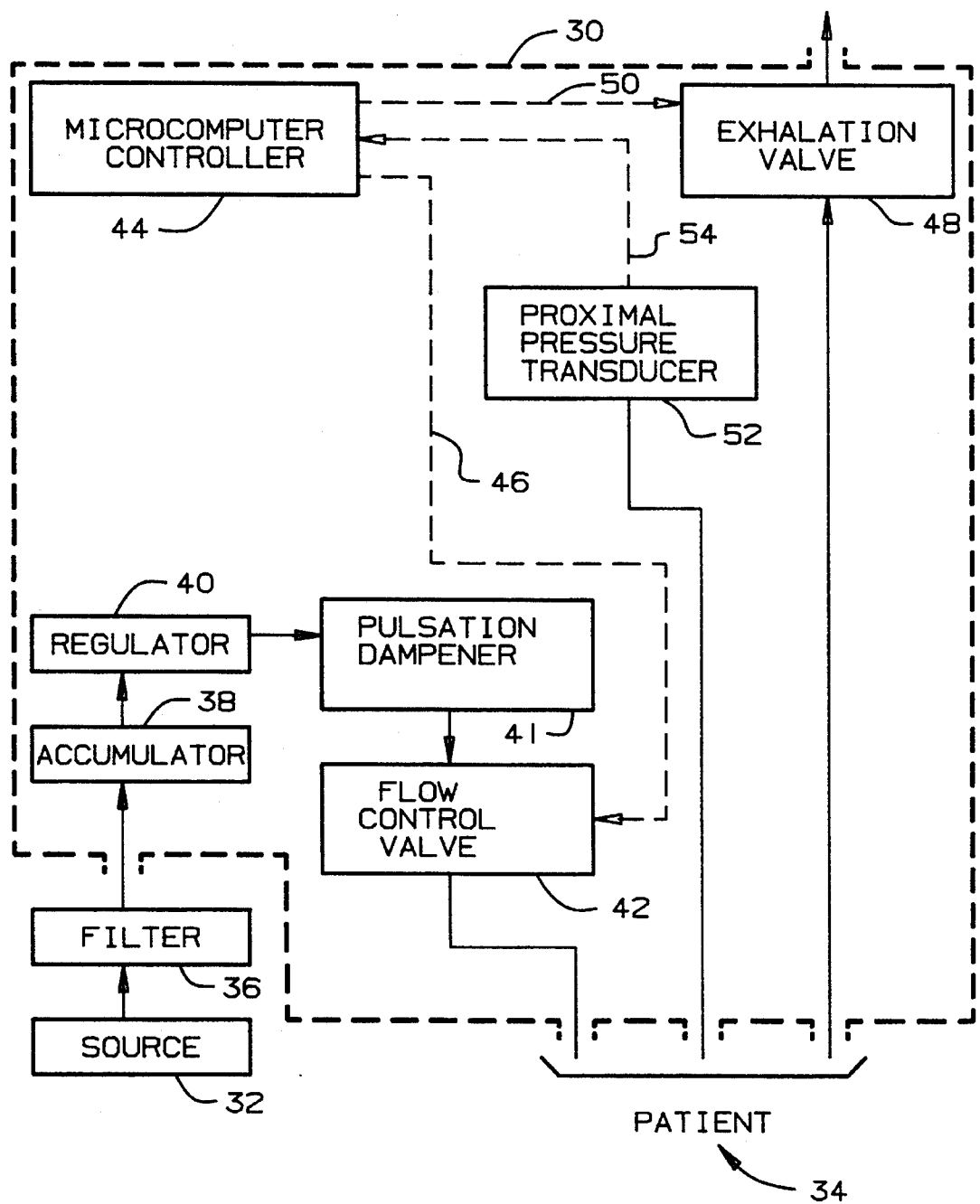
FIG. 1 is a schematic view of the pneumatic layout of a ventilator according to one embodiment of the present invention.

Referring to FIG. 1, the present ventilator is shown generally at 30. The ventilator 30 receives pressurized gas, such as air or an oxygen blend, from a source 32 and controls the flow of gas to a patient 34 so as to provide artificial respiration. As will be apparent to those skilled in the art, the schematic of FIG. 1 has been simplified by the elimination of various commonly used elements such as check valves, safety valves, pressure gauges, etc.

A description of the components illustrated in FIG. 1 and their operation will be understood from the following description of the flow path of gas through the ventilator 30. The gas initially passes from the source 32 through a coalescing filter 36, so as to remove both liquids and solids from the gas stream. After being filtered, the gas enters an accumulator 38 which is a rigid chamber for the temporary storage of the pressurized gas. The accumulator 38 acts as a reservoir from which gas is drawn during periods of peak demand, such as during inspiration by the patient. Downstream of the accumulator 38, a pneumatic regulator 40 is positioned. Gas flowing from the regulator 40 is maintained at a constant pressure of approximately 20 psig, which is referred to herein as the "system pressure."

System pressure gas enters a pulsation dampener 41 which, like the accumulator 38, is a rigid gas storage chamber. However, the volume of the pulsation dampener 41 is smaller than that of the accumulator 38, and the gas in the pulsation dampener 41 is at the system pressure. The pulsation dampener 41 compensates for pressure fluctuations due to the limited response time of the regulator 40 during periods when the flow rate through the regulator 40 is rapidly changing. Thus, the pulsation dampener 41 acts to maintain the system pressure constant at 20 psig.

The pulsation dampener 41 feeds gas to a flow control valve 42, the structure of which is discussed at length below. The flow control valve 42 regulates the flow rate of gas which is delivered to the patient 34 during inspiration. The flow control valve 42 can assume a plurality of positions, so as to permit various flow rates of gas to the patient 34. The position of the flow control valve 42 is controlled by a microcomputer controller 44. An electronic signal 46 is sent by the controller 44 to cause opening or closing of the valve 42. As is discussed in greater detail below, the controller 44 does not utilize feedback regarding flow conditions downstream of the valve 42 in order to determine what the proper position of the valve 42 should be. Thus, the valve 42 is controlled on an "open loop" basis.

Although not shown, the patient 34 is fitted with an endotracheal tube which establishes fluid communication between the patient's lungs and the ventilator 30. As is well known, the endotracheal tube is inserted in the patient's trachea, or wind pipe, and is surrounded by a balloon which forms a seal with the trachea so that all gas flow into and out of the lungs takes place through the endotracheal tube, which is in fluid communication with the flow control valve 42.

An exhalation valve 48 is provided to establish fluid communication between the patient's lungs and the atmosphere. When open, the exhalation valve 48 permits the patient 34 to exhale by venting respiratory gases to the atmosphere through the endotracheal tube. Opening and closing of the exhalation valve 48 is governed by the controller 44, which sends an electronic signal 50 to the exhalation valve 48 to effect a change in the position of the exhalation valve 48. The controller 44 determines the proper position of the exhalation valve 48 based on feedback from a proximal pressure transducer 52. The proximal pressure transducer 52 measures the pressure of the gas on the ventilator side of the seal formed by the endotracheal tube, which is referred to as the "proximal" gas. Feedback to the controller 44 is in the form of an input signal 54 from the proximal pressure transducer 52, which is an electrical analog of the proximal pressure.

When the ventilator 30 is operating in a fully controlled mode, in which the patient 34 has no control over the flow parameters, inspiration begins when the flow control valve 42 is signalled to open by the controller 44. Opening of the flow control valve 42 causes gas to enter the patient's lungs through the endotracheal tube. The exhalation valve 48 remains closed during inspiration so that the gas in the endotracheal tube does not leak to the atmosphere. When the flow control valve 42 closes on command from the controller 44, the inspiration phase of the breath terminates.

The expiration phase is commenced by the opening of the exhalation valve 48, the timing of which is determined by the controller 44. Upon opening of the exhalation valve 48, gas within the patient's lungs is automatically expelled to the atmosphere. The exhalation valve 48 closes after the patient 34 has finished exhaling. The ventilator 30 includes a positive expiration end pressure (PEEP) feature so that an operator can preset what the pressure level of the proximal gases should be at the end of each breath. During expiration, the controller 44 compares the actual proximal pressure to the predetermined pressure level (PEEP), and when the proximal pressure reaches the predetermined level, the controller 44 sends a signal 50 to cause the valve 48 to approach the closed position. The controller then "servos," or controls the position of the valve 48 on a closed loop basis, so as to maintain the actual proximal pressure equal to the preselected pressure. After the exhalation valve 48 is completely closed, the flow control valve 42 opens to end the expiration phase and begin the next inspiration phase. This cycle is repeated continuously to establish artificial respiration.

Figure 2:
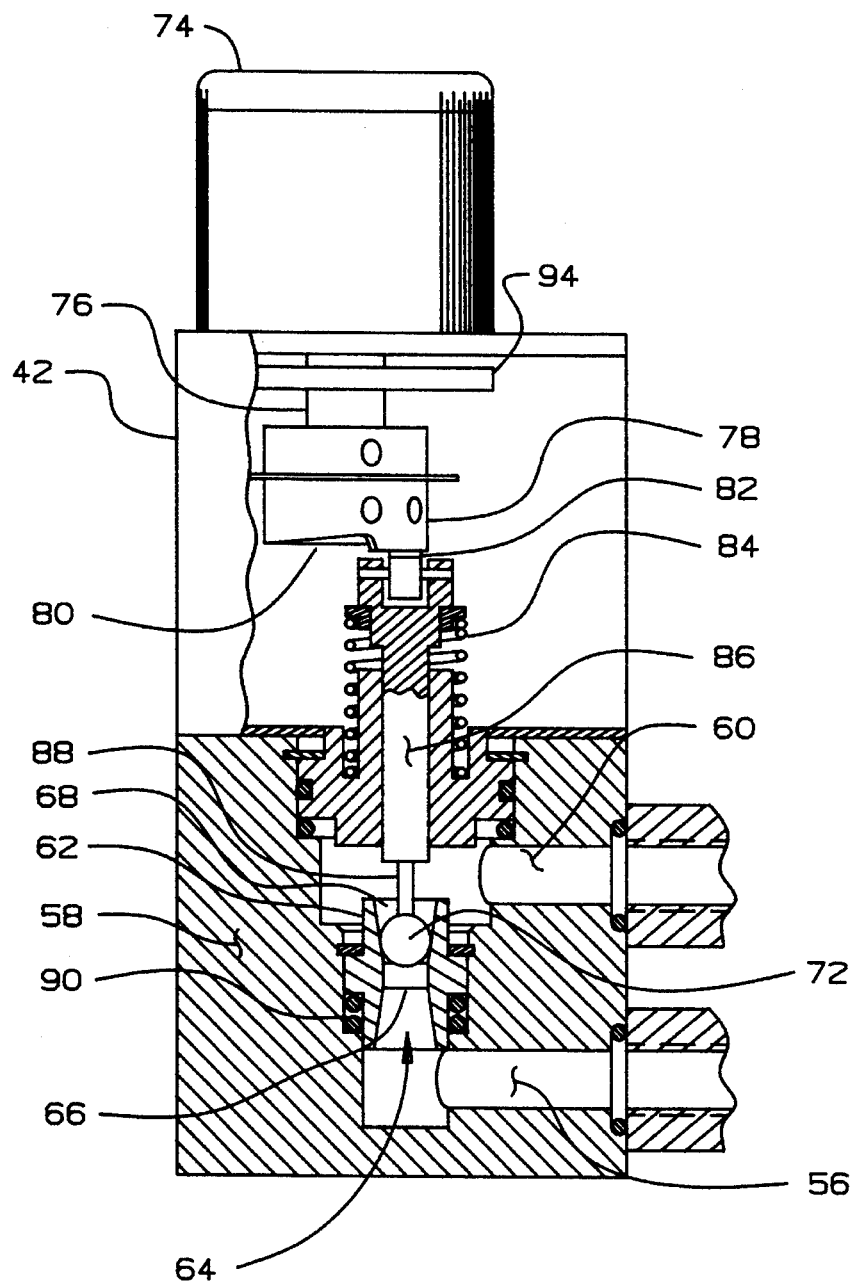
FIG. 2 is a partial cross-sectional side elevation of a flow control valve according to one embodiment of the present invention.

Turning now to FIG. 2, the flow control valve 42 is shown in greater detail. Gas from the accumulator 38 enters the flow control valve 42 through an inlet passageway 56 in a valve housing 58. Gas leaves the flow control valve 42 on the way to the patient 34 through an outlet passageway 60 in the housing 58. Between the inlet 56 and the outlet 60, a valve seat 62 is positioned. An orifice 64 extends through the valve seat 62 and permits gas to flow from the inlet 56 to the outlet 60. The orifice 64 has a converging, frusto-conical nozzle portion 66 on the side of the inlet 56 and a diverging, frusto-conical nozzle portion 68 on the side of the outlet 60.

A spherical valve member or ball 72 rests within the divergent portion 68 on the valve seat 62. The valve 42 is shown in the closed position, with the outer surface of the ball 72 in sealing engagement with the valve seat 62 so as to prevent flow through the orifice 64. The various positions of the valve 42 and the various flow rates through the valve 42 are caused by displacement of the ball 72 relative to the valve seat 62. This changes the area of the orifice 64 through which gas flow is permitted, and thus the rate of flow through the valve 42. A substantially linear relationship exists between the orifice area through which gas flows and the displacement of the ball 72.

The position of the valve 42 is changed by means of a stepping motor 74. The stepping motor 74 receives electronic signals 46 from the controller 44 which cause rotation of a stepping motor shaft 76. On the end of the shaft 76, a cam 78 is mounted. The cam 78 includes an axially facing cam surface 80. A cam follower or roller 82 is biased into engagement with the cam surface 80 by a spring 84. Thus, rotation of the shaft 76 and the cam 78 causes displacement of the roller 82 as the roller 82 follows the pitch on the cam surface 80.

Displacement of the roller 82 is translated to the ball 72 by means of an elongated, cylindrical stem 86. The stem 86 is slidable along a linear axis of motion either toward or away from the valve seat 62. The roller 82 is rotatably mounted at one end of the stem 86. At the other end of the stem 86, the ball 72 is secured to the stem 86 by means of an elongated, flexible wire 88, which is preferably formed from stainless steel and has a diameter of approximately thirty-five thousandths of an inch.

The longitudinal axis of the wire 88 is substantially parallel to the linear axis of motion of the wire 88 and the stem 86. The flexibility of the wire 88 permits the wire 88 to deviate from the axis of motion, resulting in radial displacement of the ball 72. During operation of the valve 42, the ball 72 and the valve seat 62 often become misaligned, or due to wear of either element, the radial position of the ball 72 must be changed in order to effect a tight sealing engagement between the ball 72 and the valve seat 62. Advantageously, the wire 88 automatically permits adjustments in the radial position of the ball 72 to compensate for such misalignment or wear.

The valve body 62 is surrounded by a pair of resilient O-rings 90 which form a seal between the valve seat 62 and the surrounding housing 58. To prevent damage to the ball 72 and valve seat 62 in the event of overshooting of the stem 86 past the closed position of the valve 42, compression of the O-rings 90 permits movement of the valve seat 62.

A spirally-wound spring 94 formed from a thin metallic strip surrounds the stepping motor shaft 76. The spring 94 biases the shaft 76 to rotate in a direction which causes the valve 42 to close. During normal operation, the stepping motor 74 overcomes the biasing torque generated by the spring 94 so that the spring 94 does not affect the position of the valve 42. However, in the event of a power loss, the spring 94 automatically biases the valve 42 to a closed position. This prevents a stream of system pressure gas from constantly being forced into the patient's lungs in the event of such an emergency. Although not shown in the drawings, the ventilator 30 includes a safety valve so that the patient would be allowed to breathe ambient air after the flow control valve 42 was biased closed.

Due to the structure of the flow control valve 42, the stable pressure conditions upstream of the valve 42 and the flow conditions established within the valve seat 62, a known relationship exists between the position of the ball 72 and the flow rate of gas through the valve 42. Each step of the stepping motor 74 causes a certain amount of displacement of the ball 72, which is in turn correlated to a known change in flow rate. This relationship exists for all flow conditions in the valve 42 during operation of the ventilator 30.

The major reason why flow through the valve 42 is so predictable is because a region of "sonic" or "choked" flow is established within the valve seat 62. As is well known, choked flow occurs when the ratio of the absolute pressure downstream of a nozzle or orifice relative to the absolute pressure upstream of the orifice is 0.528 or less. The significance of the choked flow condition is that variations in pressure downstream of the orifice which do not cause the 0.528 ratio to be exceeded will not change the rate of flow through the orifice. Thus, if the downstream and upstream pressures are maintained at the 0.528 ratio or below, a change in orifice area can be precisely correlated to the resulting change in flow rate, regardless of the downstream flow conditions.

In the present ventilator 30, the pressure upstream of the orifice 64 is maintained at a constant 20 psig, or approximately 34.7 psia. Enough gas is stored in the accumulator 38 during exhalation so that during the inspiration phase of each breath, the flow rate to the patient 34 can exceed the flow rate of gas into the accumulator 38 from the source 32. The pulsation dampener 41 acts as a buffer between the regulator 40 and the flow control valve 42 so as to maintain the pressure upstream of the valve 42 at a constant 20 psig. The flow control valve 42 is capable of causing very fast changes in the gas flow rate which in turn forces the regulator 40 to respond rapidly in order to maintain a constant system pressure. During these transient flow conditions, pressure fluctuations occur due to the limited response time of the regulator 40. The pulsation dampener 41 stores a small quantity of gas to minimize these pressure fluctuations.

Downstream of the orifice 64, the pressure is a function of the resistance to flow through the patient's airways and the resilience, or "compliance," of the patient's lungs. The less compliant the lungs are, the more pressure will be developed in the lungs when filled with a given volume of gas. It has been found that in adults with the least compliant lungs, the maximum back pressure which is desirable to establish within the lungs during normal ventilation is about 2 psig. Thus, the pressure downstream of the orifice 54 is always approximately 16.7 psia or less. The maximum ratio of absolute pressures then is 16.7 psia/34.7 psia, or about 0.48, which is less than the 0.528 maximum ratio required to maintain choked flow.

Due to the establishment of choked flow within the valve 42 during operating conditions, the known and constant pressure level upstream of the valve 42, and the linear relationship which exists between displacement of the ball 72 and the area of the orifice 64, the flow rate is known for all positions of the valve 42. Since the valve 42 is moved in discrete, incremental steps by the stepping motor 74, the relationship is known between the change in flow rate for each step of the stepping motor 74. As is discussed in greater detail below, since the controller 44 can keep track of the position of the valve 42, the flow rate is known to the controller 44 due to the known relationship between valve position and flow rate. As a result, the controller 44 can control the valve 42 on an open loop basis.

OPERATION

In one mode of operation, the ventilator 30 completely controls the patient's breathing. In this mode, which is usually used for severely incapacitated or unconscious patients, the patient's breath rate, the volume of air per breath (tidal volume) and the flow rate at which air is delivered are all controlled by the ventilator 30.

The ventilator 30 includes a number of switches which enable an operator to select the desired characteristics of this completely controlled ventilation provided to the patient 34. These characteristics include the peak flow rate, the tidal volume and the breath rate. The breath rate is the desired number of breaths per minute. The tidal volume is the total volume of gas delivered to the patient during each breath. The peak flow rate is the maximum rate of gas flow at which each breath is delivered.

Figure 3A:
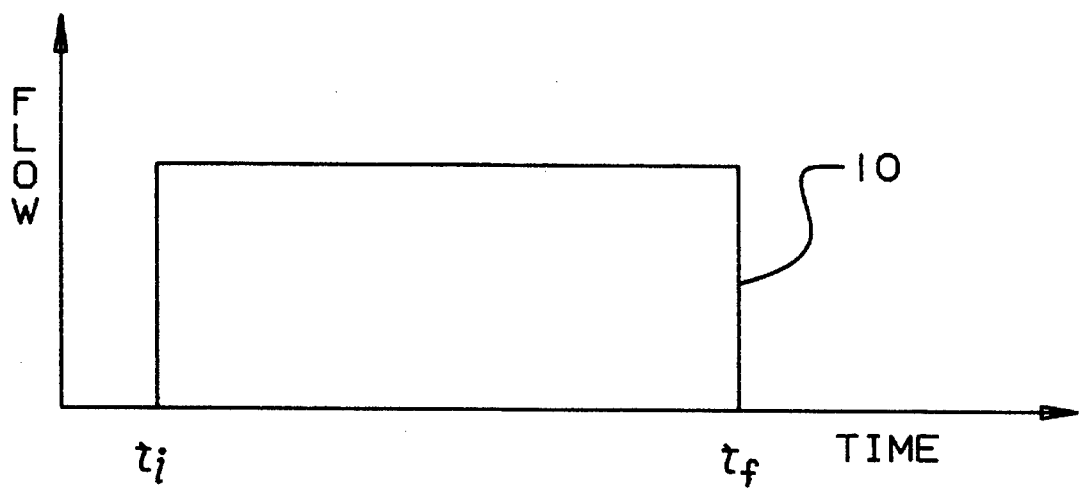
FIG. 3a is an illustration of a rectangular breath profile.
Figure 3B:
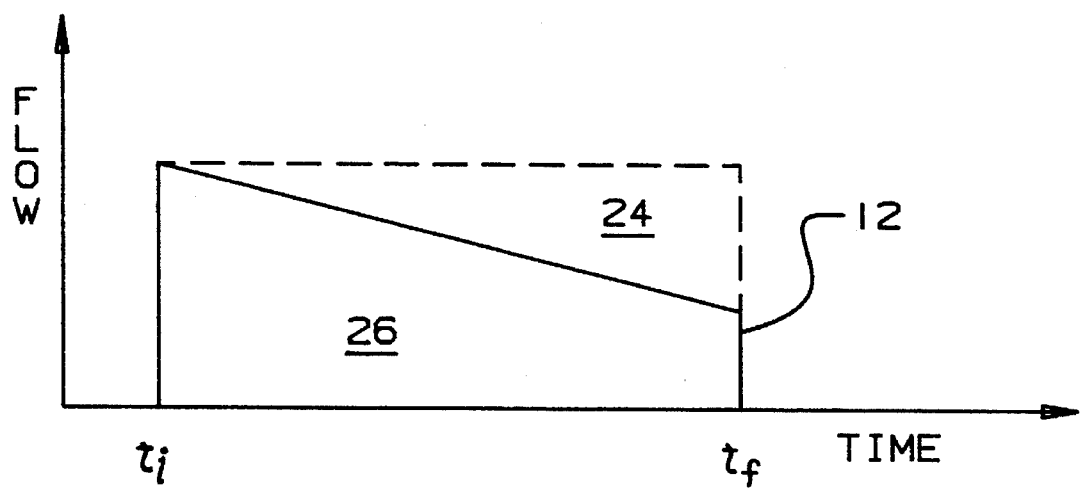
FIG. 3b is an illustration of a tapered breath profile.

The operator may also select the breath waveform, or profile. The breath profile is defined as the shape of desired rate of flow delivered to a patient versus time. A rectangular breath profile 10 and a tapered breath profile 12 are illustrated in FIGS. 3A and 3B, respectively. For the rectangular breath profile 10, the desired flow instantaneously increases from zero to the peak flow rate at time $t_i$ and instantaneously decreases from the peak flow rate to zero at time $t_f$. For the tapered breath profile 12, the desired flow increases instantaneously at time $t_i$ to the peak flow rate and gradually decreases along a straight line to one-half the peak flow rate at time $t_f$, at which point the flow instantaneously decreases to zero.

Figure 4:
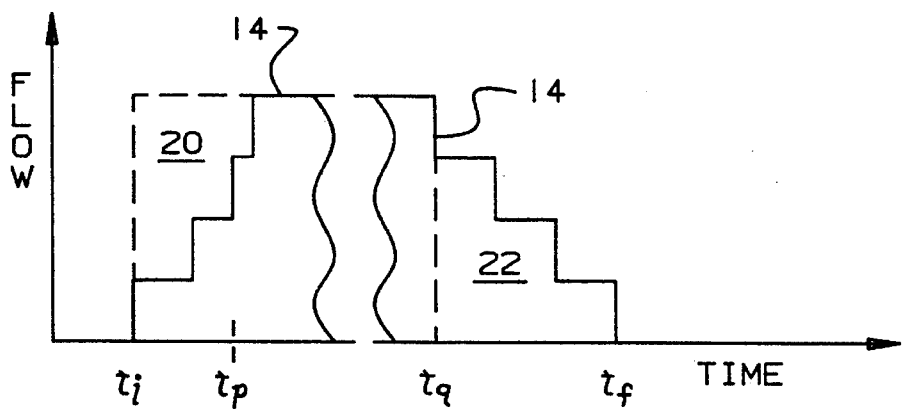
FIG. 4 is an illustration of a simplified flow profile with the intermediate portion removed of a breath with a rectangular profile.
Figure 5:
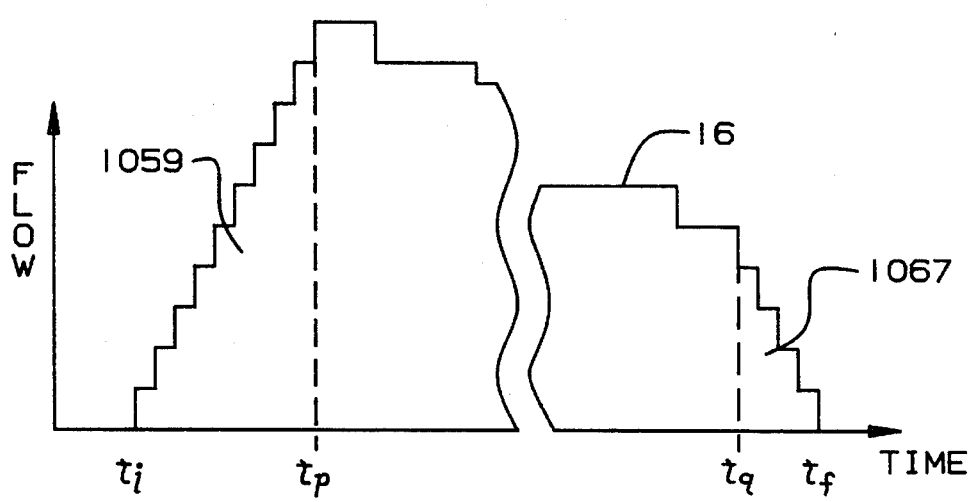
FIG. 5 is an illustration of a simplified flow profile with the intermediate portion removed of a breath with a tapered profile.
Figure 6:
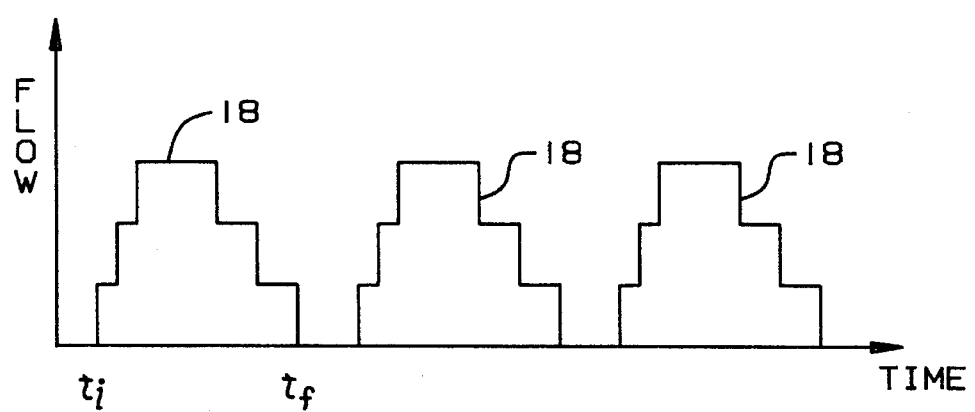
FIG. 6 is an illustration of three simplified, substantially identical flow profiles.

No ventilator can deliver a breath exactly in accordance with these breath profiles 10, 12 since no ventilator can instantaneously change the flow rate from zero to the peak flow rate, and vice versa. However, ventilators deliver flow profiles which approximate the idealized breath profiles 10, 12. A flow profile is defined as the actual rate of flow delivered to a patient versus time. FIGS. 4, 5 and 6 illustrate a number of flow profiles 14, 16, 18. In FIGS. 4 and 6, the illustrated flow profiles 14, 18 correspond to breaths having rectangular breath profiles, while the flow profile 16 in FIG. 5 corresponds to a breath having a tapered breath profile. The flow profiles 14, 16, 18 have been significantly simplified and are presented in such simplified form for purposes of clarity in the explanation of the ventilator operation.

After the ventilation characteristics have been selected by the operator, but prior to ventilating the patient 34, the ventilator 30 determines what the flow profile of a breath will be, based upon the selected characteristics, and uses the flow profile to control the delivery of ventilation to the patient 34.

In determining this flow profile, the controller 44 initially determines the number of steps through which the stepping motor 74 must be displaced to provide the discrete flow rate which most closely corresponds to the peak flow rate selected by the operator. As discussed above, the ventilator flow control valve 42 is capable of delivering many discrete flow rates. As a result, although the flow rate selected by the operator may not exactly equal one of the discrete flow rates providable by the flow control valve 42, any difference would be quite small since the flow control valve 42 is capable of delivering many discrete flow rates.

The number of steps required to provide the discrete flow rate which most closely corresponds to the selected peak flow rate is determined in accordance with the following equation:

$$\text{STEPS} = \text{INTEGER [FLOWRATE/VALVRATE} + 0.5] + \text{CONSTANT}\quad(1)$$

where FLOWRATE is the selected peak flow rate, VALVRATE is a constant which represents the incremental flow of gas through a valve 42 per step, INTEGER is the truncation function which truncates any fraction of the operand, CONSTANT represents a predetermined number of steps necessary to compensate for a nonlinear portion of the flow control valve near its closed position, and STEPS is the required number of steps corresponding to the discrete flow rate closest to the selected peak flow rate.

The INTEGER function is used since the stepping motor 74 can only be displaced through a whole number of steps. The 0.5 which is added to the value of FLOWRATE/VALVRATE before truncation by the INTEGER function compensates for the fact that the INTEGER function truncates instead of rounding to the nearest whole number.

In the particular flow control valve 42 used in this described embodiment, VALVRATE is 1.000 liter per minute per step and CONSTANT is 3. Where different flow control valves are used, VALVRATE and CONSTANT may have different values.

Equation (1) assumes that the relationship between the actual flow of gas through the flow control valve 42 and the number of steps is linear. A linear flow control valve is one that delivers additional increments of flow that are equal; that is, each further incremental opening of the valve delivers the same amount of additional flow. Even though a flow control valve may be nonlinear, such a valve may still deliver a precise or known amount of flow at each incremental opening. Such a nonlinear valve could be used in connection with this embodiment.

If a nonlinear valve is used instead of using Equation (1), a software lookup table is provided in order to derive the number of steps corresponding to the discrete flow rate closest to the selected peak flow rate. Such a software lookup table includes the actual flow rate that is delivered at each incremental opening of the flow control valve so that the actual flow rate most closely corresponding to the selected peak flow rate can be retrieved from the table along with the corresponding number of steps.

After determining the number of steps necessary to provide the closest discrete flow, the actual flow rate is determined so that the actual tidal volume delivered to the patient 34 may be made equal to the tidal volume selected by the operator.

In order to calculate the actual flow from the number of steps determined in accordance with Equation (1), the following equation is used, where the flow is linear with the number of steps:

$$\text{FLOW} = (\text{STEPS} - \text{CONSTANT}) \times (\text{VALVRATE}) \quad (2)$$

where STEPS is the number of steps that was calculated in Equation (1) which would yield the actual discrete flow closest to the desired peak flow, CONSTANT is the number used to compensate for a nonlinear portion of the flow control valve, VALVRATE is the constant which represents the incremental flow through the valve 42 per step, and FLOW is the actual flow delivered.

If the flow rate provided by the flow control valve 42 is not linear with the number of steps, the software lookup table described above can be used to provide the actual flow from the number of steps. In this case, instead of just comparing the selected peak flow rate with each of the discrete actual flow rates and only retrieving the number of steps corresponding to the closest actual flow rate, the actual flow rate is retrieved as well.

After the number of steps and the corresponding actual peak flow rate are determined, the controller 44 determines a breath delivery period which determines the length of time that a breath is delivered to the patient 34. In general, a breath delivery period is broadly defined as any period of time which is used to determine how long the duration of a breath should be. While a breath delivery period is defined broadly, one particular definition is set forth below to aid in the explanation of the ventilator 30 of the described embodiment.

An important feature of the ventilator 30 is directed to the delivery to the patient 34 of an actual tidal volume which is substantially equal to the tidal volume preselected by the operator. The delivery of such a precise actual tidal volume is accomplished by adjusting the magnitude of the breath delivery period.

One simplified method of determining the breath delivery period necessary to deliver the tidal volume selected by the operator would be to divide the preselected tidal volume by the actual peak flow rate determined in accordance with Equation (1). This simplified method assumes that the flow rate is instantaneously increased to the peak flow rate at the beginning of a breath and instantaneously decreased at the end of a breath. However, since a flow control valve 42 cannot be opened instantaneously, the actual volume delivered during the initial portion of the breath is somewhat less than the amount expected by the idealized method. This volumetric difference is referred to as the undelivered volume that would be lost during the increase of the flow rate during the initial portion of the breath. Also, since the flow control valve 42 is not closed instantaneously at the end of a breath, there is an extra volume delivered that is not taken into account by the simplified method. In FIG. 4, the undelivered volume that would be lost corresponds to the area 20 bounded by the dotted line and the extra volume that would be delivered corresponds to the area 22 bounded by the dotted line. Since the flow control valve 42 may not be opened and closed at identical rates, the undelivered volume lost may not be equal to the extra volume delivered, so that the actual volume delivered will not equal the preselected tidal volume. In order to account for this volumetric error, the controller 44 adjusts the breath delivery period so that the actual volume delivered is substantially equal to the preselected tidal volume.

For purposes of the following discussion, a breath delivery period is defined as including the initial portion of a breath during which the flow rate is rapidly increasing and the intermediate portion of the breath just prior to the rapid decrease of flow during the final portion of the breath, but excluding this final portion of the breath. Thus, in FIGS. 4 and 5, the breath delivery period starts at time $t_i$ and ends at time $t_q$. The breath delivery period is precisely defined in this manner only for purposes of explanation of the ventilator's operation.

The breath delivery period is determined in accordance with the following equation:

$$BDP = (V_X + \text{VOLUME} - V_Y)/\text{FLOW} \quad (3)$$

where $V_X$ is the undelivered volume that would be lost while the valve is opening, $V_Y$ is the extra volume that would be delivered while the valve is closing, VOLUME is the selected tidal volume, FLOW is the actual flow rate closest to the preselected flow rate, and BDP is the breath delivery period.

Thus, as it can be seen from Equation (3), if the undelivered volume that would be lost, $V_X$, is larger than the extra volume that would be delivered, $V_Y$, the breath delivery period is increased to account for this difference. If the undelivered volume lost, $V_X$, is less than the extra volume delivered, $V_Y$, the breath delivery period is shortened to accommodate this difference. If it happens that the extra volume delivered is exactly equal to the undelivered volume lost, the breath delivery period is unaffected. Thus, the adjustment of the breath delivery period in this manner ensures that the actual volume delivered will substantially equal the preselected tidal volume.

The undelivered volume lost and the extra volume delivered, which are stored in a software lookup table, can be computed as a summation of time-flow products, a time-flow product being defined as a volume computed as the product of the actual flow delivered at one of the incremental openings of the flow control valve and the length of time the valve is opened to that incremental opening. More particularly, the undelivered volume that would be lost is determined in accordance with the following equation:

$$V_X = \sum_{n=i}^{p} (\text{FLOW} - A_n) \times (t_n) \quad (4)$$

where FLOW is the actual peak flow, $A_n$ is the actual flow delivered by the flow control valve in its nth incremental position, $t_n$ is the amount of time that the flow control valve is in the nth position, and $V_X$ is the undelivered volume lost.

The extra volume that would be delivered during the closing of the flow control valve 42 is determined in accordance with the following equation:

$$V_Y = \sum_{n=q}^{f} (A_n) \times (t_n) \quad (5)$$

where $A_n$ is the actual flow delivered by the flow control valve in its nth incremental position, $t_n$ is the amount of time the flow control valve 42 is in the nth position, and $V_Y$ is the extra volume delivered while the flow control valve 42 is closing during the final portion of a breath.

Instead of computing the extra volume delivered and undelivered volume lost as the summation of a plurality of time flow products, these volumes can also be determined empirically by direct volumetric measurement. Regardless of how they are determined, these volumes are stored in a software lookup table which provides the total cumulative undelivered volume lost and the extra volume delivered for each actual peak flow position of the flow control valve.

The controller 44 also includes conventional ramp-up and ramp-down profiles contained in a plurality of software tables for the flow control valve stepping motor. The ramp-up profile for the stepping motor 74 determines the rate at which the motor 74 accelerates, and the ramp-down profile determines the rate at which the motor decelerates. Each of the software tables comprises a series of time delays which govern the rate at which the stepping motor is energized. Different ramp tables are provided for the stepping motor 74 depending upon (1) the direction in which the flow control valve 42 is being moved, opened or closed, (2) the number of steps through which the stepping motor 74 must be displaced to move the flow control valve 42 to its desired position, and (3) the spring force range. Different ramp tables are provided based upon direction because the flow control valve 42 is spring-biased closed, as described above, which affects the rates at which the stepping motor 74 can be accelerated and decelerated. Thus, if the valve 42 is being opened, the stepping motor 74 must be accelerated more slowly since it must overcome the force of the spring 84, while if the valve is being closed, the stepping motor 74 can be accelerated more rapidly. Different ramp tables are provided based on the number of steps in order to minimize the travel time of the stepping motor 74. For example, if the desired valve position is 12 steps away from the current valve position, a particular ramp table is used. If the desired valve position is only 6 steps away, a different ramp table is used. The ramp tables are developed in a conventional well-known manner, and the particular time delays contained therein depend upon the stepping motor 74 used and the mass and friction of the coupling between the stepping motor 74 and the flow control valve 42, in addition to direction, distances, and spring force range as described above.

The ventilator uses the stepping motor ramp profiles, the breath delivery period and the number of steps required to deliver the discrete flow rate closest to the selected peak flow rate to deliver each of a plurality of breaths to a patient. Since each breath is based upon the same predetermined ramp profiles, breath delivery period and number of steps, each breath has a substantially identical flow profile. In addition, the tidal volume of each breath is substantially identical to the preselected tidal volume since the breath delivery period is adjusted to compensate for the variability of the flow rate.

Referring now to FIG. 4, in delivering a breath with a rectangular profile, the ventilator selects a particular ramp table for the acceleration of the motor 74. Then, the ventilator accelerates the stepping motor 74 in accordance with the selected ramp table to start delivering flow at time $t_i$. The stepping motor 74 is decelerated in accordance with a selected ramp table until the stepping motor 74 reaches at time $t_p$ the step predetermined in Equation (1) corresponding to the discrete flow closest to the selected peak flow. The flow remains substantially constant until a later time $t_q$ at which point the stepping motor 74 is stepped in accordance with selected ramp tables to gradually close the flow control valve until it is completely closed at time $t_f$. More specifically, at time $t_q$, the stepping motor 74 is accelerated in accordance with a selected ramp table, which is different than the ramp table used to open the valve 42 at time $t_i$, since the direction is different. The stepping motor 74 is then decelerated in accordance with a selected ramp table, which is also different, since the valve direction has changed until the valve 42 completely closes at time $t_f$.

The ventilator 30, when desired, also delivers breaths with a tapered breath profile. Referring now to FIG. 5, a breath having this profile is delivered by rapidly increasing the flow from zero to a peak flow rate, gradually decreasing the peak flow rate to one-half the peak flow rate, and then rapidly decreasing the flow rate back to zero during the final portion of the breath. The flow profile 16 shown in FIG. 5 is a piece-wise linear approximation of the tapered breath profile 12 in FIG. 3B.

The delivery of a plurality of breaths having tapered profiles requires several additional preliminary steps than those needed to deliver a plurality of breaths with a rectangular profile. First, the breath delivery period must be adjusted for the tapered profile. More particularly, after the ventilator has determined the number of steps necessary to provide the discrete flow closest to the selected peak flow and the breath delivery period as described above, if the breath is to have a tapered profile, the controller 44 increases the breath delivery period by one-third in order to accommodate for the gradual decrease of the peak flow rate at the start of a breath to one-half the peak flow rate at the end of a breath. Referring now to FIG. 3b, it can be seen that the tidal volume delivered in a breath with a tapered profile is less than the tidal volume of a breath with a rectangular profile having an equal duration by an area equal to the dotted area 24. This dotted area 24 is equal to one-third of the area 26 underneath the breath profile 12. Thus, in order to provide the tapered profile 12 and yet still deliver the same tidal volume, the breath delivery period is increased by one-third for breaths with a tapered profile.

In addition to increasing the breath delivery period, the controller 44 performs several other steps in order to deliver a breath with a tapered profile. The controller 44 determines the number of steps required to deliver one-half the peak flow rate by dividing the value of STEPS determined in Equation (1) by two.

During the gradual decrease of the flow rate from the peak flow rate to one-half the peak flow rate during the intermediate portion of the breath, the controller 44 closes the flow control valve 42 by one or more steps each time a predetermined time interval elapses. The number of time intervals required to gradually decrease the flow from the peak flow rate to one-half the peak flow rate may be equal to the number of steps required to accomplish the same if one step is moved each time interval.

Each time interval has an equal duration which is determined by dividing the increased breath delivery period for the tapered profile by the number of steps required to move the flow control valve 42 from its peak flow position to one-half the peak flow position. After the duration of the time intervals is calculated, the ventilator 30 may deliver breaths with a tapered profile.

Now referring to FIG. 5, the flow profile 16 is delivered by rapidly increasing the flow rate at an initial time $t_i$ to a peak flow rate at a later time $t_p$, gradually decreasing the flow rate during the intermediate portion of the breath to one-half the peak flow rate at time $t_q$, and then rapidly decreasing the flow rate to zero at a time $t_f$. The gradual decrease of the flow rate from the peak flow rate to one-half the peak flow rate during the intermediate portion of the breath is accomplished by closing the flow control valve 42 one or more steps as each of the intervals described above elapses. More particularly, as soon as the flow rate reaches the peak flow rate at the time $t_p$, the ventilator waits one-half of an interval after the time $t_p$ before closing the flow control valve by one or more steps. Thereafter, as each full interval elapses, the flow control valve 42 is closed by one or more steps until the flow rate decreases to one-half the peak flow rate, at which time the controller 44 waits one-half of an interval before rapidly closing the flow control valve 42 to end the breath.

Upon completing the delivery of a single breath of either profile, the ventilator 30 waits a predetermined period of time based upon the preselected breath rate before delivering another breath. Each subsequent breath delivered by the ventilator 30 is also based upon the same peak flow rate, actual flow rate, breath delivery period and ramp profiles used to deliver the initial breath, all of which were calculated prior to the delivery of the breaths. Thus, each of the breaths has the same flow profile, and the breaths are substantially identical and have substantially identical tidal volumes, as is illustrated in FIG. 6.

ENGINEERING DESIGN DETAILS OF A PREFERRED EMBODIMENT

Figure 7:
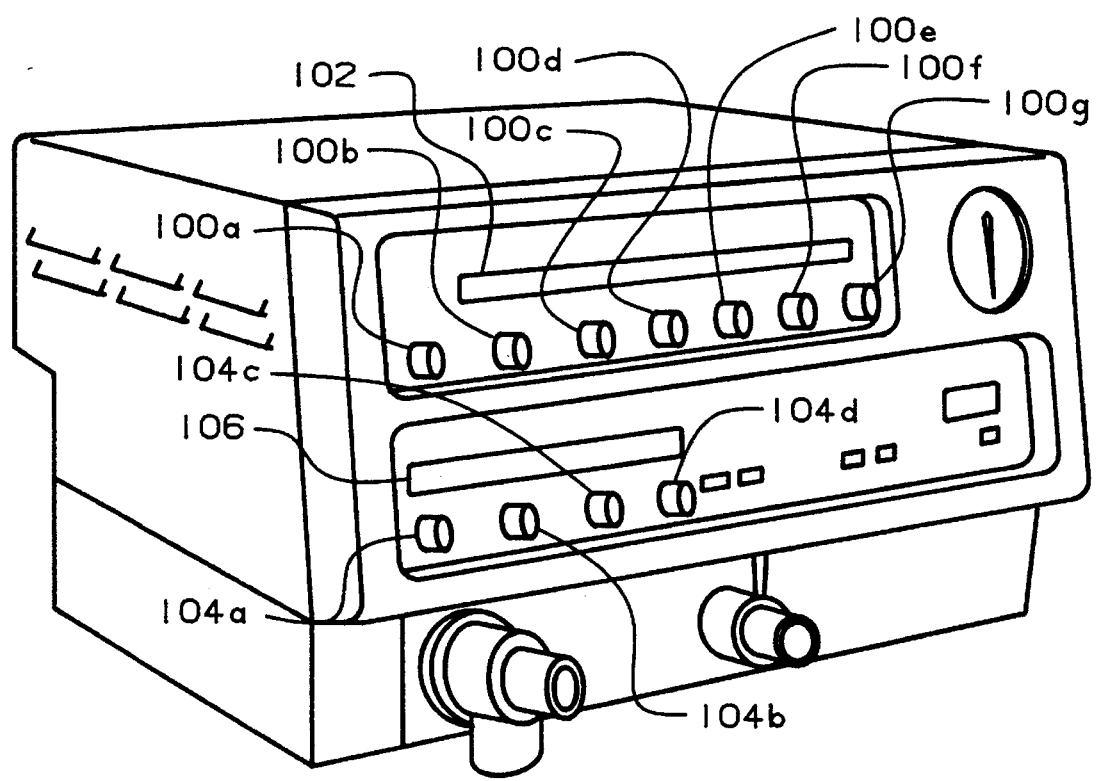
FIG. 7 is a perspective view of the front control panel of the ventilator.

Now referring to FIG. 7, the ventilator 30 has a control panel which includes an upper row of controls and a lower row of controls. The upper row of controls includes a mode control knob 100a that selects the four modes of operation of the ventilator, which include a first mode in which a volume-controlled square breath profile is delivered, a second mode in which a volume-controlled tapered breath profile is delivered, and third and fourth modes which are synchronized intermittent mandatory ventilation (SIMV) modes. SIMV modes of ventilation are well known in the ventilator art. Only the first and second modes, the volume-controlled modes, are germane to this invention since these are the two modes in which breaths with predetermined flow profiles as described above are delivered to the patient.

The upper row of controls also includes a knob 100b which may be set to a selected tidal volume, a knob 100c that may be set to a selected peak flow rate, a knob 100d that may be set to a selected breath rate, a knob 100e that may be set to a selected PEEP/CPAP pressure, a knob 100f that may be set to a selected pressure sensitivity, and a knob 100g that may be set to a selected pressure support. The PEEP/CPAP pressure is defined in the ventilator art as the minimum pressure existing within the patient's lungs at all times during inspiration and exhalation. The pressure sensitivity and support controls have a function well known in the art. The upper row of controls also includes an LED display 102 that displays the selected values above their respective control knobs.

The lower row of controls includes a number of control knobs which control various alarm limits in the ventilator 30. In particular, the lower row includes a knob 104a that may be set to a selected the high pressure alarm limit, a knob 104b that may be set to a selected low peak pressure alarm limit, a knob 104c that may be set to a selected low PEEP pressure alarm limit, and a knob 104d that may be set to a selected low inspiratory tidal volume alarm limit. The high pressure alarm limit determines the highest acceptable pressure that will be delivered to the patient without triggering the alarm. The peak pressure is defined as the highest pressure delivered to the patient during the inspiratory phase of a breath. The low peak pressure limit determines the lowest acceptable pressure to be delivered to the patient. The lower row of controls also includes an LED display 106 that displays the selected alarm limit settings above their respective control knobs 104.

Spirally-Wound Spring

Figure 2A:
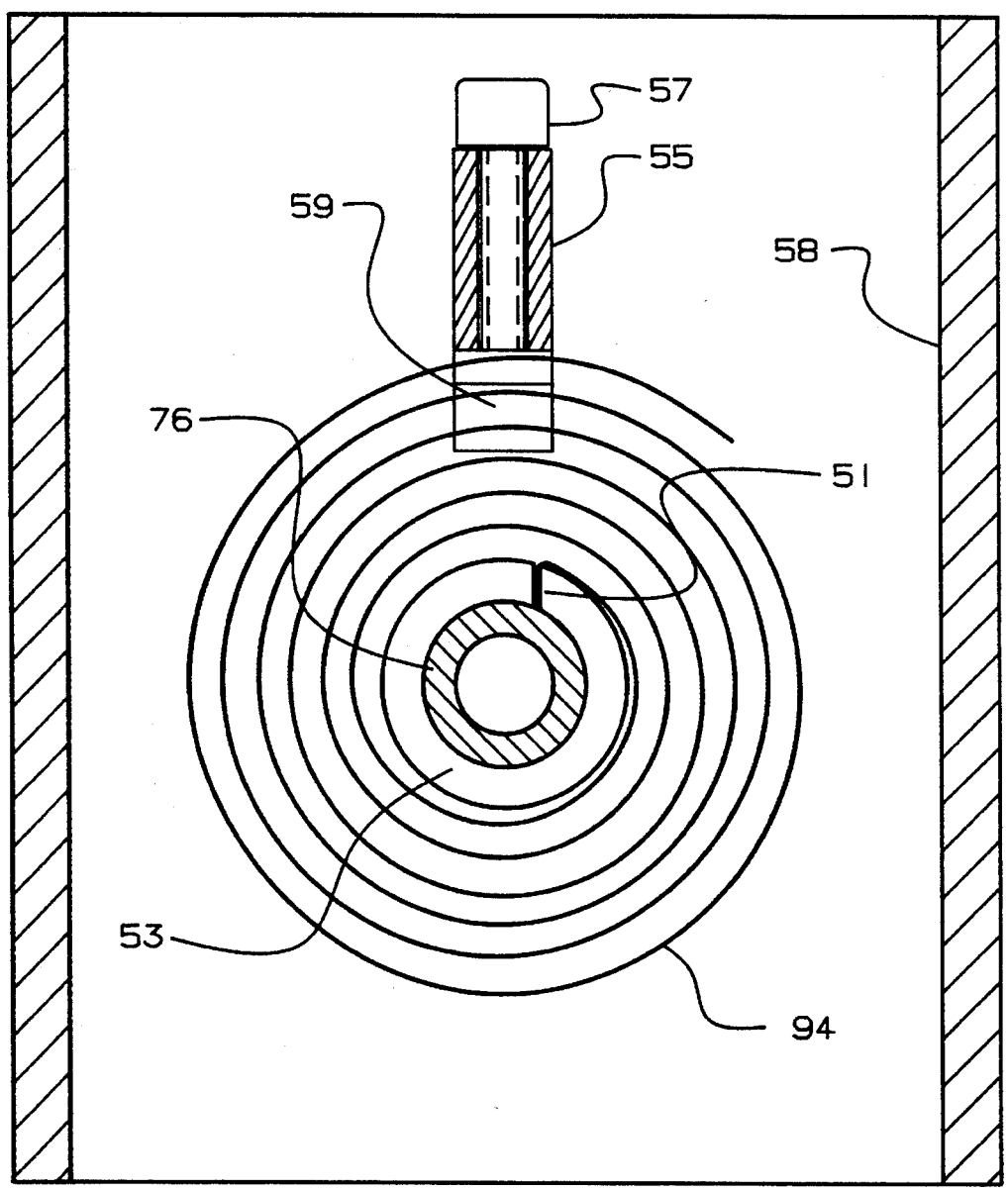
FIG. 2a is a partial cross-sectional view of the housing of the flow control valve.

The spirally-wound spring 94, a side view of which is shown in FIG. 2a, is made of AISI-1095 (American Iron and Steel Institute) spring temper steel 0.010 inches thick having a length of 27.1 inches and a width of 0.15 inches. One end of the spring is attached to the shaft 76 by means of a hub 53 having a slot 51 formed therein. The hub 53 is fixably attached to the shaft 76. The end of the spring attached to the hub 53 is bent, and the bent portion is inserted into the slot 51. The spring 94 is wrapped around the shaft approximately 9 times. The other end of the spring 94 is attached to the interior of the housing 58 by means of a bracket 55 attached to the interior of the housing 58. The bracket 55 includes a clamp. The end of the spring inserted between the bracket 55 and a clamp 59, which clamp the end and the spring when a bolt 57 is tightened. The end of the spring 94 may be clamped at different positions with respect to the bracket 55 to make minor adjustments in the working load of the spring 94, as described in detail below. When clamped, the innermost winding of the spring 94 has a diameter of approximately 0.4 inches and the outermost winding has a diameter of approximately 1.5 inches.

Since the spring 94 biases the flow control valve closed, when the flow control valve motor causes the flow control valve to open, the working load of the spring 94 increases. In particular, when the flow control valve is opened to positions 0–31, as defined in full steps of the stepping motor, position 0 representing the position in which the flow control valve is fully closed and position 127 representing the fully open position of the valve, the spring 94 exerts an average working load of 1.4 inch-ounces. When the flow control valve is opened to positions 32–95, the spring 94 exerts an average working load of 1.75 inch-ounces. When the flow control valve is opened to positions 96–127, the spring 94 exerts an average working load of 2.1 inch-ounces. These are the three spring force ranges that are used in connection with the ramp profiles explained in detail below.

Circuitry Details

Figure 8:
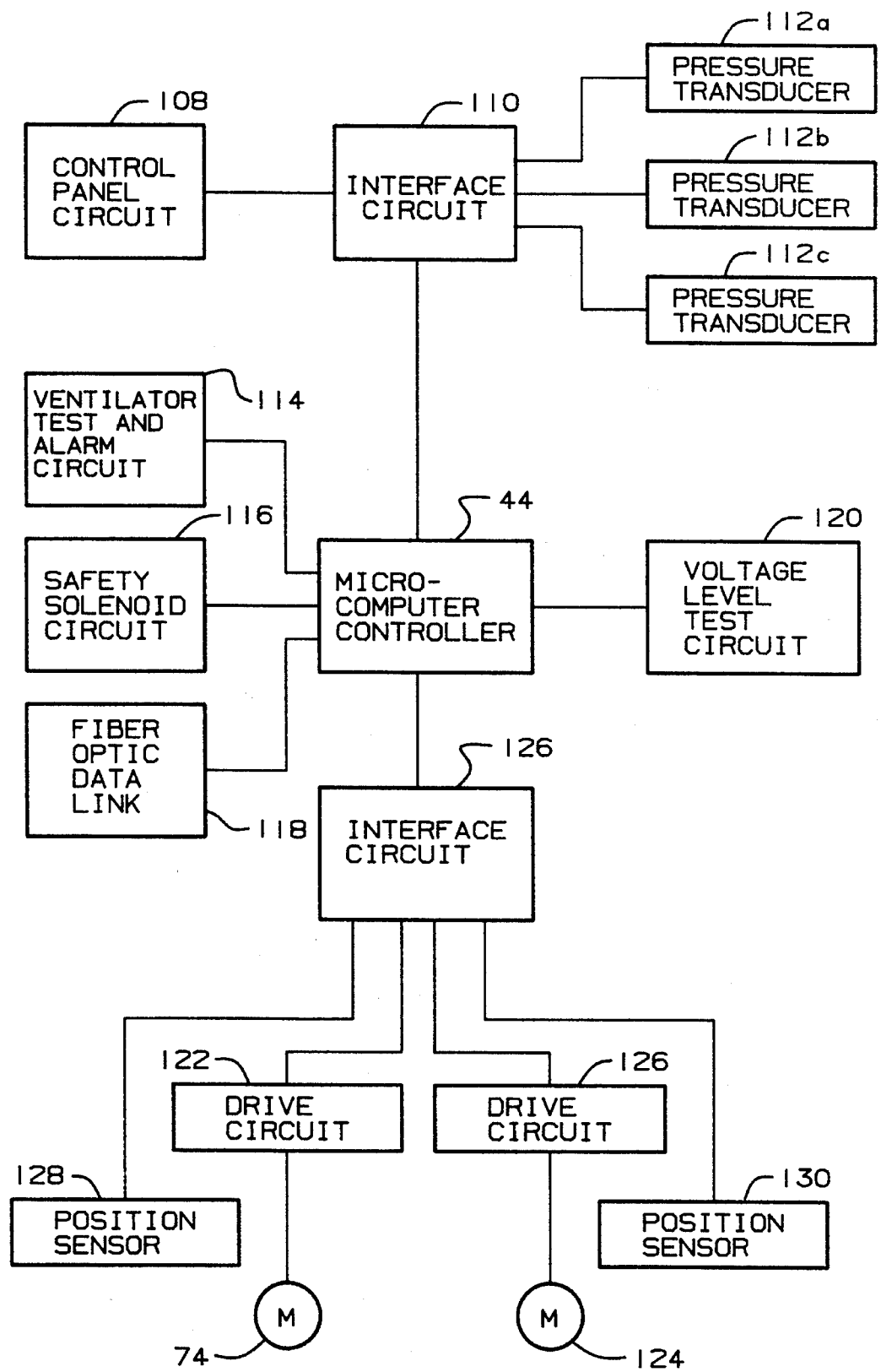
FIG. 8 is a block diagram of the detailed circuitry of the ventilator.

A block diagram of the circuitry of the ventilator is shown in FIG. 8. The microcomputer controller 44 is connected to a control panel circuit 108 through an interface circuit which allows the controller 44 to read the various control knob settings from the control panel and send control signals to the appropriate LED displays 102, 106 on the control panel to display the current settings of the knobs. The controller is also connected to three pressure transducers, a proximal pressure transducer 112a, a machine pressure transducer 112b, and a system pressure transducer 112c, through the interface circuit 110. The proximal pressure transducer 112a measures the air pressure supplied by the flow control valve 42 at a point near the patient, the machine pressure transducer 112b measures the air pressure supplied by the flow control valve 42 at a point just downstream of the valve at the exit of the ventilator, and the system pressure transducer 112c measures the air pressure upstream of the flow control valve as delivered by the pulsation dampener 41, which as indicated above is approximately 20 psi. As is described in detail below, the interface circuit 110 comprises primarily a pair of analog-to-digital converters which read the analog signals developed by potentiometers in the control panel and the pressure transducers 112 and convert these analog signals to digital signals on a multiplexed basis.

The controller 44 is also connected to a ventilator test and alarm circuit 114, a safety solenoid circuit 116, a fiber optic data link 118, and a voltage level test circuit 120. The ventilator test and alarm circuit 114 includes circuitry that periodically tests the ventilator to determine whether it is functioning properly. If the ventilator is not functioning properly, the ventilator is shut down, and an ventilator inoperative (VENT INOP) signal is generated to sound an alarm. The alarm is also sounded if one of the preselected alarm limit settings is exceeded. The VENT INOP signal activates a solenoid via the safety solenoid circuit 116 in order to cut off the flow of air being delivered to the patient and allow the patient to breathe normally by venting both the flow control valve 42 and the exhalation valve 48 to the atmosphere.

In response to the selected breath characteristics as set by the control knobs on the control panel, the controller 44 drives the stepping motor 74 for the flow control valve 42 through a drive circuit 122 and a stepping motor 124 for the exhalation valve 48 through a second drive circuit 126. The stepping motor drive circuits are connected to the controller 44 via an interface circuit 125. The controller is also connected to a first position sensor 128, or home switch, that senses when the stepping motor 74 has completely shut the flow control valve and a second position sensor 130 which senses when the stepping motor 124 has completely shut the exhalation valve 48. At all times, the controller 44 keeps track of the position of the flow control valve 42 as a number of steps of the stepping motor 74 ranging from zero, which indicates that the flow control valve is fully closed, to 127, which indicates that the flow control valve 42 is fully open. Similarly, at all times the controller 44 keeps track of the position of the exhalation valve 48 as a number of steps of the exhalation valve stepping motor 124 ranging from zero, indicating that the exhalation valve is completely closed, to 127, indicating that the exhalation valve is fully open.

The fiber optic data link 118 is connected to a communication channel of the controller and is connectable to an external device (not shown) for purposes of communicating information concerning the operation of the ventilator. This information and the messages in which it is sent is described in detail below. The voltage level test circuit 120 tests the voltage levels being supplied to the ventilator to ensure that they do not fluctuate enough to affect the operation of the ventilator.

The block diagram of FIG. 8 illustrates the generalized interconnection of the electrical circuitry elements for purposes of understanding this description of the technical details of the preferred embodiment; however, the detailed electrical circuit schematics shown in FIGS. 9–19 illustrate the exact interconnections of the circuitry. These figures include signal names and connector and pin numbers specifying the exact interconnections of the circuits. For example, the designation J3-12 in the figures refers to pin 12 of connector J3. Where a signal name includes an asterisk (*) or an overstrike following the name of the signal, the signal is active if it is logic 0, or has a small positive voltage, for example, 0.5 volts, and is inactive if it is logic 1, or has a large positive voltage, for example, 4.5 volts. Otherwise, the signal is active when logic 1 and inactive when logic 0 as defined above. If no connector pin numbers or signal names that specify the exact interconnection are shown, double capital letters are used to specify the interconnections. For example, the five signal lines labeled AA, shown in FIG. 10a, are connected to the five signal lines also labeled AA in FIG. 10b.

Figure 9A:
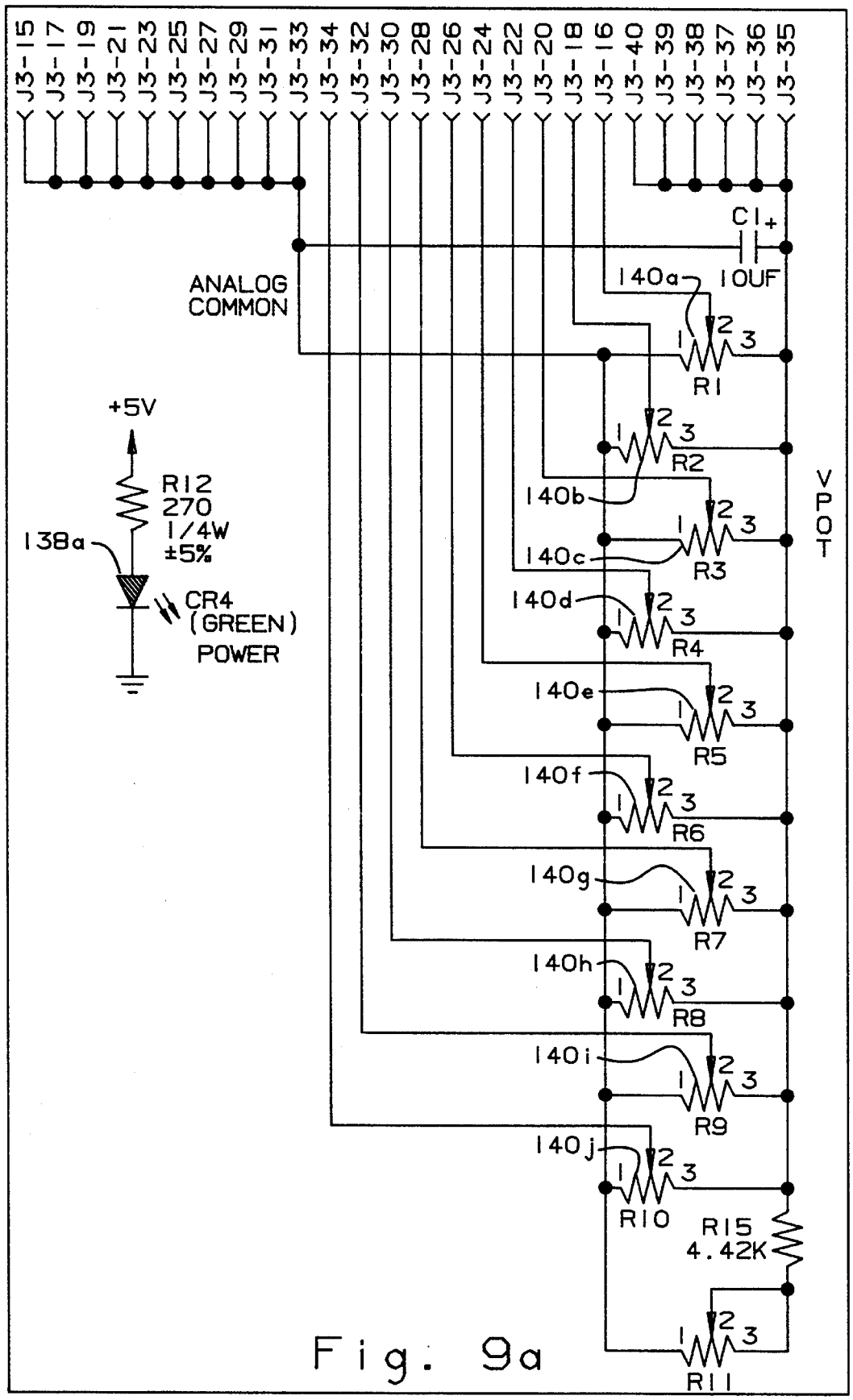
FIG. 9 is a detailed circuit diagram of a first portion of the control panel circuit shown in FIG. 8.
Figure 9B:
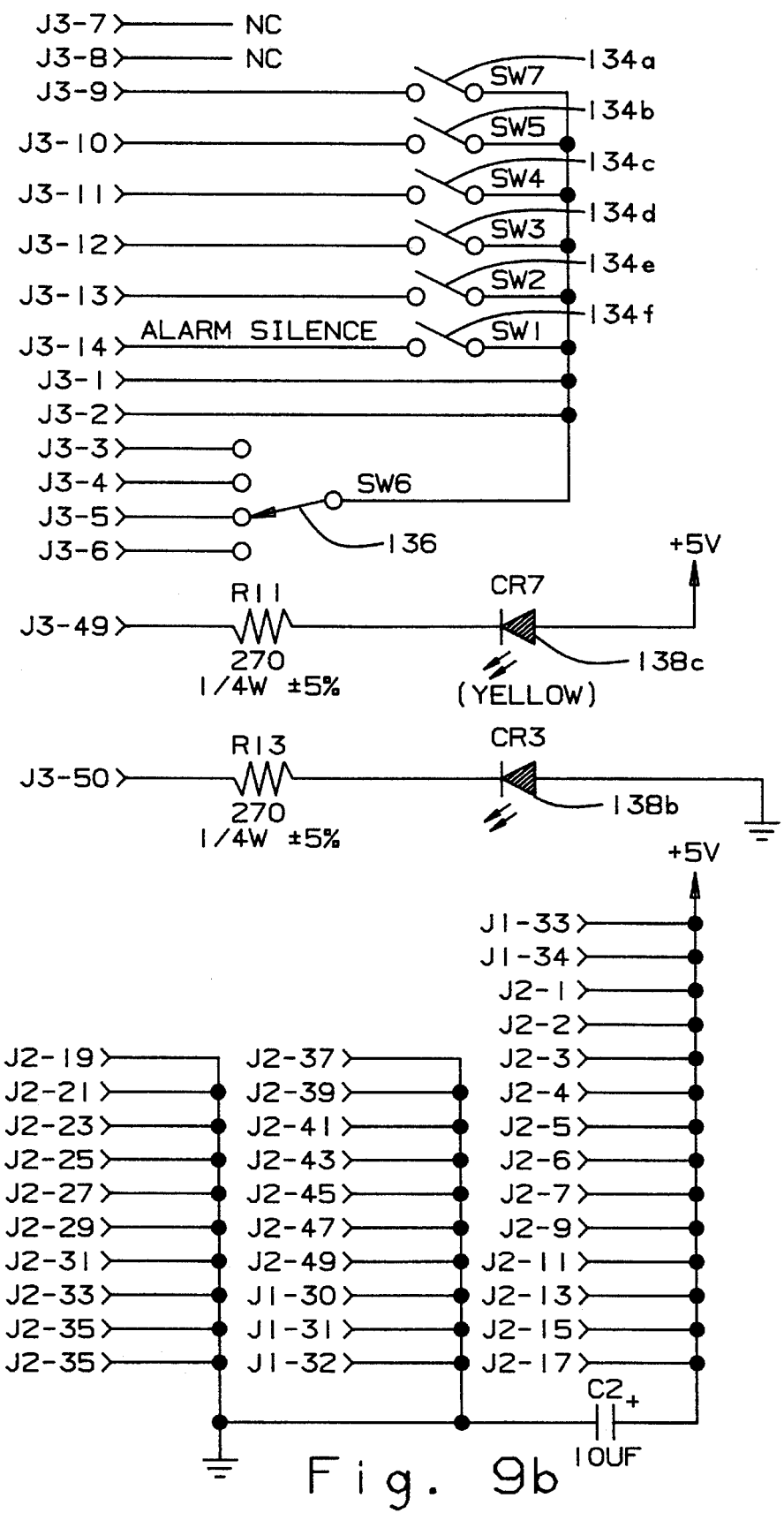

FIGS. 9 and 10 illustrate the detailed circuitry of the control panel circuit 108, shown schematically in FIG. 8. Now referring to FIG. 9, the control panel circuit 108 includes ten potentiometers 140, each of which is connected to a respective control knob 100 or alarm knob 104 on the control panel. The rotation of the control knobs and alarm knobs alters the wiper positions of the potentiometers 140 in a conventional manner, and as a result, various analog voltages are produced on the connector pins to which the wipers are connected. In this case, these connector pins are the even-numbered pins from J3-16 through J3-34. A number of pushbutton switches 134 are used for various functions including alarm silence, alarm reset, sigh breath, manual breath, and display select. A four position switch 136 is connected to the mode control knob 100a described above in order to specify in which of the four modes the ventilator is to operate. The pushbutton and mode switches are connected either directly or indirectly to the controller 44 via connector lines J3-1 through J3-14. FIG. 9 also illustrates a number of light-emitting diodes (LEDs) 138 that indicate the state of various conditions including power, the state of a battery (not shown), and a ventilator inoperative state. Also shown in FIG. 9 are various connections of connectors 1, 2 and 3 of the ventilator.

FIGS. 10a through 10d illustrate the portion of the interface circuit which causes the various control settings of the knobs 100, 104 to be displayed on the LED displays 102, 106. Now referring to FIG. 10a–10d, a first source driver is connected to and provides a source of current to each of a plurality of LED display circuits 142 in the upper LED display 102 through signal lines A–H, and a second source driver 144 is connected to and provides a source of current to each of a plurality of the LED display circuits 146 in the lower LED display 106 through signal lines A–H. The first source driver 140 is driven by logic signals supplied on the even-numbered connector lines J2-20 through J2-34 by the controller 144 through an interface circuit 110, and the second source driver 144 is logically driven by signals supplied on the even-numbered connector lines J2-36 through J2-50 also supplied from the controller 44 via the interface circuit 110.

Each of the LED display circuits 142, 146 has a cathode that is connected to a respective Darlington amplifier of a Darlington amplifier circuit 148. The circuits 148 provide a current sink so that when the Darlington amplifier is activated, current flows through the LED display circuits 142, 146 and illuminates the LEDs contained therein. Each Darlington amplifier is connected to each of two LED display circuits 142, 146 in a vertical row (the top rows of LED display circuits appear to be unconnected and are shown in that manner for purposes of clarity).

The Darlington amplifiers in the Darlington amplifier circuits 148 are selectively activated by binary logic signals provided by three 3-to-8 decoder circuits 150. Each of the 3-to-8 decoder circuits 150 is connected to a respective Darlington amplifier circuit 148, and each of the 3-to-8 decoder circuits 150 is connected to three control lines via connector pins J2-14, J2-16 and J2-18. These three control lines activate exactly one of the outputs of the decoder circuits 150, which turns on one of the Darlington amplifiers and causes the LEDs in the vertical row to which the Darlington amplifier is connected to be illuminated. Only one of the 3-to-8 decoder circuits 150 is enabled at a time by the chip select lines which are input on connector lines J2-8, J2-10 and J2-12.

In operation, the LED digit displays 142, 146 in each vertical row are illuminated periodically on a multiplexed basis at a frequency high enough to give the appearance that the LED digit displays 142, 146 are constantly illuminated. In order to display a pair of digits, the two source drivers 140, 144 are selectively driven according to the binary signals supplied on the connector J2 pins so that the appropriate parts of the numerals in the LED digit displays 142, 146 are provided a source of current, while at the same time the two LED digit displays 142, 146 in one of the vertical rows is provided a current sink through one of the Darlington amplifiers.

Figure 10A:
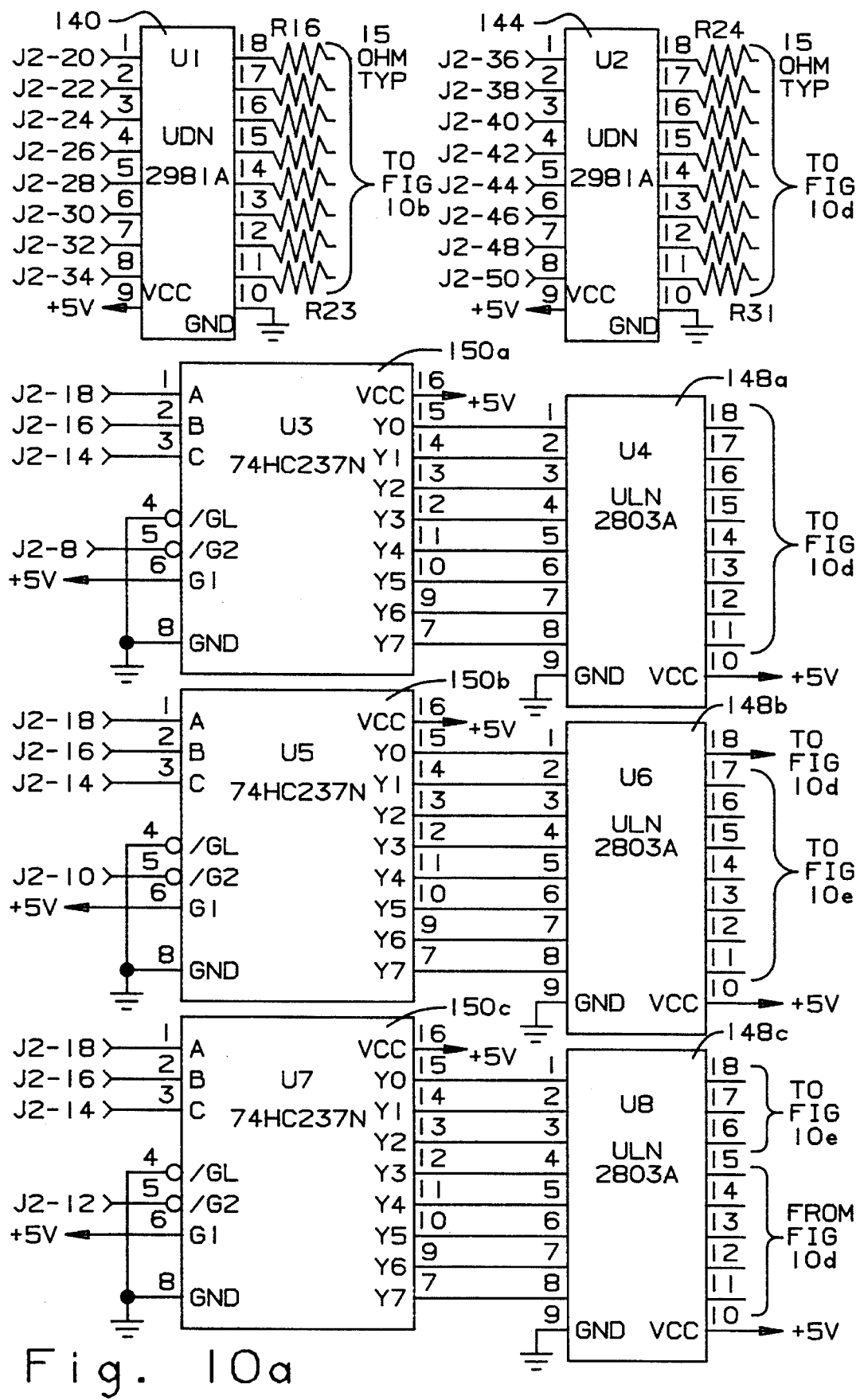
FIG. 10a is a detailed circuit diagram of a second portion of the control panel circuit shown in FIG. 8.
Figure 10B:
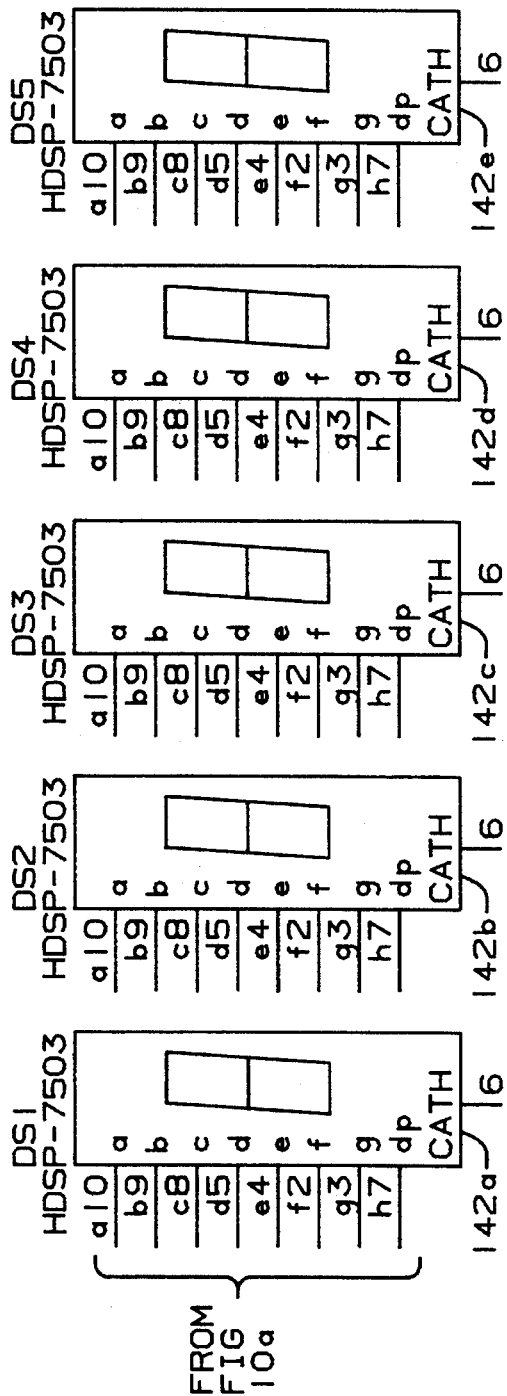
FIG. 10b is a detailed circuit diagram of a third portion of the control panel circuit shown in FIG. 8.
Figure 10B:
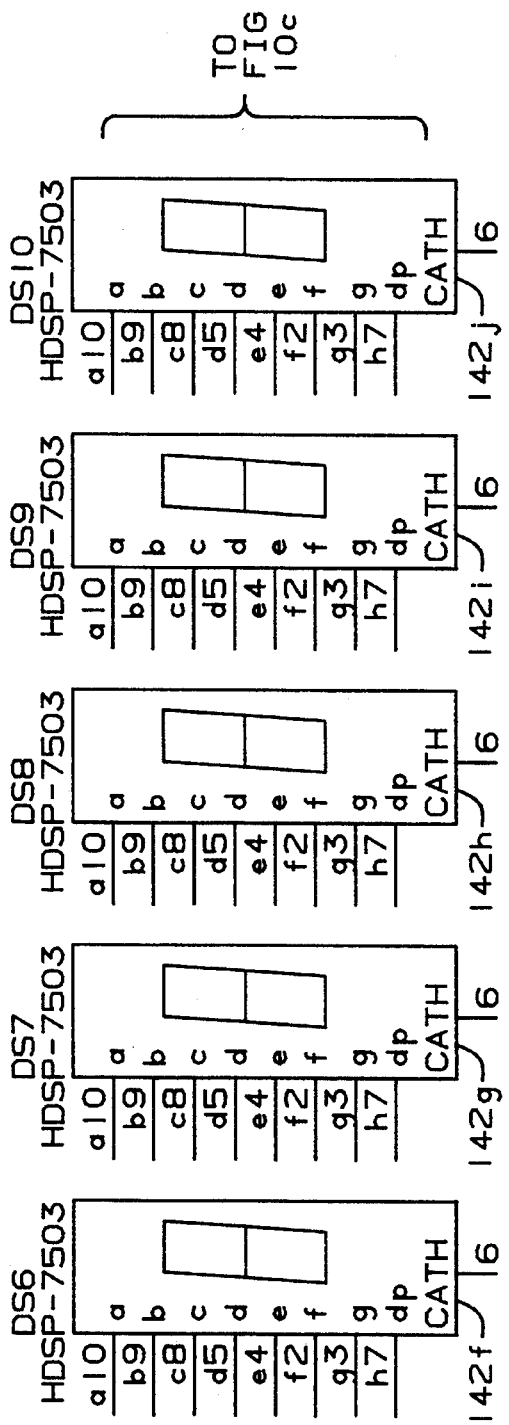
Figure 10C:
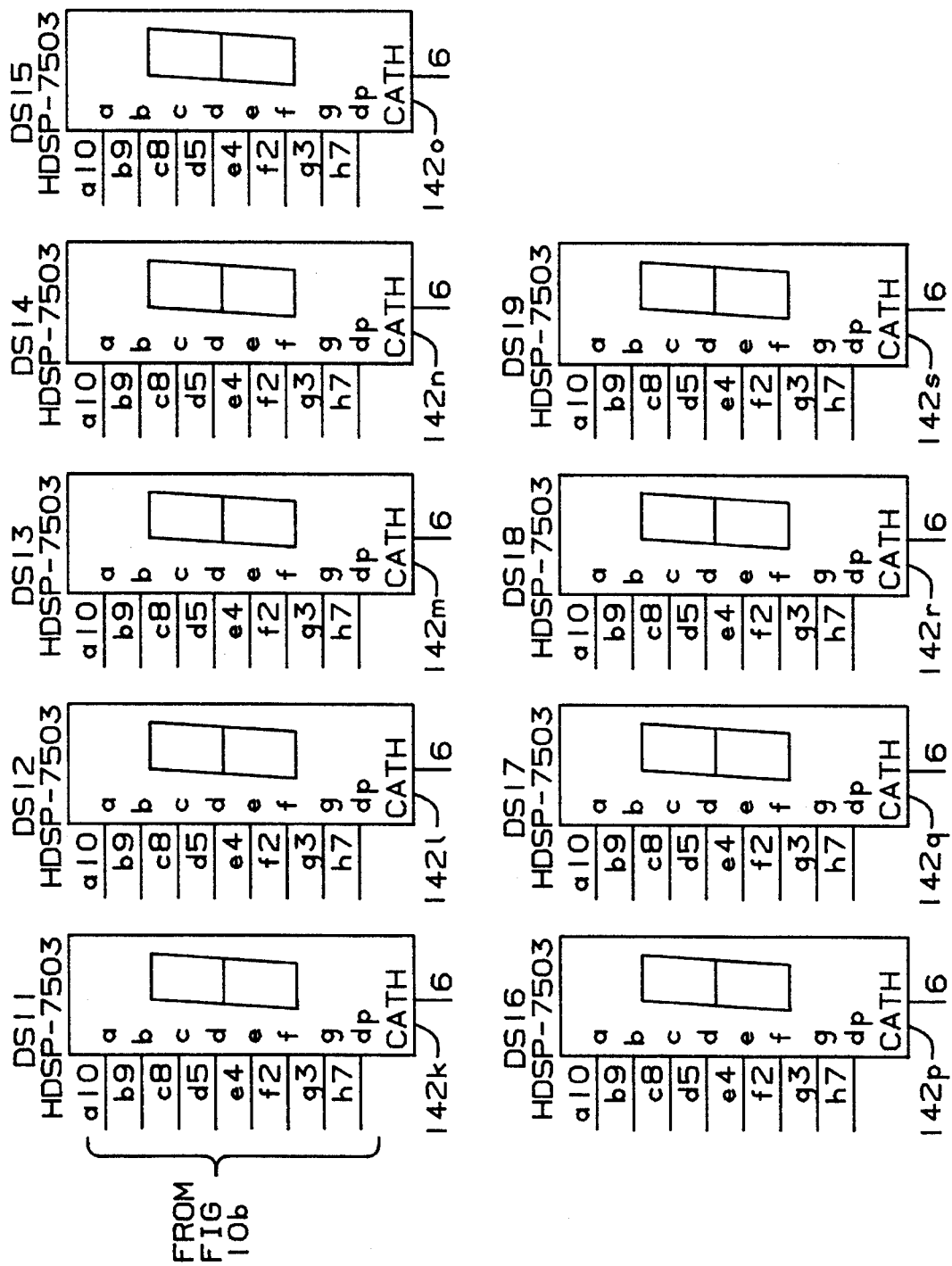
FIG. 10c is a detailed circuit diagram of a fourth portion of the control panel circuit shown in FIG. 8.
Figure 10D:
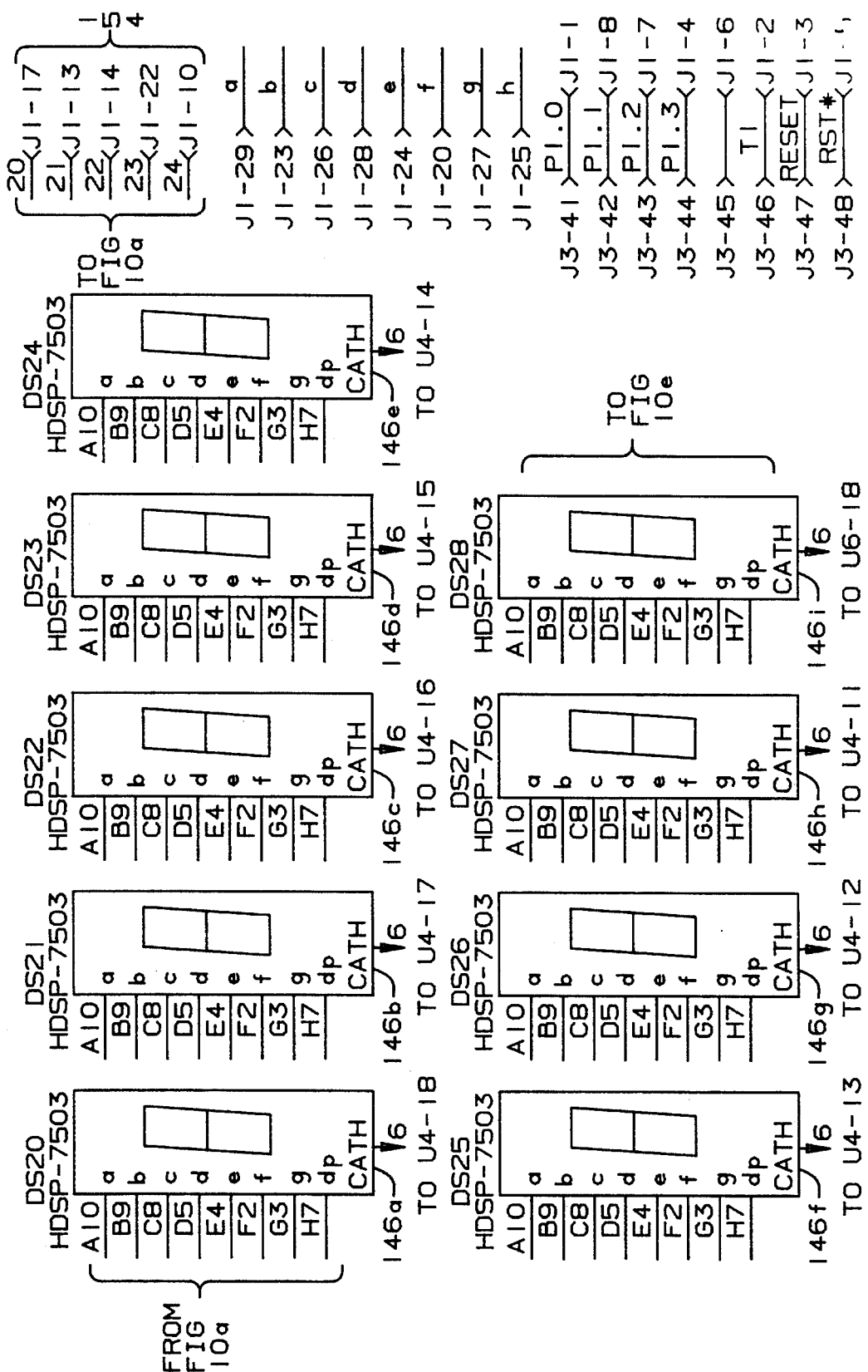
FIG. 10d is a detailed circuit diagram of a fifth portion of the control panel circuit shown in FIG. 8.
Figure 10E:
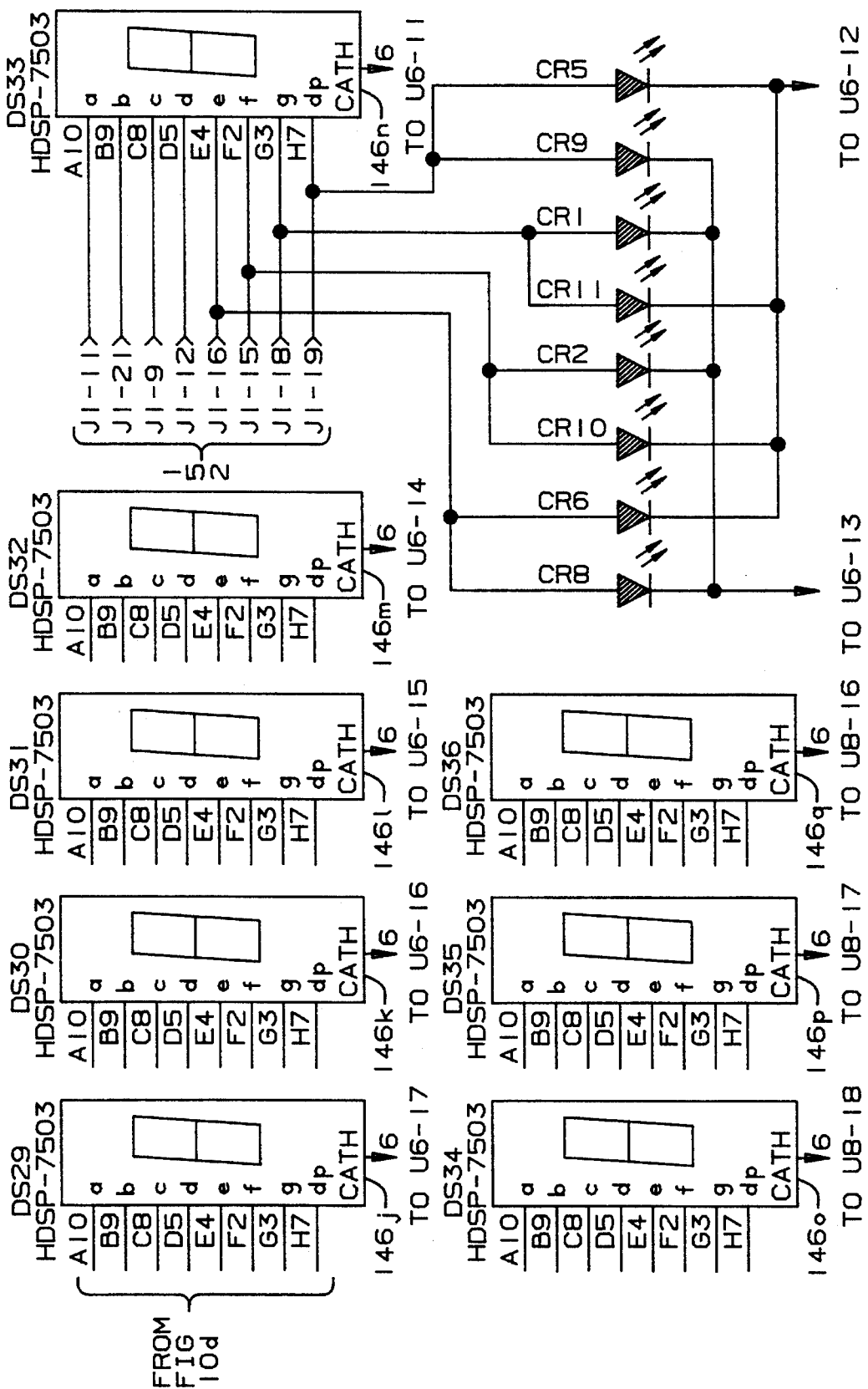

Eight connector pins 152 ranging from J1-9 through J1-21 are shown connected to the LED digit displays 142, 146 in FIG. 10d. These connector pins 152 were used for test purposes during the development of the ventilator and are not currently used. The five cable connections 154 ranging from J1-10 through J1-22 connected to the lowest Darlington amplifier circuit 148c shown in FIG. 10a are not used.

The detailed circuitry of the interface circuit 110 is shown in FIGS. 11a–11d. The interface circuit 110 includes two analog data acquisition (ADA) units 156, 158 connected in parallel, each of which contains an internal analog-to-digital converter and a multiplexer for providing the conversions on a multiplexed basis. Dual ADA units are provided as a matter of safety design. Each of the ADA units 156, 158 is periodically checked by the controller 44, and the results are compared to make sure that both the ADA units are functioning properly.

Figure 11A:
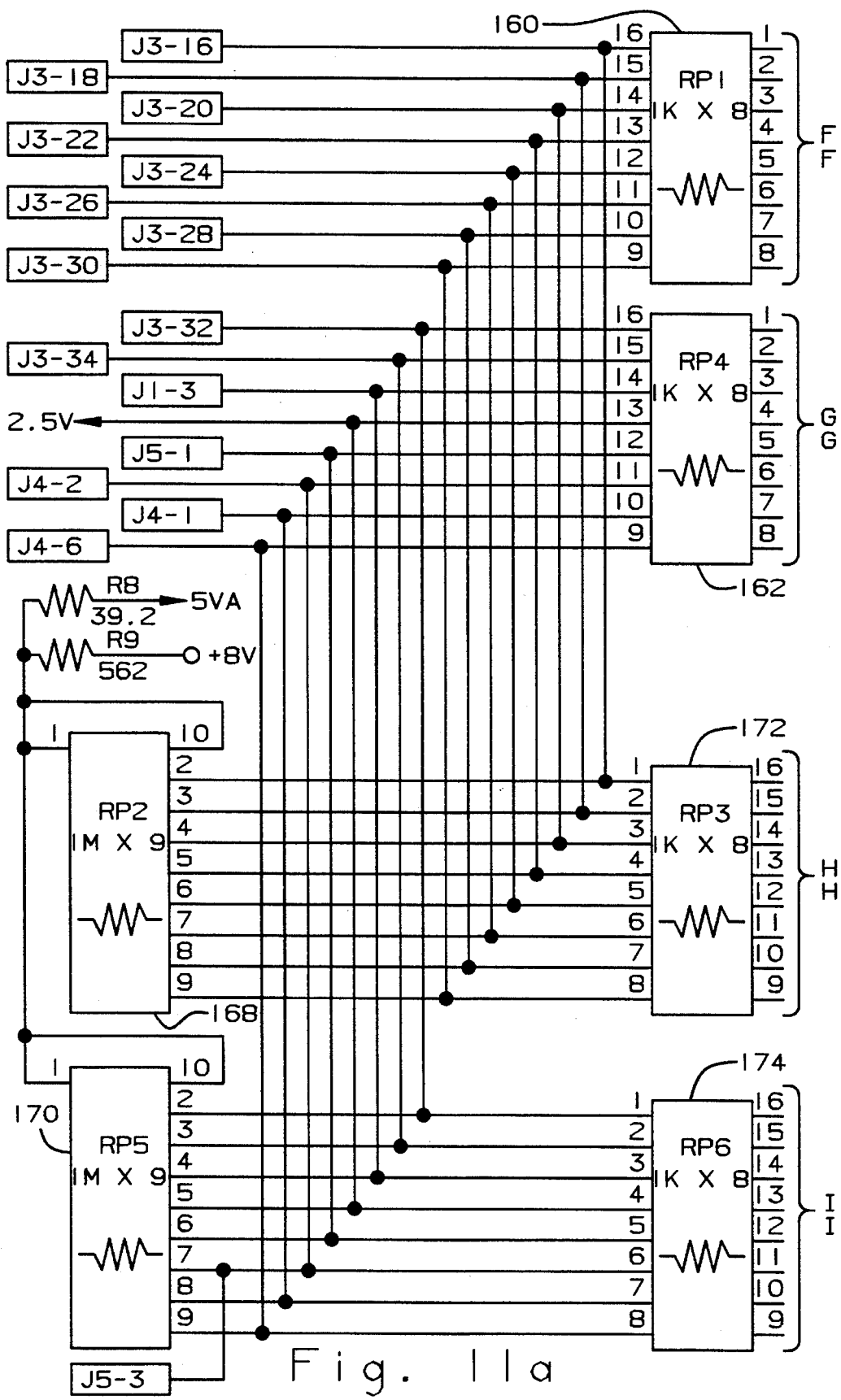
FIG. 11a is a detailed circuit diagram of a first portion of the interface circuit 110 shown in FIG. 8.
Figure 11B:
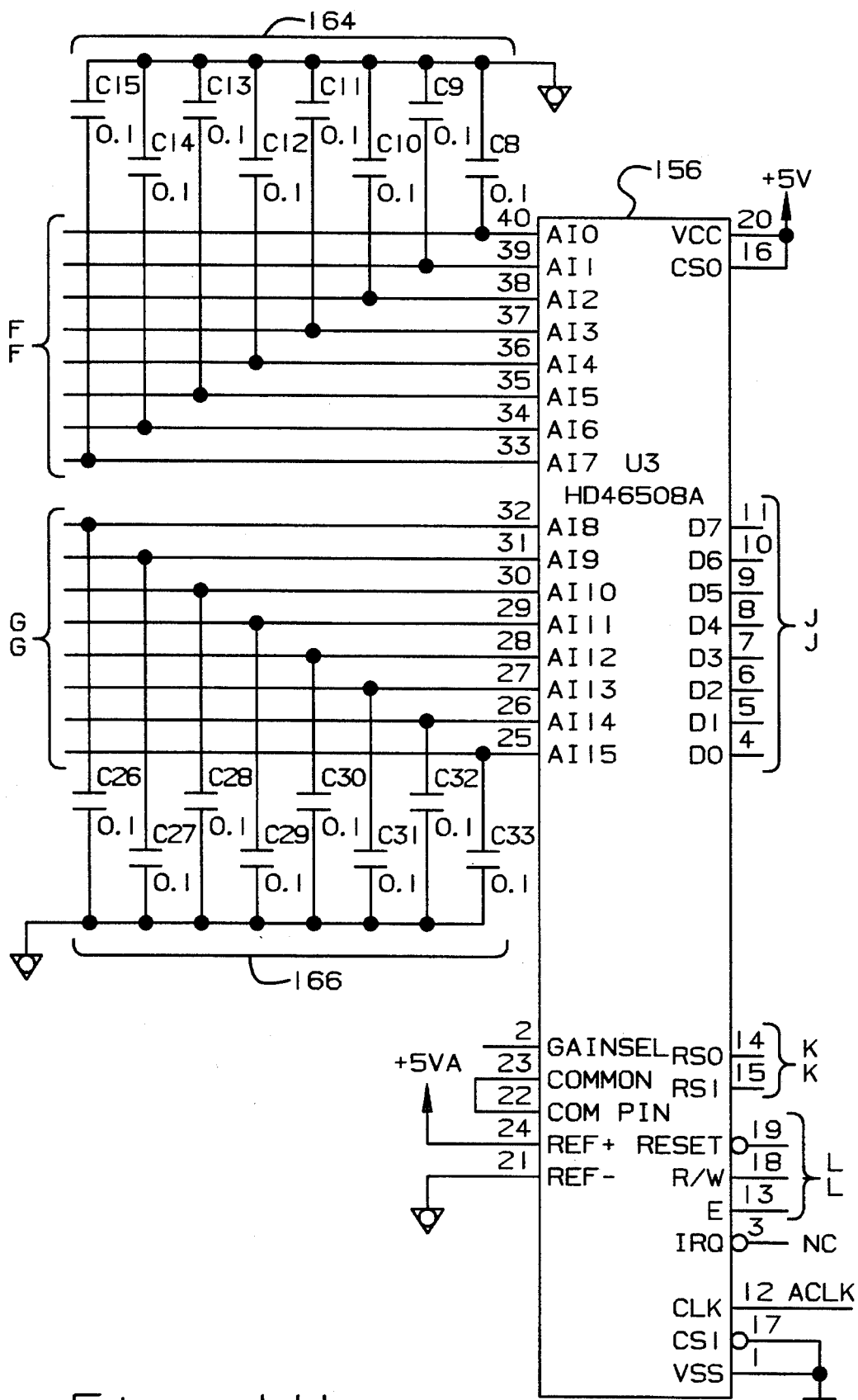
FIG. 11b is a detailed circuit diagram of a second portion of the interface circuit 110 shown in FIG. 8.
Figure 11C:
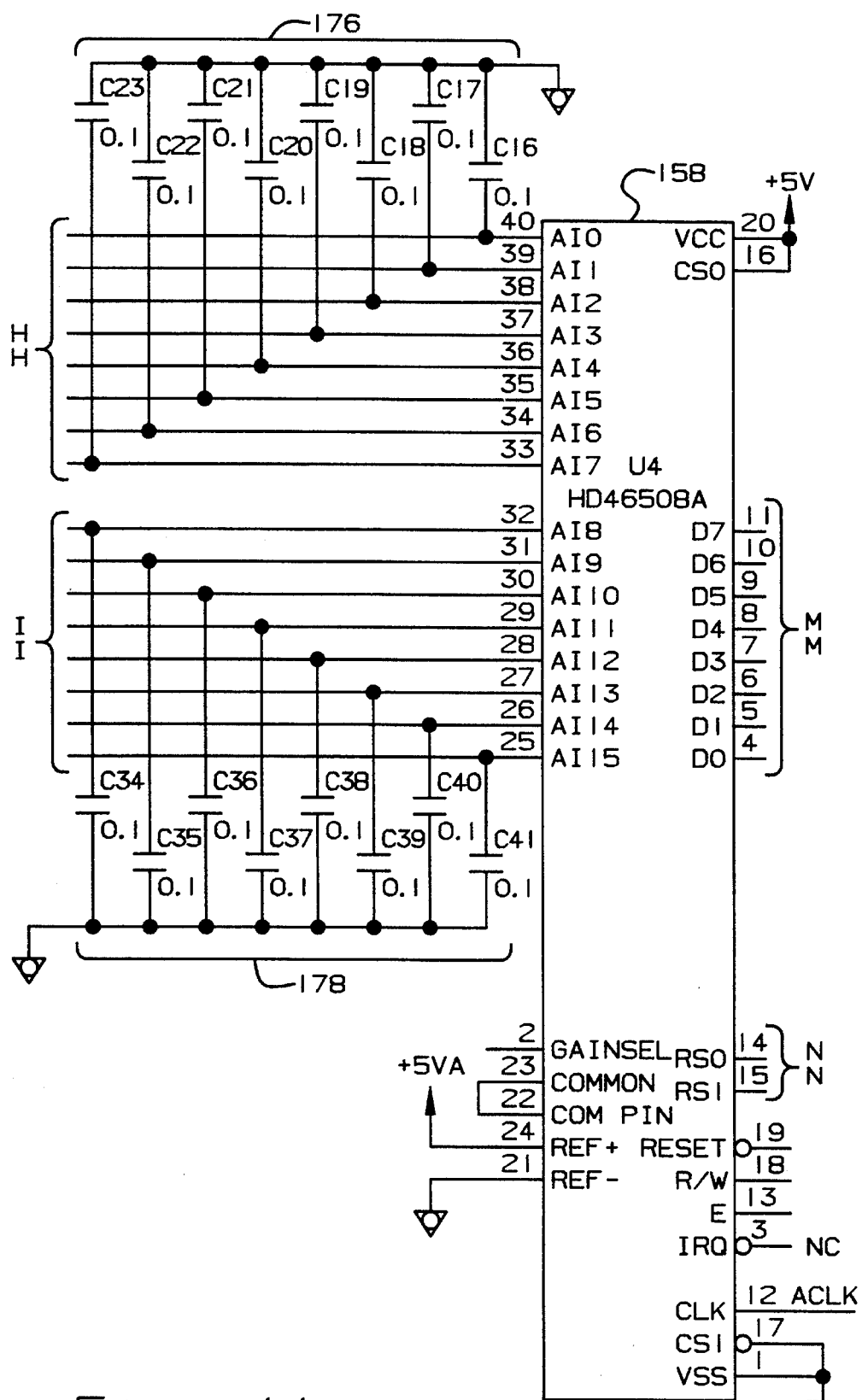
FIG. 11c is a detailed circuit diagram of a third portion of the interface circuit 110 shown in FIG. 8.

Now referring to FIGS. 11a and 11b, the analog signals provided by the ten control knob potentiometers 140 described above are supplied to the even-numbered connector pins J3-16 through J3-34. These signals are provided to the first ADA unit 156 through resistors in two pairs of resistor packs 160, 162. Capacitors in a pair of capacitor banks 164, 166 are connected to the FF and GG signal lines that are connected to the first ADA unit 156. The resistors in the resistor packs 160, 162 and the capacitors in the capacitor banks 164, 166 cooperate to act as a low pass filter to filter out any high-frequency noise on the analog signal lines input to the first ADA unit 156.

The signal lines provided to the resistor packs 160, 162 are also connected to two resistor packs 168, 170 of pull-up resistors. The pull-up resistors in the two resistor packs 168, 170 have a relatively large resistance of one megohm so that if one of the wiper arms of the potentiometers 140 breaks off, the analog signal supplied to the ADA units 156, 158 will be pulled out of the range expected by the ADA units and an appropriate error signal will be generated. The HH and II signal lines input to the second ADA unit 158 have a pair of resistor packs 172, 174 and a pair of capacitor banks 176, 178 attached which also act together as a low-pass filter.

Each of the ADA units 156, 158, which is a conventional integrated circuit chip, receives 16 analog signals and converts each to a set of digital signals on a multiplexed basis. Now referring to FIGS. 11b and 11c, the digital signals are transmitted from the D0–D7 outputs of the ADA units 156, 158 to a pair of communication circuits 180, 182, respectively, each of which has four data ports. The communication circuit 180 has a first data port having signal lines PA0 through PA7 that is connected to receive the converted digital signals from the first ADA unit 156. The second data port having signal lines PB0 through PB7 is connected to connector pins J3-7 through J3-13 from the pushbutton switches 134 of the control panel circuit 108. These signal lines are also connected to a resistor pack 184 of pull-up resistors. A third data port having signals lines PC0 through PC5 is connected to the first ADA unit control signals RS0, RS1, RESET, R/W and E. The fourth data port having signal lines AD0 through AD7 is connected to an address/data bus 186 of a main microprocessor 188 of the controller 44.

The second communication circuit 182 has four data ports connected to the second ADA unit 158 in a manner similar to that of the first communication circuit 180, with the exception that the data port having signal lines PB0–PB7 is connected to a bank 190 of switches connected to a pack 192 of pull-up resistors which are set to the ventilator identification number, which uniquely identifies each ventilator. The ventilator identification number is not needed in the normal operation of the ventilator, but may be used in connection with the fiber optic data link 118 to identify which ventilator information is being transmitted from.

Figure 11D:
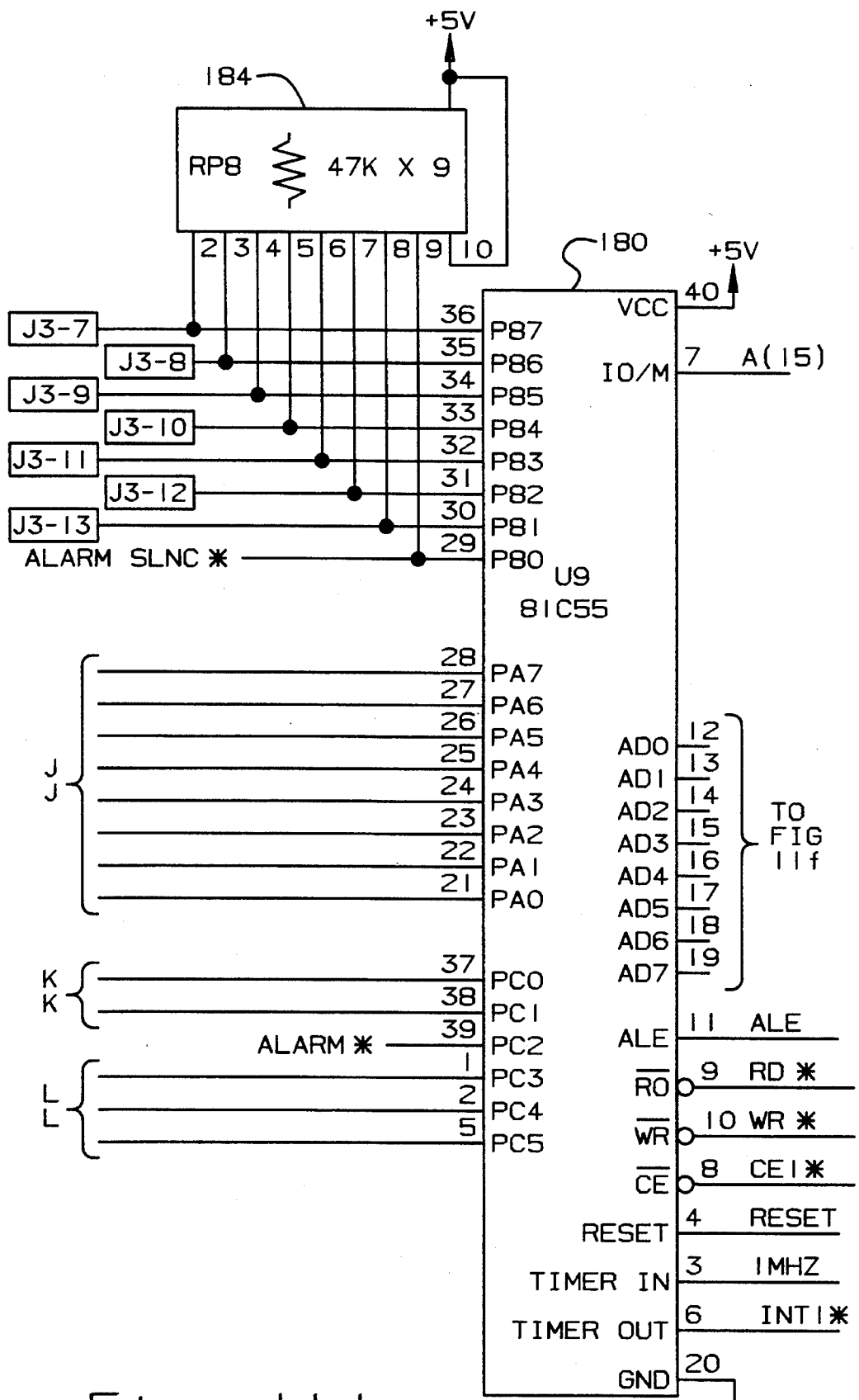
FIG. 11d is a detailed circuit diagram of a fourth portion of the interface circuit 110 shown in FIG. 8.
Figure 11E:
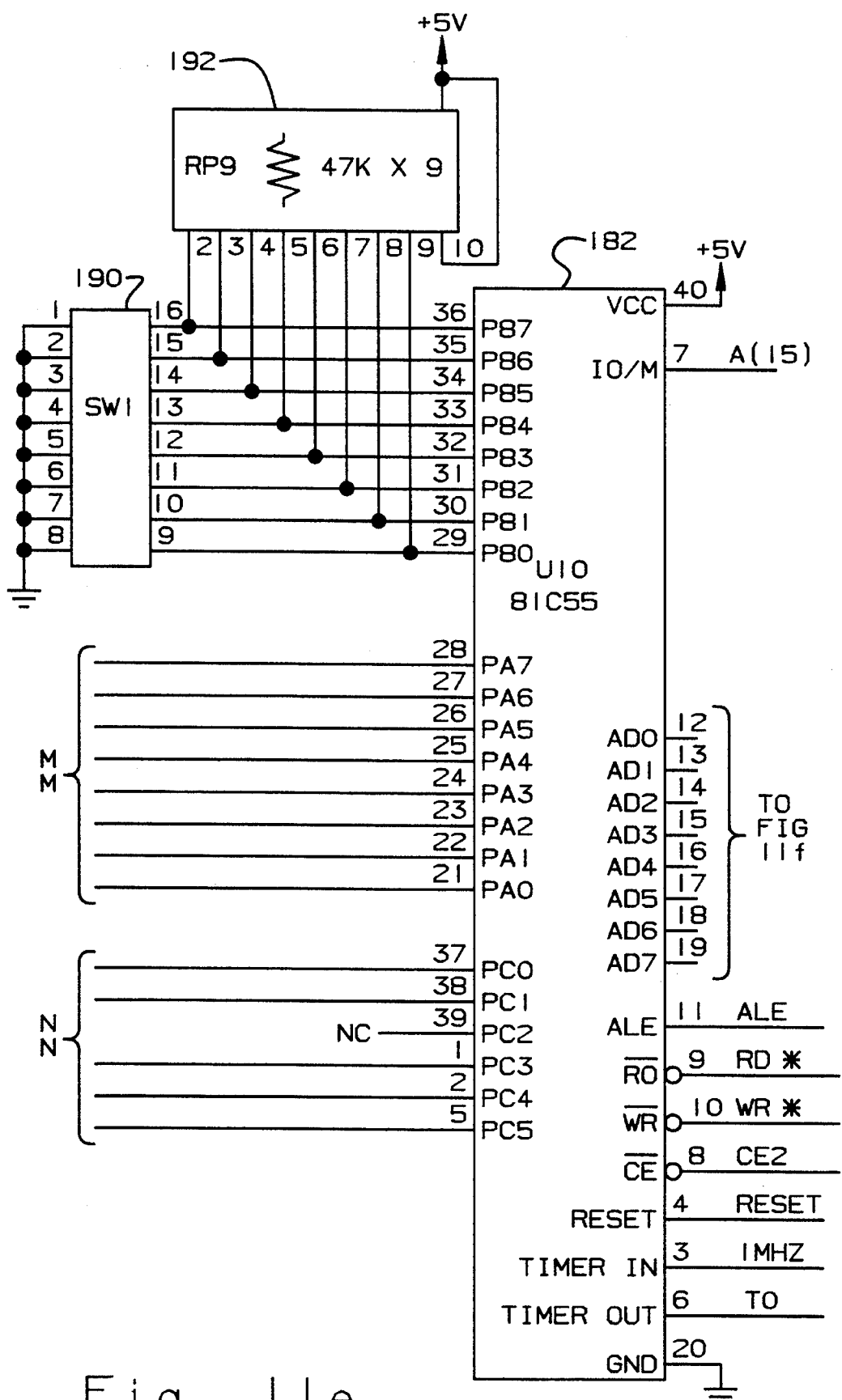
Figure 11F:
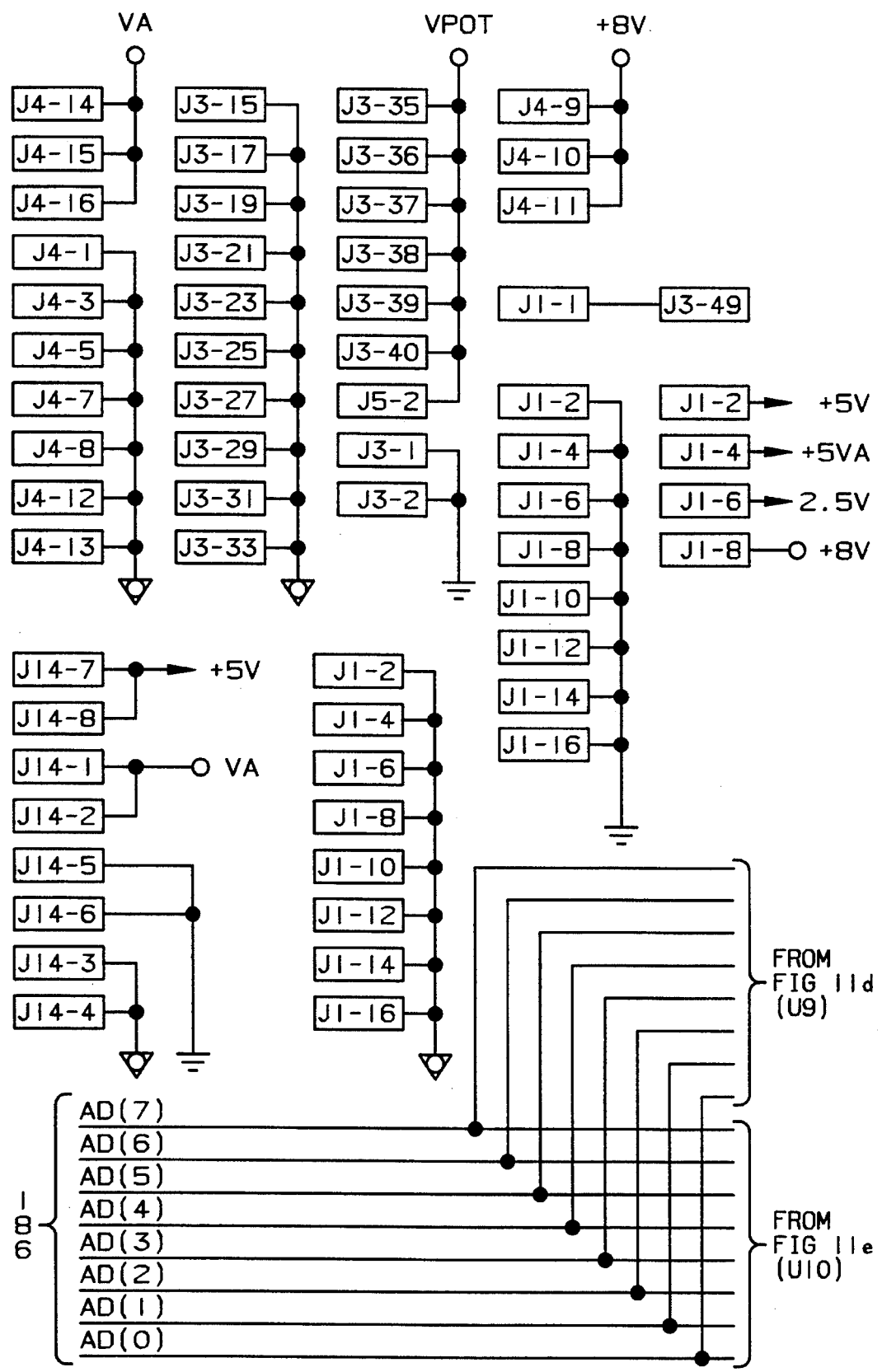

Now referring to FIG. 11d, the interface circuit 110 includes another communication circuit 194 with four data ports. A first of these data ports having signal lines AD0 through AD7 is connected to the address/data bus 186 of the main microprocessor 188 of the controller 44, a second of these ports having signal lines PB0 through PB7 is connected to the first source driver 140 via the even-numbered connector pins J3-20 through J3-34, a third data port having signal lines PA0 through PA7 is connected to the second source driver 144 via the even-numbered connector pins J3-36 through J3-50, and the fourth data port having signal lines PC0 through PC5 is connected to the 3-to-8 decoders 150.

Figure 12B:
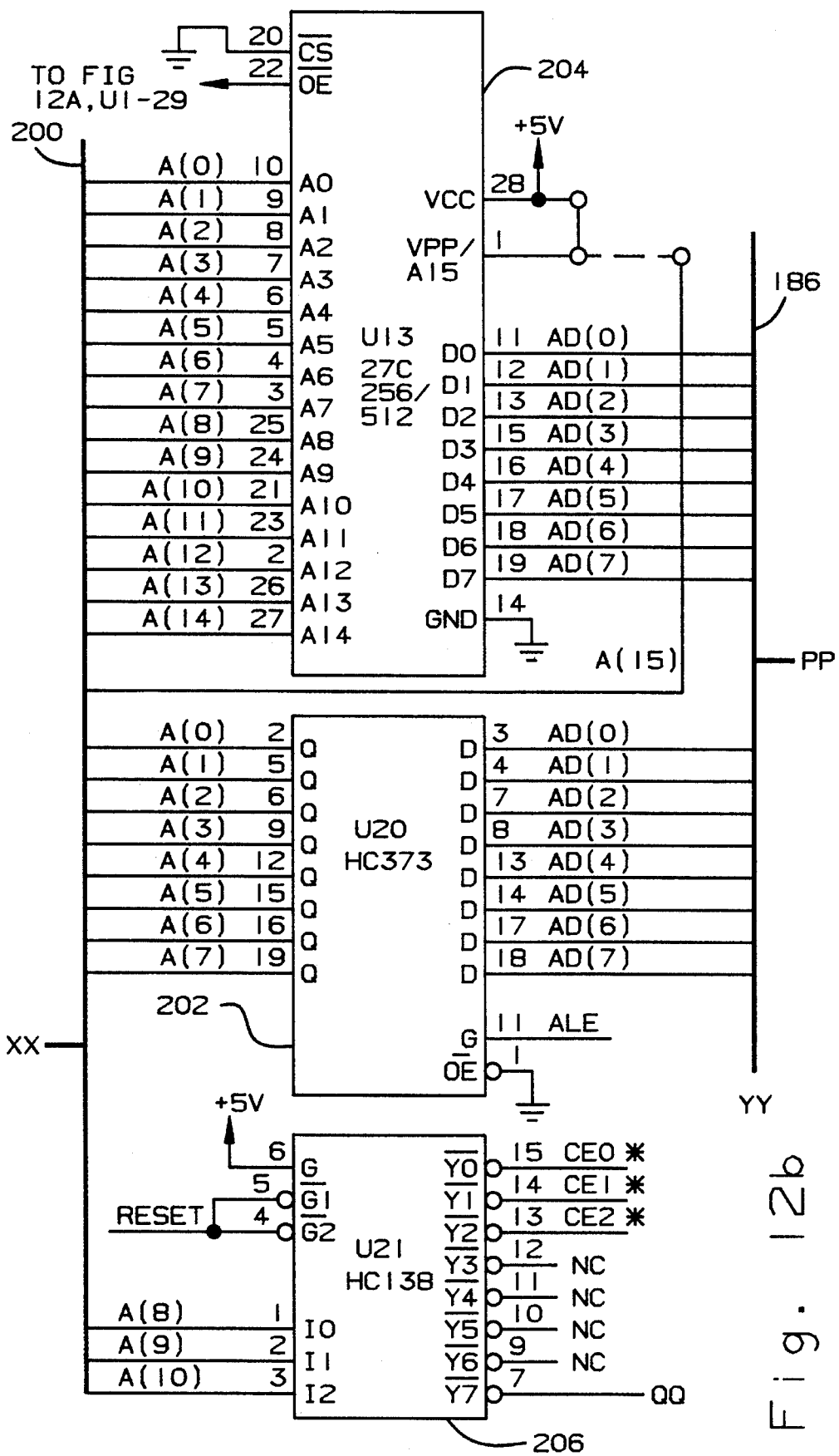
FIG. 12b is a detailed circuit diagram of a second portion of the microcomputer controller shown in FIG. 8.
Figure 12C:
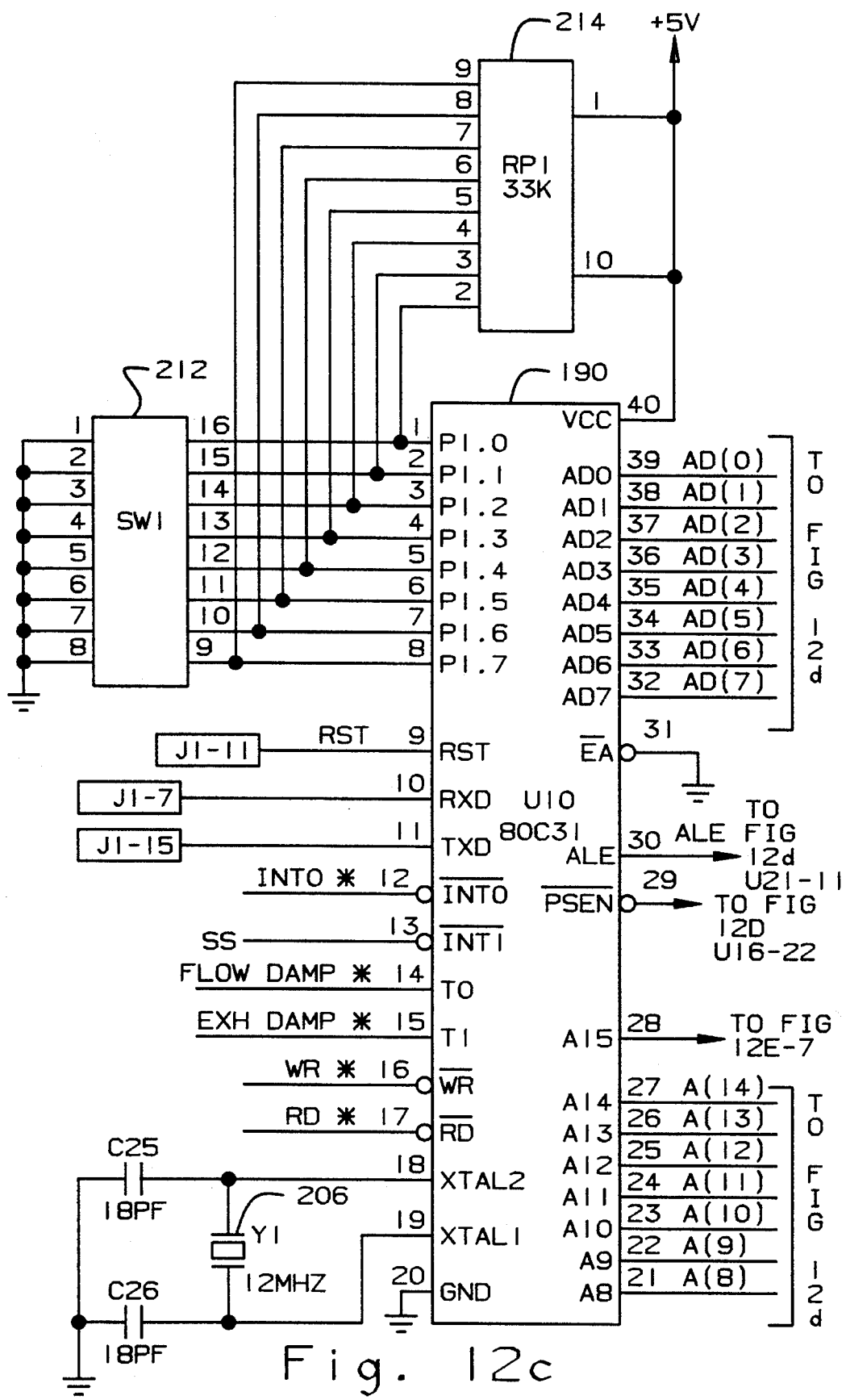
FIG. 12a is a detailed circuit diagram of a first portion of the microcomputer controller shown in FIG. 8.
Figure 12D:
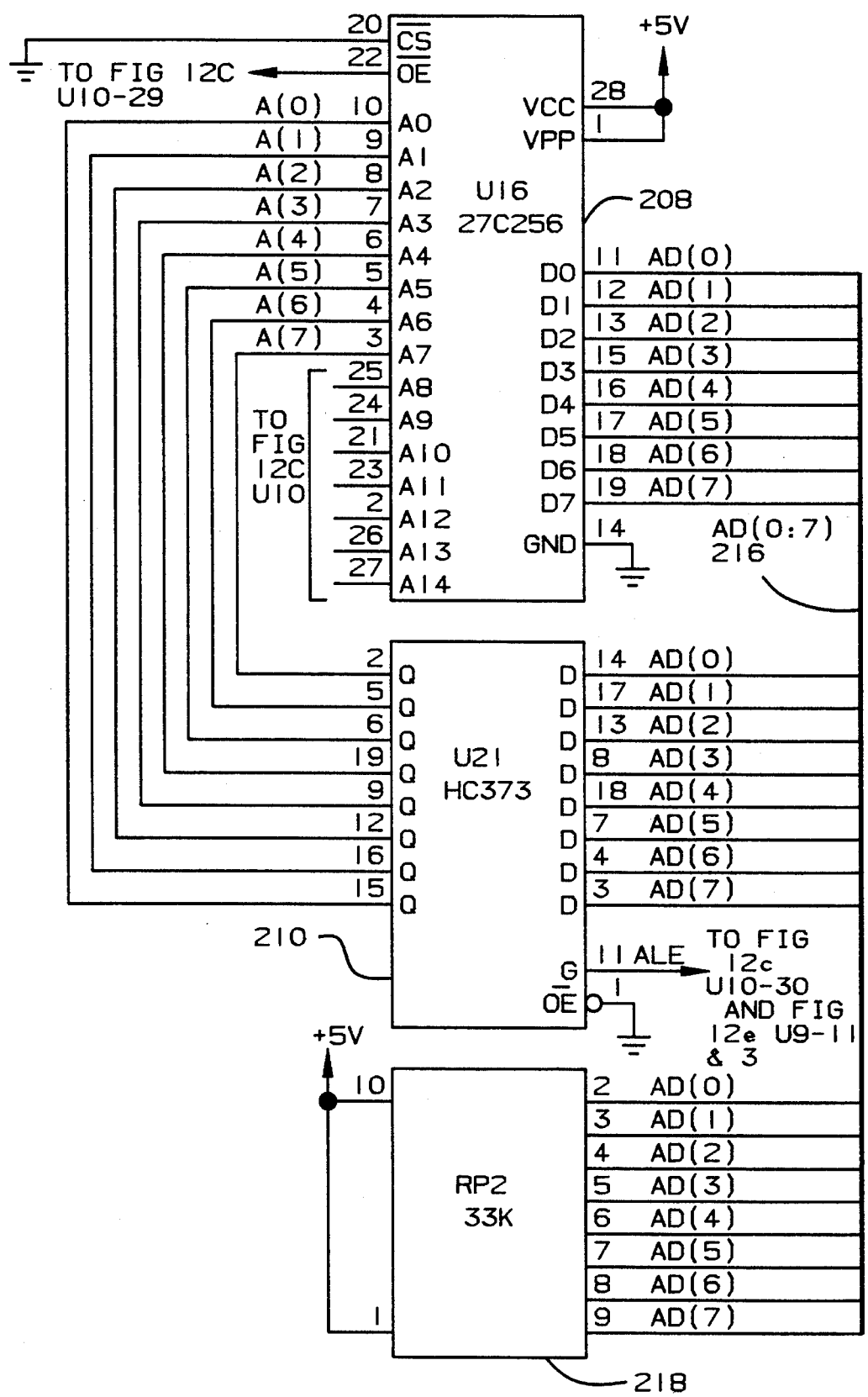
Figure 12E:
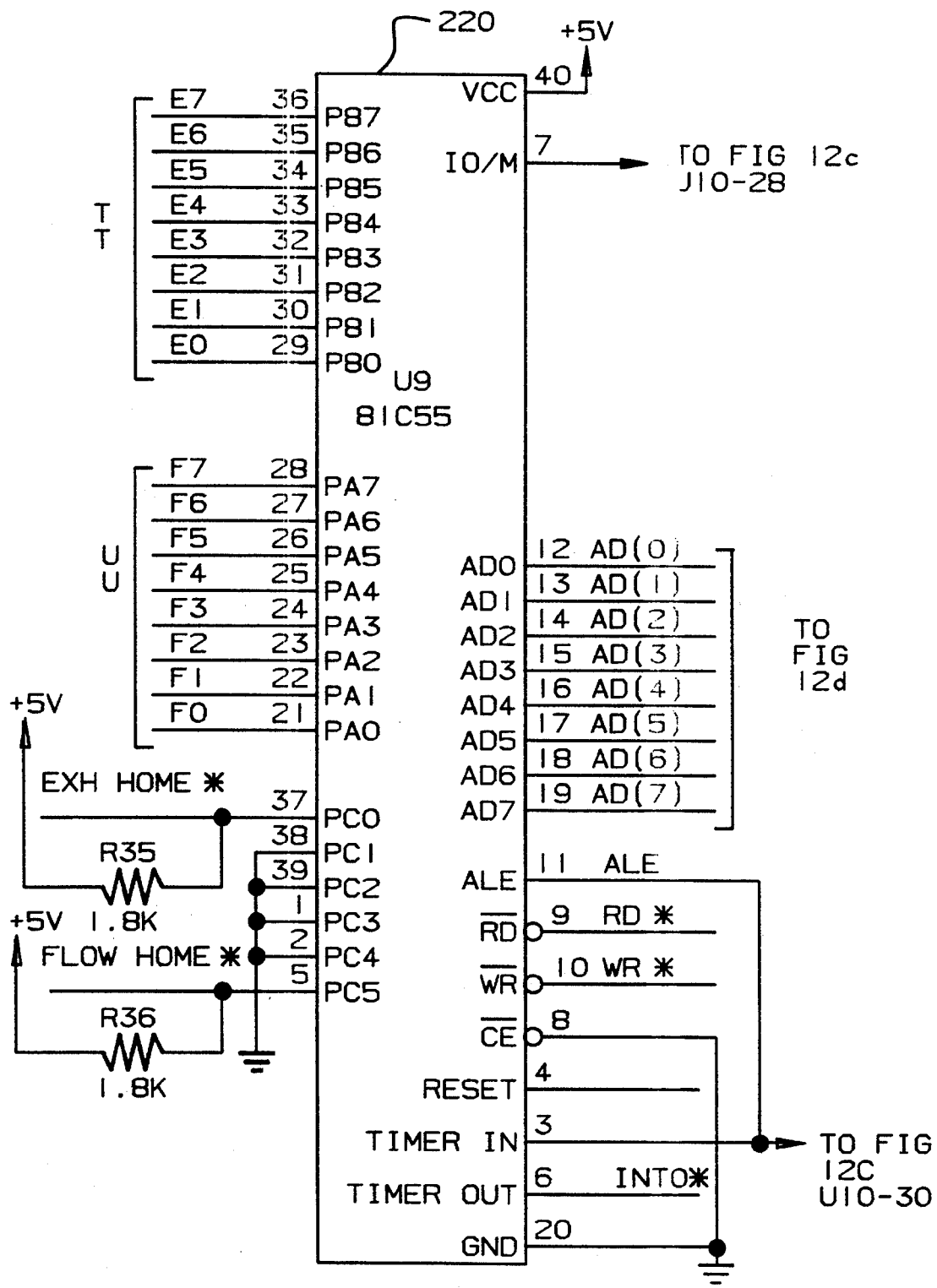

The detailed circuitry of the microcomputer controller 44 is shown in FIGS. 12a and 12b. The controller 44 comprises a pair of conventional microprocessors that are interconnected in a conventional manner. One of the microprocessors, the main microprocessor 188 executes a main computer program which controls the overall operation of the ventilator. The other microprocessor 190, the motor control microprocessor, executes a motor control computer program that controls the operation of the stepping motors 74, 124 which drive the flow control valve 42 and the exhalation valve 48.

The main processor 188 is driven by an external oscillator 192. The oscillator 192 is driven by a crystal 194 and generates a number of clock signals used by the ventilator circuitry. These clock signals include the OSC, PCLK, ACLK and 1MHZ signals. The ACLK and 1MHZ clock signals are generated by a pair of interconnected 4-bit ripple counters 196, 198.

The main processor 188 contains a data port having signal lines P1.0 through P1.7 that is connected to the ventilator mode switch 136 via connectors J3-3 through J3-6. The connectors J3-41 through J3-44 to which the data port is also attached are not currently used, but may used in case of expansion of the number of ventilator modes from four to eight. The main processor 188 has an address/data port having signal lines AD0–AD7 which is connected to the 8-bit wide address/data bus 186 and a high address port having signal lines A8 through A15 connected to a 16-bit wide address bus 200. The address/data bus 186 is connected to a latch 202, and the output of the latch 202 is connected to the eight lower order address bits of the address bus 200. The address bus 202 is also connected to the A0 through A14 inputs of an erasable programmable read-only memory (EPROM) 204 in which the main computer program is stored. The EPROM 204 provides data output via its D0–D7 outputs to the address/data bus 186. The main processor 188 is also connected to a 3-to-8 decoder 206 which outputs a number of chip enable signals that enable the various integrated circuit chips to which they are attached.

In operation, the main processor 188 fetches and executes the main computer program instructions stored in the EPROM 204. The address/data bus 186 is time multiplexed.

During the first instruction fetch cycle of the processor 188, the lower order address bits are transmitted to the address/data bus 186 to be temporarily stored in the latch 202. During the next instruction fetch cycle, the high order address bits are transmitted to the EPROM 204 via the high order address bus 200. At the same time, the lower order address bits are transmitted from the latch 202 to the EPROM 204. In response to the address so provided, the EPROM 204 supplies the instruction to be executed by the main processor 188 on the address/data bus 186 for transmission to the processor 188, which then executes the instruction.

The main processor communicates with the motor control processor via a serial interface utilizing connector pins J1-15 and J1-7 which are connected to the RXD and TXD pins of the main processor 188, respectively.

Now referring to FIG. 12b, the motor control microprocessor 190 is driven by a crystal 206 and connected to a second EPROM 208 via a latch 210. A dual in-line package (DIP) switch 212, which is not currently used, is connected to a port of the microprocessor 190 having signal lines P1.0 through P1.7 through a bank 214 of pull-up resistors. An address/data bus 216 is connected to a bank 218 of pull-up resistors. The TXD and RXD pins of the motor control processor 190 are connected to the main processor 188 via connectors J1-7 and J1-15. The communication format by which the two processors 188, 190 communicate is described in detail below. The operation of the motor control processor 190 is substantially the same as the operation of the main processor 188, except that the motor control program stored in the EPROM 208 is executed.

Now referring to the right-hand side of FIG. 12b, the interface circuit 125 shown schematically in FIG. 8 comprises a communication circuit 220 having four ports. A first of these ports having data lines AD0 through AD7 is connected to the address/data bus 216 of the motor control processor 190 and enables the communication circuit 220 to communicate with that processor. A second of the data ports having signal lines PB0 through PB7 is connected to the motor driver circuit 126 which drives the stepping motor 124 connected to the exhalation valve 48, a third of these data ports having signals lines PA0 through PA7 is connected to the motor driver circuit 122 connected to the stepping motor 74 that drives the flow control valve 42, and the fourth data port having signal lines PC0 through PC5 is connected to an exhalation valve home (EXH HOME) signal and a flow control valve (FLOW HOME) signal. When active, these two signals indicate that the exhalation valve 48 is at its home position and the flow control valve 42 is at its home position, respectively.

Figure 13A:
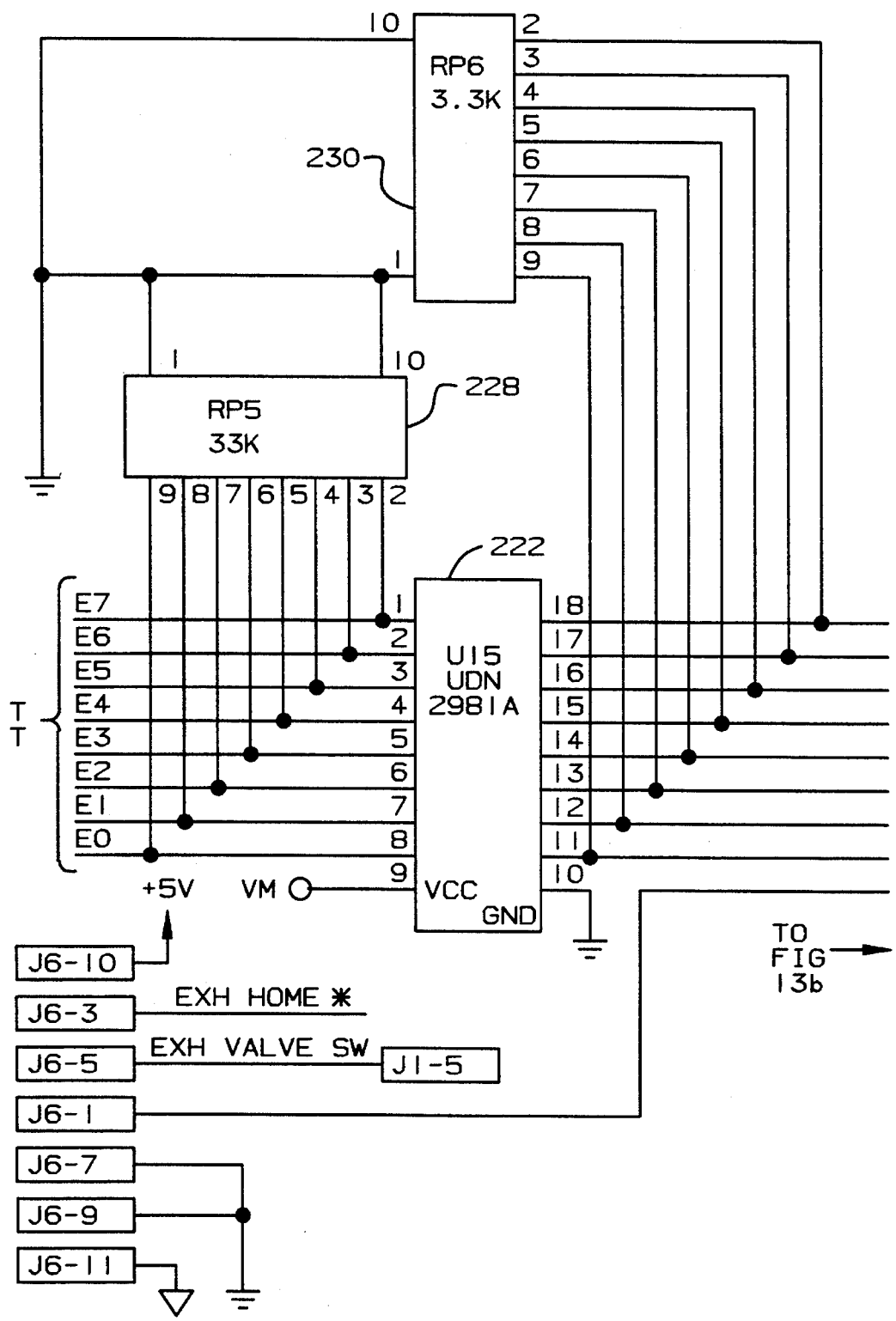
FIG. 13a is a detailed circuit diagram of the drive circuit 126 shown in FIG. 8.

The exhalation valve motor driver circuit 126 schematically shown in FIG. 8 is shown in detail in FIG. 13a. This circuit comprises an 8-channel driver circuit 222 having eight inputs F0 through F7 which are received from the interface circuit 125 and eight outputs, each of which is supplied to a respective Darlington switch 224, 226 which controls the supply of power to four wires connected to connector pins J7-2, J7-4, J7-6 and J7-8. The input signal lines E0–E7 are connected to a resistor pack 228 which pulls them to logic 0 as a safety design feature in case the inputs E0–E7 are not properly driven, for example, in case of failure of the motor control processor 190. The signal lines output from the driver circuit 222 are connected to a resistor pack 230 which is used to adjust the level of the drive current supplied by the driver circuit 222.

The stepping motor 124 used to drive the exhalation valve 48 is a two-phase motor having two coils through which current may be induced in either direction. Four of the Darlington switches 224 shown in the upper portion of FIG. 13a control the flow of current through one of the coils of the motor, and the remaining four switches 226 shown in the lower portion of FIG. 13a control the flow of current through the other coil. The current is supplied by a pair of current regulators 232, 234 connected to the switches.

Since the operation of the circuit which supplies current to each of the coils is substantially the same, the operation is only described with reference to the upper portion of FIG. 13a. The connectors J6-6 and J6-8 are each connected to a respective side of one of the two coils (not shown) of the motor 124. The motor is driven in its half-stepping mode of operation, which is well known, and in this mode, a coil has either (1) no current flowing through it; (2) current flowing through it in a first direction; or (3) current flowing through it in a second direction opposite the first direction.

In order to provide no current flow through the coil, each of the switches 224 is provided a logic 0 input so that it remains open and the current regulator is not connected to either connector J6-6 or J6-8. To provide a current flow through the coil in a first direction, two diagonally opposed switches 224a, 224d are turned on by the provision of a logic 1 signal, which in this case happens to be approximately 18 volts, and the current source is connected to one of the connectors J6-6, J6-8, causing current to flow through this connector, the coil, the other connector, and then through a resistor 236 to ground. To provide a current flow through the coil in the opposite direction, the other two diagonally opposed switches 224b, 224c are turned on by the provision of a logic 1 signal, and the current source 232 is connected to the other of the connectors J6-6, J6-8, causing current to flow through this connector, the coil, the other connector, and then through the resistor 236 to ground. The lower portion of the circuitry in FIG. 13a drives the other coil of the motor 124 in the same manner.

The connector pin J6-3 shown in the lower left-hand portion of FIG. 13a is connected to receive the exhalation valve home (EXH HOME*) signal from the exhalation valve position sensor 130, and the connector J6-5 is connected to a microswitch (not shown) that senses when the exhalation valve body has been removed from the ventilator, for example, for cleaning.

Figure 13B:
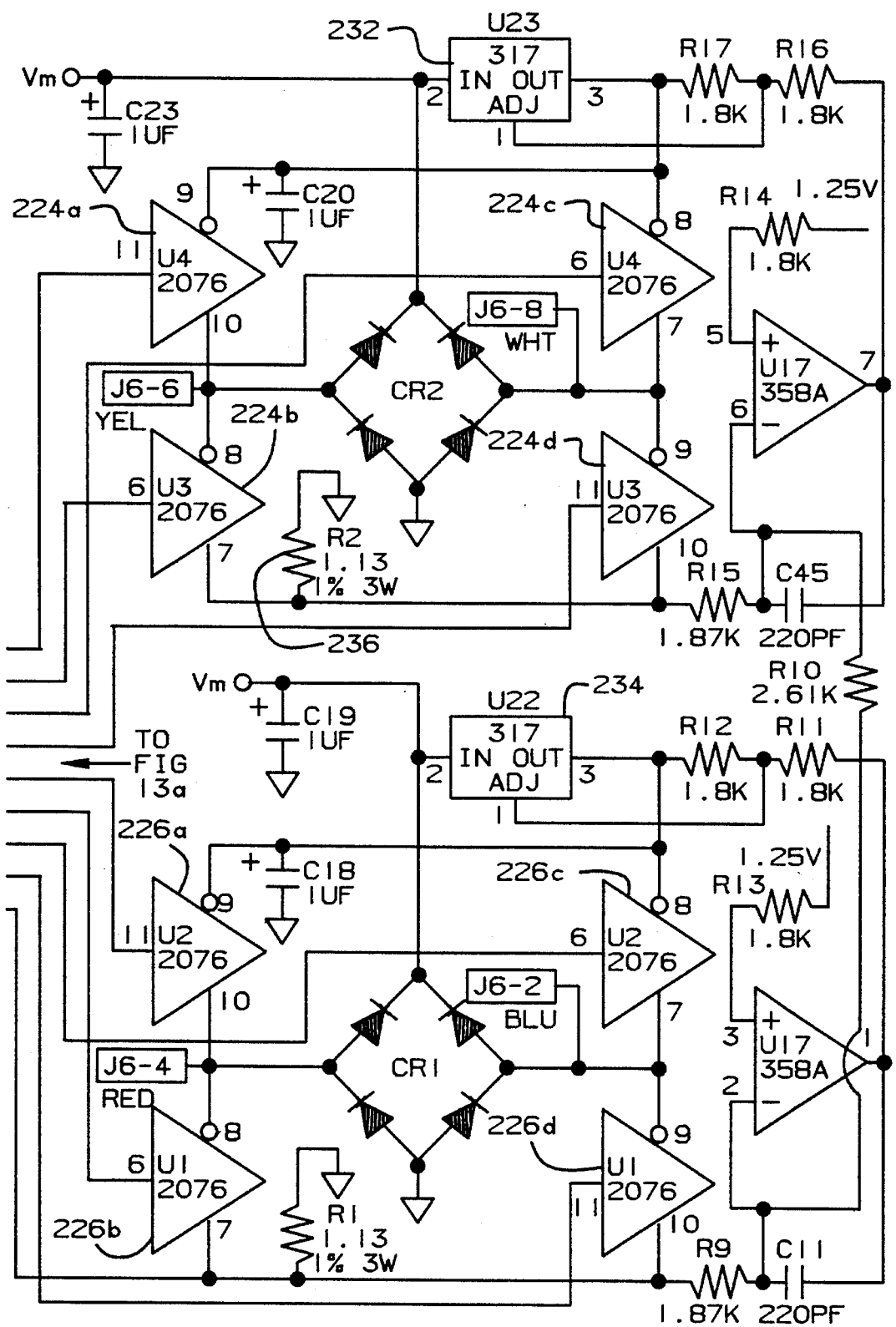
FIG. 13b is a detailed circuit diagram of the drive circuit 122 shown in FIG. 8.
Figure 13C:
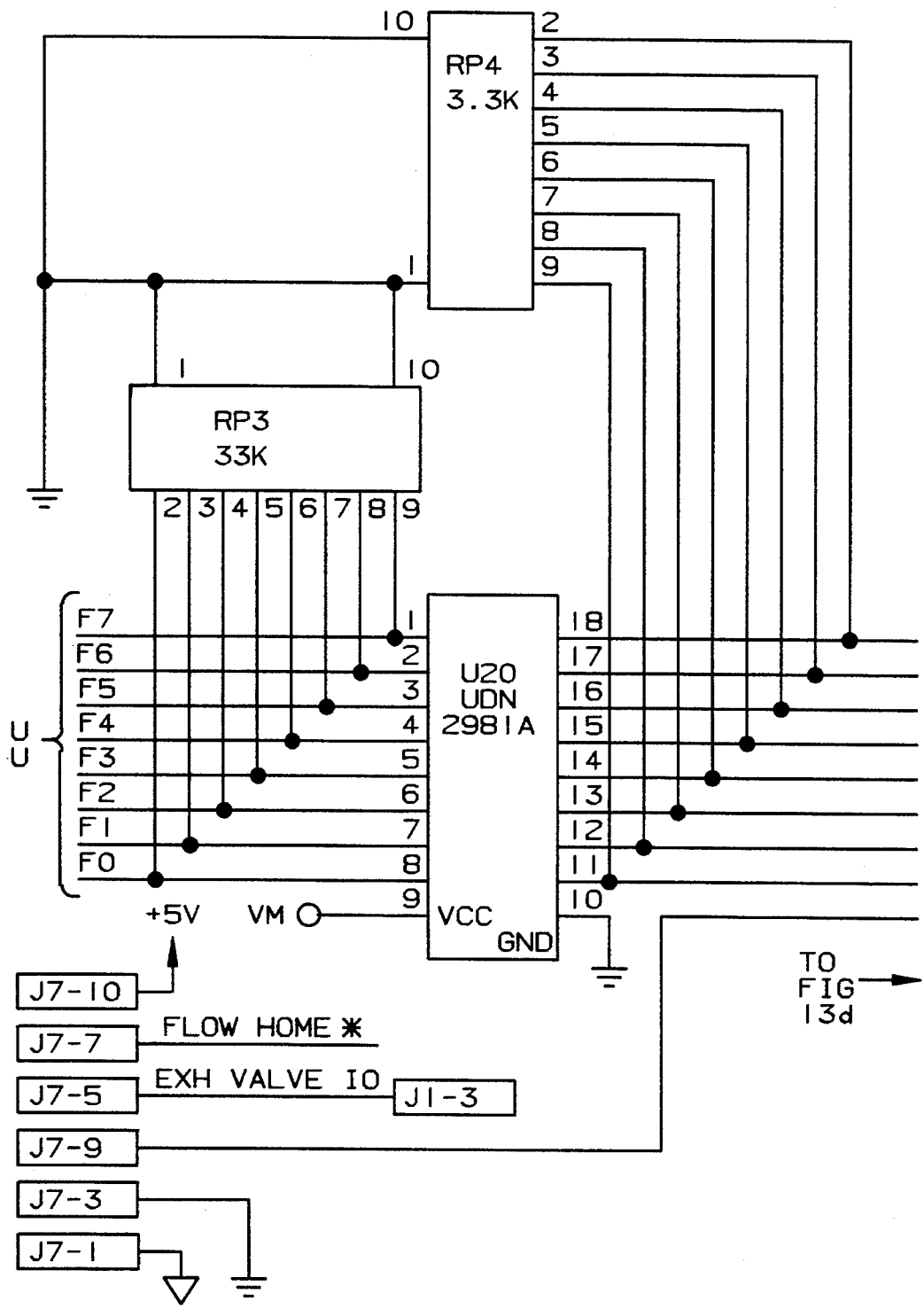
Figure 13D:
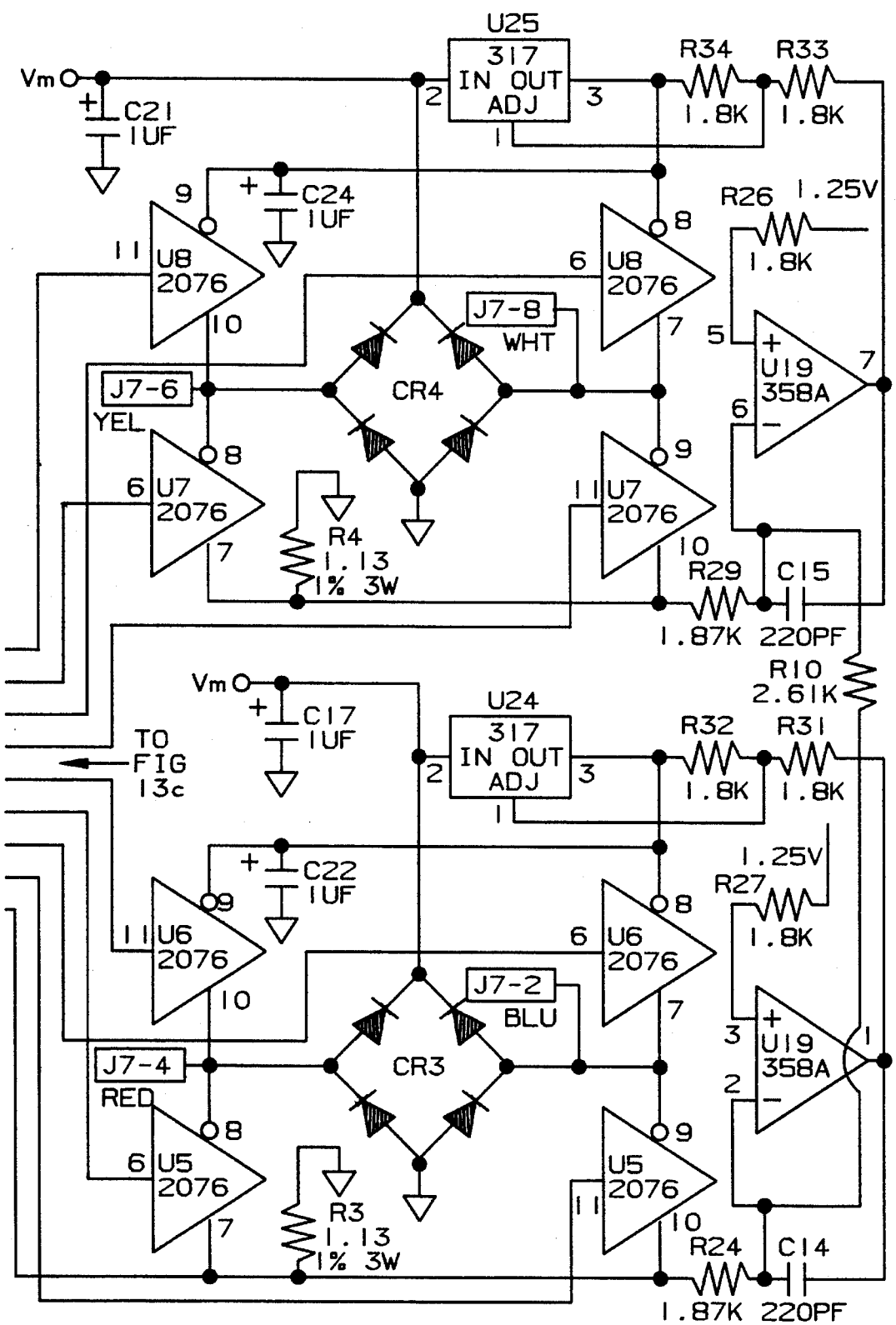

The motor driver circuit 122 for the flow control valve 42 is shown in FIG. 13b and operates in substantially the same manner as the driver circuit 126 for the exhalation valve 48 explained in connection with FIG. 13a. The connector pin J7-7 shown in the lower left-hand portion of FIG. 13b is connected to receive the flow control valve home (FLOW HOME*) signal from the flow control valve position sensor 128, and the connectors J7-1, J7-5 and J7-9 are not used.

Figure 14:
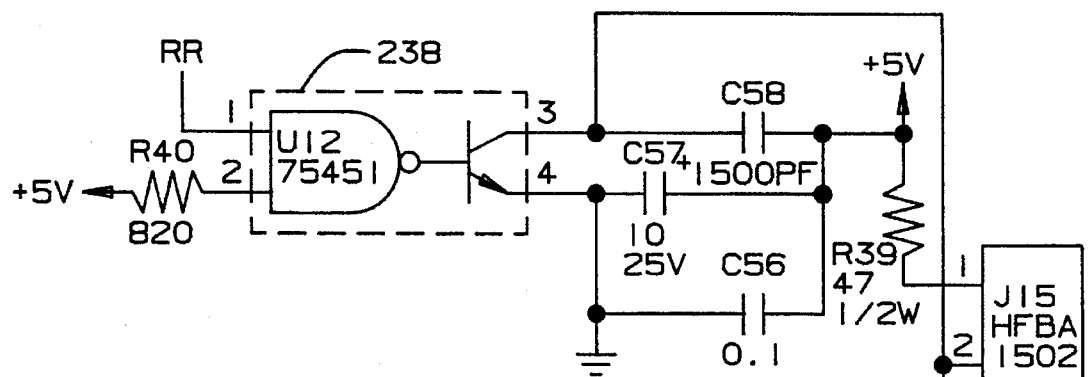
FIG. 14 is a detailed circuit diagram of the fiber optic data link shown in FIG. 8.

The fiber optic data link circuit 118 schematically shown in FIG. 8 is shown in detail in FIG. 14. The circuit 118 includes a NAND gate 238 having an input on pin 1 that is connected to the TXD pin of the main microprocessor 188. The digital information output from the TXD pin is supplied to the NAND gate 238 and causes the same digital information to be output via a fiber optic transmitter 240. The transmitter 240 transmits the information over a fiber optic cable to be received by a fiber optic receiver (not shown), and then the received digital information may be decoded in accordance with the communication format between the microprocessors 188 described below. The fiber optic data link circuit 118 is not necessary for the operation of the ventilator, and it is only provided for informational purposes.

Figure 15:
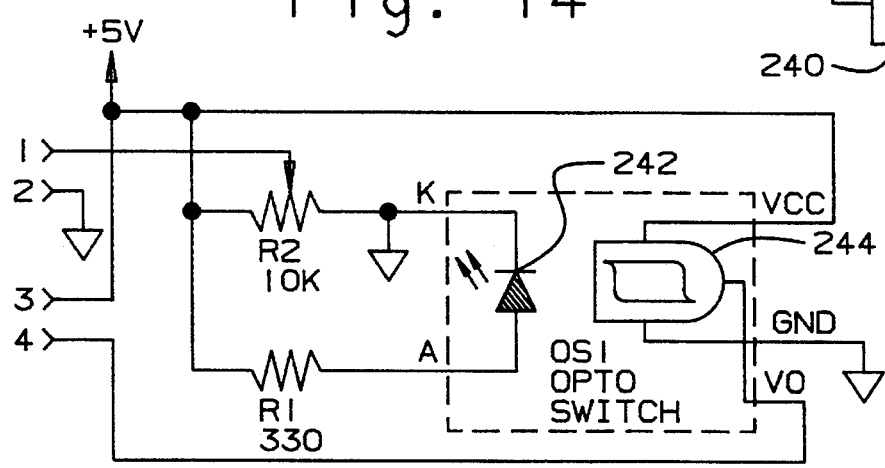
FIG. 15 is a detailed circuit diagram of the position sensors shown in FIG. 8.

One of the position sensors 128, 130 schematically shown in FIG. 8 is shown in detail in FIG. 15. The two position sensors 128, 130 detect when the flow control and exhalation valves are fully closed, or in their home position. This home position is used as a reference position to keep track of the exact position of the two valves 42, 48 at all times. Since the two position sensors 128, 130 are identical, only one is shown.

As explained above, the controller 44 keeps track of the position of the flow control valve 42 as a number of steps of the stepping motor 74 ranging from zero, which indicates that the flow control valve 42 is fully closed, to 127, which indicates that the flow control valve is fully open. Similarly, at all times the controller 44 keeps track of the position of the exhalation valve 48 as a number of steps of the exhalation valve stepping motor 124 ranging from zero, indicating that the exhalation valve is completely closed, to 127, indicating that the exhalation valve is fully open.

The position sensor shown includes an LED 242 that emits light that is detected by a photodetector 244 that develops a voltage that corresponds to the amount of light detected. When one of the two valves 42, 48 is in its fully closed position, a mechanical element (not shown) on the valve lies between the LED 242 and the detector 244, interrupting the light path, and the light detected by the detector 244 decreases. This decrease can be detected by the controller 44 which senses the reduced voltage developed by the detector 244. These reduced voltages, which are developed on pin 4 in FIG. 15, are supplied to the appropriate pins on the connectors shown in FIGS. 13a and 13b as described above.

Figure 16:
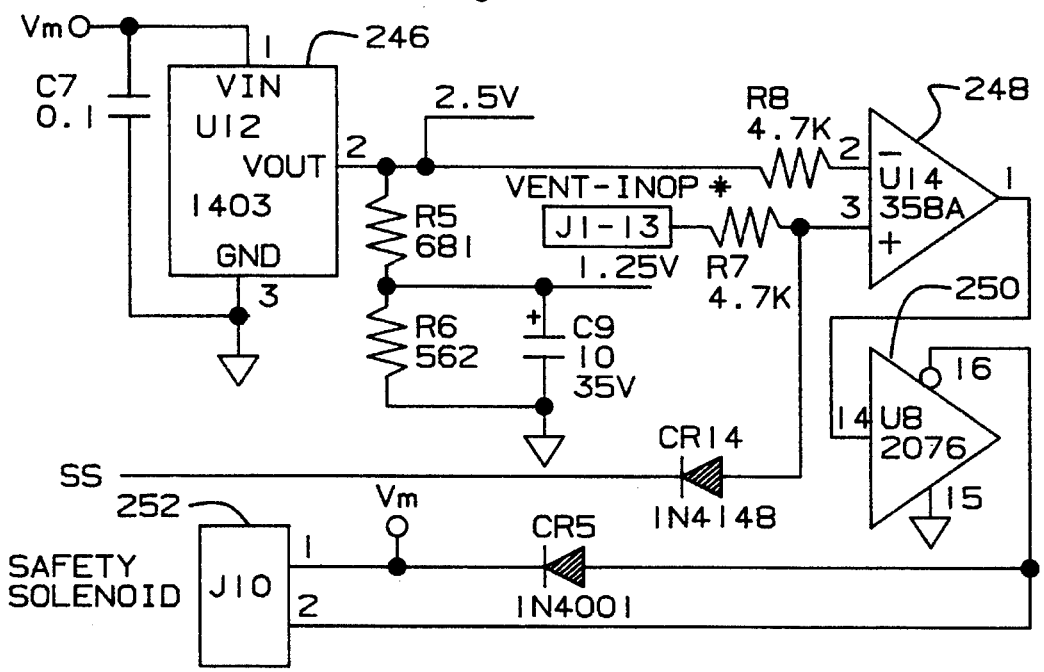
FIG. 16 is a detailed circuit diagram of the safety solenoid circuit shown in FIG. 8.
Figure 17:
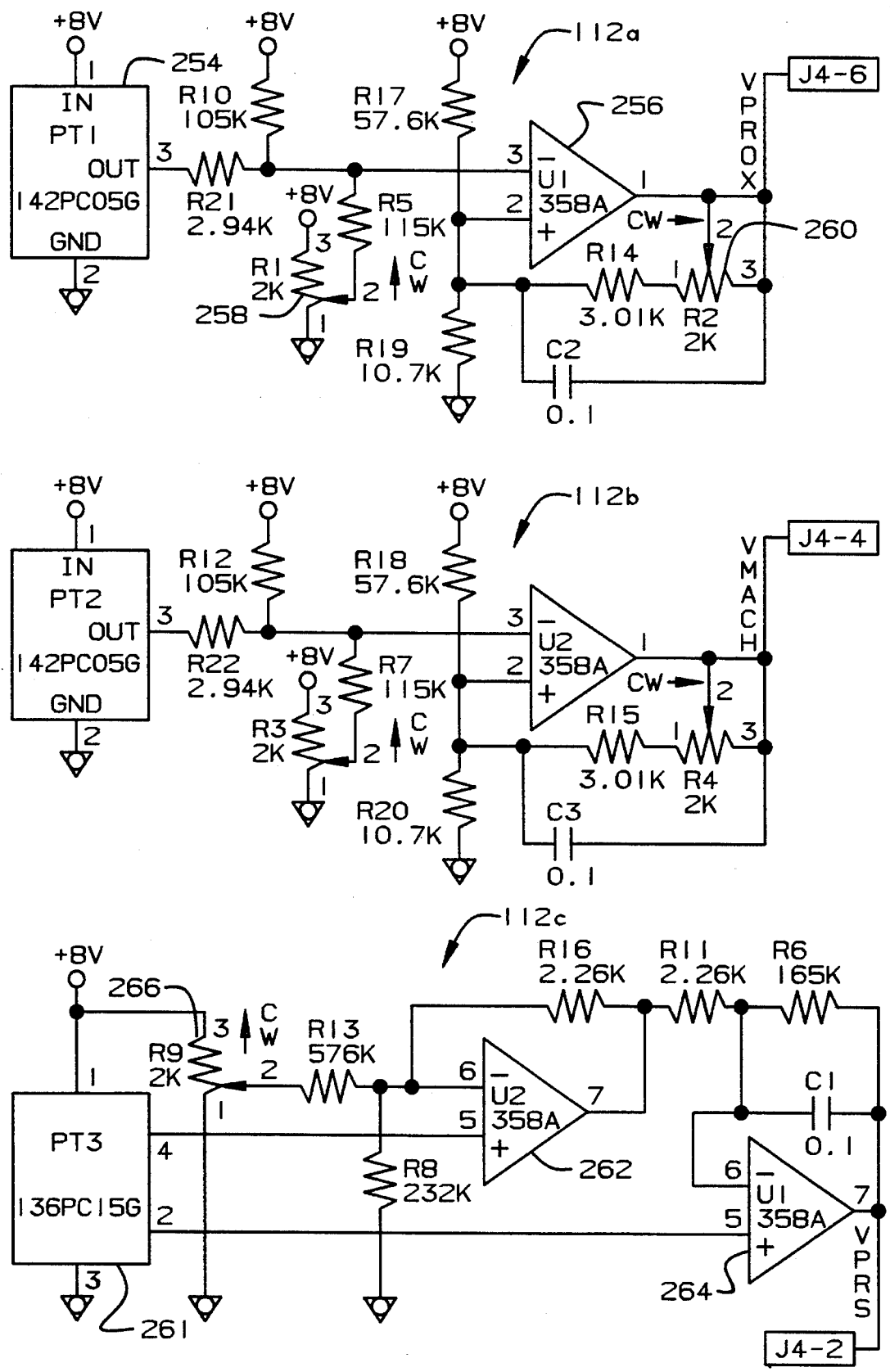
FIG. 17a is a detailed circuit diagram of the pressure transducer 112a shown in FIG. 8.
FIG. 17b is a detailed circuit diagram of the pressure transducer 112b shown in FIG. 8.
FIG. 17c is a detailed circuit diagram of the pressure transducer 112c shown in FIG. 8.
Figure 18A:
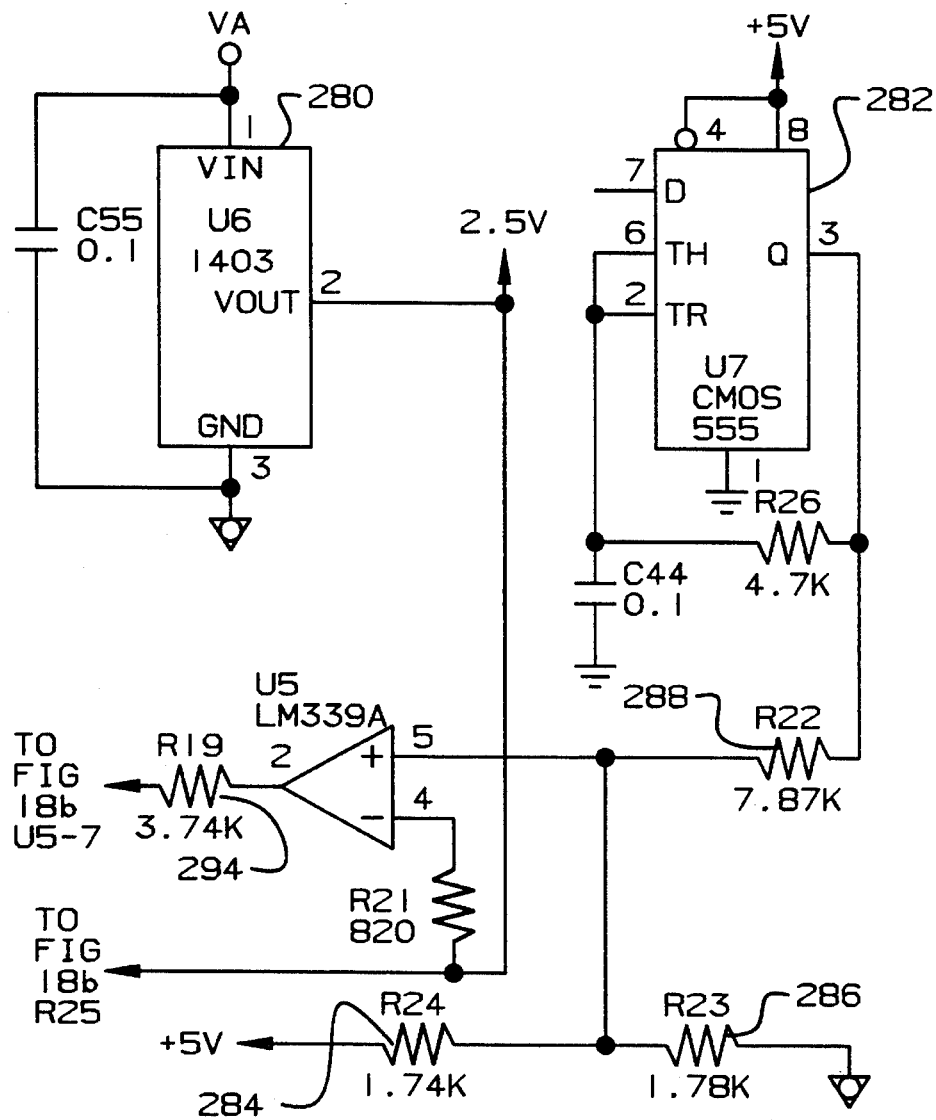
FIG. 18 is a detailed circuit diagram of the voltage level test circuit shown in FIG. 8.
Figure 18B:
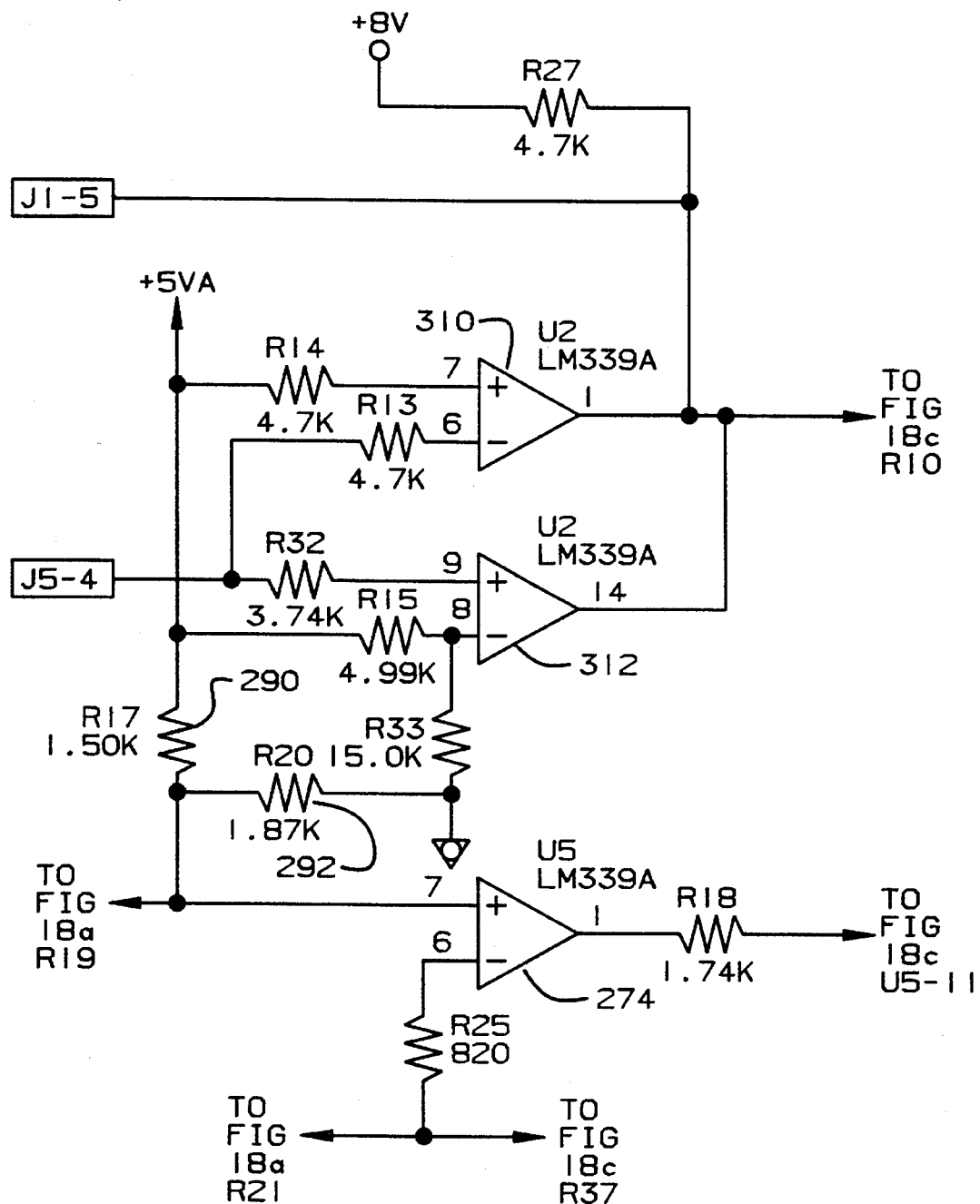
Figure 18C:
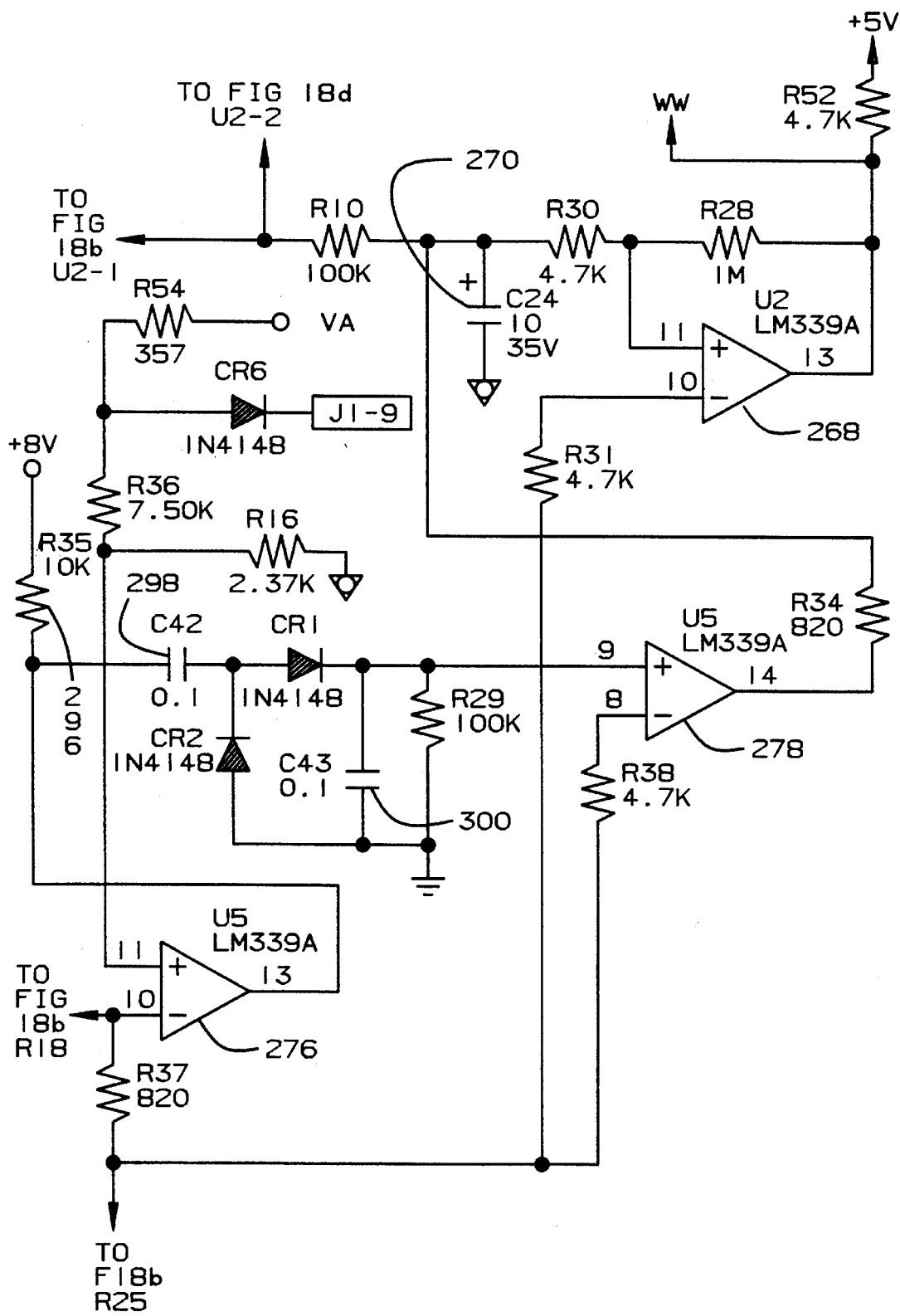
Figure 18D:
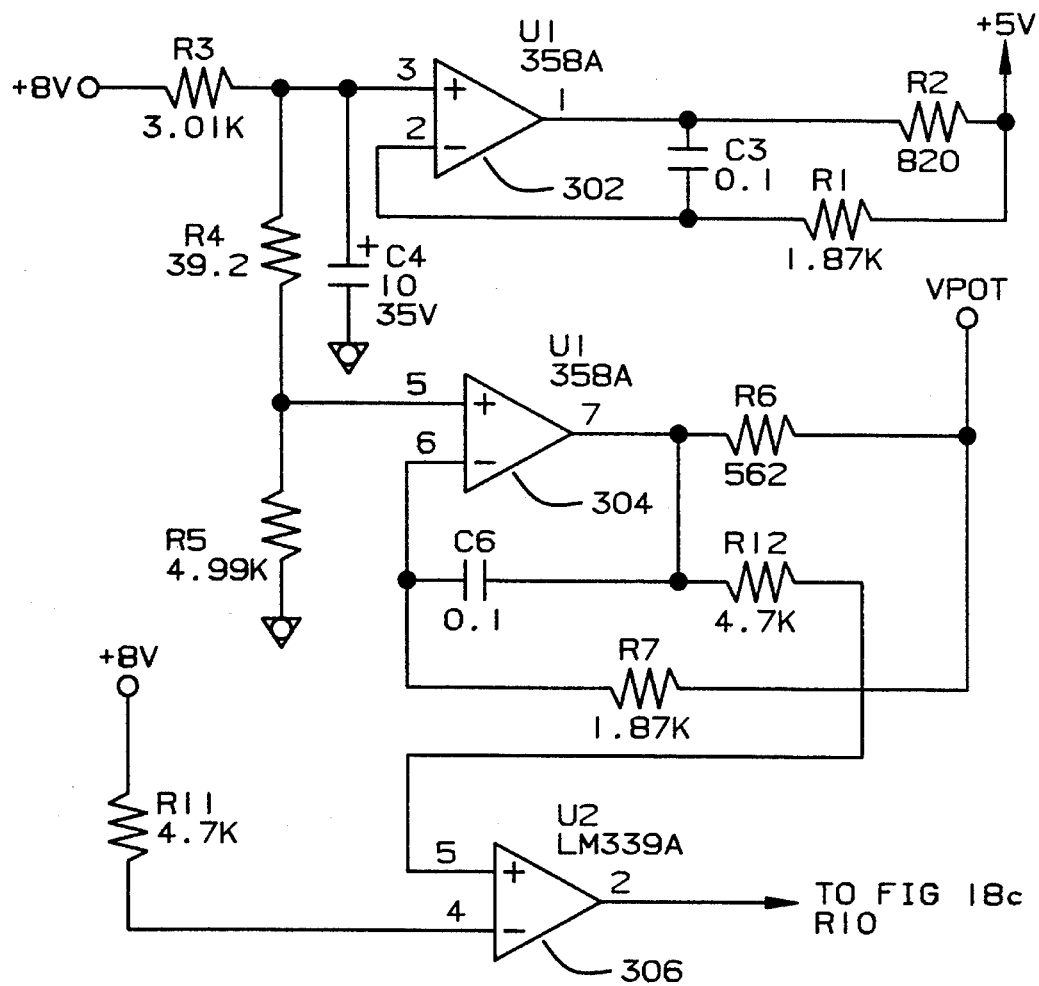

The safety solenoid circuit 116 schematically shown in FIG. 8 is shown in detail in FIG. 16. The principal components of the safety solenoid circuit 116 are a 2.5 volt voltage reference 246 connected to the inverting input of an operational amplifier 248, the output of which drives a Darlington switch 250 coupled to a dual pin connector 252 that is connected to the safety solenoid (not shown). The safety solenoid is connected to a safety valve that, when activated by the solenoid, vents the inspiratory leg of the patient air passage to the atmosphere so that the patient can breathe normally in case of ventilator malfunction.

During normal operation of the safety solenoid circuit 116, a 2.5 volt signal is supplied to the non-inverting input of the operational amplifier 248, which in this case is used as a comparator, and a high voltage is supplied to the non-inverting input of the amplifier 248. As a result, the amplifier 248 outputs a high voltage which causes the Darlington switch 250 to be on, so that it presents a current path through the jumper and the solenoid, thus energizing the solenoid in which state the solenoid holds the safety valve in a closed position. However, if the ventilator malfunctions and the VENT INOP* signal becomes logic 0, the output of the amplifier 248 produces a low voltage, which causes the Darlington switch 250 to be off, so that it does not present a current path through the jumper and the solenoid, thus de-energizing the solenoid in which state the solenoid opens the safety valve allowing the patient to breathe the atmosphere. The non-inverting input of the amplifier 248 is also connected to the INT1* signal line of the motor control microprocessor 190 which allows that processor to activate the safety solenoid as well. Although the INT1* signal line would appear to be an interrupt line, this pin is programmable and in this case is used as an output.

The pressure transducer circuits 112a, 112b, 112c schematically shown in FIG. 8 are shown in detail in FIGS. 17a, 17b and 17c, respectively. Now referring to FIG. 17a, the proximal pressure transducer circuit 112a comprises a conventional pressure transducer 254 that develops a voltage proportional to the sensed pressure. This voltage is supplied to the non-inverting input of an operational amplifier 256 having its output coupled to the connector pin J4-6 that is supplied to the main processor 188 via the interface circuit 110 after it is converted to digital form. The proximal pressure transducer circuit 112a includes a first potentiometer 258 coupled to the non-inverting amplifier input which acts as a zero level adjust and a second potentiometer 260 coupled to the amplifier output which acts as a gain adjust for purposes of shaping the pressure versus analog voltage waveforms most advantageously for interfacing with the ADA units 156, 158.

The machine pressure transducer circuit shown in 17b operates in substantially the same manner as the proximal pressure transducer circuit just described.

The system pressure transducer circuit shown in FIG. 17c includes a pressure transducer 261 connected to a pair of operational amplifiers 262, 264 to develop an analog voltage proportional to pressure at the output of the second operational amplifier 264. This circuit, which is slightly different since a different type of pressure transducer is used, includes a single potentiometer 266 that is used as zero level adjust.

The voltage level test circuit 120 schematically shown in FIG. 8 is shown in detail in FIG. 18. This circuit 120 functions to develop several voltages used by the ventilator circuitry and to test the voltage levels used by the ventilator circuitry. A comparator 268 outputs a signal that, when logic 1, indicates that the various voltage levels within the ventilator circuitry are within acceptable ranges. This comparator continuously senses the voltage supplied to its positive input by a capacitor 270. When all voltages are within acceptable ranges, the capacitor is supplied a high voltage, which prevents it from discharging and activating the comparator 268. When any of the voltage levels being tested is out of range, the capacitor is supplied a low voltage, causing it to discharge and activate the comparator.

A number of voltage levels are tested by a chain of four comparators 272, 274, 276, 278 coupled to a 2.5 volt reference 280 and a timer 282. The reference 280 supplies a 2.5 volt signal to each of the negative inputs of the comparators 272, 274, 276, 278, 268. The positive input of the comparator 272 is supplied with an approximate 2.5 volt d.c. signal supplied from the 5 volt system source after being divided down by a pair of resistors 284, 286. Superimposed on the 2.5 volt d.c. signal is a square waveform of a smaller magnitude, for example 1 volt, that defines the acceptable voltage range of the 5 volt supply. The square waveform is developed by the timer, which produces a waveform having a five volt magnitude, and reduced in magnitude by a resistor 288. As a result of the variation in voltage at the positive input of the comparator induced by the small magnitude square waveform, the comparator 272 will output a square waveform if the five volt supply is within its acceptable range.

The five volt analog supply, +5VA, is supplied to the positive input of the comparator 272 through a pair of resistors 290, 292. To the d.c. voltage supplied thereby, a square waveform is superimposed from the output of the comparator 272 and reduced through a resistor 294. When the +5VA supply is within acceptable limits, the output of the comparator 274 will be a square wave just like the output of the 272. The unregulated analog supply Va is supplied to the positive input of the comparator 276, just as the +5V, +5VA supplies. The output of the comparator 276 will generate a square waveform if the Va supply is within range. If any of the comparators 272, 274 fails to provide a square wave output, then the succeeding comparator will also fail to provide a square waveform since the output of each comparator is caused to swing by the small magnitude square waveform superimposed on the d.c. input supplied to its positive input. As a result, if all of the voltage levels +5V, +5VA, Va are within range, the output of the comparator 276 will be a square waveform. Any d.c. component of this square waveform is removed by the combination of a resistor 296 and a capacitor 298 and the remaining a.c. portion causes an integrating capacitor 300 to remain charged with a voltage sufficient to prevent the positive input of the comparator 278 from going below its negative input. If the a.c. portion disappears for a predetermined period of time, indicating that one of the voltage levels has gone out of range, the capacitor 300 will discharge, and this will cause the output of the comparator 278 to be pulled low, the capacitor 270 to start discharging, and the output of the comparator 268 to be pulled low.

Another portion of the circuit 120 comprising a pair of operational amplifiers 302, 304 develops the +5VA and $V_{POT}$ voltage levels from the +8V level. A comparator 306 senses a reduced voltage when one of the potentiometers of the control panel circuit malfunctions, which triggers a low signal at its output which in turn causes the capacitor 270 to discharge and cause the VENT INOP state.

A pair of comparators 310, 312 are connected to receive the output of the system pressure transducer at pin J5-4, and they sense when the system pressure does not come within predetermined pressure limits. As a result, the output of the comparators 310, 312 goes low, causing the capacitor 270 to discharge and the VENT INOP state to be entered. Finally, the capacitor 270 is caused to discharge and the VENT INOP state to be entered when the exhalation valve is disassembled, which is indicated by the output of a microswitch going low, the output of the microswitch being supplied to the J1-5 pin.

Figure 19A:
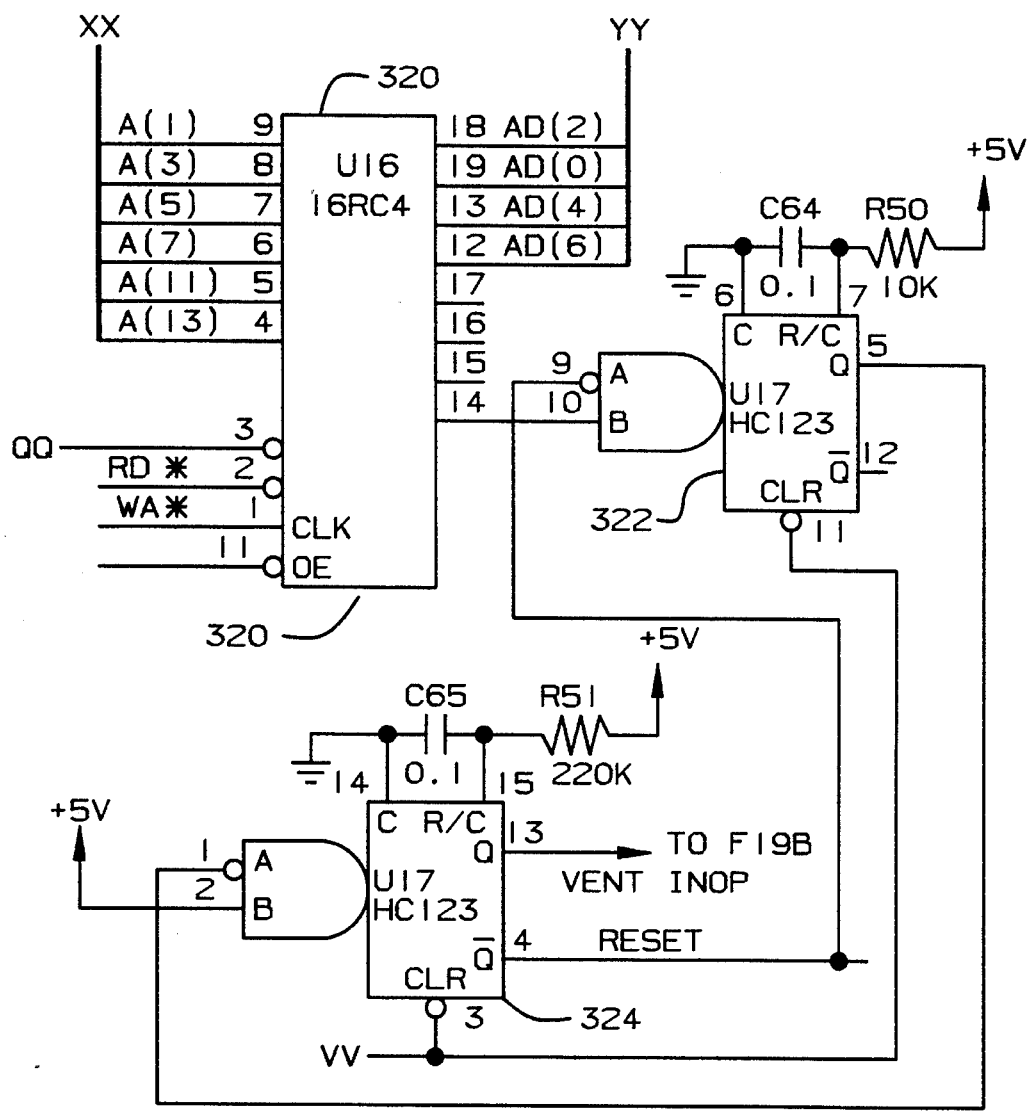
FIG. 19 is a detailed circuit diagram of the ventilator test and alarm circuit shown in FIG. 8.
Figure 19B:
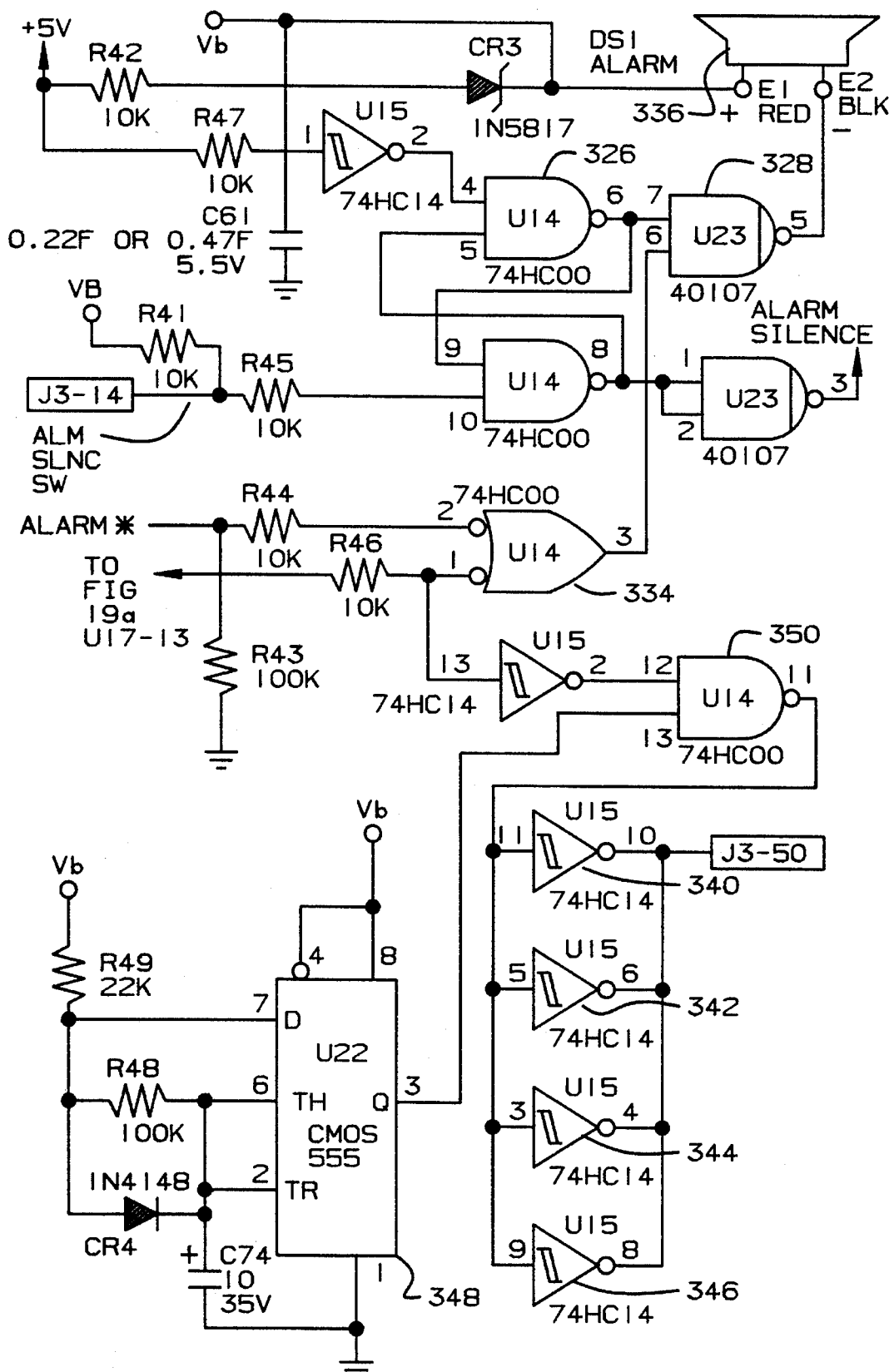

The ventilator test and alarm circuit 114 schematically shown in FIG. 8 is shown in detail in FIG. 19. Now referring to FIG. 19, this circuit includes a watchdog timer 320 which ensures that the main microprocessor is functioning properly. The watchdog timer 320 is implemented with a programmable-array logic (PAL) integrated circuit chip which is programmed as a state machine by a set of PAL equations included as part of the microfiche index referred to above. The watchdog timer, the operation of which is explained below, periodically outputs a signal via its pin 14 which periodically retriggers a first monostable multivibrator 322 the output of which is connected to a second monostable multivibrator 324. If the main processor is not functioning properly, the watchdog timer 320 will not retrigger the first multivibrator 322, and as a result, output of the second multivibrator 324 will go low, and the VENT INOP signal will be activated. This VENT INOP signal is supplied to a set-reset (SR) flip-flop comprising four NAND gates 326, 328, 330, 332 through a NOR gate 334 with complemented inputs. When activated, the VENT INOP signal causes an alarm to sound. The alarm may be temporarily deactivated by the alarm silence switch on the ventilator control panel, the output of which is supplied to the SR flip-flop through the connector pin J3-14. The activation of the VENT INOP signal also causes a visual alarm that is activated by four drivers 340, 342, 344, 346. The visual alarm blinks, which is caused by a timer 348 coupled to the drivers via a NAND gate 350.

The second multivibrator 324 is connected to receive the signal output from the oscillator, the output of which may be activated by the voltage level supply and test circuit as described above. When the W signal output from the oscillator is so activated, the second multivibrator 324 outputs an active VENT INOP signal.

Figure 20:
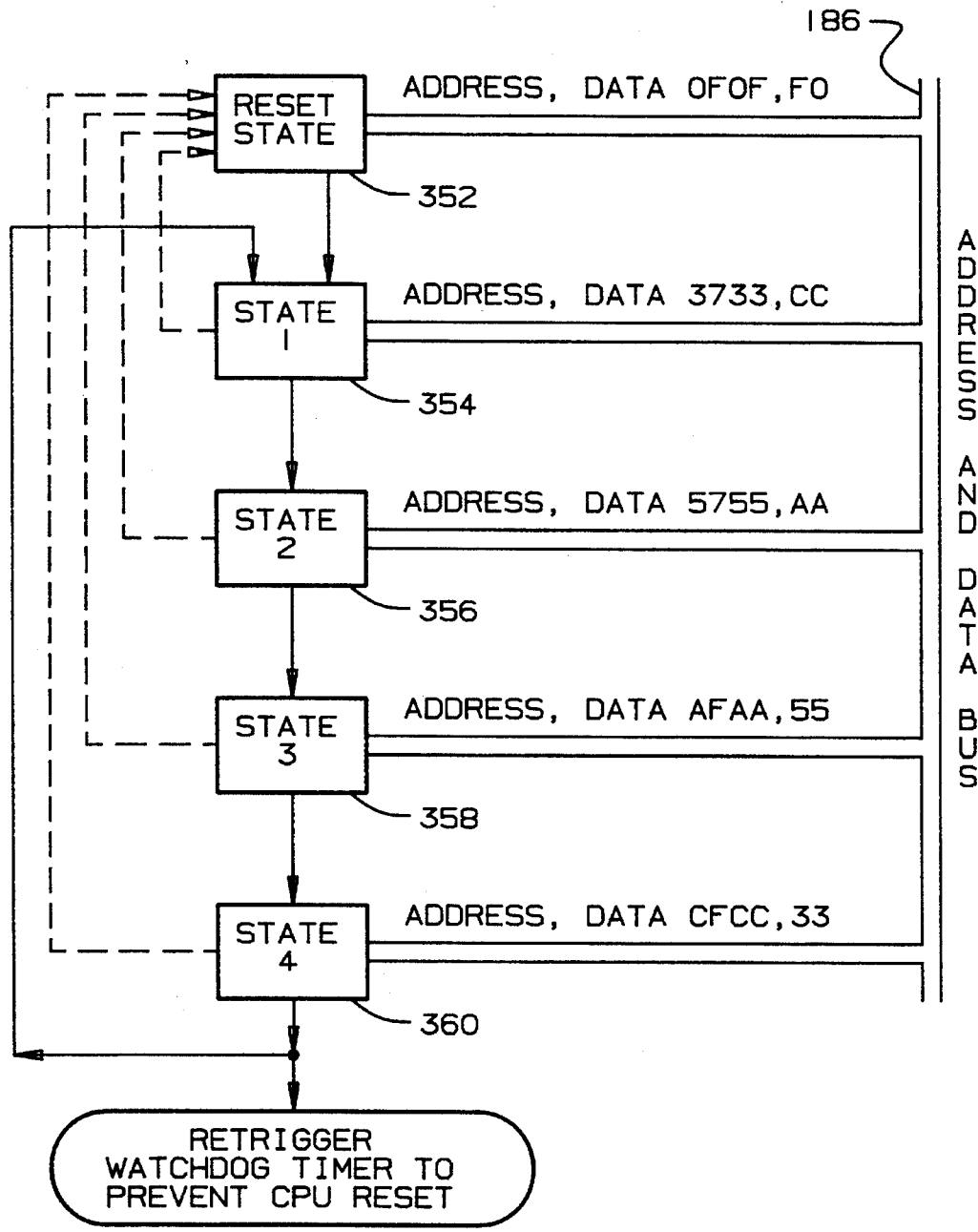
FIG. 20 is a state diagram of the watchdog timer of FIG. 19.

Now referring to FIG. 20, a diagram of the state machine of the watchdog timer is shown. State machines are conventional and commonly used in circuit design. The state machine shown in FIG. 20, which is implemented with the PAL equations included in the microfiche appendix, has five states which it can be in at any time. These five states include a reset state 352, a first state 354, a second state 356, a third state 358, and a fourth state 360. The watchdog timer 320 is connected to the main processor 188 via the address/data bus 186 and the address bus 200.

The operation of the watchdog timer is as follows. When the ventilator is initially turned on, the watchdog timer 320 is initialized to the reset state. During normal operation of the ventilator, the main processor 188 periodically requests the current state of the watchdog timer 320 by the hexadecimal address 0F0F, which contains the current state of the watchdog timer. When the main processor 188 receives the current state, it then transmits a predetermined pair of hexadecimal numbers to a predetermined address, depending upon which state the watchdog timer 320 is in.

Specifically, if the watchdog timer 320 is in the first state 354, the main processor transmits the data CC to the address 3733. If the watchdog timer 320 is in the second state 356, the main processor transmits the data AA to the address 5755. If the watchdog timer 320 is in the third state 358, the main processor transmits the data 55 to the address AFAA. If the watchdog timer 320 is in the fourth state 360, the main processor transmits the data 33 to the address CFCC.

If the watchdog timer 320 receives the expected data at the expected address, it moves to the next state. Whenever the watchdog timer 320 moves from its fourth state 360 to its first state 354, it transmits a retrigger signal to the first multivibrator 322, which prevents the VENT INOP signal from being activated. However, if the watchdog timer 320 does not progress through its four states 354, 356, 358, 360 normally, which would be caused by a main processor malfunction that causes the wrong data or address to be sent to the watchdog timer 320, then the retrigger signal will not be provided and the VENT INOP signal will be activated by the second multivibrator 324.

Communication Format Between Microprocessors

The two microprocessors 188, 190, which communicate with each other via a serial interface created by interconnecting their RXD and TXD pins as described above, use a communication format shown in FIGS. 21a and 21b. The two processors communicate with each other by sending messages which include a header byte indicating which type of message is being sent. The header byte may be followed by one or more data bytes.

During normal operation, the main processor 188 may send any of the messages shown in FIG. 21a to the motor control processor 190. Now referring to FIG. 21a, the main processor may send a message to the motor control processor, requesting that it move the flow control valve to its home position and then acknowledge when the valve has been so moved. This FLOW VALVE POSITION 0 message consists of a single header byte containing the hexadecimal number 13. The main processor may send another message requesting that the motor control processor send the exhalation valve to its home position and acknowledge when it has done so. This EXH VALVE POSITION 0 message is transmitted by sending a single header byte containing the hexadecimal number 14.

The main processor may also send a STATUS REQUEST message to the motor control processor, and this message comprises a single header byte containing the hexadecimal number 00.

The main processor can also request that the motor control processor either open or close the safety valve. The OPEN SAFETY VALVE message is a single header byte containing the hexadecimal number 25, and the CLOSE SAFETY VALVE message is a single header byte containing the hexadecimal number 26.

The last message comprising only a single header byte is the ITV ACCUMULATOR 0 message, which requests that the inspired tidal volume accumulator be set to zero, and is indicated by a single header byte containing the hexadecimal number 0F.

Three messages consist of a single header byte followed by either one or two data bytes. These messages include a FLOW VALVE POSITION message that is sent by the main processor to the motor control processor and requests that the latter move the flow control valve to a requested position. The FLOW VALVE POSITION message is indicated by a header byte containing either the hexadecimal numbers 03 or 83. If the current breath is not a sigh breath, the header byte is 03, and if the current breath is a sigh breath, the header byte is 83. Two additional data bytes are transmitted following the header byte. The first data byte following the header byte is a binary integer ranging from zero to 127 which represents the step position to which the flow control valve is requested to be positioned. The second data byte following the header byte is a binary integer ranging from zero to 255 which represents the last position of the flow control valve, in half steps, that was reported by the motor control processor to the main processor. Strictly speaking, this byte is not necessary to the motor control processor since it, at all times, keeps track of where the flow control valve is positioned. However, this data may be of interest to diagnostic devices which utilize the fiber optic data link described below.

The main processor may also send a message requesting that the motor control processor move the exhalation control valve to a requested position. This EXH VALVE POSITION message is indicated by a header byte containing the hexadecimal number 04 and two data bytes which follow. The first data byte which follows the header byte is a binary integer ranging from zero to 127 which represents the step position to which the exhalation control valve should be positioned. The second data byte following the header byte is a binary integer ranging from zero to 255 which represents the last reported position of the exhalation valve, in half steps, as reported by the motor control processor. This second data byte is also strictly not required since the motor control processor knows where the exhalation control valve is at all times, but may be used for diagnostic devices connected to the fiber optic data link.

A message indicating that the ventilator is inoperative may also be transmitted. This VENT INOP message includes a single header byte containing the hexadecimal number EE and a single data byte following the header byte which contains a binary integer ranging from zero to 255 that represents the cause of the ventilator inoperative state.

The remaining four messages of the communication format between the main processor and the motor control processor include a single header byte followed by 16 data bytes. These messages include an INSPIRATORY BREATH message that is transmitted at the end of each inspiration cycle and includes data relating to the inspiratory breath. The INSPIRATORY BREATH message includes a header byte containing the hexadecimal number AA followed by 16 data bytes. The data bytes 0–3 contain the ASCII representation of the inspiratory time: data byte 0 contains the most significant integer digit of the inspiratory time; data byte 1 contains the least significant integer digit of the inspiratory time; data byte 2 contains the most significant fractional digit of the inspiratory time; and data byte 3 contains the least significant fractional digit of the inspiratory time. The next four data bytes contain the breath rate: data byte 4 contains the most significant integer digit of the breath rate; data byte 5 contains the next most significant integer digit of the breath rate; data byte 6 contains the next most significant integer digit of the breath rate; and data byte 7 contains the least significant integer digit of the breath rate. The next four bytes contain the calculated minute volume of the breath: data byte 8 contains the most significant integer digit of the minute volume; data byte 9 contains the next most significant integer digit of the minute volume; data byte A contains the next most significant integer digit of the minute volume; and data byte B contains the least significant integer digit of the minute volume. The last four data bytes of the INSPIRATORY BREATH message contain data indicating the inspired tidal volume: data byte C contains the most significant integer digit of the inspired tidal volume; data byte D contains the next most significant integer digit of the inspired tidal volume; data byte E contains the next most significant integer digit of the inspired tidal volume; and data byte F contains the least significant integer digit of the inspired tidal volume.

An EXPIRATORY BREATH message, which is indicated by a header byte containing the hexadecimal number 55, is transmitted after the end of each exhalation. The sixteen data bytes which follow the header byte contain information relating to the exhalation control process described in more detail below.

A CONTROL PANEL message is transmitted every 32 milliseconds after being requested. This message contains the control panel settings, current status code, if any, and the DIP switch settings from both the main and motor control processors. The CONTROL PANEL message has a header byte that contains the hexadecimal number 5A. This header byte is followed by 16 data bytes. Data bytes 0 and 1 contain the most significant byte and least significant byte, respectively, of the current setting of the tidal volume control on the front panel of the ventilator. The data are all positive 2-byte binary integers ranging from 50 through 2000 milliliters. Data byte 2 contains a binary integer representing the most current setting of a peak flow rate control on the front panel of the ventilator. The data are all positive 1-byte binary integers ranging from 10 to 120 liters per minute. Data byte 3 contains the most current setting of the breath rate control on the front panel of the ventilator. The data are all positive 1-byte binary integers ranging from zero to 80 breaths per minute. Data byte 4 contains the binary integer representing the most current setting of the PEEP control knob on the front panel of the ventilator. The data are all positive 1-byte binary integers ranging from zero to 30 centimeters $H_2O$. Data byte 5 contains a binary integer representing the most current setting of the assist sensitivity control on the front panel of the ventilator. The data are positive 1-byte binary integers ranging from 1 to 20 centimeters $H_2O$, plus the off selection state which is represented by the hexadecimal number FF. The off position of this control is equivalent to requiring an infinitely large patient effort to trigger a breath. Since an infinite effort cannot be created by a human patient, the effect is simply to disable patient-initiated breaths. The data byte 6 of the CONTROL PANEL message contains a binary integer representing the most current setting of the pressure support control on the front panel of the ventilator. The data are positive 1-byte binary integers ranging from 1 to 50 centimeters H$_2$O, plus the off selection state which is represented by the hexadecimal number FF. The off position of this control is equivalent to a pressure support of zero, which is no support. Data byte 7 contains the most current setting of the high peak pressure alarm control on the front panel of the ventilator. The data are positive 1-byte binary integers ranging from zero to 140 centimeters H$_2$O. Data byte 8 contains the most current setting of the low peak pressure alarm on the front panel of the ventilator. The data are positive 1-byte binary integers ranging from zero to 140 centimeters H$_2$O. Data byte 9 contains the most current setting of the low PEEP/CPAP pressure alarm on the front panel of the ventilator. The data are signed 1-byte binary integers ranging from −20 to +30 centimeters H$_2$O. Two's complement form is used so that, for example, the quantity −2 appears as the hexadecimal number 0FE. The data byte A and data byte B contain the most significant byte and least significant byte, respectively, of the most current setting of the low inspired tidal volume alarm on the front panel of the ventilator. The data are positive 2-byte binary integers ranging from 20 to 2000 milliliters. The data byte C contains the most current setting of the 8-bit main board DIP switch. The state of the switch is read in real-time and transmitted in this message. A closed switch appears as a zero, while an open switch appears as a one. The data byte D contains the last status code generated by the software. At power-up, the code is zero indicating no unusual events have occurred. As each unusual event occurs (if any do occur), the new code number overwrites the previous code number. The codes range from the hexadecimal numbers 00 to FF, or zero to 255 decimal. The data byte E contains the power-up setting of the 8-bit DIP switch associated with the motor control processor. The state of the switch is read in at system initialization time only and transmitted thereafter in this message. A closed switch appears as a zero, while an open switch appears as a one. Data byte F is a spare data byte in which the hexadecimal number 00 is currently transmitted.

The last message in the communication format that the main processor 188 sends the motor control processor 190 is a SYSTEM STATUS message which is transmitted every 32 milliseconds after being requested by the file task O currently executed in time slot 29. The header byte for this message contains the hexadecimal number A5. The data bytes 0–6 following the header byte contain various mode switch flags, LED flags, data flags, alarm flags and miscellaneous flags. Data byte 6 contains the most current measured pressure data for the 20 pounds per square inch regulated gas supply. Data bytes 7, 8 and 9 contain the most current measured pressure data for the machine outlet pressure transducer. Data bytes A, B and C contain the most current measured pressure data for the proximal pressure transducer. Data bytes D and E contain various high pressure and pressure mismatch alarm flags. Data byte F is not used and a hexadecimal 00 is currently transmitted there.

The motor control processor 190 may send any of the messages shown in FIG. 21b to the main processor 188. Each of these messages may include a single header byte which may be followed by one or more data bytes. Now referring to FIG. 21b, a FLOW VALVE DATA message may be sent which contains information relating to the flow control valve. The header byte for this message is the hexadecimal number 0B. This header byte is followed by a first data byte containing a binary integer ranging from 0 to 255 which represents the current position of the flow control valve in half steps. The second, third, fourth and fifth data bytes following the header comprise a 4-byte binary integer representing the current sum in the tidal volume integrating accumulation register. The second byte is the most significant byte, and the fifth byte is the least significant byte of the 4-byte number.

An EXH VALVE DATA message may be sent by the motor control processor to the main processor. This message has a header byte containing the hexadecimal number 0C, a first data byte containing a binary integer ranging from 0 to 255 which represents the current position of the exhalation valve in half steps, and a second data byte containing a binary integer ranging from 0 to 255 which represents the length of time, in units of 8 microseconds, until the next exhalation valve step interrupt will occur. This data is primarily for diagnostic use.

The next message is a FLOW VALVE BUSY message that is indicated by a header byte containing the hexadecimal number 1B. This message is sent whenever the motor control processor receives a request from the main processor to move the flow control valve, but cannot do so because a home operation is in progress.

An EXH VALVE BUSY message may be sent which contains a header byte containing the hexadecimal number 1C. This message is sent whenever the motor control processor receives a request from the main processor to move the exhalation valve, but cannot do so because a home operation is in progress.

A motor control processor ready (MCP READY) message may be sent which contains a header byte containing the hexadecimal number 0F. The header byte is followed by five data bytes which contain information regarding the motor control processor. The first, second, third and fourth data bytes following the header byte comprising a 4-character software revision code for the motor control processor. The fifth data byte following the header byte is the current setting of the DIP switch on the motor control processor.

The next message that may be sent is a FLOW VALVE HOME message, which contains a header byte containing the hexadecimal number 23, and is used to indicate that the motor control processor has completed a verification test on the correctness of the home position of the flow control valve.

The EXH VALVE HOME message, which is indicated by a header byte containing the hexadecimal number 24, is sent when the motor control processor completes a verification test on the correctness on the home position of the exhalation valve.

A SAFETY VALVE CLOSED message, which consists of a header byte containing the hexadecimal number 28H, is sent whenever the motor control processor changes the status of the safety valve, or when inquiry about its status is received from the main processor.

A SAFETY VALVE OPEN message, indicated by a header byte containing the hexadecimal number 29H, is sent whenever the motor control processor changes the status of the safety valve, or when inquiry about its status is received from the main processor.

A DATA BYTE MISSING message, which is represented by a header byte containing the hexadecimal number DB, is sent whenever the motor control processor receives a message from the main processor which does not contain the expected number of data bytes.

A HEADER BYTE MISSING message, which is represented by a header byte containing the hexadecimal DC, is sent by the motor control processor to the main processor when a header byte was missing from a message previously received.

Finally, a VENT INOP message may be transmitted. This message is indicated by a header byte containing the hexadecimal number EE, and indicates that the ventilator is in a malfunction state. The header byte is followed by one data byte which contains a code number corresponding to the reason the motor control processor has forced a ventilator malfunction state.

Overall Operation of Main Ventilator

Figure 22:
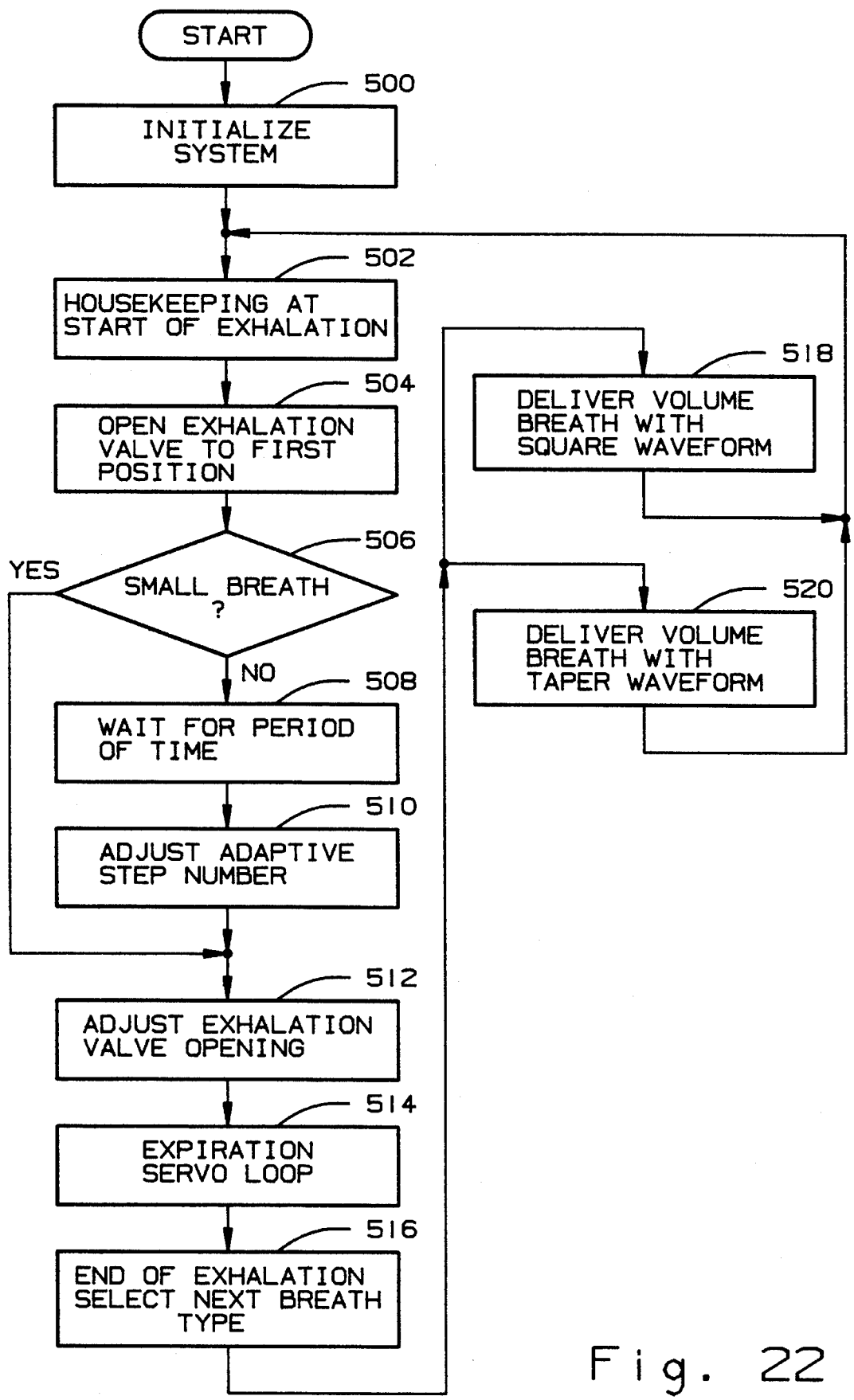
FIG. 22 is a flow chart of the main ventilator computer program.

A general flow chart of the main computer program stored in the EPROM in the main processor is shown in FIG. 22. The execution of the main computer program by the main processor 188 causes the patient to be automatically ventilated. In this ventilation process, as described above, the patient is delivered breaths with a predetermined flow profile between which the patient is caused to exhale. FIG. 22 illustrates the overall flow chart of this process. At step 500, the system is initialized by performing a number of processor tests and initializations. At step 502, various housekeeping chores are performed before the beginning of exhalation. At step 504, the exhalation valve is opened to an initial position. This position is an initial position which is based upon the proximal pressure that is measured during the exhalation of the patient. Next, at step 506, the tidal volume of the previously delivered breath is tested to determine if a small breath was delivered. If a small breath was not delivered, the program branches to step 508 during which it waits for a period of time after the initial opening of the valve. This waiting period is also based upon the proximal pressure sensed during exhalation. Next, at step 510, the program adjusts the adaptive step number so that the valve opening can be adjusted in the next step 512. If the breath just delivered by the ventilator was a small breath, as determined in step 506, the program branches to step 512, at which point the ventilator adjusts the opening position of the exhalation valve. At step 514, the ventilator enters an expiration servo loop during which time the motor control processor uses pressure feedback in order to keep the patient's expiratory pressure at a particular value. Next, at step 516, the exhalation process ends and the program branches to its inspiratory leg during which either a volume-controlled breath having a square waveform at step 518 is delivered or a volume-controlled breath having a tapered waveform at step 520 is delivered. A computer program corresponding to FIG. 22 is included in the microfiche appendix incorporated herein by reference.

System Initialization

Figure 23A:
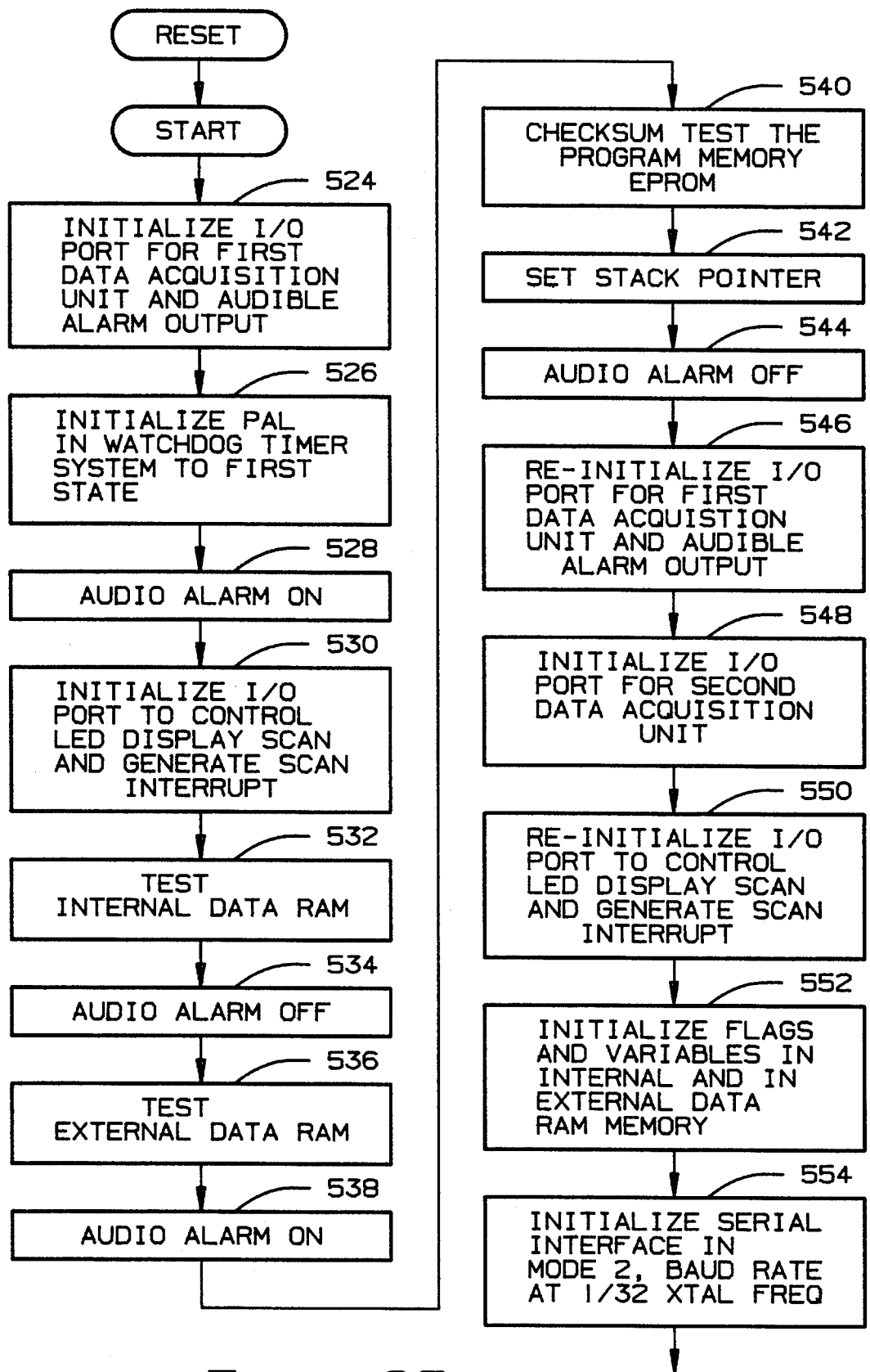
FIG. 23 is a detailed flow chart of a first portion of step 500 of FIG. 22.
Figure 23B:
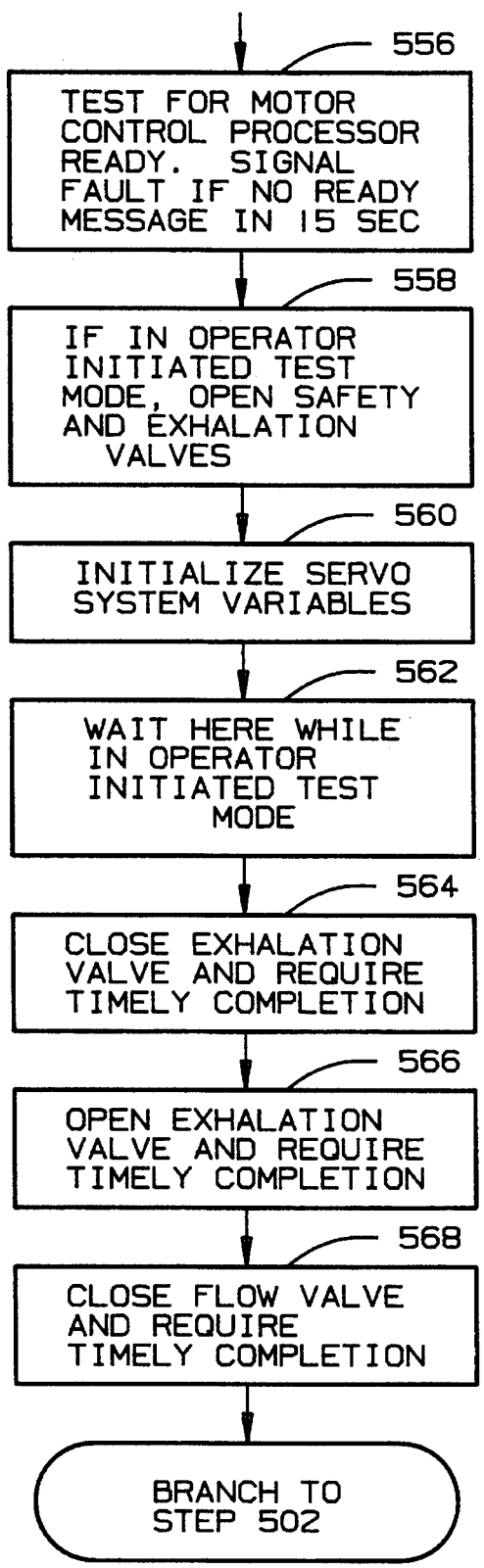
Figure 24:
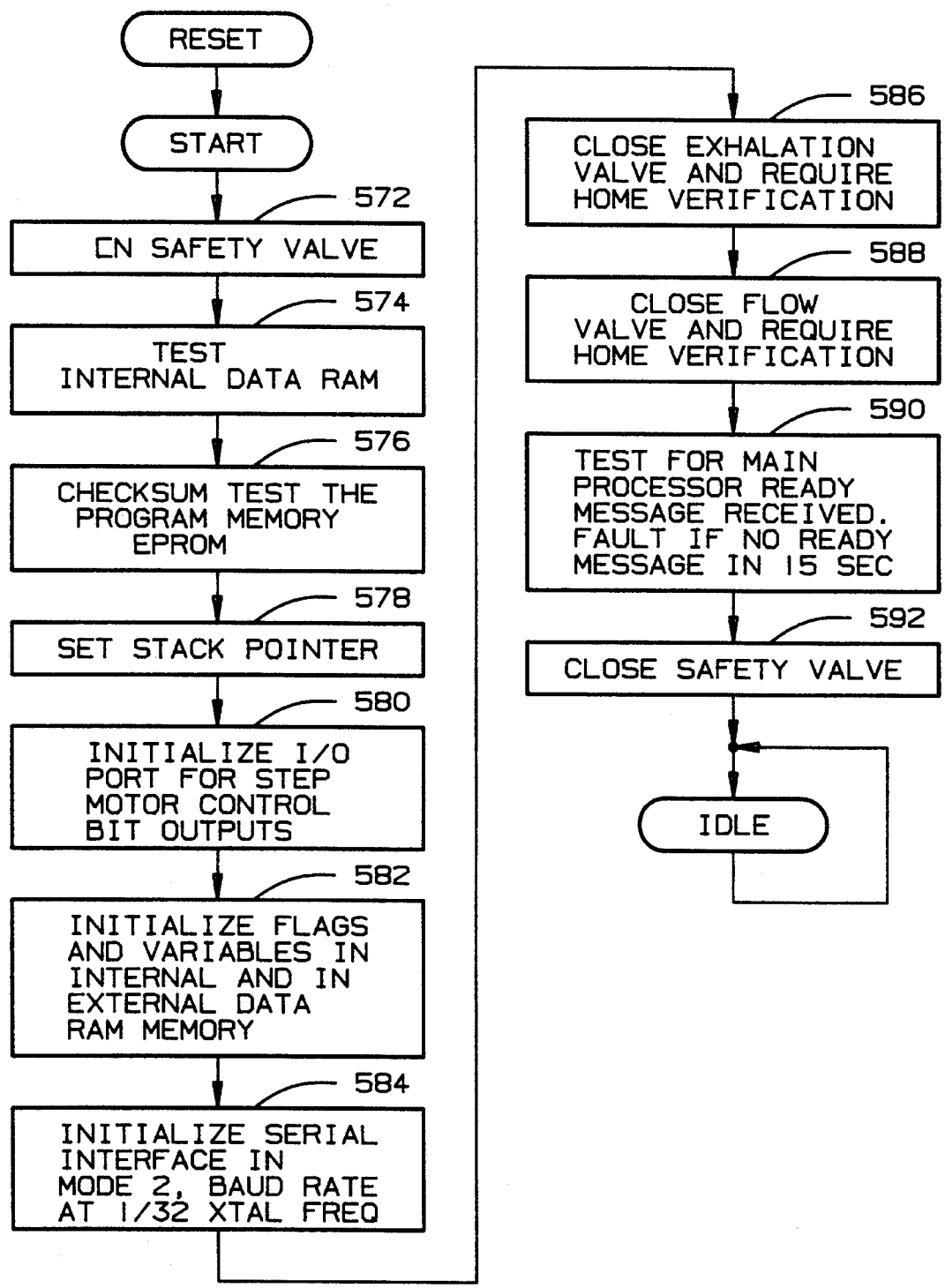
FIG. 24 is a detailed flow chart of a second portion of step 500 of FIG. 22.

A detailed flow chart of the initialization step 500, schematically shown in FIG. 22, is set forth in FIGS. 23 and 24. Now referring to FIG. 23, when the system is either powered up or reset, at step 524, the I/O port for the first ADA unit is initialized. At step 526, the watchdog timer circuit is initialized and set to its first state, as described above. At step 528, the audio alarm is turned on. At step 530, the I/O port to control the LED display scan and generate scan interrupt is initialized. At step 532, the internal data RAM of the main processor is tested. At step 534, the audio alarm is turned off. At step 536, the external data RAM of the main microprocessor is tested. At step 538, the audio alarm is turned on again. At step 540, the program memory in the EPROM is tested by performing a check sum on its contents. At step 542, the stack pointer of the main processor is initialized. At step 544, the audio alarm is turned off. At step 546, the I/O port for the first ADA unit is reinitialized. At step 548, the I/O port for the second ADA unit is initialized. At step 550, the I/O port to control the LED display is reinitialized and an interrupt is generated that causes the scan to be performed. At step 552, the flags and variables contained in the internal and external data RAM memory of the main microprocessor are initialized. At step 554, the serial interface between the two processors 188, 190 is initialized. At step 556, the main processor communicates to the motor control processor to determine if the processor is ready. If the motor control processor 190 does not respond within 15 seconds, a fault is activated. Next, at step 558, the safety and exhalation valves are opened if the ventilator is in an operator-initiated test mode. At step 560, the servo system variables are initialized. Step 562 is a processor wait state that waits until the operator-initiated test mode is completed. At step 564, the main processor sends a close exhalation valve message to the motor control processor 190 and requires that the processor 190 respond with an acknowledgment in a timely manner. At step 566, the main processor 188 requests that the motor control processor 190 open the exhalation valve and waits to see if the processor 190 acknowledges the request in a timely manner. At step 568, the main processor requests that the motor control processor 190 close the flow control valve, and the processor 188 checks to determine if an acknowledgment is received from the processor 190 in a timely manner. At step 570, the program branches to the routine shown in FIG. 41.

The detailed flow chart shown in FIG. 24 is part of the system initialization of step 500 which relates to the initialization of the motor control processor 190. During this initialization process, at step 572, the safety valve is opened. At step 574, the internal data RAM of the processor 190 is tested. At step 576, the program memory of the EPROM connected to the processor 190 is tested using a check sum. At step 578, the stack pointer of the motor control processor 190 is set. At step 580, the I/O port for the step motor control is initialized. At step 582, the flags and variables in the internal and external data RAM memory are initialized. At step 584, the serial interface between the processors 188, 190 is initialized. At step 586, the exhalation valve is closed and tested to see if it is at home. At step 588, the flow control valve is closed and tested to see if it is at home. At step 590, the main processor 188 is sent a message to determine if it is ready yet. A fault signal is activated if no ready message is received by the processor 190 in 15 seconds. At step 592, the safety valve is closed, and at step 594, the processor 190 remains in an idle state until it receives a command from the main processor 188.

Data Acquisition Interrupt Service Routine

Figure 25:
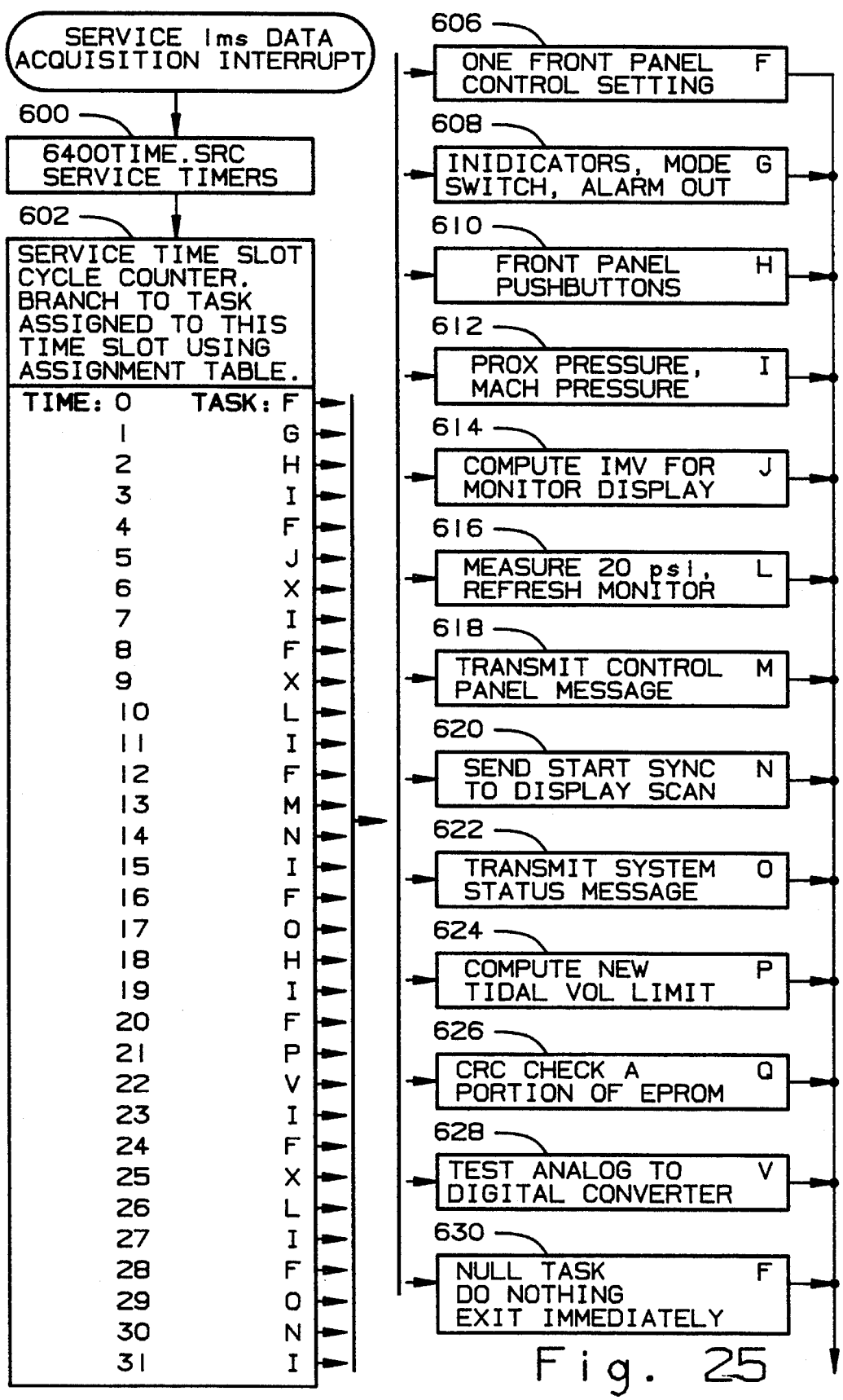
FIG. 25 is a flow chart of the data acquisition interrupt service routine.

A general flow chart of the operation of the data acquisition interrupt routine is shown in FIG. 25. This routine is called every 1 millisecond on an interrupt basis, principally in order to read the control and alarm knob settings on the front panel of the ventilator. At step 600, various software generated timers are updated. These software timers, which are explained in further detail below, are used for various tasks.

At step 602, the program branches to one of 13 different tasks that is performed on a multiplexed basis. The table set forth in step 604 includes 32 time slots numbered 0 through 31 and an associated task corresponding to each time slot. The time slots are kept track of by a service time slot cycle counter which counts from zero to 31 repeatedly. The particular task that is performed during this step 604 is determined by the count of the cycle counter. These tasks are labeled F through X. The basic function of task F at step 606 is to retrieve one front panel control knob setting. Task G at step 608 checks various alarm states and activates the corresponding alarms if the alarm state is active. Task H at step 610 reads the values of the momentary contact switches on the front control panel. During task I at step 612, the controller reads the proximal pressure and machine pressure from the corresponding pressure transducers and checks for the existence of certain pressure alarm states. During task J at step 614, the main controller calculates the inspired minute volume (IMV) for display on the control panel. During task L at step 616, the main processor reads the system pressure from the system pressure transducer and checks for the existence of the system pressure alarm state. Task M at step 618 provides for data communication via the fiber optic data link. Task N at step 620 synchronizes the LED display scan with the time slot in which task N is executed. Task O at step 622 causes a system status message to be transmitted to the fiber optic data link. During task P at step 624, the main processor calculates the inspiratory tidal volume. During task Q at step 626, a portion of the main processor EPROM is checked with a cyclic redundancy check. During task V at step 628, the ADA units are checked for accuracy. Task X at step 630 is a null task during which nothing is done.

Figure 26:
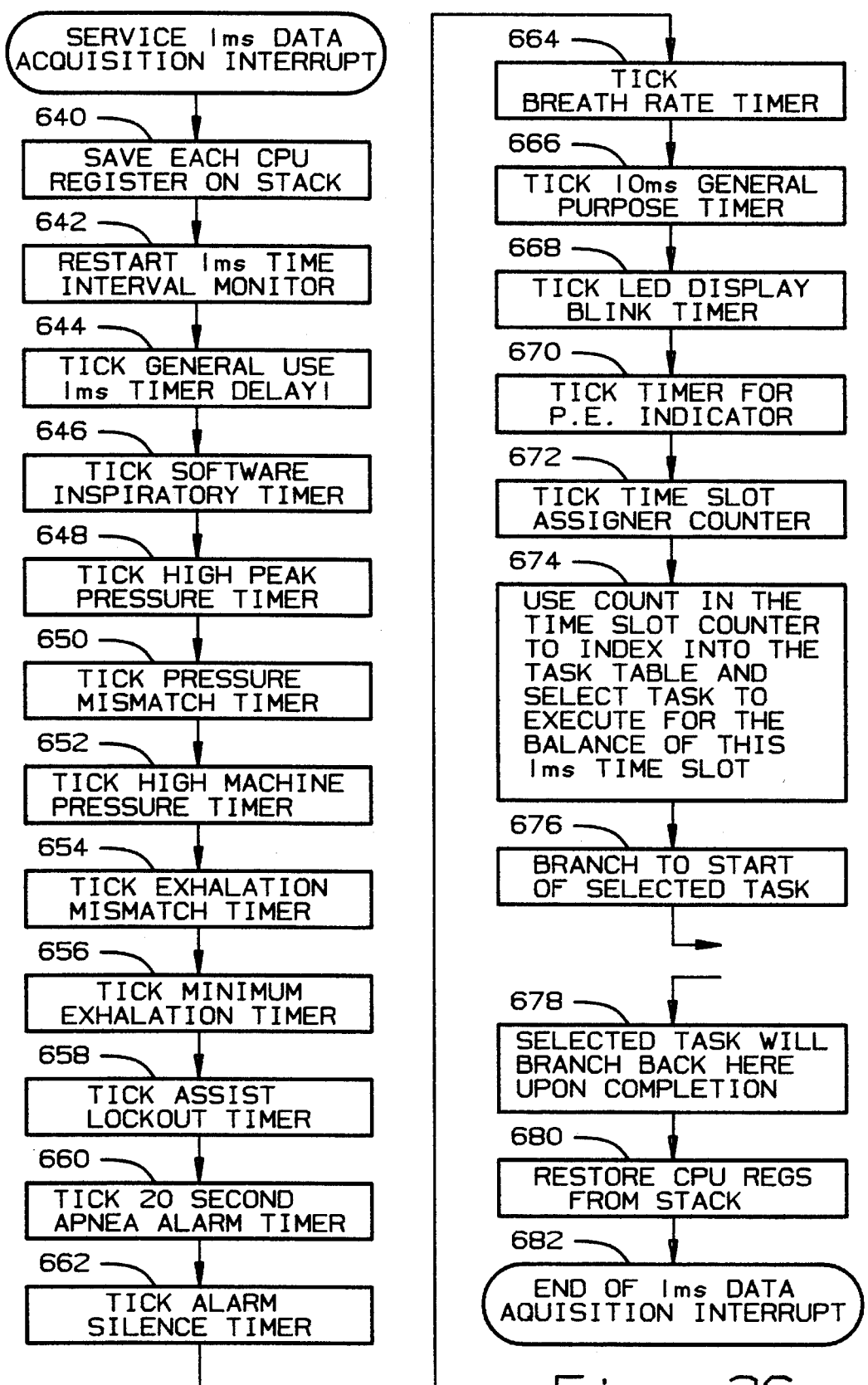
FIG. 26 is a detailed flow chart of steps 600 and of FIG. 25.

Now referring to FIG. 26, a detailed flow chart corresponding to the step 600 shown in FIG. 25 is provided. At step 640, the CPU registers of the main processor are saved onto the stack so that subsequent operations can be performed without losing their contents. Next, at step 642, the 1 millisecond time interval monitor that is used in connection with the data acquisition interrupt routine is restarted. At step 644, the 1 millisecond general use timer DELAY 1 is ticked. At step 646, the software inspiratory timer is ticked. At step 648, the high peak pressure timer is ticked. At step 650, the pressure mismatch timer is ticked. At step 652, the high machine pressure timer is ticked. At step 654, the exhalation mismatch timer is ticked. At step 656, the minimum exhalation timer is ticked. At step 658, the assist lock-out timer is ticked. At step 660, the apnea alarm timer is ticked. At step 662, the alarm silence timer is ticked. At step 664, the breath rate timer is ticked. At step 666, the general purpose timer is ticked. At step 668, the LED display blink timer is ticked. At step 670, the timer for the patient effort (PE) indicator is ticked. At step 672, the time slot assigner counter is ticked. At step 674, the 1 millisecond task table is indexed using the current count in the time slot counter, and the corresponding task is selected for execution for the remaining portion of the 1 millisecond time slot. Next, at step 676, the corresponding task is branched to. This corresponding task may be any one of the tasks F through X shown in the right-hand portion of FIG. 23. After the particular task is executed, the program branches back from the task to step 678 upon completion. Finally, at step 680, the CPU registers of the main processor are restored from the stack.

Figure 27A:
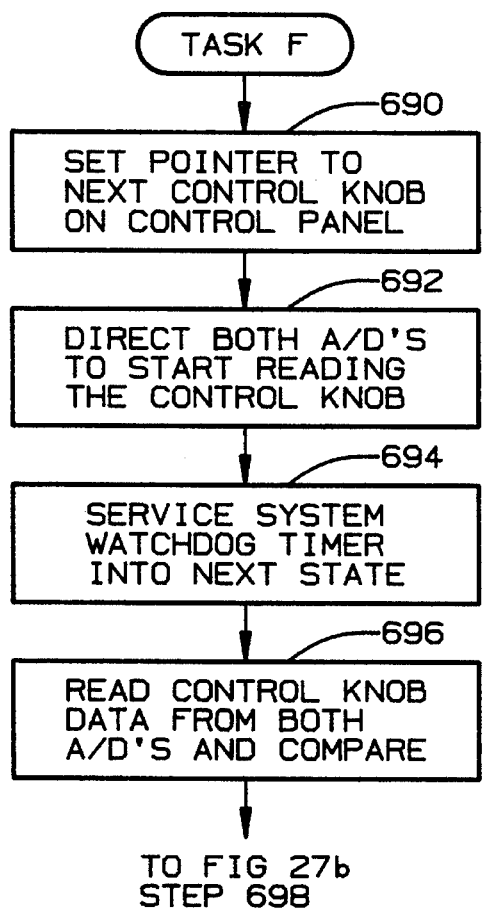
FIG. 27 is a detailed flow chart of step 606 of FIG. 25.
Figure 27B:
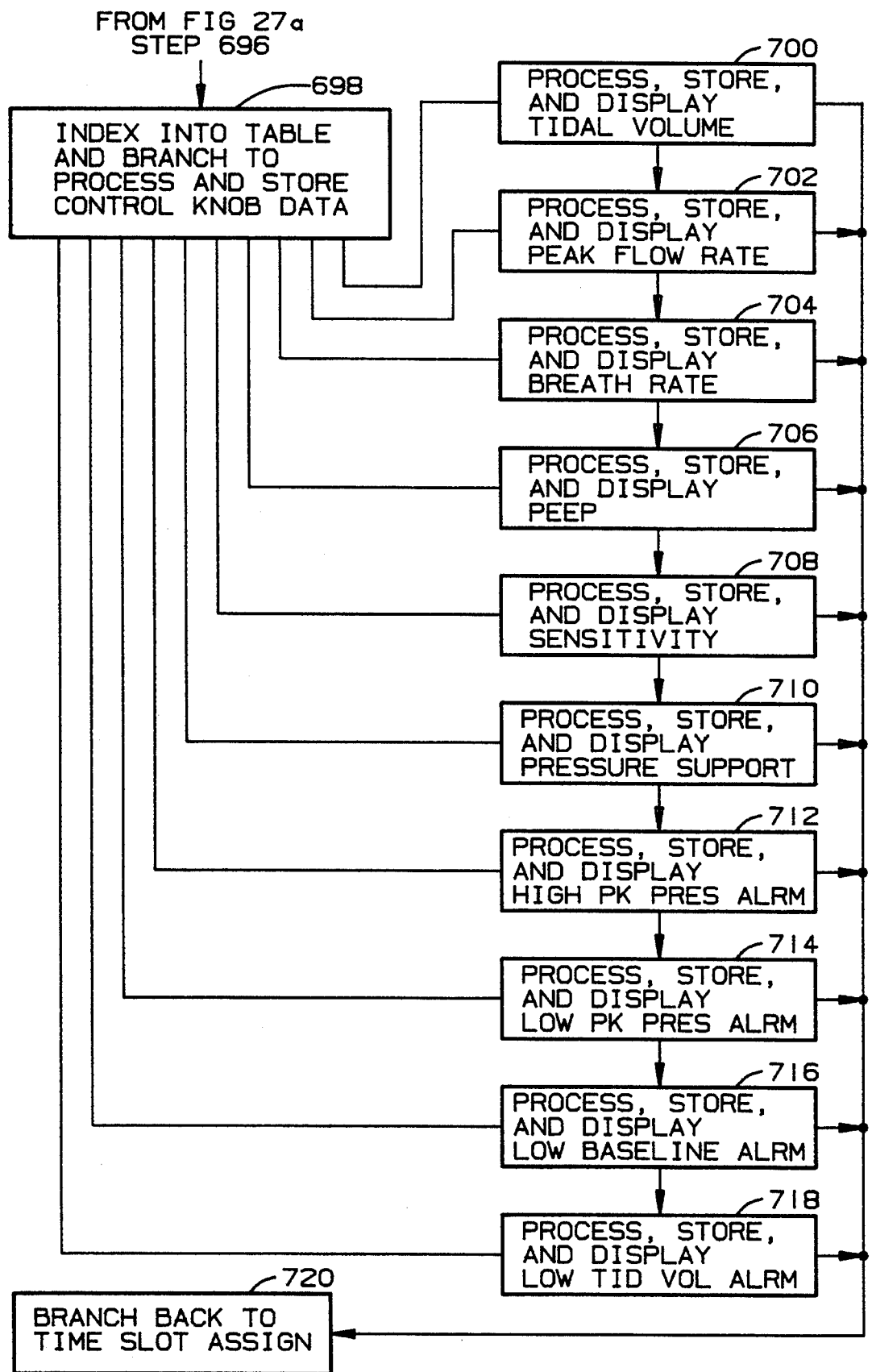
Figure 28:
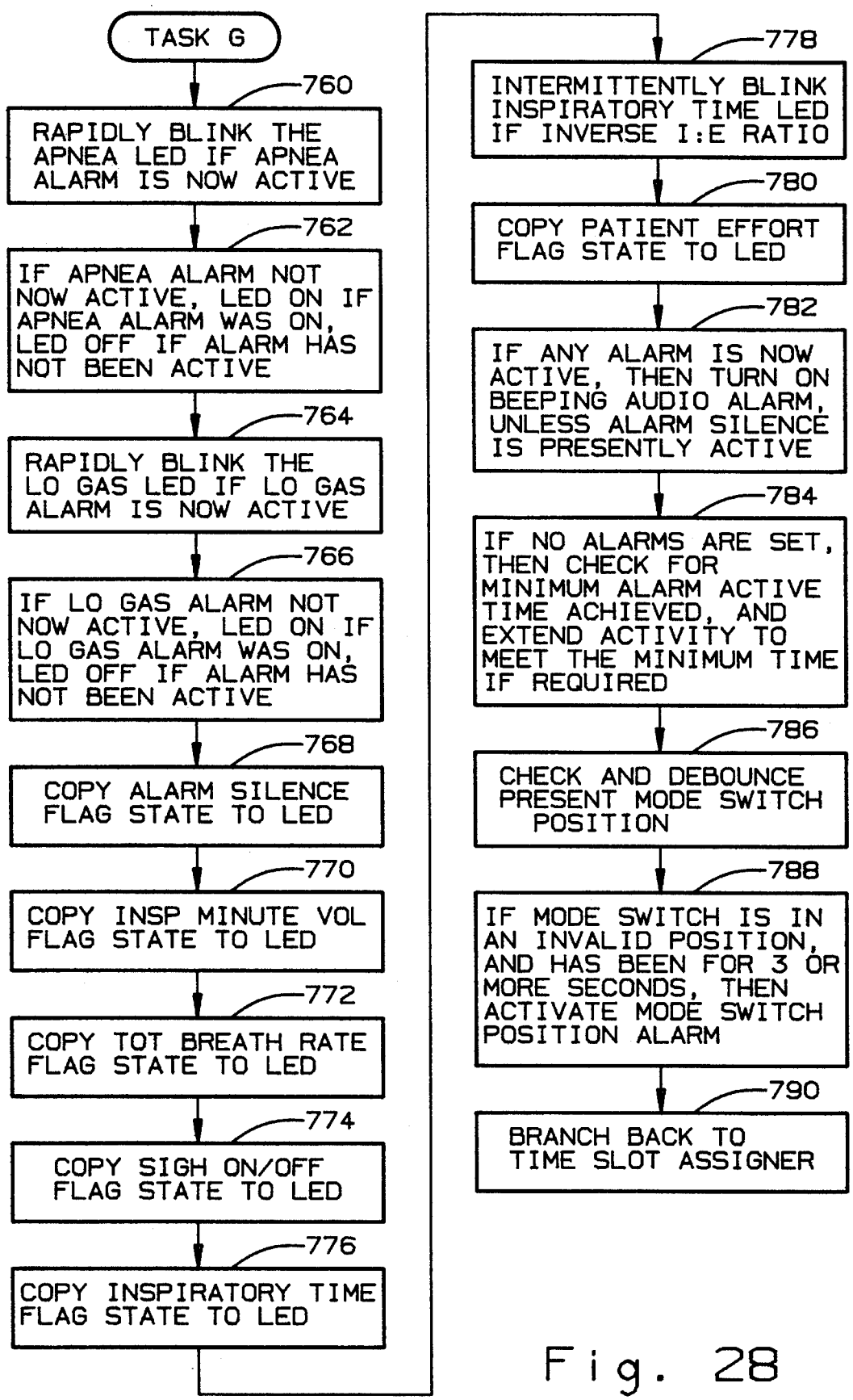
FIG. 28 is a detailed flow chart of step 608 of FIG. 25.

A detailed flow chart of the task F shown generally in FIG. 25 is set forth in FIG. 27. The purpose of task F is to retrieve one of the control or alarm knob settings from the front panel of the ventilator. At step 690, a pointer is set to the next control knob which needs to be read. At step 692, the main processor causes both of the ADA units to start reading the potentiometer associated with the control knob which is to be read. At step 694, the watchdog timer is serviced. At step 696, the digital data corresponding to the control knob setting that was read is read from both of the ADA units and compared to see if it corresponds.

The main ventilator computer program includes a small software table that includes a set of control signals that specifies which of the ten control and alarm knobs is read by the ADA units. The pointer referred to in step 690 points to one entry in this software table, and as a result, the corresponding set of control signals causes one of the ten control and alarm knob settings to be read. At step 698, this table is indexed, and the program branches to one of the step numbers at which the appropriate parameter from the control or alarm knob setting is processed, stored and displayed on the LED display. At step 720, the program branches back to the time slot assignment program.

Figure 29:
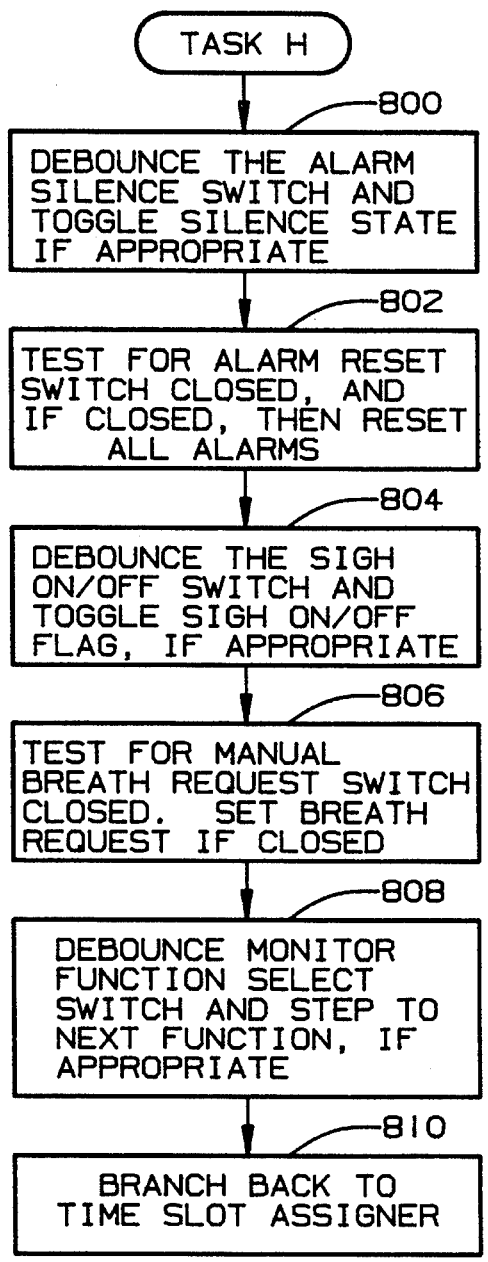
FIG. 29 is a detailed flow chart of step 610 of FIG. 25.

A detailed flow chart of task G, which is illustrated generally in FIG. 25, is set forth in FIG. 29. Now referring to FIG. 29, at step 760, the apnea LED is rapidly blinked if the apnea alarm is active. At step 762, the apnea alarm LED is turned off if the apnea alarm has not been active if the apnea alarm LED was previously on. At step 764, the low gas LED is rapidly blinked if the low gas alarm is currently active. At step 766, the low gas alarm LED is turned off if this alarm is no longer active. At step 768, the state of the alarm silence flag state is transmitted to the alarm silence LED. At step 770, the inspiratory minute volume flag state is transmitted to the LED. At step 772, the total breath rate flag state is transmitted to the corresponding LED. At step 774, the sigh on/off flag state is transmitted to the LED. Next, at step 776, the inspiratory time flag state is transmitted to the LED. At step 778, the inspiratory time LED is blinked intermittently if the previous inspiratory time was greater than one-half the breath period. Next, at step 780, the patient effort flag state is transmitted to the LED. Next, at step 782, a beeping audio alarm is turned on if any of the alarms is active, unless the alarm silence switch has been activated. At step 784, if an alarm has been activated but is no longer active, the minimum alarm time is checked to force the alarm to be activated for a predetermined period of time, for example three seconds, so that all alarms last at least that long. At step 786, the position of the mode switch on the ventilator control panel is checked to make sure that it is in one of the four valid positions. Next, at step 788, a mode switch position alarm is activated if the mode switch has been in an invalid position for more than 3 seconds. Finally, at step 790, the program branches back to the time slot assigned.

Figure 30:
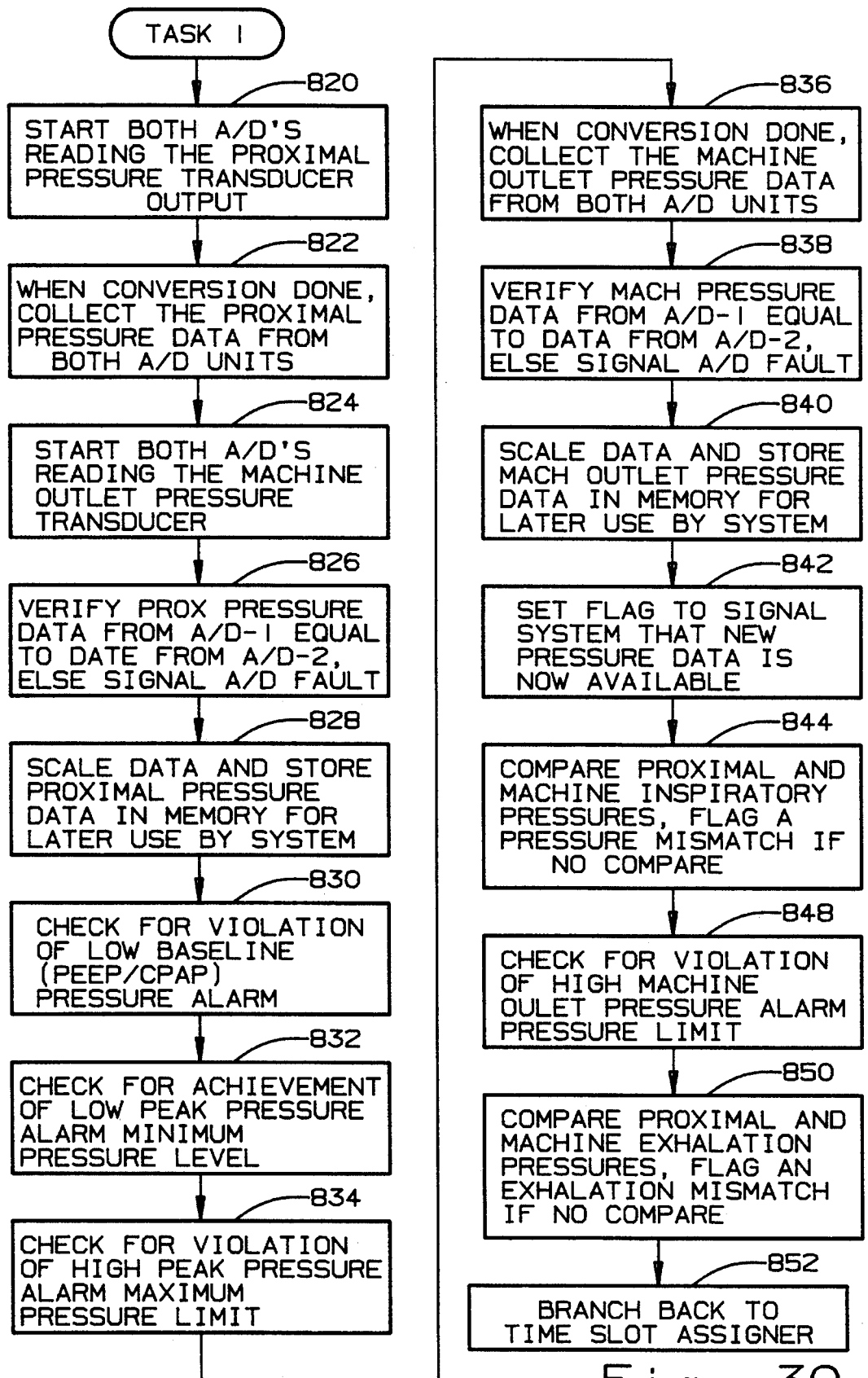
FIG. 30 is a detailed flow chart of step 612 of FIG. 25.

A detailed flow chart of the task H, which is shown schematically in FIG. 25, is shown in FIG. 30. During task H, the main processor monitors and debounces the control panel push button switches. Specifically, at step 800, the alarm silence switch is debounced and read, and if the switch has changed state, the silence state is toggled. At step 802, the alarm reset switch is tested to see if it is closed, and all alarms are reset if the switch is closed. At step 804, the sigh on/off switch is debounced and read, and the sigh on/off flag is toggled if the switch has changed state. At step 806, the manual breath request switch is tested to determine if it is closed. If it is closed, the breath request flag is set. Next, at step 808, the monitor function select switch is debounced and read, and the next function is stepped to if appropriate. At step 810, the program branches back to the time slot assigner.

Figures 31, 32:
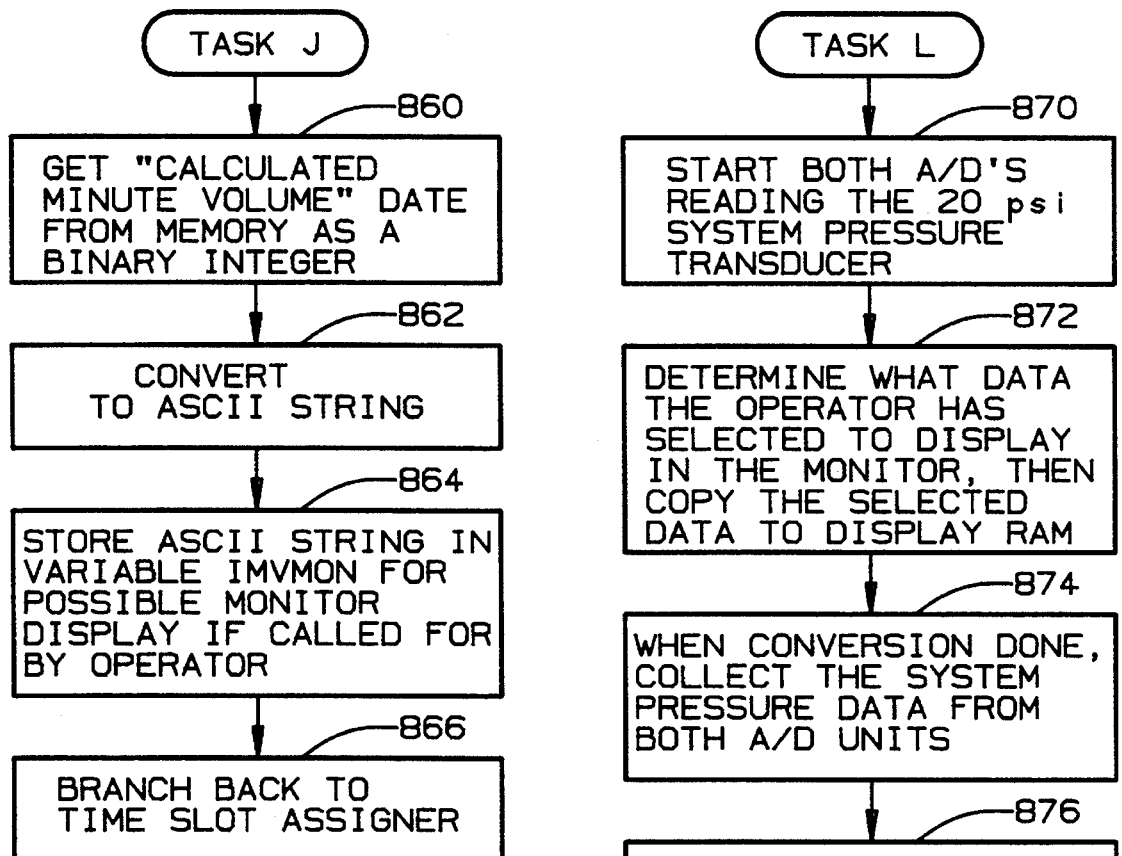
FIG. 31 is a detailed flow chart of step 614 of FIG. 25.
FIG. 32 is a detailed flow chart of step 616 of FIG. 25.

A detailed flow chart of task I, which is schematically shown in FIG. 25, is set forth in FIG. 31. During task I, the proximal pressure and machine outlet pressure is measured to determine whether it is compliance with the pressure alarm limits. Specifically, at step 820, the main controller causes both ADA units to read the output of the proximal pressure transducer. Next, at step 822, the proximal pressure data is read from both ADA units. At step 824, the main controller causes both ADA units to read the machine outlet pressure from the machine outlet pressure transducer. At step 826, the proximal pressure data from the first ADA unit is compared with the same data from the second ADA unit, and an ADA fault signal is activated if the data is not equal. At step 828, the proximal pressure data as read by the ADA units is scaled and stored in memory for later use by the system. At step 830, the proximal pressure is tested for a violation of the low baseline pressure alarm. At step 832, the proximal pressure is compared to the low peak pressure alarm limit to determine if a minimum peak pressure is present. At step 834, the proximal pressure limit is checked for a violation of the high peak pressure alarm maximum pressure limit. At step 836, the main processor reads the machine outlet pressure from the ADA units after the A-to-D conversion is completed. At step 838, the machine pressure read from the first ADA unit is compared to the same data from the second ADA unit, and an ADA fault signal is activated if the data are not substantially the same. At step 840, the machine outlet pressure data is scaled and stored in the memory of the main processor for later use by the system. At step 842, a flag is set to signal that new pressure data is available. At step 844, the proximal pressure is compared with the machine pressure to determine if these two pressures are within predetermined limits. Since the proximal pressure is measured at the patient and the machine pressure is measured just outside the flow control valve, these two pressures should be substantially the same, except that there will be a small pressure drop caused by the air flow through the air supply tube from the ventilator to the patient. At step 848, the machine outlet pressure is checked for a violation of the high machine outlet pressure alarm limit. At step 850, the proximal and machine exhalation pressures are compared to determine if there is an exhalation mismatch. Finally, at step 852, the program branches back to the time slot assigner.

A detailed flow chart of task J, which is schematically shown in FIG. 25, is shown in FIG. 32. Task J converts the calculated minute volume from a binary number to an ASCII number so that it can be displayed on the ventilator LED display. At step 860, the calculated minute volume is retrieved from memory as a binary integer. Next, at step 862, the binary number is converted to an ASCII string in a conventional manner. At step 864, the converted ASCII string is stored in the variable IMVMON so that it can be displayed on a monitor if requested by an operator. Finally, at step 866, the program branches back to the time slot assigner.

A detailed flow chart of task L, which is schematically shown in FIG. 25, is set forth in FIG. 33. During task L, the main controller measures the 20 pounds per square inch system gas supply and updates the monitor data display. Specifically, at step 870, the main processor causes the ADA units to read the system pressure transducer. At step 872, the main controller determines what data the operator has selected to display in the monitor, and then the selected data is copied to the display RAM. At step 874, when the A-to-D conversion is done, the system pressure is read from both ADA units. At step 876, the output of the two ADA units are compared to determine if they are substantially the same. If they are not substantially the same, an ADA fault signal is activated. At step 878, the system pressure data is scaled and stored in memory for later use by the main processor. Next, at step 880, the system pressure is checked to determine whether it is below the expected 20 pounds per square inch. In this case, the gas pressure alarm is activated. Finally, at step 882, the program branches back to the time slot assigner.

A detailed flow chart of task M, which is schematically shown in FIG. 25, is shown in FIG. 34. During task M, the main processor requests transmission of the control panel parameters data string over the fiber optic data link. At step 890, a flag is set to request transmission of the control panel parameters data string over the fiber optic data link. At step 892, if the serial interface has requested a transmit interrupt wake-up in 2 milliseconds, the wake-up request is cancelled and a transmit interrupt is issued. Finally, at step 894, the program branches back to the time slot assigner.

A detailed flow chart of task N, which is schematically shown in FIG. 25, is shown in FIG. 35. During task N, a start/sync signal is sent to the LED display scan interrupt generator. This signal is sent at step 900 so that the scan will start in sync with the particular time slot during which task N is executed. At step 902, the program branches back to the time slot assigner.

Figure 36:
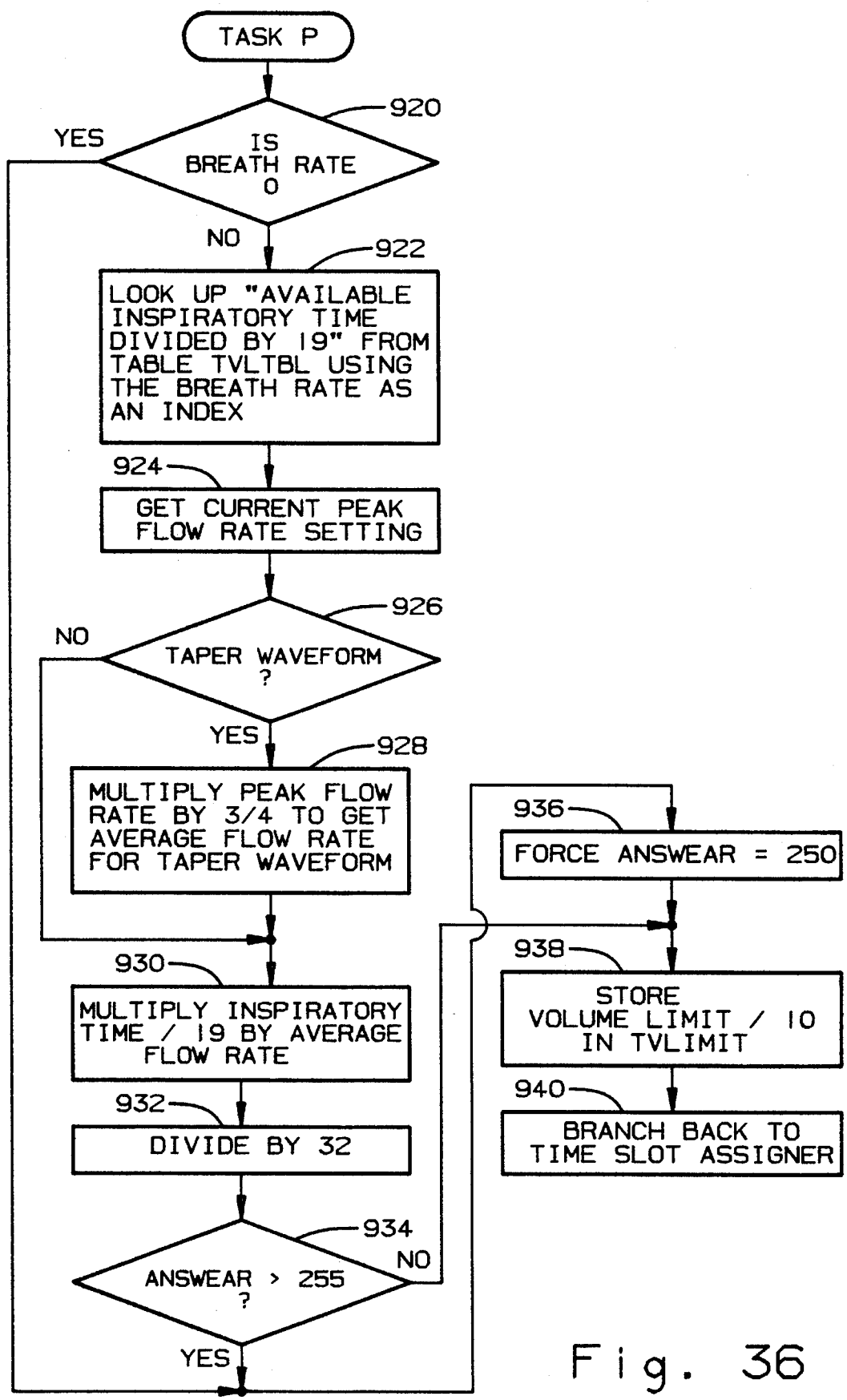
FIG. 36 is a detailed flow chart of step 624 of FIG. 25.

A detailed flow chart of task O, which is schematically shown in FIG. 25, is set forth in FIG. 36. During task O, the main processor requests transmission of the system status data string over the fiber optic data link. At step 910, a flag is set to request transmission of the system status message data string over the fiber optic data link. At step 912, if the serial interface has requested a transmit interrupt wake-up in 2 milliseconds, the wake-up request is cancelled and a transmit interrupt now is issued. At step 914, the program branches back to the time slot assigner.

Figure 37:
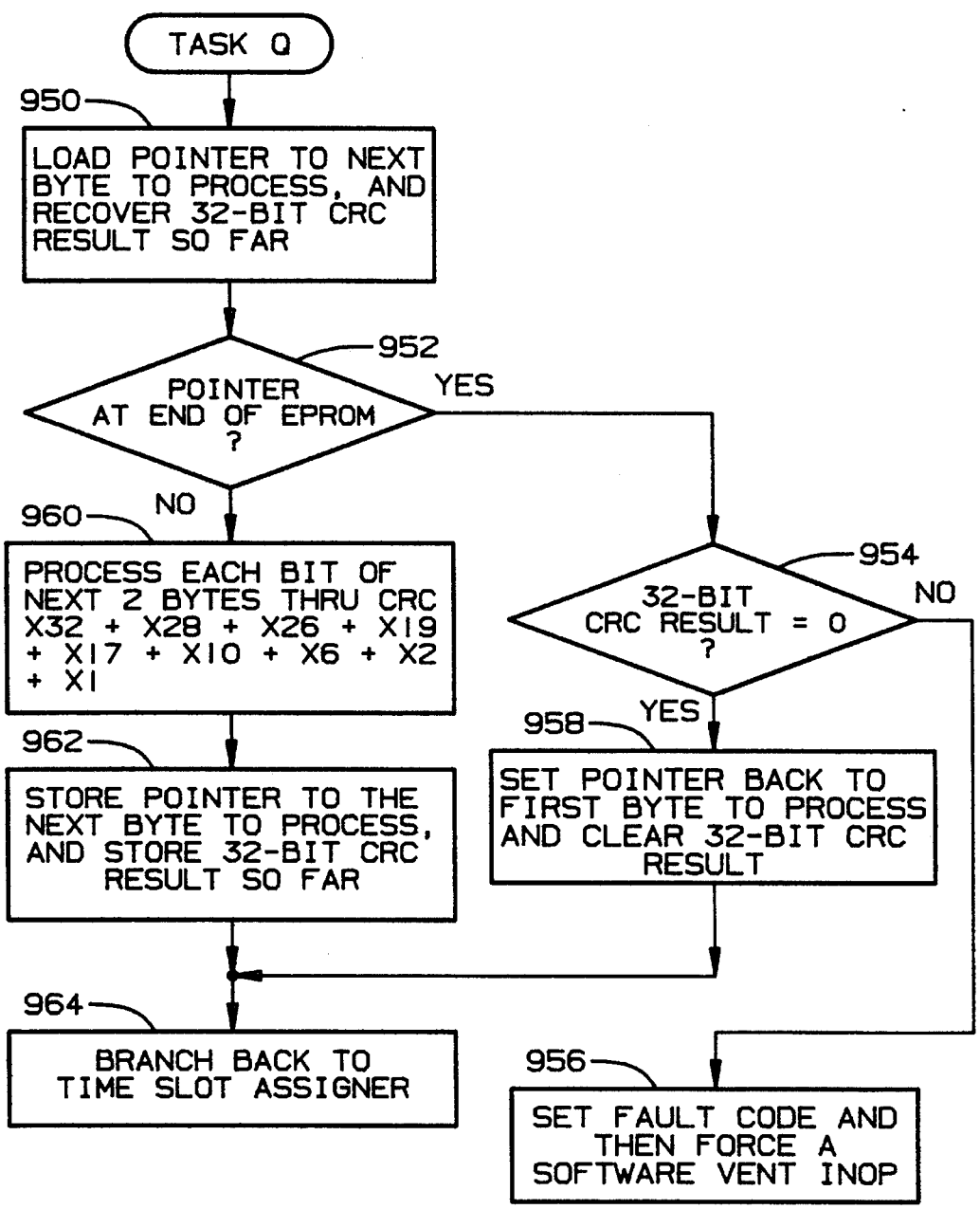
FIG. 37 is a detailed flow chart of step 626 of FIG. 25.

A detailed flow chart of task P, which is schematically shown in FIG. 25, is set forth in FIG. 37. During task P, the main processor determines the tidal volume limit based upon the selected peak flow and the breath rate settings. At step 920, the stored breath rate setting is tested to determine if it is zero. If it is zero, the ventilator has enough time to deliver any sized breath that is possible for the operator to select, and the program branches to step 936 where the volume limit is forced to equal 250 so that it will be greater than the maximum volume possible for the operator to select. If the breath rate is not zero, the program proceeds to step 922 where the available inspiratory time divided by 19 is retrieved from a table TVLTBL using the breath rate as an index. Next, at step 924, the current peak flow rate is retrieved from the memory of the main processor. Next, at step 926, the waveform shape flag is checked to determine if the waveform is a taper waveform. If the waveform is not a taper waveform, the waveform must be a rectangular waveform, and the program branches to step 930. If it is a taper waveform, the program at step 928 multiplies the peak flow rate by three-fourths to get the average peak flow rate for the taper waveform. Next, at step 930, the inspiratory time divided by 19 is multiplied by the average peak flow rate. Next, the product of the inspiratory time divided by 19 times the average peak flow rate is divided by 32 to calculate the tidal volume limit based on the current peak flow and breath rate settings. This product is compared with the binary number 255, which is the maximum allowable limit value, to determine if the tidal volume limit is within the valid range. If this value is greater than 255, the limit, representing the maximum volume which there is time for the ventilator to deliver, is in excess of the volume that it is possible for the operator to select, and the program branches to step 936 where the volume limit is forced to equal 250. If the volume limit is less than 255, the program branches to step 938 where the volume limit is stored in the variable TVLIMIT. Finally, at step 940, the program branches back to the time slot assigner.

A detailed flow chart of task Q, which is schematically shown in FIG. 25, is shown in FIG. 37. During task Q, the contents of a portion of the EPROM are tested with a cyclic redundancy check (CRC). Such testing is conventional. This task Q may be skipped since it is included only to add an extra safety factor to the operation of the ventilator. Now referring to FIG. 37, at step 950 a pointer is loaded to the next byte to process and the corresponding 32-bit CRC result is recovered. At step 952, if the pointer is at the end of the EPROM, the program branches to step 952 at which point the 32-bit CRC result, which should equal zero if there were no CRC errors, is tested to determine if it is zero. If not, the program branches to step 956 where the VENT INOP signal is activated since there was a fault in the EPROM. If the 32-bit CRC result was zero, the program branches to step at which the pointer is set so that it will point to the first byte in memory, and the program branches to step 964 where it branches back to the time slot assigner.

If the pointer is not at the end of the EPROM as determined at step 952, the program branches to step 960 at which the next two bytes are test with the CRC equation $X32+X28+X26+X19+X17+X10+X6+X2+X1$. At step 962, the pointer is set to the next byte to process, and the result 32-bit CRC result is stored, at which point the program branches back to the time slot assigner.

Figure 38:
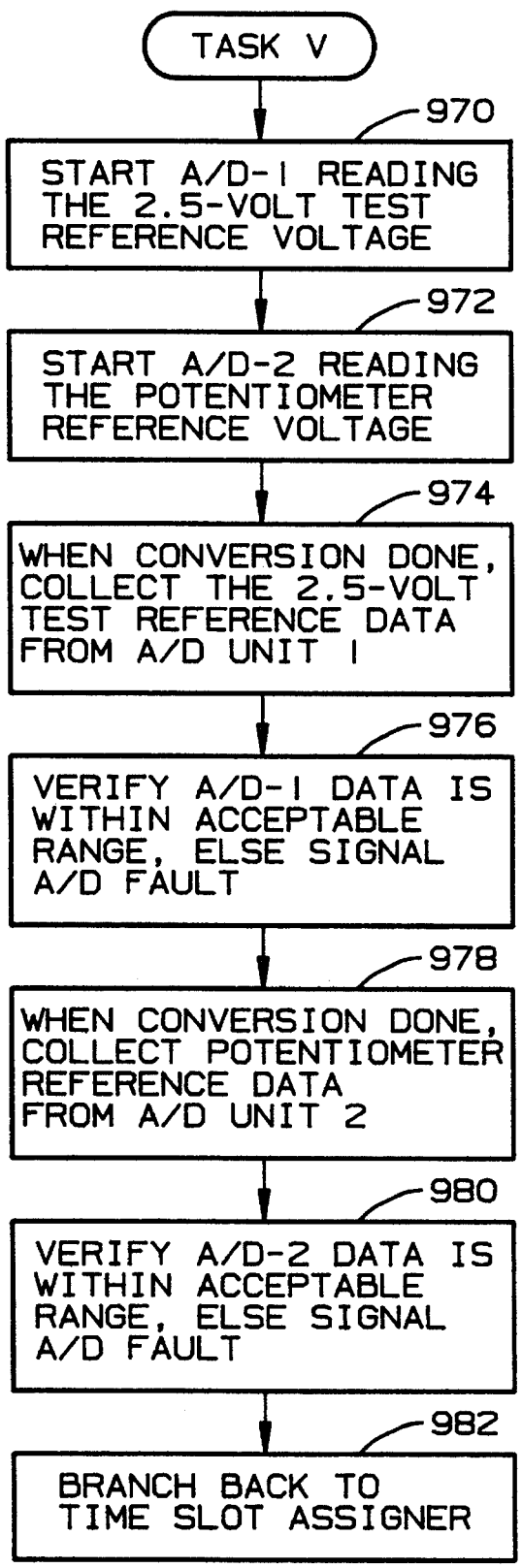
FIG. 38 is a detailed flow chart of step 628 of FIG. 25.

A detailed flow chart of task V, which is schematically shown in FIG. 25, is shown in FIG. 38. During task V, the main processor tests each of the ADA units using a test reference voltage. At step 970, the main processor starts the first ADA unit reading the 2.5 volt test reference voltage. Then, at step 972, the main processor starts the second ADA unit reading the potentiometer reference voltage. At step 974, when the A-to-D conversion is completed, the test reference data is collected from the first ADA unit. Next, at step 976, the data from the first ADA unit is compared to a predetermined data range to see whether it falls within the range. If it does not, an ADA fault is activated. When the second ADA unit has completed the A-to-D conversion, the potentiometer reference data is read by the main processor. If this potentiometer reference data does not fall within a predetermined acceptable range, an ADA fault signal is generated. At step 982, the program branches back to the time slot assigner.

Delivery of a Breath Having a Rectangular Profile

Figure 39A:
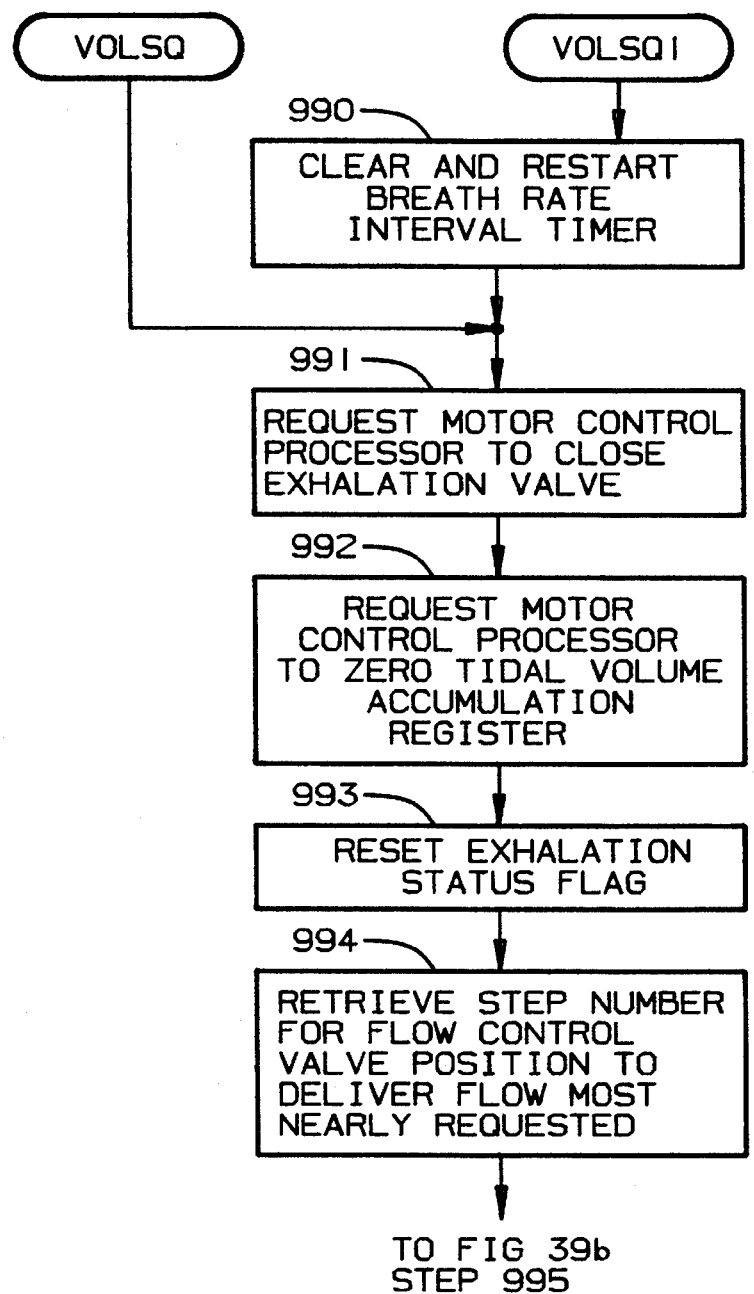
FIG. 39a is a detailed flow chart of a first portion of step 518 of FIG. 22.
Figure 39B:
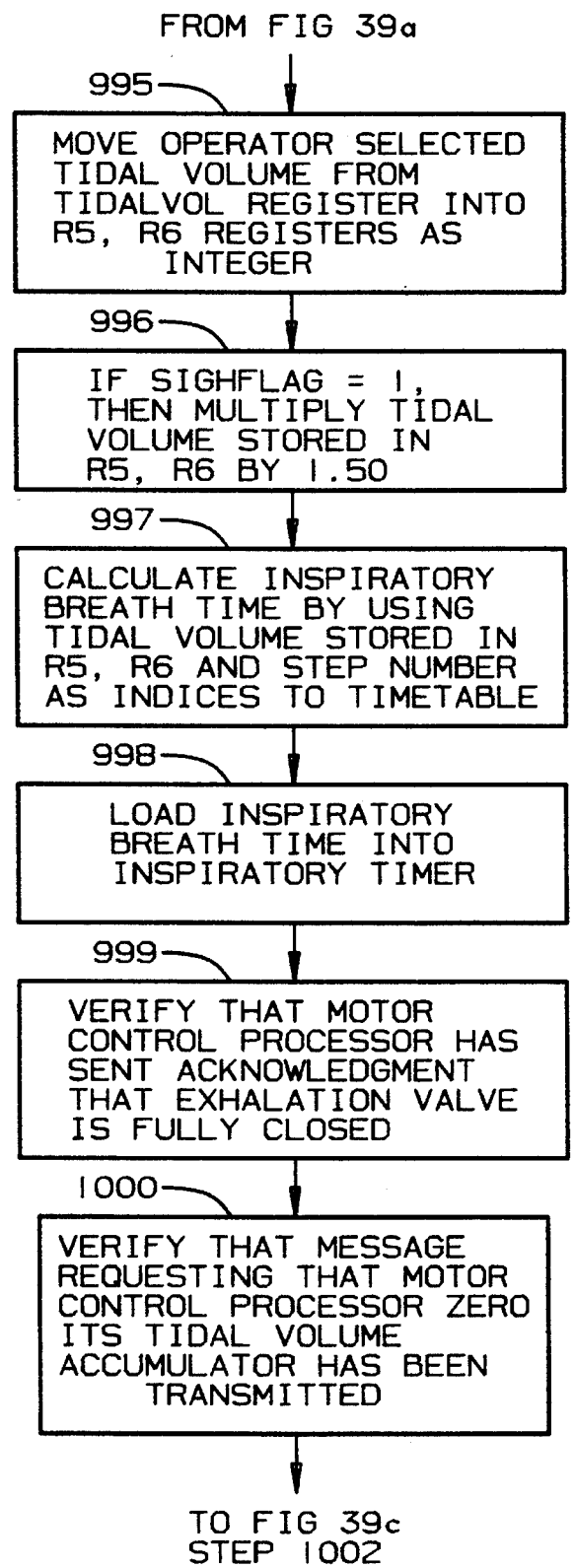
FIG. 39b is a detailed flow chart of a second portion of step 518 of FIG. 22.
Figure 39C:
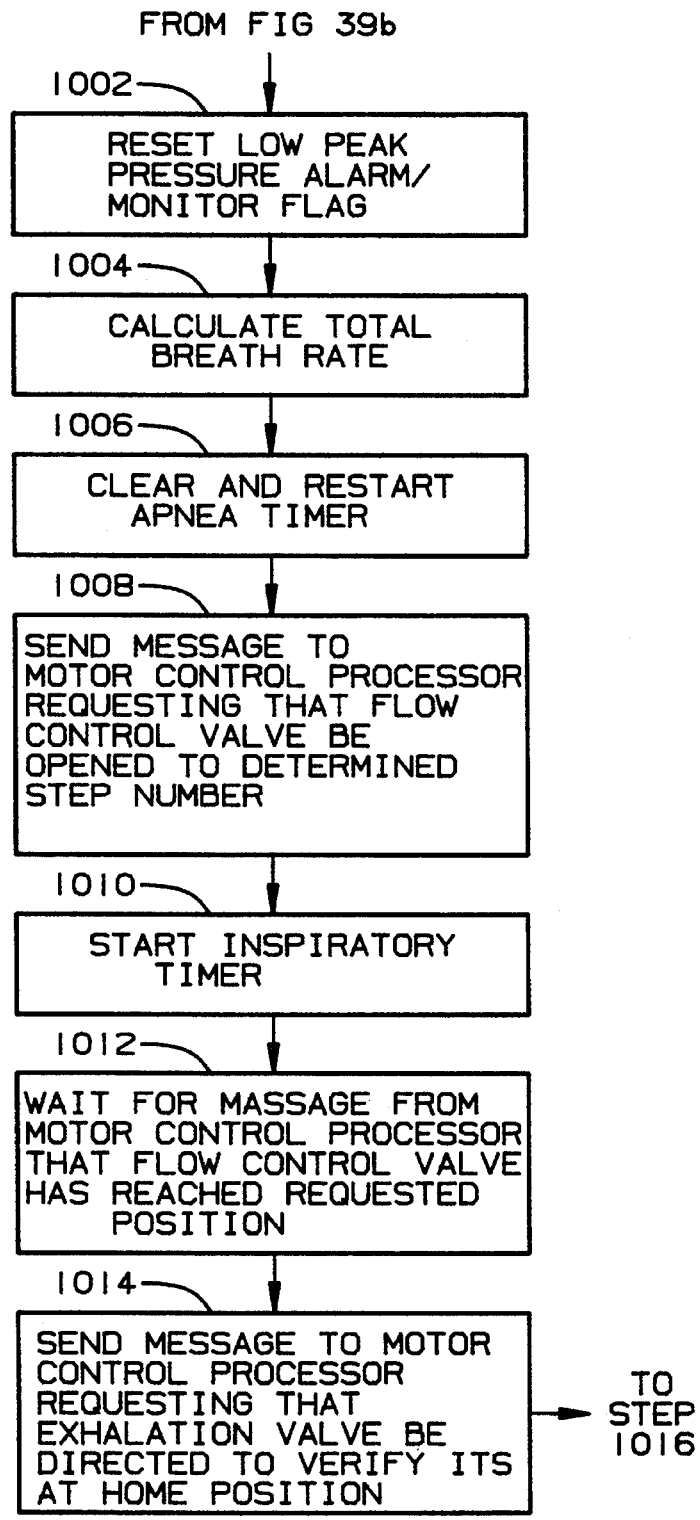

A detailed flow chart of step 518, which is shown schematically in FIG. 22, is set forth in FIGS. 39a and 39b. When executed, the flowchart shown in FIGS. 39a and 39b cause the ventilator to deliver a breath having a rectangular waveform and a predetermined flow profile. The flow profile is predetermined before the breath is delivered, based upon the operator selected peak flow rate and tidal volume.

Now referring to FIG. 39a, at step 990, the breath rate interval timer is cleared and restarted. This timer triggers the delivery of breaths in accordance with the breath rate selected by the operator. At step 991, the processor 188 requests the motor control processor 190 to fully close the exhalation control valve. At step 992, the processor 188 requests that the processor 190 reset the tidal volume accumulation register. This register keeps track of the actual tidal volume delivered to the patient on a real-time basis so that this information may be transmitted to the fiber optic data link. At step 993, the exhalation status flag is reset since the ventilator is not exhalating the patient at this time, but is inspirating the patient. Next, at step 994, the operator-selected peak flow rate, which is stored in the FLOWRATE register, is used as an index to access a software table having a plurality of step numbers stored in it in order to retrieve the step number for the flow control valve position to deliver the flow most nearly requested.

Table 1 set forth below shows a portion of the actual software table used. Now referring to Table 1, the discrete flow rates in liters per minute which the ventilator is capable of delivering are set forth in the left-hand column, and the corresponding step opening of the flow control valve stepping motor necessary to achieve this flow rate is set forth in the right-hand column. For example, if the operator has selected four liters per minute as the peak flow rate, the main processor 188 accesses the table and retrieves the number seven as the number of steps that the motor will be driven to cause the flow control valve to deliver a four liter per minute peak flow. While each step listed in Table 1 delivers the same incremental flow, this relationship could be made nonlinear.

TABLE 1

| FLOWRATE (INT) | STEPS |
| --- | --- |
| 0 | 3 |
| 1 | 4 |
| 2 | 5 |
| 3 | 6 |
| 4 | 7 |
| 5 | 8 |

Next, at step 995, the operator selected tidal volume is moved from the TIDALVOL register in which it is stored into the registers R5, R6 of the main processor as an integer. At step 996, the SIGH flag is tested to determine if the breath to be delivered should be a sigh breath. If the control panel pushbutton corresponding to the sigh breath is activated, the ventilator will deliver one sigh breath infrequently, for example, once every 100 breaths. If the SIGH flag is set, the processor 188 multiplies the operator-selected tidal volume in the registers R5, R6 by 150% since, by definition, a sigh breath is larger than a normal breath by this amount. Next, at step 997, the inspiratory time is determined from the tidal volume stored in registers R5 and R6 and the number of steps that was retrieved from the software table in step 994. The tidal volume stored in the R5, R6 registers is a binary number in which each binary bit represents the presence or absence of a portion of the tidal volume.

The calculation of the inspiratory time is explained with reference to Table 2, which is a portion of the actual software table used. Now referring to Table 2, each row of the table lists a sequence of times corresponding to a particular flow control valve position in steps when the valve is delivering the peak flow rate. The times listed in a particular horizontal row of the table represent the time it would take, at the corresponding valve step position, to deliver a specified portion of the tidal volume, as indicated by the $T_n$ header at the top of each column. Each of these $T_n$ headers corresponds to the portion of the tidal volume represented by each binary bit in the tidal volume stored in the R5, R6 registers. The inspiratory breath time is calculated by selectively adding together the times set forth in the row corresponding to the valve step number, each time being included only if the corresponding bit in the registers R5, R6 is logic 1.

For example, assume that the operator-selected peak flow rate was four liters per minute, in which case the ventilator would have retrieved the step number seven at step 994. In order to calculate the inspiratory breath time, only the row of times adjacent step seven is used since these correspond to that flow rate. Next suppose that the tidal volume in registers R5, R6 consisted of a five bit binary number 11010, each bit representing a fraction of the specified volume, the most significant bit being the leftmost "1" and the least significant bit being the rightmost "0" as is standard binary representation. Now referring to Table 2, the calculated inspiratory breath time would be calculated as 229+114+0+29+0=372 time units, for example milliseconds. Only the 229, 114, and 29 were added since the corresponding bits in the representation of the tidal volume were 1. The flows given in Table 2 are not used, but are provided only for purposes of clarity in the explanation.

The individual time entries in Table 2 are obtained by simply dividing the corresponding volume portion by the corresponding flow rate delivered. For example, if the $T_1$ column represented one milliliter of tidal volume and the corresponding flow rate was 4.20 liters per minute, the corresponding time entry would be (1.0 milliliter/4200 milliliters per minute) * (60,000 milliseconds per minute), or 14 milliseconds.

TABLE 2

| FLOW | STEPS | $T_{16}$ | $T_8$ | $T_4$ | $T_2$ | $T_1$ |
|---|---|---|---|---|---|---|
| 0 | 3 | 512 | 256 | 128 | 64 | 32 |
| 1.05 | 4 | 512 | 256 | 128 | 64 | 32 |
| 2.10 | 5 | 457 | 229 | 114 | 57 | 29 |
| 3.15 | 6 | 305 | 152 | 76 | 38 | 19 |
| 4.20 | 7 | 229 | 114 | 57 | 29 | 14 |

Next, at step 998, the inspiratory timer is loaded with the inspiratory time period calculated in step 997. At step 999, the processor 188 checks to see that it has received a message over the serial interface from the motor control processor 190 indicating that the exhalation valve has been fully closed. At step 1000, the main processor 188 also checks to determine that it has received a message from the motor control processor 190 that the tidal volume accumulator has been zeroed. At step 1002, the low peak pressure detected alarm/monitor flag is reset. At step 1004, the total breath rate is made available for display on the monitor. At step 1006, the apnea timer is cleared and restarted since a new inspiration is about to begin.

At step 1008, the main processor 188 sends a message to the motor control processor 190 requesting that the flow control valve be opened to the step position determined in step 994 to most nearly deliver the selected flow, and the breath starts to be delivered to the patient. At step 1010, the inspiratory timer is started. At step 1012, the main processor 188 waits for a message from the motor control processor 190 indicating that the flow control valve has reached the requested position. At step 1014, the main processor sends a message to the processor 190 requesting that the exhalation valve be directed to verify the integrity of its at home position. At step 1016, the main processor 188 waits for the inspiratory timer to expire. In the meantime, the processor 188 tests for high peak pressure alarm, high machine output pressure alarm, or pressure mismatch alarm. If any of these alarms are activated, the processor performs an emergency exit in order to terminate the inspiration process and proceed immediately to exhalation. Next, at step 1022, since the inspiratory timer has expired, indicating that the desired breath delivery period is over, the main processor 188 sends a message to the motor control processor 190 requesting that the flow control valve by fully closed to end the breath.

At step 1024, the main processor 188 waits for a message from the motor control processor 190 indicating that the flow control valve has reached its fully closed position. At step 1026, the current contents of the apnea timer are read and converted from binary to ASCII so that they can be displayed on the ventilator monitor if necessary. The ASCII string is also saved in the variable INSPMON, which allows for display on the ventilator monitor, if desired. At step 1028, the inspiratory time in INSPMON is compared against 50% of the breath period for the currently selected breath rate. If the inspiratory time is larger, an inverse I:E ratio warning is set, which indicates that the inspiratory time to exhalation time ratio is too large. Next, at step 1030, the main processor 188 waits 5 milliseconds for the accumulated tidal volume to be sent from the motor control processor 190. The actual tidal volume delivered in each breath is calculated for informational purposes. During step 1030, the accumulated tidal volume data just received from the processor 190 is converted into an ASCII string and stored in ITVMON, and is also stored as a two-part integer in registers R5 and R6 in the main processor 188. At step 1032, the breath inspiratory parameters are transmitted to the fiber optic data link. Finally, at step 1036, the program branches to the exhalation portion of the program so that the patient will be made to breath out.

Steps 1038–1040 are the steps the main processor 188 performs if there is a pressure alarm limit exceeded in step 1016. At step 1038, the main processor 188 sends a message to the motor control processor 190 requesting that the flow control valve be fully closed, and at step 1040 the program proceeds to the exhalation portion of the program.

Delivery of a Breath Having a Tapered Profile

A detailed flow chart of step 520, shown schematically in FIG. 22, is set forth in FIGS. 40a–40d, which describe the delivery of a breath having a tapered waveform. The delivery of a breath having a tapered waveform is quite similar to the delivery of a breath having a rectangular waveform. Now referring to FIG. 40a, at step 1050, the breath rate interval timer is cleared and restarted. This timer triggers the delivery of breaths in accordance with the breath rate selected by the operator. At step 1052, the processor 188 requests the motor control processor 190 to fully close the exhalation control valve. At step 1054, the processor 188 requests that the processor 190 reset the tidal volume accumulation register. This register keeps track of the actual tidal volume delivered to the patient on a real-time basis so that this information may be transmitted to the fiber optic data link. At step 1055, the exhalation status flag is reset since the ventilator is not exhalating the patient at this time, but is inspirating the patient. At step 1056 the step number corresponding to the selected peak flow rate is retrieved from a software table, as is explained in detail above in connection with step 994.

Next, at step 1057, the operator-selected tidal volume is moved from the TIDALVOL register in which it is stored into the registers R5, R6 of the main processor as an integer. At step 1058, the SIGH flag is tested to determine if the breath to be delivered should be a sigh breath. As explained above, if the control panel pushbutton corresponding to the sigh breath is activated, the ventilator will deliver one sigh breath infrequently, for example, once every 100 breaths. If the SIGH flag is set, the processor 188 multiplies the operator-selected tidal volume in the registers R5, R6 by 150% since, by definition, a sigh breath is larger than a normal breath by this amount.

At step 1060, the program retrieves a predetermined volume from a software table in order to compensate for the extra volume delivered while the flow control valve is opening and closing. One method of accounting for the undelivered volume lost while the flow control valve is opening and the extra volume delivered while the flow control valve is closing is explained above in connection with FIGS. 4 and 5.

A second method of accounting for these volumes may be used in the delivery of a breath having a tapered waveform. In this second method, the volume delivered while the valve is opening is considered to be extra volume delivered. This volume is represented by the volume 1059 shown in FIG. 5. The volume delivered while the valve is closing from one-half of its peak flow rate is also considered to be extra volume delivered. This volume is represented by the volume 1067 shown in FIG. 5. In this second method, the breath inspiratory period is defined to be the time between $t_p$ and $t_q$ shown in FIG. 5. Consequently, any volume delivered outside of those times is accurately defined to be extra volume delivered.

Figure 40A:
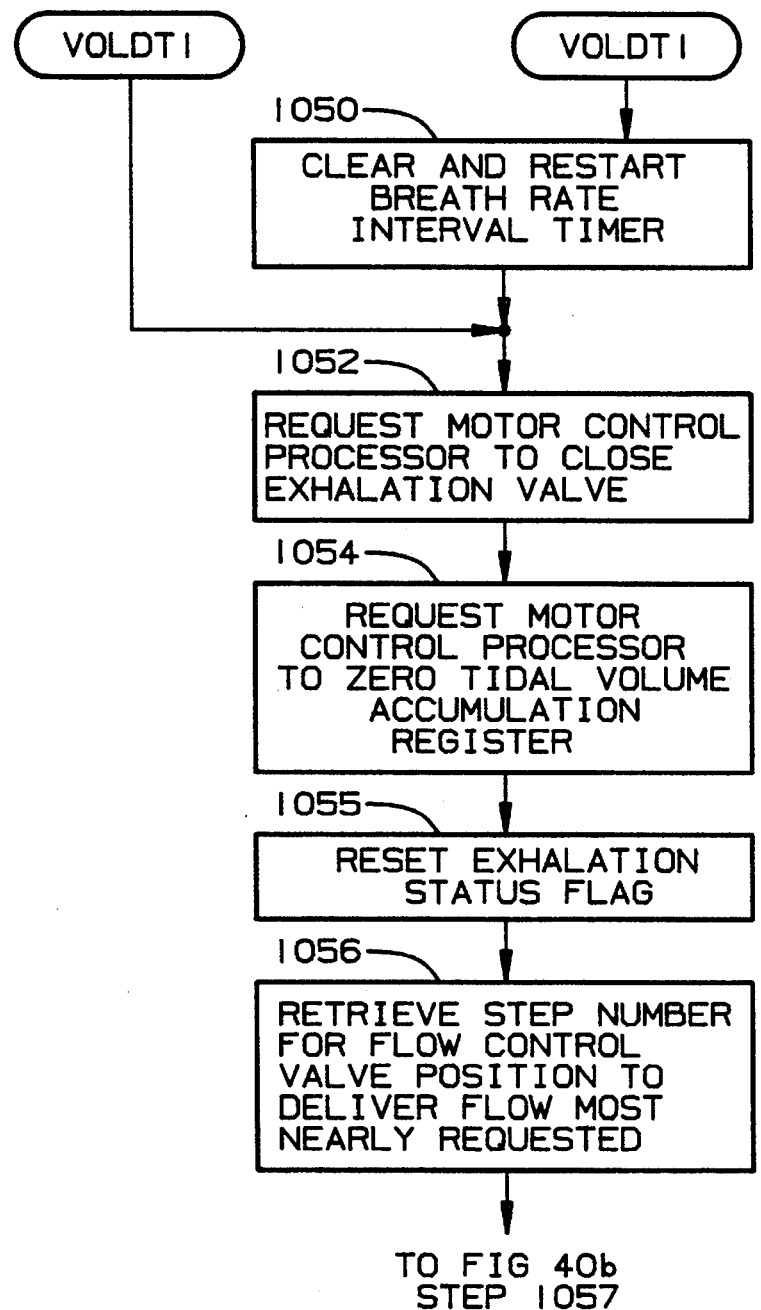
FIG. 40a is a detailed flow chart of a first portion of step 520 of FIG. 22.
Figure 40B:
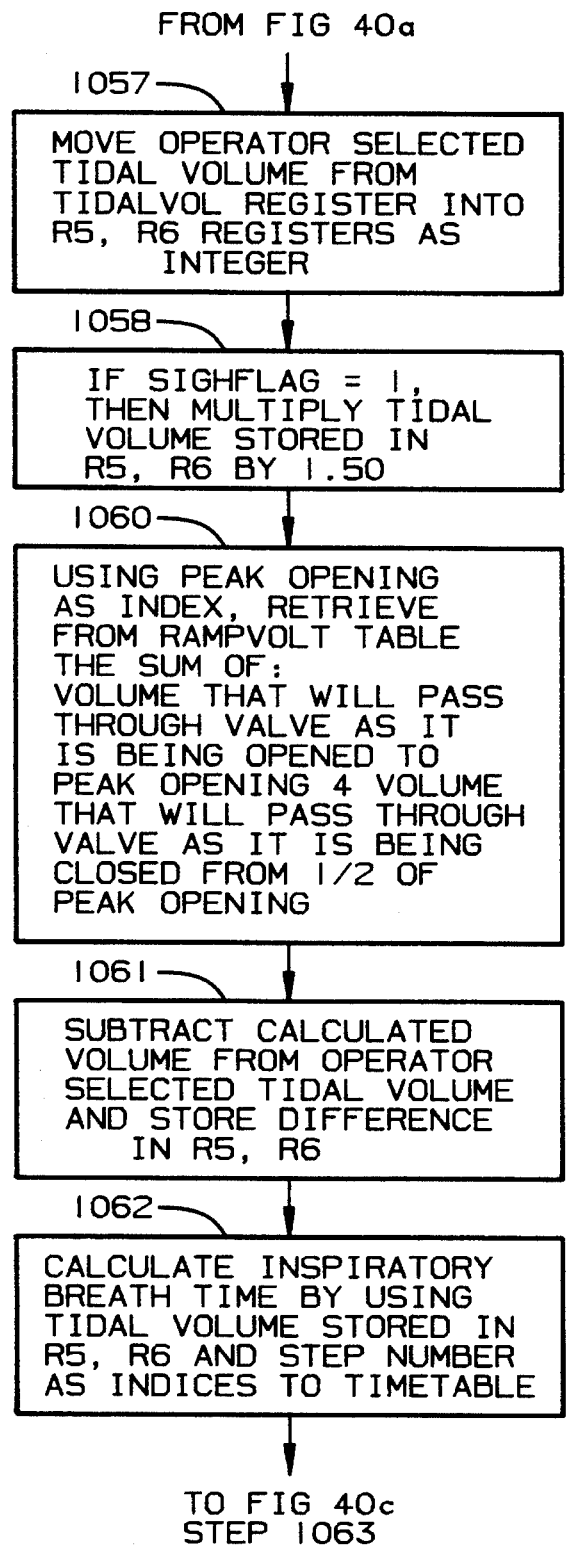
FIG. 40b is a detailed flow chart of a second portion of step 520 of FIG. 22.
Figure 40C:
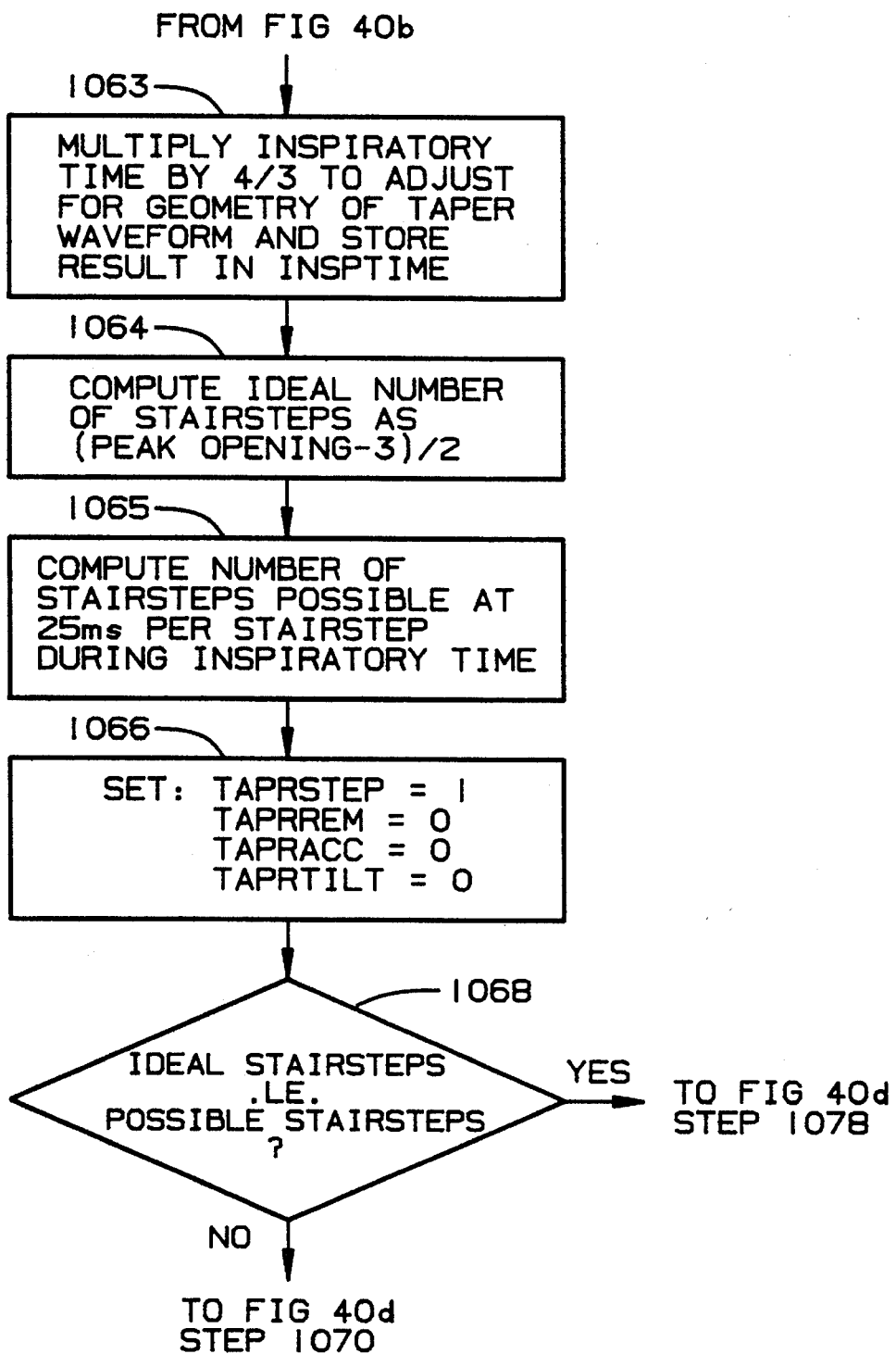
FIG. 40c is a detailed flow chart of a third portion of step 520 of FIG. 22.
Figure 40D:
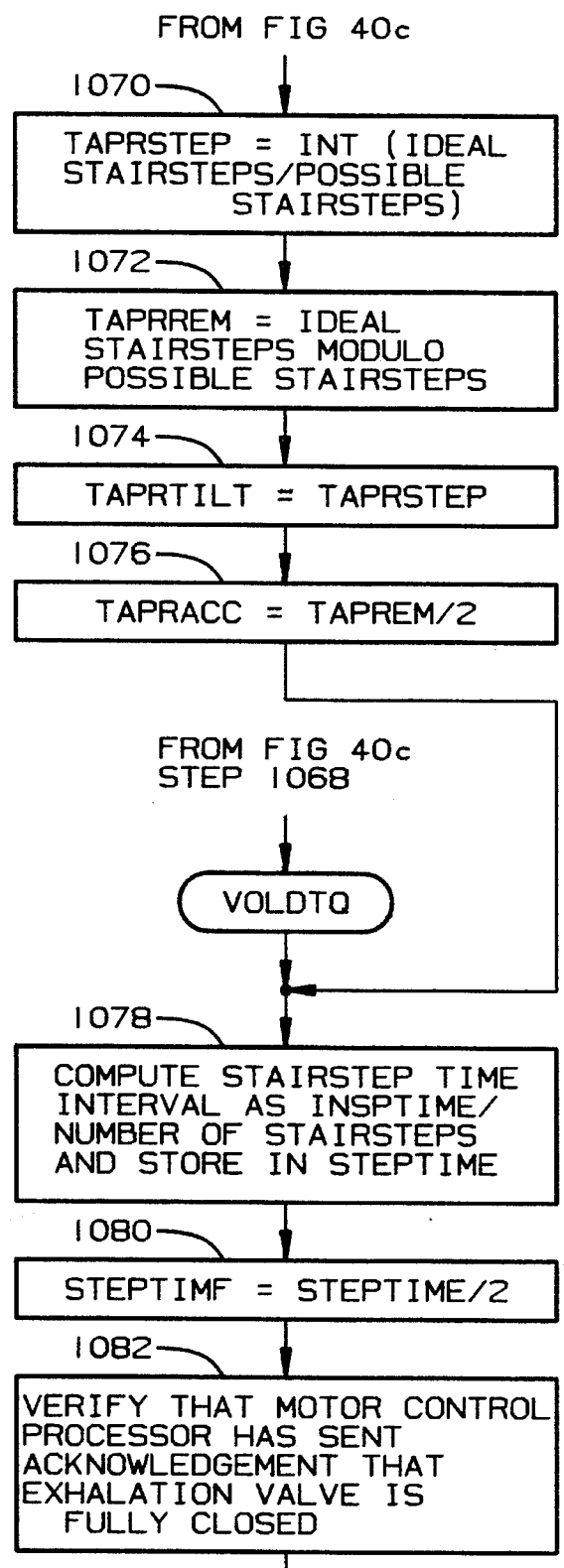
FIG. 40d is a detailed flow chart of a fourth portion of step 520 of FIG. 22.
Figure 40E:
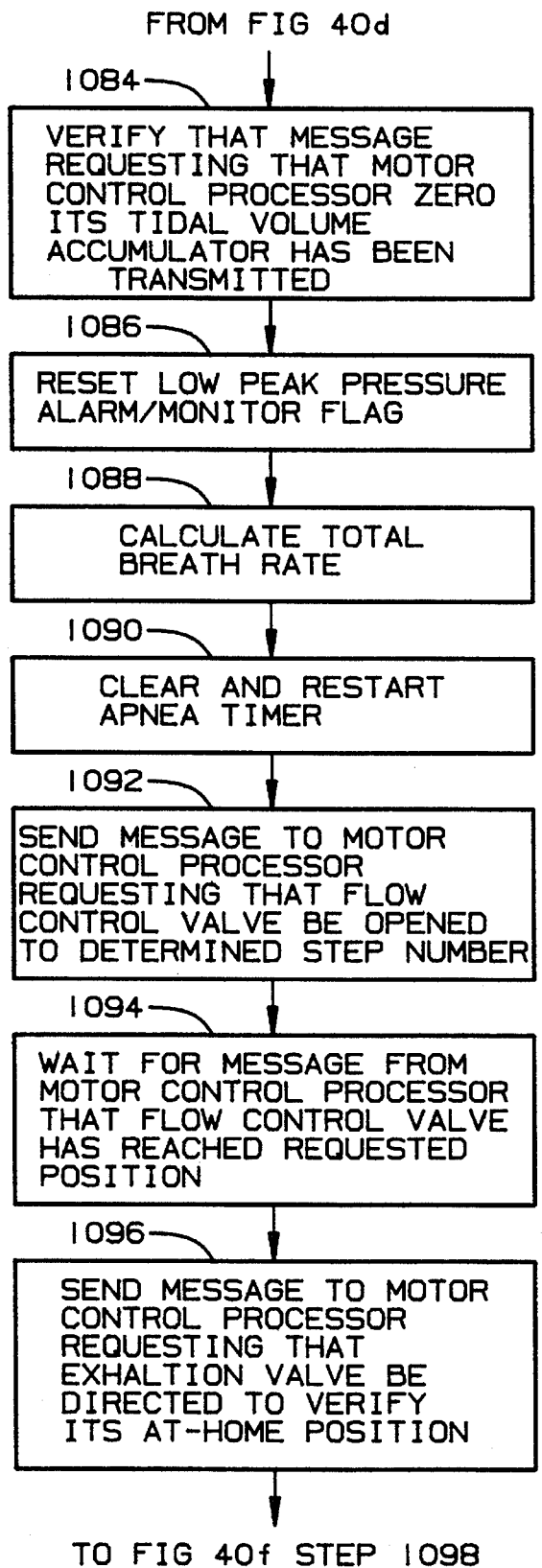
Figure 40F:
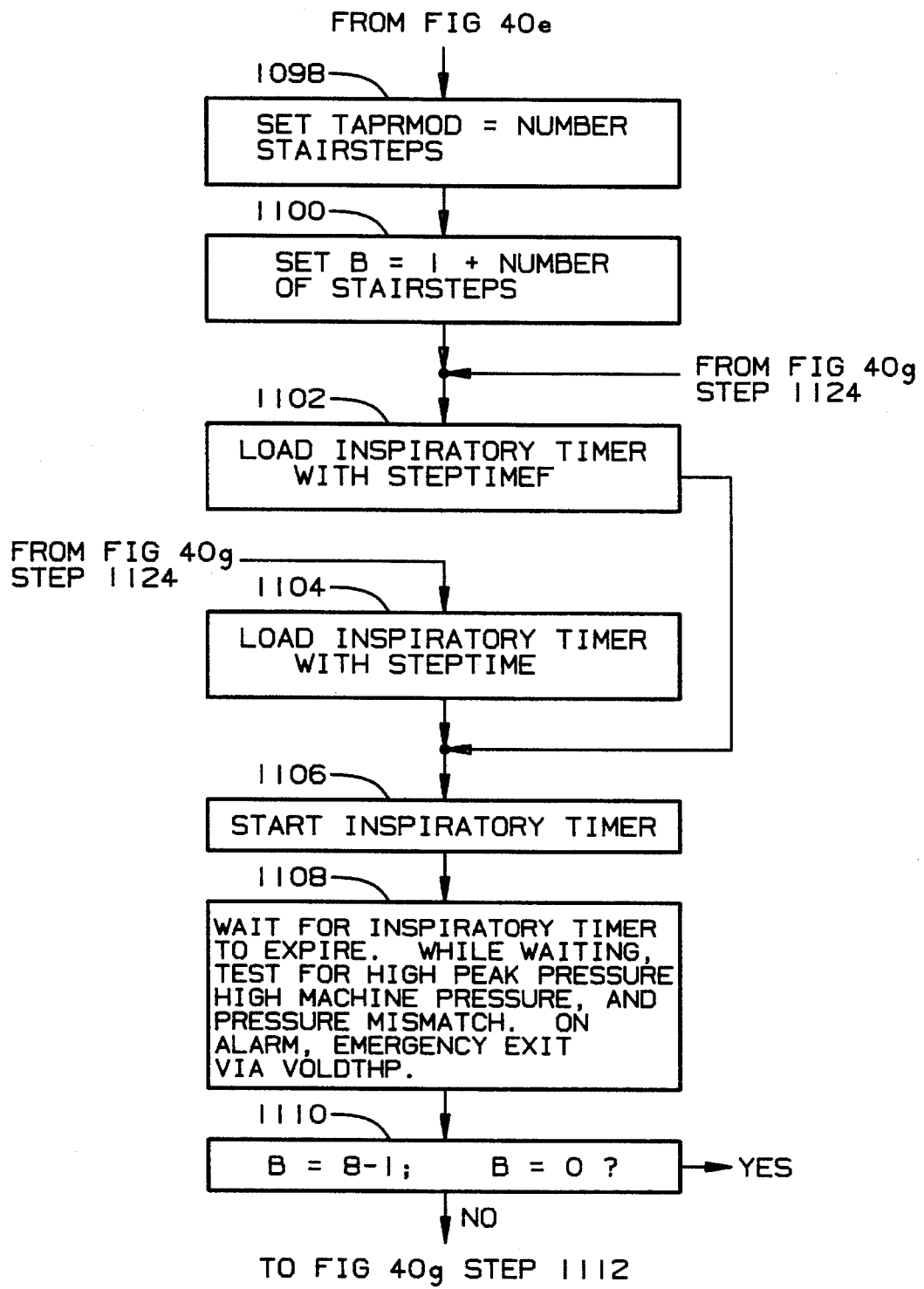
Figure 40H:
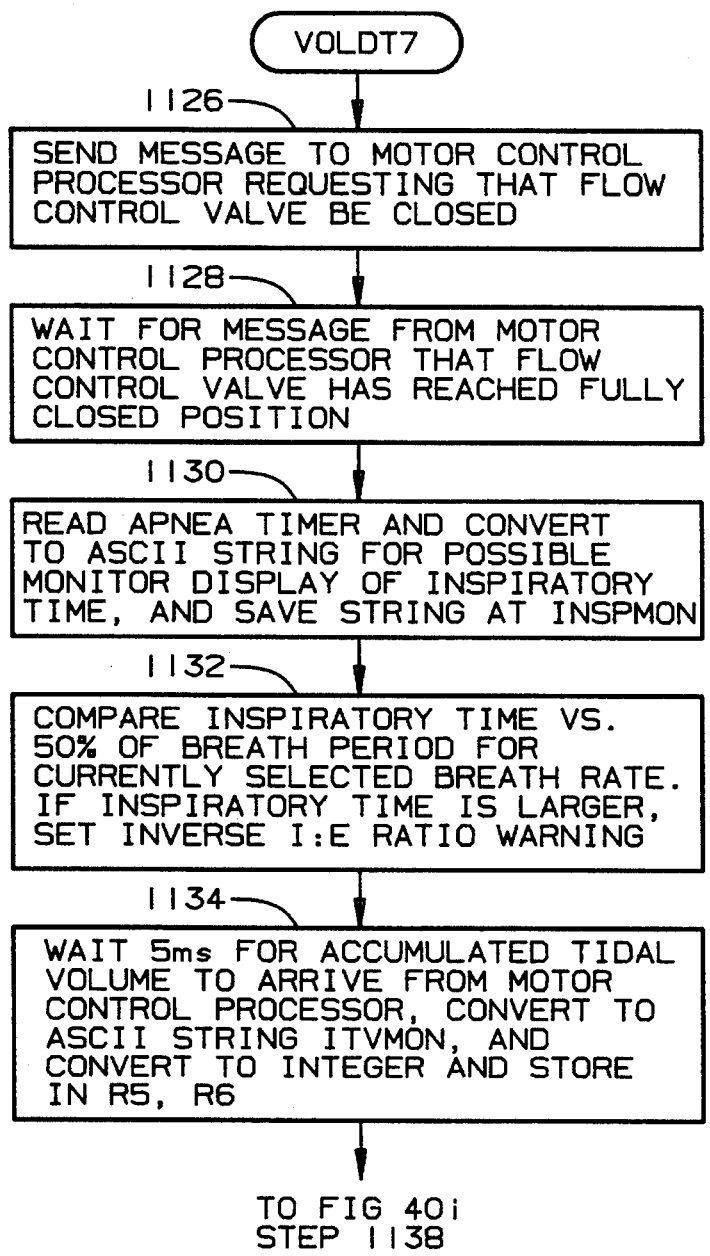
Figure 40I:
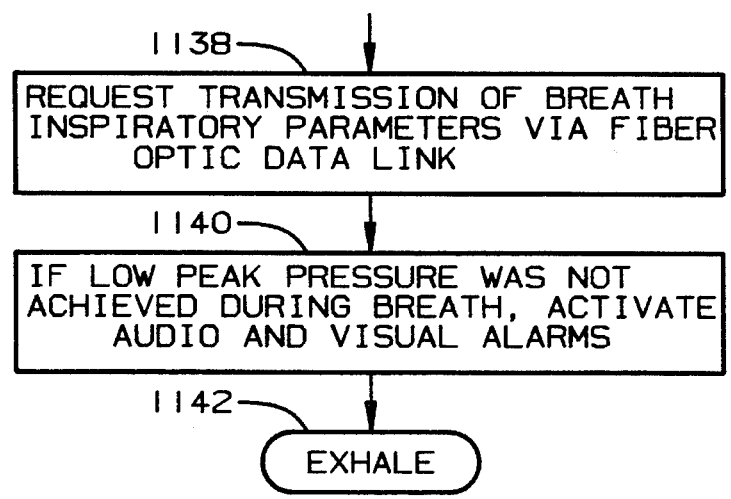
Figure 40I:
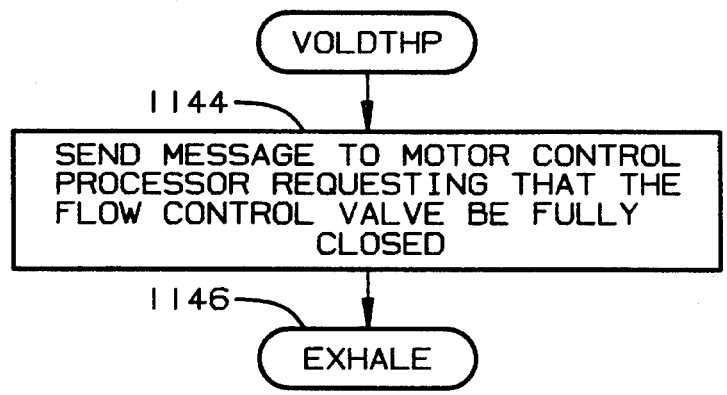

Now referring to FIG. 40a, this extra volume delivered is retrieved from a software table a portion of which is shown in Table 3 below. For each peak flow rate that the flow control valve can deliver, there is a precalculated extra volume delivered, which comprises the sum of the volume that will pass through the valve as it is being opened to the peak opening and the volume that will pass through the valve as it is being closed from one-half of its peak opening. The program retrieves this extra volume delivered from the software table by using the peak valve position as an index and retrieving the associated volume. For example, referring to Table 3, if the peak valve position for the tapered breath was 44, the program would retrieve the volume 12 milliliters.

The volumes in the software table were precalculated as the summation of a plurality of time-flow products. Now referring to FIG. 5, each of these time-flow products is the product of the time which the valve occupies the particular position times the actual flow delivered at that valve position. The times that are used are the time delays from the appropriate ramp-up and ramp-down tables used to drive the flow control valve stepping motor.

TABLE 3

| VALVE POSITION | EXTRA VOLUME |
| --- | --- |
| 40 | 10 |
| 41 | 11 |
| 42 | 11 |
| 43 | 12 |
| 44 | 12 |
| 45 | 13 |

After the extra volume is retrieved from the software table, at step 1061 the extra volume is subtracted from the operator-selected tidal volume held in the registers R5, R6 in the processor 188 to reduce the inspiratory breath period that will be calculated from the tidal volume to compensate for the extra volume that will be delivered as explained above. The new slightly reduced tidal volume is stored as a 2-byte integer in registers R5, R6. Next, at step 1062, the inspiratory breath period is calculated from the peak flow rate and the tidal volume in the manner described above in connection with step 997. At step 1063, the inspiratory time held in registers R5 and R6 is multiplied by 4/3 to adjust for the geometry of the taper waveform, as explained above. This inspiratory time is then converted to a floating point format and stored in registers R5, R6 and R7. The floating point format is also stored in a 3-byte variable INSPTIME.

The next portion of the program performs a number of housekeeping tasks necessary to deliver the taper waveform. As explained above, in the delivery of a taper waveform, the flow control valve is opened to deliver a peak flow, and then is gradually closed during the intermediate portion of the breath in a number of "stair steps" to one-half of the peak flow rate, and then is rapidly closed (see FIG. 5). At step 1064, the ideal number of stair steps of the stepping motor is computed by subtracting 3 from the initial number of opening steps and dividing this result by two. Next, the possible number of stairsteps is determined at step 1065 by dividing the inspiratory time period stored in the variable INSPTIME by 25 (representing 25 milliseconds per stair step) in order to determine the number of stair steps possible while stepping the motor from the peak flow rate to one-half the peak flow rate. This number is converted from a floating point format to a binary integer, and the fractional places are truncated in the process.

At step 1066, a number of variables are initialized, based upon the assumption that the taper waveform will have exactly one valve step per stair step, and that the number of stair steps will equal the number of steps from the peak flow rate to one-half the peak flow rate. This type of taper waveform is referred to as a "standard taper." Nonstandard taper waveforms have either multiple valve steps per stair step or have a peak flow rate such that the number of steps needed to close the valve from the peak flow rate to one-half the peak flow rate is not divisible by the number of stair steps, so that each of the stair steps is not of equal valve steps.

Now referring to step 1066, the variable TAPRSTEP, which contains the number of valve steps in each of the stair steps is initialized to one. The variable TAPRREM, which represents the "extra" number of steps which are left over when the total number of steps from the peak flow rate to one-half the peak flow rate are divided by the number of stair steps. For example, if there are 19 valve steps from the peak flow rate to one-half the peak flow rate and the number of stair steps is four, the remainder when 19 is divided by four is three. In this case, TAPRREM would be three. The variable TAPRACC is used as an accumulator for various calculations performed during this procedure, and is initialized to zero at step 1066. The variable TAPRTILT, which is used to make the first stair step twice as large as the other stair steps in order to enhance its visual taper appearance, is also initialized to 0 at step 1066.

At step 1068, the ideal number of stair steps calculated in step 1064 is compared to the possible number of stair steps calculated in step 1065. If the ideal number is less than or equal to the possible number, then the program branches to step 1078; otherwise, the program branches to step 1070. At step 1070, the ideal number of stair steps divided by the possible number of stair steps, the result is truncated by the integer function and stored in TAPRSTEPS. For purposes of explanation, the following example will be used. Assume that the number of valve steps from the peak flow rate to one-half the peak flow rate is 19, and also assume that the possible number of stair steps is 4. At step 1070, TAPRSTEP in this case would be set to 4 since 19/4 with the quotient truncated is 4. At step 1072, TAPRREM would be set to 3 since that is the remaining number of steps left over in the division in step 1070. At step 1074, TAPRTILT is set to TAPRSTEP, which in this case equals four. At step 1076, TAPRACC is set equal to one-half of TAPRREM, truncating any remainder, which in this case is INT (3/2), which equals one.

At step 1078, the time interval for each stair step is calculated as the total inspiratory time for the breath divided by the number of stair steps in the breath, and the result is stored in the variable STEPTIME, which contains the time for each of the stair steps. At step 1080, one-half of the value of STEPTIME is store in STEPTIMF, which is the time that the very first stair step will last, since the first stair step only lasts one-half the time that the other stair steps last.

At step 1082, the processor 188 checks to see that it has received a message over the serial interface from the motor control processor 190 indicating that the exhalation valve has been fully closed. At step 1084, the main processor 188 also checks to determine that it has received a message from the motor control processor 190 that the tidal volume accumulator has been zeroed. At step 1086, the low peak pressure detected alarm/monitor flag is reset. At step 1088, the total breath rate is made available for display on the monitor. At step 1090, the apnea timer is cleared and restarted since a new inspiration is about to begin.

At step 1092, the main processor 188 sends a message to the motor control processor 190 requesting that the flow control valve be opened to the step position determined in step 1056 to most nearly deliver the selected flow, and the breath starts to be delivered to the patient. At step 1094, the main processor 188 waits for a message from the motor control processor 190 indicating that the flow control valve has reached the requested position. At step 1096, the main processor sends a message to the processor 190 requesting that the exhalation valve be directed to verify the integrity of its at home position.

Next, at step 1098, the variable TAPRMOD is set equal to the number of stair steps, which in the above example is four. TAPRMOD is used in a calculation explained below. At step 1100, the variable B is initialized to the number of stair steps plus one. B is used as a counter, which is decremented each time a stair step is moved, to determine when the taper breath is over and the flow control valve should be closed.

At step 1102, the inspiratory timer is loaded with the time period for the first stair step, and the program branches to step 1106. Note that the normal inspiratory time, STEPTIME, is loaded for each subsequent stair step at step 1104. At step 1106, the inspiratory timer is started, and the peak flow is delivered to the patient. At step 1108, the main processor 188 waits for the inspiratory timer to expire. In the meantime, the processor 188 tests for high peak pressure alarm, high machine output pressure alarm, or pressure mismatch alarm. If any of these alarms are activated, the processor performs an emergency exit in order to terminate the inspiration process and proceed immediately to exhalation.

At step 1110, B is decremented since there is one less stair step to perform. If B equals zero, the program branches to step 1126 since the taper breath is finished and the valve should be closed.

Step 1112 acts to compensate for cases in which the total number of steps from the peak flow rate to one-half the peak flow rate is not evenly divisible by the number of stair steps. TAPRACC acts to accumulate the number of fractional "remainder" steps that were not moved during each stair step. In the above example, the total number of steps to be closed over four stair steps is 19. If the motor could be moved a fractional number of steps, each stair step would consist of 4.75 valve steps. In this case, there is a fractional 0.75 remainder step left over for each stair step. TAPRACC accumulates these fractional steps and adds a single integral step to the next stair step down whenever the accumulated fractions reach a total of a whole step. This function is accomplished by the equation TAPRACC=(TAPRACC+ TAPRREM) MODULO TAPRMOD set forth in step 1112. Using the above example, this equation is TAPRACC= (TAPRACC+3) MODULO 4. Each time step 1112 is performed, a three is added to TAPRACC, and by the well known modulo arithmetic, any difference over four is retained.

An extra step is periodically added to the next stair step down by the C variable shown in step 1112. C is a variable which represents an additional step that is added to the closing of the flow control valve to compensate where the total number of steps from the peak flow rate to one-half the peak flow rate is not evenly divisible by the number of stair steps. In the above example, the total number of steps to be closed over four stair steps is 19. If the motor could be moved a fractional number of steps, each stair step would consist of 4.75 valve steps. However, since the motor can only be moved by an integral number of steps, the variable C causes the motor to close the valve by a fifth step for 75% of the stair steps. For example, instead of the step sequence 4.75, 4.75, 4.75, 4.75 to close the valve by 19 steps, the variable C acts to cause the step sequence to be 5, 5, 5, 4, for example, so that the valve is still closed 19 steps.

In step 1112, the equation C=INTEGER [(TAPRACC+ TAPRREM)/TAPRMOD] causes the extra step to be periodically added to the next stair step down. Using the above example, this equation reduces to C= INTEGER [(TAPRACC+3)/4]. It can be seen that whenever the accumulated count in TAPRACC is one or more, which occurs 75% of the time, an extra step will be added to the stair step down.

At step 1116 the new flow control valve destination, FDESTIN, is determined from the equation FDESTIN= FDESTIN– C–TAPRSTEP–TAPRTILT. Using the above example, and after the first stair step down when TAPRTILT equals zero, this equation reduces to FDESTIN=FDESTIN– C–4. The new destination is always smaller, meaning that the flow control valve is being closed, by at least four steps, and is periodically smaller by five steps when the value of C is one, as explained above.

At step 1118, FDESTIN is compared to determine if it is less than or equal to zero, in which case the program branches to step 1126. At step 1120, the main processor requests that the motor control processor move the flow control valve to the position it has just calculated. At step 1122, the variable TAPERTILT is set to zero so that it no longer contributes to the calculation of the valve position after the first stair step. At step 1124, the value of the stair step counter B is tested to determine if it is the last stair step in the sequence. If it is, then the program branches to step 1102 so that the last stair step in the sequence is one-half the duration of the other stair steps, as is the very first stair step in the sequence; otherwise, the program branches to step 1104 to load the inspiratory timer so that another breath can be delivered.

Next, at step 1126, since the inspiratory timer has expired, indicating that the desired breath delivery period is over, the main processor 188 sends a message to the motor control processor 190 requesting that the flow control valve be fully closed to end the breath.

At step 1128, the main processor 188 waits for a message from the motor control processor 190 indicating that the flow control valve has reached its fully closed position. At step 1130, the current contents of the apnea timer are read and converted from binary to ASCII so that they can be displayed on the ventilator monitor if necessary. The ASCII string is also saved in the variable INSPMON, which allows for display on the ventilator monitor, if desired. At step 1132, the inspiratory time in INSPMON is compared against 50% of the breath period for the currently selected breath rate. If the inspiratory time is larger, an inverse I:E ratio warning is set, which indicates that the inspiratory time to exhalation time ratio is too large. Next, at step 1134, the main processor 188 waits 5 milliseconds for the accumulated tidal volume to be sent from the motor control processor 190. The actual tidal volume delivered in each breath is calculated for informational purposes. During step 1134, the accumulated tidal volume data just received from the processor 190 is converted into an ASCII string and stored in ITVMON, and is also stored as a two-part integer in registers R5 and R6 in the main processor 188. At step 1138, the breath inspiratory parameters are transmitted to the fiber optic data link. At step 1140, audio and visual alarms are activated if the minimum peak pressure was not achieved during the breath. Finally, at step 1142, the program branches to the exhalation portion of the program so that the patient will be made to breath out.

Steps 1144–1146 are the steps the main processor 188 performs if there is a pressure alarm limit exceeded in step 1108. At step 1144, the main processor 188 sends a message to the motor control processor 190 requesting that the flow control valve be fully closed, and at step 1146 the program proceeds to the exhalation portion of the program.

Exhalation

After a breath is delivered to the patient using either a volume-controlled rectangular or taper waveform as described above, the patient is caused to exhale. Detailed flow charts of the exhalation portion of the program schematically shown at steps 502–516 in FIG. 22 are set forth in FIGS. 41–47. The computer program that controls the exhalation portion of the ventilator operation is also included in the microfiche appendix referred to above. The proximal pressure that the proximal pressure transducer senses is used at various points during the exhalation phase of a breath. This proximal pressure is sensed at a point near the patient, approximately twelve inches upstream of the point at which the endotracheal tube is inserted into the patient's windpipe, via a relatively small diameter pressure sensing line.

Figure 41:
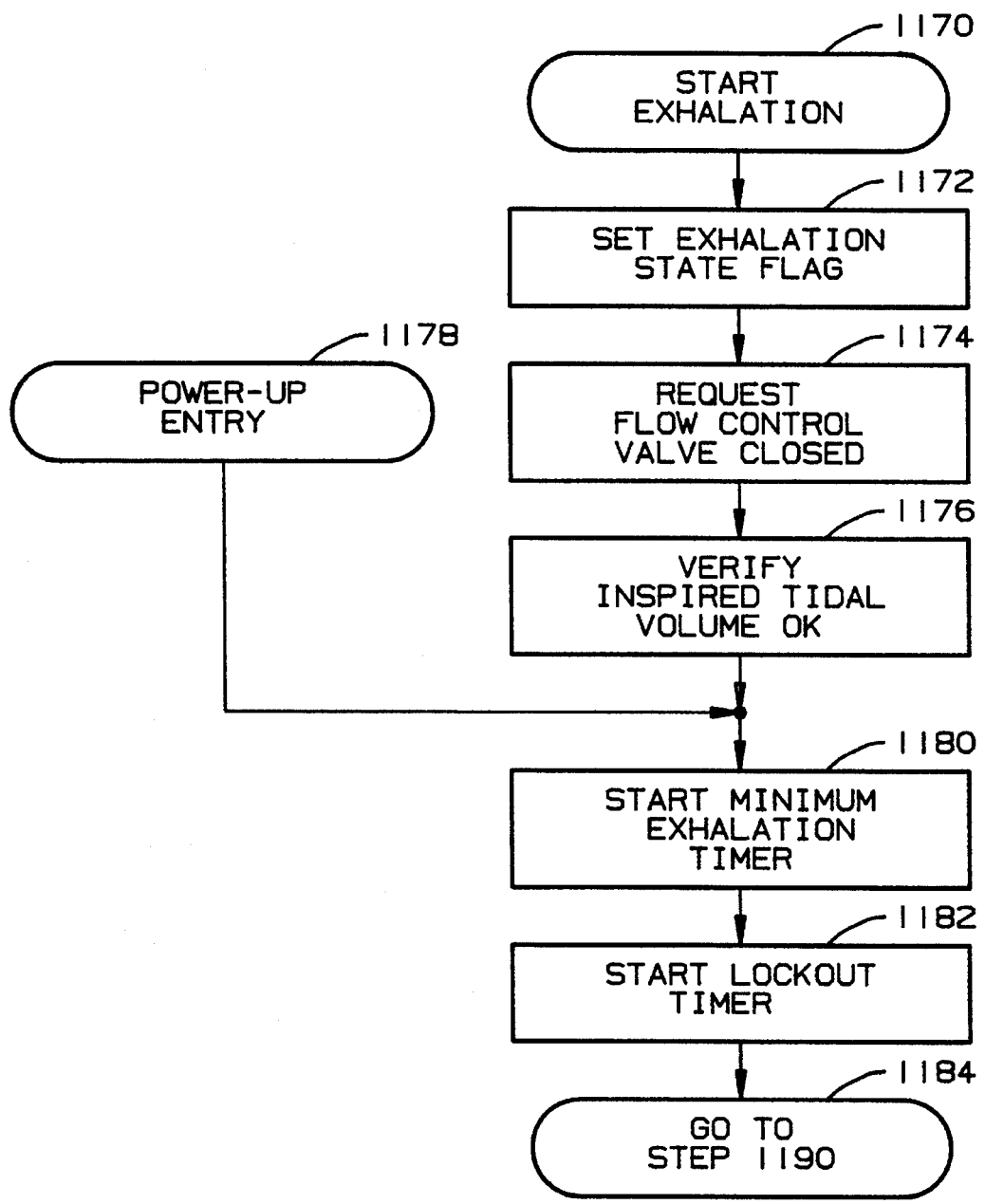
FIG. 41 is a detailed flow chart of step 502 of FIG. 22.

A flow chart of step 502, which is schematically shown in FIG. 22, is set forth in FIG. 41. Now referring to FIG. 41, after each inspiratory period, the main program branches to step 1170 in order to start exhalation. At step 1172, the exhalation state flag is set since exhalation has begun, and the ventilator is no longer inspirating the patient. At step 1174, the main processor 188 requests that the flow control valve 42 be closed. At step 1176, the main processor 188 determines whether the inspired tidal volume on the previous breath was within limits. At step 1180, the minimum exhalation timer is started. This timer prevents interruption of the exhalation portion of the ventilator operation for a short predetermined period of time, for example 100 milliseconds, in order to prevent the ventilator from autocycling, or rapidly switching back and forth between the inspiration and exhalation modes of operation. At step 1182, the lockout timer is started. The lockout timer prevents the patient from initiating a breath. At step 1184, the program branches to step 1190, at which point the step 504 schematically shown in FIG. 22 is executed.

Figure 42:
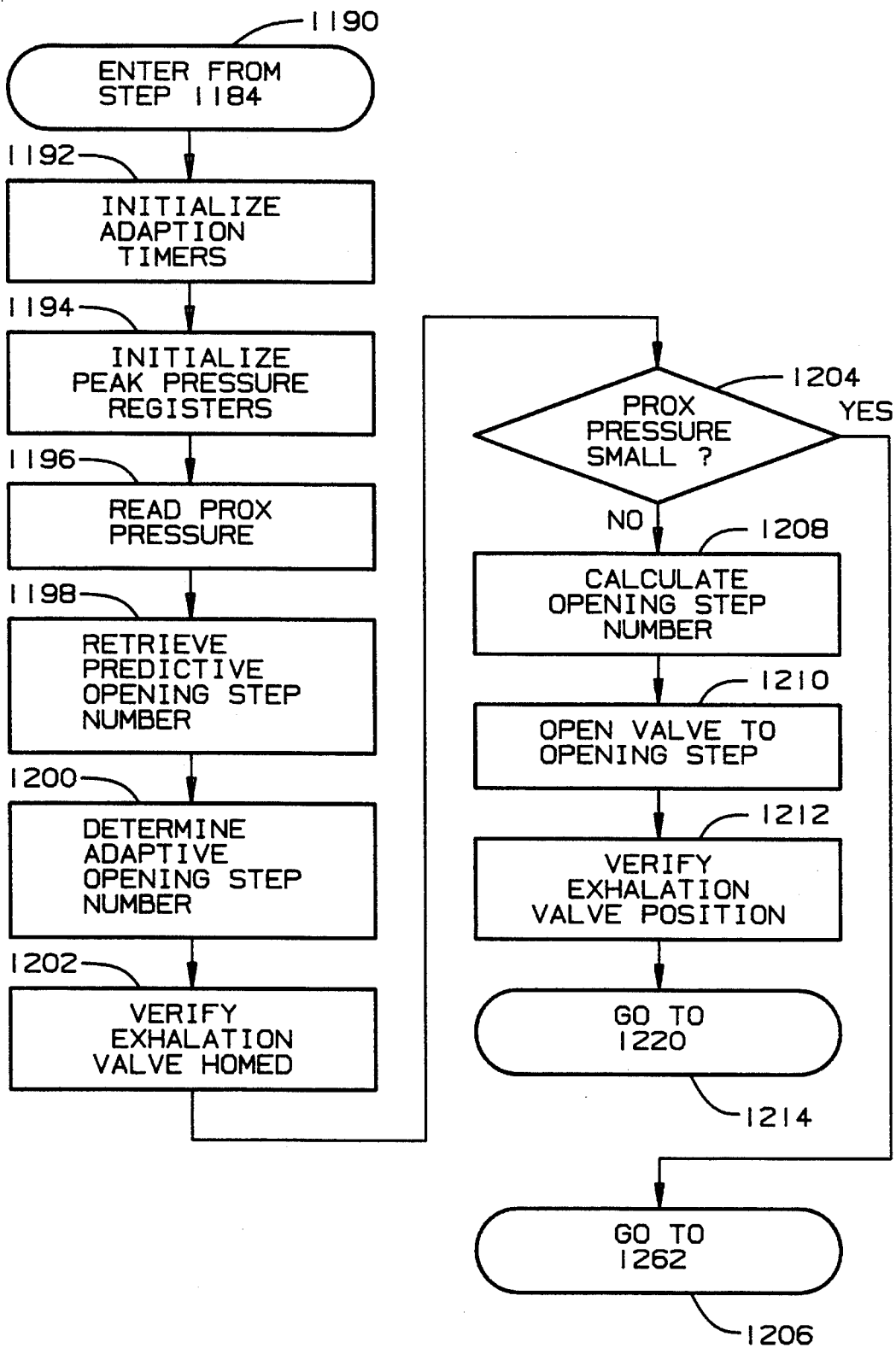
FIG. 42 is a detailed flow chart of step 504 of FIG. 22.
Figure 43:
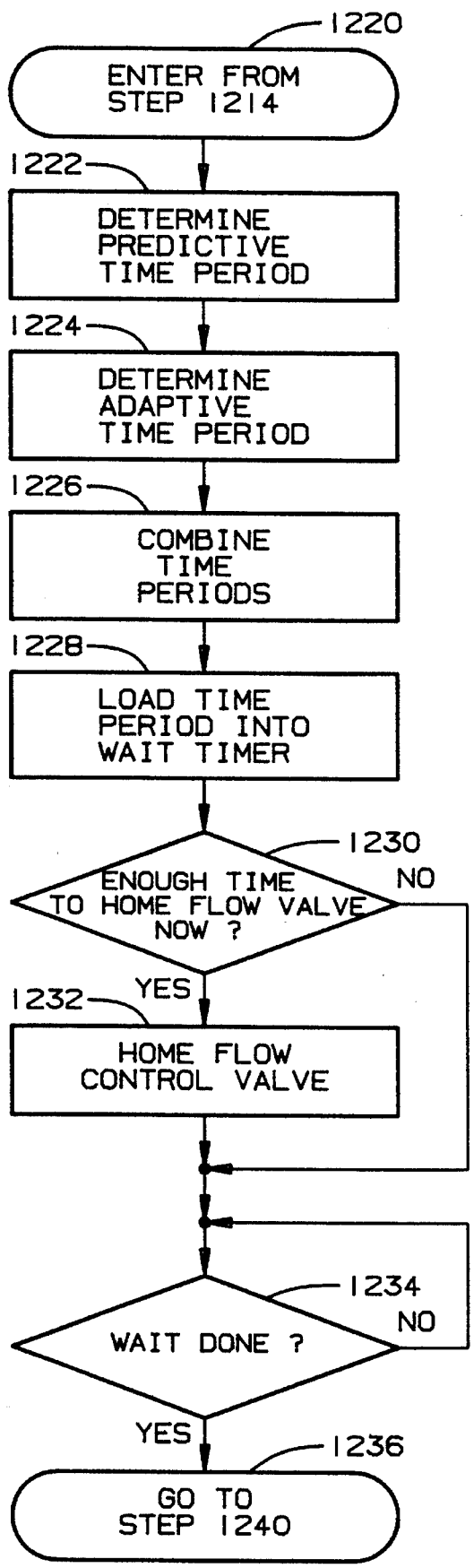
FIG. 43 is a detailed flow chart of step 508 of FIG. 22.

A detailed flowchart of step 504 of FIG. 22 is set forth in FIG. 42. The portion of the exhalation portion of the program set forth in FIG. 42 causes the exhalation valve to be opened to a predetermined position, based upon a predictive valve step number and an adaptive step number.

Now referring to FIG. 42, at step 1192, a number of adaption timers used by the main processor are initialized. At step 1194, a number of registers in which the peak pressures read from the proximal pressure transducer are initialized. At step 1196, the proximal pressure is read from the proximal pressure transducer.

At step 1198, the predictive valve opening step number is retrieved. The predictive step number is determined either from Table 4 or from Equation (6) set forth below.

TABLE 4

| Po-PEEP | 1 | 2–3 | 4–5 | 6–7 | 8–9 |
|---------|-----|-----|-----|-----|-----|
| 7–10    | 66  | 51  | 41  | 38  | 35  |
| 11–15   | 74  | 60  | 48  | 44  | 42  |
| 16–21   | 77  | 65  | 53  | 47  | 44  |
| 22–28   | 82  | 69  | 58  | 51  | 48  |
| 29–36   | 92  | 69  | 59  | 52  | 50  |
| 37–45   | 98  | 75  | 66  | 61  | 59  |
| 46–55   | 105 | 82  | 71  | 68  | 62  |
| 56–66   | 107 | 84  | 77  | 72  | 69  |
| 67–78   | 115 | 93  | 80  | 77  | 73  |
| 79–91   | 119 | 100 | 84  | 82  | 78  |
| 92–105  | 119 | 103 | 88  | 86  | 82  |
| 106+    | 119 | 107 | 92  | 89  | 85  |

Now referring to Table 4, each column of the table contains a number of predetermined exhalation valve step openings that depend upon the PEEP pressure that was preselected by the operator of the ventilator. Thus, during this portion of the program, only one of the columns set forth in Table 4 above is used. Each row of Table 4 contains a number of predetermined valve step openings that depend upon the difference of the proximal pressure that was sensed by the proximal pressure transducer when exhalation was first started, $P_o$, and the preselected PEEP pressure, or ($P_o$–PEEP). As a general rule, the predictive step openings set forth in Table 4 above increase as ($P_o$–PEEP) increases. This is to be expected, since if the pressure difference is larger then the exhalation valve must be opened more quickly in order to more quickly stabilize these pressures. The predictive step openings set forth in Table 4 above also decrease as the preselected PEEP pressure increases. This is also to be expected since if the desired PEEP pressure is higher, the exhalation valve should be opened more slowly.

The predictive opening step number is retrieved from Table 4 by retrieving the step number in the column corresponding to the preselected PEEP pressure and in the row corresponding to the difference ($P_o$–PEEP).

If the preselected PEEP pressure is higher than 9 cm $H_2O$, then Equation (6), which is set forth below, is used.

$$\text{Opening Step Number} = (P_o - \text{PEEP})/2 + 39 \qquad (6)$$

At step 1200, an adaptive opening step number is added. This adaptive opening step number is based upon physical characteristics of the exhalation air supply hose connecting the patient to the ventilator.

At step 1202, the main processor 188 verifies that the exhalation valve has been homed. At step 1204, the main processor compares the proximal pressure read in step 1196 to determine whether it is smaller than a predetermined limit. If it is, the program branches to step 1206, at which the program branches to step 512, which is schematically shown in FIG. 22. If the proximal pressure is larger than a predetermined limit, the predictive and adaptive step numbers as computed above are combined at step 1208 in order to create an initial opening of exhalation valve. At step 1210, the main processor 188 sends a message to the motor control processor 190 requesting that the exhalation valve be opened to this initial opening, and then at step 1212, the main processor 188 verifies that exhalation valve has been moved to this position. At step 1214, the program branches to step 1220, at which point the step 504 schematically shown in FIG. 22 is executed.

After the exhalation valve has been moved to its initial opening position described above, the exhalation portion of the program waits a period of time before the exhalation valve is moved again. This period of time is determined in a manner similar to the manner in which the initial exhalation valve opening was determined. Now referring to FIG. 43, which is a detailed flow chart of step 508 shown schematically in FIG. 22, at step 1222, a predictive time period is either retrieved from Table 5 set forth below or calculated using Equation (7).

TABLE 5

| Po-PEEP | PEEP | | | | | | |
|---|---|---|---|---|---|---|---|
| | 1 | 2–3 | 4–5 | 6–7 | 8–9 | 10–11 | 12–13 |
| 7–10 | 128 | 160 | 172 | 180 | 192 | 168 | 144 |
| 11–15 | 160 | 172 | 184 | 188 | 192 | 180 | 160 |
| 16–21 | 192 | 196 | 200 | 204 | 208 | 192 | 176 |
| 22–28 | 224 | 224 | 224 | 224 | 224 | 208 | 192 |
| 29–36 | 252 | 252 | 252 | 252 | 252 | 224 | 208 |
| 37–45 | 252 | 252 | 252 | 252 | 252 | 240 | 224 |
| 46–55 | 252 | 252 | 252 | 252 | 252 | 252 | 240 |
| 56+ | 252 | 252 | 252 | 252 | 252 | 252 | 252 |

Now referring to Table 5, each column of the table contains a number of predetermined time periods in milliseconds which correspond to a respective PEEP pressure preselected by the ventilator operator. Each row of the table contains a number of predetermined time periods which correspond to a respective pressure difference, ($P_o$– PEEP), as described above. At step 1222, the program retrieves the appropriate time period from Table 6 based upon the PEEP pressure and the pressure difference ($P_o$– PEEP). If the PEEP pressure is higher than 13 cm $H_2O$, then Equation (7) set forth below is used.

$$\text{Time Period} = 4*[(P_o-\text{PEEP})/4+\text{PEEP OFFSET}] \quad (7)$$

Equation (7), which yields the desired time period in milliseconds, utilizes a PEEP OFFSET variable which varies with the PEEP pressure as listed in Table 6 below.

TABLE 6

| PEEP | PEEP OFFSET |
|---|---|
| 14 | 37 |
| 15 | 35 |
| 16 | 32 |
| 17 | 30 |
| 18 | 27 |
| 19 | 25 |
| 20 | 22 |
| 21 | 20 |

TABLE 6-continued

| PEEP | PEEP OFFSET |
|---|---|
| 22+ | 20 |

At step 1224, an adaptive time period is determined. This adaptive time period, which is based upon the physical characteristics of the exhalation air supply hose connecting the patient to the ventilator, is determined by multiplying the appropriate entry in Table 8, which is set forth and described below, by the number four in order to obtain the adaptive time period. At step 1226, the predictive and adaptive time periods determined above are combined, and at step 1228, the resulting time period is loaded into a wait timer. At step 1230, if the main processor 188 has enough time to home the flow control valve, it does so at step 1232. If not, the program branches to step 1234 during which time the program waits until the wait timer has expired, at which point the program at step 1236 branches to step 1240, at which point the step 510 schematically shown in FIG. 22 is executed.

Figure 44:
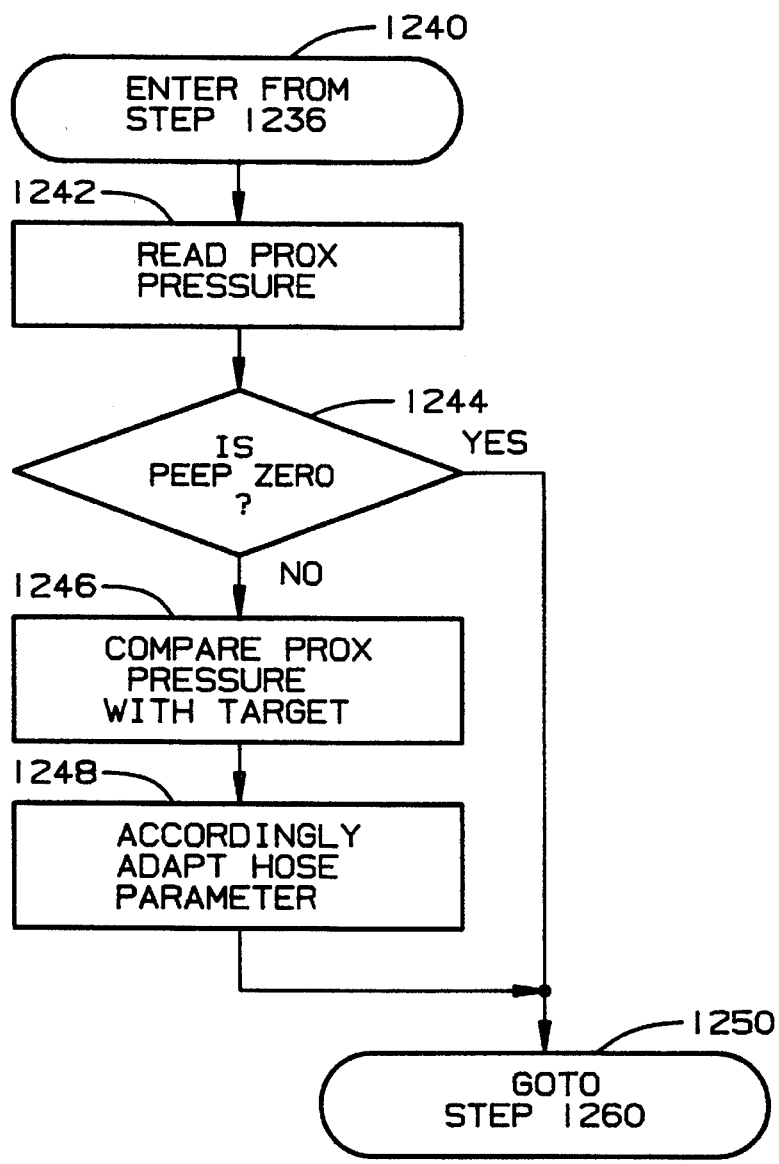
FIG. 44 is a detailed flow chart of step 510 of FIG. 22.

A detailed flow chart of step 510 is set forth in FIG. 44. At step 1242, the proximal pressure is read from the proximal pressure transducer. At step 1244, the proximal pressure is tested to determine if it is zero. If it is zero, the program branches to step 1260 at which point the step 512 schematically shown in FIG. 22 is executed. If the proximal pressure is not zero, the program branches to step 1246 where the proximal pressure is compared with a predetermined target pressure. At step 1248, the air supply hose parameter described below is adapted is adapted according to the difference between the proximal pressure and the target pressure. The program then branches to step 1250 at which point it branches to step 1260 where the step 512 schematically shown in FIG. 22 is executed.

Figure 45:
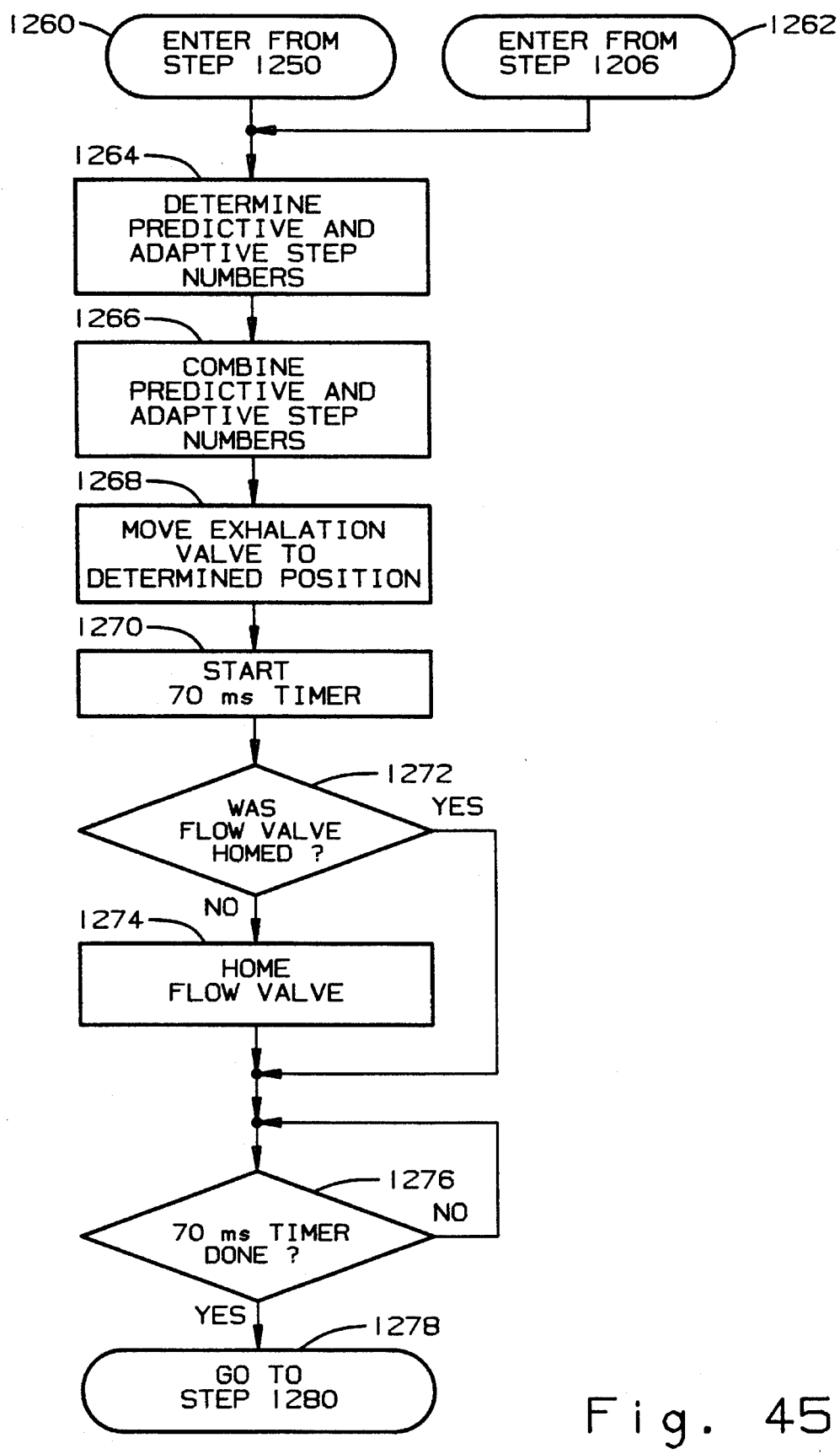
FIG. 45 is a detailed flow chart of step 512 of FIG. 22.

A detailed flow chart of step 512, which is schematically shown in FIG. 22, is set forth in FIG. 45. The program may branch into the flow chart shown in FIG. 45 from either step 1250 or step 1206. The flow chart shown in FIG. 45 causes the position of the exhalation valve to be adjusted. The valve is adjusted based upon predictive and adaptive step numbers in a manner similar to that described above.

At step 1264 the predictive and adaptive step numbers are determined. The predictive step number is retrieved from Table 7 set forth below.

TABLE 7

| Po-PEEP | PEEP | | | | | | | |
|---|---|---|---|---|---|---|---|---|
| | 1 | 2–3 | 4–5 | 6–7 | 8–9 | 10–11 | 12–13 | 14–15 |
| negative | 0 | 0 | 0 | 0 | 0 | 0 | 0 | 0 |
| 0–1 | 16 | 8 | 7 | 6 | 5 | 4 | 3 | 3 |
| 2–3 | 24 | 14 | 13 | 12 | 11 | 10 | 9 | 8 |
| 4–6 | 32 | 30 | 28 | 25 | 22 | 19 | 16 | 14 |
| 7–10 | 48 | 44 | 37 | 34 | 32 | 28 | 28 | 28 |
| 11–15 | 63 | 46 | 43 | 37 | 34 | 31 | 30 | 30 |
| 16–21 | 68 | 55 | 48 | 44 | 40 | 36 | 34 | 34 |
| 22–28 | 68 | 59 | 51 | 45 | 44 | 40 | 36 | 36 |
| 29–36 | 75 | 66 | 53 | 48 | 44 | 42 | 42 | 42 |
| 37–45 | 78 | 67 | 54 | 54 | 45 | 43 | 43 | 45 |
| 46–55 | 84 | 76 | 62 | 54 | 52 | 52 | 45 | 47 |
| 56–66 | 91 | 82 | 68 | 65 | 59 | 56 | 52 | 54 |
| 67–78 | 98 | 89 | 75 | 68 | 63 | 58 | 56 | 57 |

TABLE 7-continued

| Po-PEEP | PEEP | | | | | | | |
|---|---|---|---|---|---|---|---|---|
| | 1 | 2–3 | 4–5 | 6–7 | 8–9 | 10–11 | 12–13 | 14–15 |
| 79–91 | 102 | 93 | 79 | 77 | 67 | 64 | 61 | 65 |
| 92–105 | 108 | 99 | 87 | 80 | 70 | 67 | 66 | 68 |
| 106+ | 112 | 103 | 90 | 83 | 73 | 70 | 69 | 71 |

Now referring to Table 7, each column of the table contains a number of predetermined exhalation valve step openings that depend upon the PEEP pressure that was preselected by the operator of the ventilator. Thus, during this portion of the program, only one of the columns set forth in Table 7 above is used. Each row of Table 7 contains a number of predetermined valve step openings that depend upon the difference of the proximal pressure $P_o$ and the preselected PEEP pressure, or ($P_o$–PEEP).

The predictive opening step number is retrieved from Table 7 by retrieving the step number in the column corresponding to the preselected PEEP pressure and in the row corresponding to the difference ($P_o$–PEEP).

If the preselected PEEP pressure is higher than 15 cm H$_2$O, then Equation (8), which is set forth below, is used.

$$\text{Predictive Step Number} = P_o + 16 - (5/4) * \text{PEEP} \tag{8}$$

At step 1264, an adaptive opening step number is also determined. This adaptive opening step number, which is based upon physical characteristics of the exhalation air supply hose connecting the patient to the ventilator, is determined from Table 8 set forth below.

TABLE 8

| TARGET PRESSURE $T_p$ | HOSE PARAMETER |
|---|---|
| $T_p$ > PEEP + 10 | +8 |
| PEEP + 10 > $T_p$ > PEEP + 6 | +4 |
| PEEP + 6 > $T_p$ > PEEP + 1.5 | +1 |
| PEEP + 1.5 > $T_p$ > PEEP – 5 | –1 |
| PEEP – 5 > $T_p$ | –4 |

At step 1266 the adaptive and predictive step numbers determined in step 1264 are added, and at step 1268 the main processor transmits a message to the motor control processor requesting that it move the exhalation valve to the position determined in step 1264. At step 1270 a 70 millisecond timer is started to initiate a predetermined waiting period. At step 1272, the main processor determines if the flow control valve was sent to its home position, and at step 1274 if the flow control valve was not sent to its home position, the main processor transmits a message to the motor control processor requesting that it do so. At step 1276 the program waits until the 70 millisecond timer times out, and then branches to step 1280, at which point the program enters the exhalation servo portion illustrated in FIG. 22 as step 514.

Figure 46A:
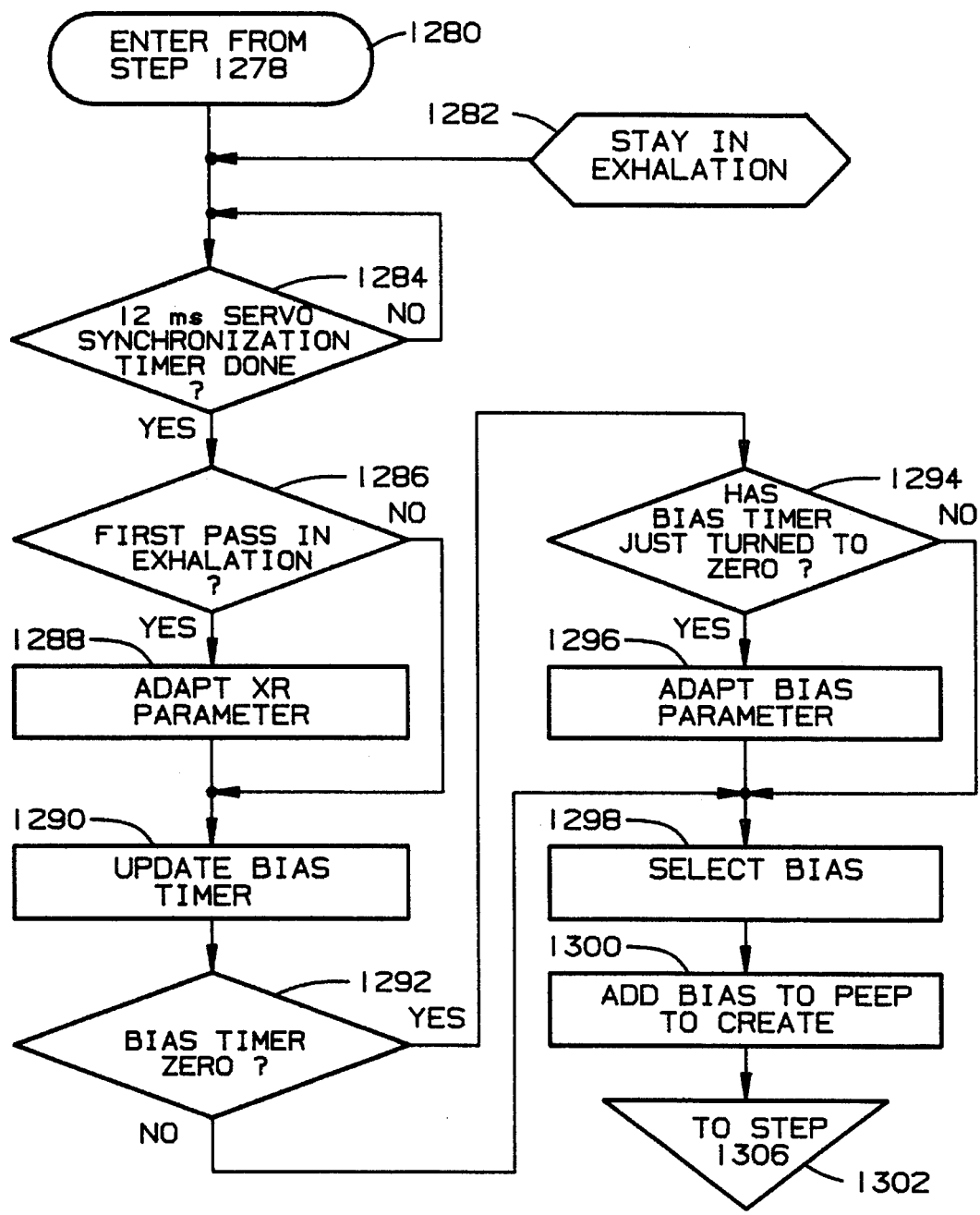
FIG. 46a is a detailed flow chart of a first portion of step 514 of FIG. 22.

A first portion of the exhalation servo portion of the program is set forth in FIG. 46a. Now referring to FIG. 46a, at step 1284, the servo synchronization timer is tested to determine if it has timed out yet. The 12 millisecond timer is used to cause the exhalation portion of the program to adapt to the exhalation process every 12 milliseconds during the exhalation phase of the breath. If the timer has not timed out yet, the program stays at step 1284. When the 12 millisecond servo synchronization timer times out, the program branches to step 1286 during which the program determines whether the program has just entered the exhalation phase for the first time. If it is the first pass, the program branches to step 1288; otherwise, the program branches to step 1290.

At step 1288, the XR parameter, which represents an adjustment factor in motor steps, is adapted depending upon the target pressure in accordance with Table 9 set forth below.

TABLE 9

| TARGET PRESSURE $T_p$ | XR PARAMETER |
|---|---|
| $T_p$ > PEEP + 4.5 | +4 |
| PEEP + 4.5 > $T_p$ > PEEP + 2.5 | +1 |
| PEEP + 2.5 > $T_p$ > PEEP + .5 | –1 |
| .5 > $T_p$ | –4 |

At step 1290, the bias timer is ticked. The bias timer is a software driven timer that keeps track of how long the servo portion of the exhalation phase has been in execution. At step 1292, the bias timer is tested to determine if it is zero. If the bias timer is not zero, as determined in step 1292, the program branches to step 1298. At step 1298, the bias parameter is selected as a number of cm H$_2$O, based upon the size of the breath as determined in step 506 and upon the proximal pressure, as set forth in Tables 10A and 10B below, Table 10A being used for small breaths and Table 10B being used for all other breaths.

TABLE 10A

| PROXIMAL PRESSURE $P_p$ | BIAS |
|---|---|
| $P_p$ > PEEP + 2 | –3 |
| PEEP + 2 > $P_p$ > PEEP + .5 | –1 |
| PEEP + .5 > $P_p$ | +2 |

TABLE 10B

| PROXIMAL PRESSURE $P_p$ | BIAS |
|---|---|
| $P_p$ > PEEP + 3 | –3 |
| PEEP + 3 > $P_p$ > PEEP + 1.5 | –1 |
| PEEP + 1.5 > $P_p$ | +2 |

If the bias timer is not zero, the program branches to step 1294 at which point the program determines if the bias timer has just turned to zero. If it has, the bias parameter is adapted at step 1296, and at step 1300, the bias is added to the PEEP pressure to create the target pressure which the system servos.

Figure 46B:
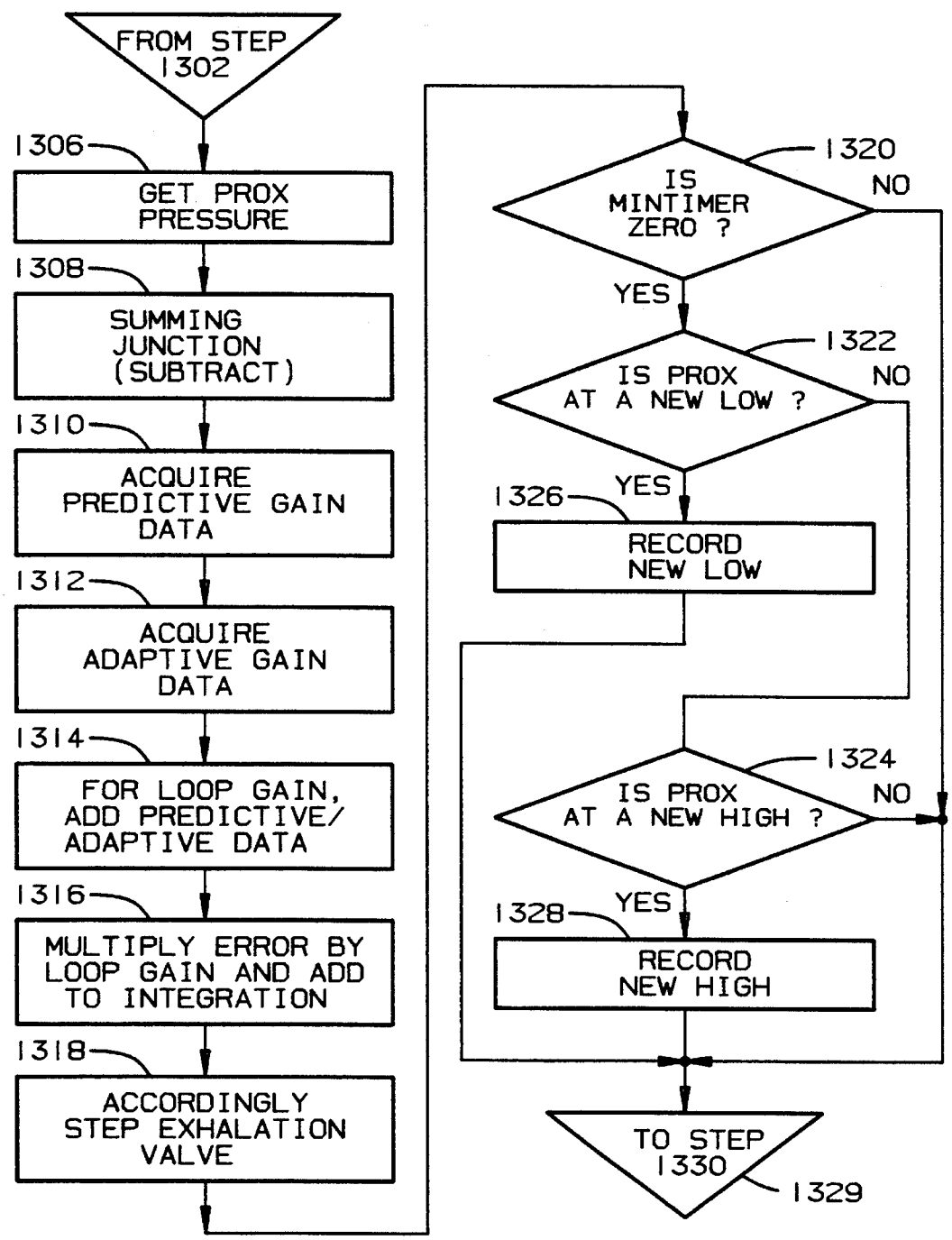
FIG. 46b is a detailed flow chart of a second portion of step 514 of FIG. 22.

A second portion of the exhalation servo routine is set forth in FIG. 46b. Now referring to FIG. 46b, steps 1306–1316 determine the next position to which the flow control valve is going to be opened during the servo portion of the exhalation program. At step 1306 the proximal pressure is read. At step 1308, the target pressure is subtracted from this proximal pressure in order to determine the servo error.

At step 1310, a positive predictive gain value is retrieved from Table 11 set forth below, and a negative predictive gain value is retrieved from Table 12 set forth below.

TABLE 11

| Po-peep | 0-1 | 2-3 | 4-5 | 6-7 | 8-9 | 10- | 12- | 14- | 16- | 18- | 20- | 22- | 24- | 26- | 28- | 30 |
|---|---|---|---|---|---|---|---|---|---|---|---|---|---|---|---|---|
| negative | 90 | 90 | 90 | 80 | 70 | 60 | 50 | 40 | 40 | 40 | 40 | 40 | 30 | 30 | 30 | 30 |
| 0-1 | A0 | 90 | 90 | 80 | 70 | 60 | 60 | 50 | 50 | 50 | 40 | 40 | 38 | 38 | 38 | 38 |
| 2-3 | A0 | 90 | 90 | 80 | 70 | 60 | 60 | 50 | 50 | 50 | 40 | 40 | 38 | 38 | 38 | 38 |
| 4-7 | A0 | 90 | 90 | 80 | 70 | 60 | 60 | 50 | 50 | 50 | 40 | 40 | 38 | 38 | 38 | 38 |
| 7-10 | 80 | 70 | 70 | 70 | 60 | 60 | 50 | 40 | 40 | 40 | 38 | 38 | 38 | 38 | 38 | 38 |
| 11-15 | 70 | 60 | 60 | 60 | 50 | 50 | 50 | 40 | 38 | 38 | 38 | 38 | 38 | 38 | 38 | 38 |
| 16-21 | 60 | 50 | 50 | 50 | 40 | 40 | 40 | 40 | 38 | 38 | 38 | 38 | 38 | 38 | 38 | 38 |
| 22-28 | 50 | 40 | 40 | 40 | 40 | 40 | 40 | 40 | 38 | 38 | 38 | 38 | 30 | 30 | 30 | 30 |
| 29-36 | 40 | 40 | 40 | 40 | 40 | 40 | 40 | 40 | 38 | 38 | 30 | 30 | 28 | 28 | 28 | 28 |
| 37-45 | 40 | 40 | 40 | 40 | 40 | 40 | 38 | 30 | 30 | 30 | 28 | 28 | 20 | 20 | 20 | 20 |
| 46-55 | 40 | 40 | 40 | 38 | 38 | 38 | 38 | 30 | 28 | 28 | 20 | 20 | 18 | 18 | 18 | 18 |
| 56-66 | 38 | 38 | 38 | 30 | 30 | 30 | 30 | 28 | 20 | 20 | 18 | 18 | 18 | 14 | 14 | 14 |
| 67-78 | 34 | 34 | 30 | 28 | 24 | 20 | 20 | 20 | 18 | 18 | 18 | 18 | 18 | 14 | 14 | 14 |
| 79-91 | 28 | 28 | 28 | 28 | 24 | 20 | 20 | 20 | 18 | 18 | 18 | 14 | 14 | 14 | 14 | 14 |
| 92-105 | 28 | 28 | 28 | 28 | 24 | 20 | 20 | 20 | 18 | 18 | 18 | 14 | 14 | 14 | 14 | 14 |
| 106+ | 28 | 28 | 28 | 28 | 24 | 20 | 20 | 20 | 18 | 18 | 14 | 14 | 14 | 14 | 14 | 14 |

Now referring to Table 11, each column of the table contains a plurality of positive predictive gain values that depend upon the PEEP pressure that was preselected by the operator of the ventilator. Thus, during this portion of the program, only one of the columns set forth in Table 11 above is used. Each row of Table 11 contains a plurality of positive predictive gain numbers that depend upon the difference of the proximal pressure $P_o$ and the preselected PEEP pressure, or ($P_o$–PEEP).

The positive predictive gain number is retrieved from Table 11 by retrieving the step number in the column corresponding to the preselected PEEP pressure and in the row corresponding to the difference ($P_o$–PEEP).

TABLE 12

| | | | | | | PEEP | | | | | | | | | | |
|---|---|---|---|---|---|---|---|---|---|---|---|---|---|---|---|---|
| Po-peep | 0-1 | 2-3 | 4-5 | 6-7 | 8-9 | 10- | 12- | 14- | 16- | 18- | 20- | 22- | 24- | 26- | 28- | 30 |
| negative | 90 | 90 | 90 | 90 | 90 | 80 | 80 | 80 | 80 | 80 | 70 | 70 | 70 | 70 | 60 | 60 |
| 0-1 | A0 | A0 | 90 | 90 | 90 | 90 | 90 | 80 | 80 | 80 | 70 | 70 | 70 | 70 | 70 | 70 |
| 2-3 | A0 | A0 | 90 | 90 | 90 | 90 | 90 | 80 | 80 | 80 | 70 | 70 | 70 | 70 | 70 | 70 |
| 4-6 | A0 | A0 | 90 | 90 | 90 | 90 | 90 | 80 | 80 | 80 | 70 | 70 | 70 | 70 | 70 | 70 |
| 7-10 | A0 | 90 | 90 | 90 | 90 | 90 | 80 | 70 | 70 | 70 | 70 | 70 | 70 | 70 | 70 | 70 |
| 11-15 | 90 | 90 | 90 | 90 | 90 | 80 | 80 | 80 | 70 | 70 | 70 | 70 | 70 | 70 | 70 | 70 |
| 16-21 | 90 | 90 | 90 | 90 | 80 | 80 | 80 | 80 | 70 | 70 | 70 | 70 | 70 | 70 | 60 | 60 |
| 22-28 | 90 | 90 | 90 | 80 | 80 | 80 | 80 | 70 | 70 | 70 | 70 | 60 | 60 | 60 | 50 | 50 |
| 29-36 | 80 | 80 | 80 | 80 | 80 | 80 | 70 | 70 | 70 | 60 | 60 | 50 | 50 | 50 | 40 | 40 |
| 37-45 | 80 | 80 | 80 | 80 | 80 | 80 | 70 | 60 | 60 | 50 | 50 | 40 | 40 | 40 | 30 | 30 |
| 46-55 | 80 | 80 | 70 | 70 | 70 | 70 | 50 | 50 | 40 | 40 | 40 | 30 | 30 | 30 | 28 | 28 |
| 56-66 | 70 | 70 | 60 | 60 | 60 | 60 | 50 | 40 | 40 | 40 | 30 | 30 | 28 | 28 | 28 | 28 |
| 67-78 | 60 | 60 | 60 | 50 | 50 | 50 | 40 | 40 | 30 | 30 | 30 | 30 | 28 | 28 | 28 | 28 |
| 79-91 | 50 | 50 | 50 | 50 | 50 | 40 | 40 | 40 | 30 | 30 | 28 | 28 | 28 | 28 | 28 | 28 |
| 92-105 | 50 | 50 | 50 | 50 | 40 | 40 | 40 | 30 | 30 | 28 | 28 | 28 | 28 | 28 | 28 | 28 |
| 106+ | 50 | 50 | 50 | 40 | 40 | 40 | 30 | 30 | 28 | 28 | 28 | 28 | 28 | 28 | 28 | 28 |

Now referring to Table 12, each column of the table contains a plurality of negative predictive gain values that depend upon the PEEP pressure that was preselected by the operator of the ventilator. Thus, during this portion of the program, only one of the columns set forth in Table 12 above is used. Each row of Table 12 contains a plurality of negative predictive gain numbers that depend upon the difference of the proximal pressure $P_o$ and the preselected PEEP pressure, or ($P_o$–PEEP).

The negative predictive gain number is retrieved from Table 12 by retrieving the step number in the column corresponding to the preselected PEEP pressure and in the row corresponding to the difference ($P_o$–PEEP).

At step 1312, the adaptive gain factor, which is determined based upon the occurrence of a proximal pressure ripple in servo of 1 cm $H_2O$ peak-to-peak, is retrieved from Table 13 set forth below.

TABLE 13

| RIPPLE (cm) | RIPPLE FACTOR |
|---|---|
| 0 | 1 |
| 1 | 7/8 |
| 2 | 3/4 |
| 3 | 5/8 |
| 4 | 1/2 |

TABLE 13-continued

| RIPPLE (cm) | RIPPLE FACTOR |
|---|---|
| 5 | 3/8 |
| 6 | 1/4 |
| 7 | 1/8 |

At step 1314, the positive and negative predictive gain data determined in step 1310 are added and the sum is multiplied by the ripple factor determined in step 1312 in order to determine the loop gain. Then, at step 1316, this loop gain is multiplied by the error determined in step 1308. Since the servo system is an integrating-type servo, the loop gain multiplied by the error is added to the current integration, or the accumulation of all previous error in order to determine the next opening of the exhalation valve. At step 1318, the exhalation valve is opened to the position determined in step 1316.

At step 1320, the minimum exhalation timer is tested to determine whether it is zero. If it is not zero, the program branches to step 1332 in FIG. 46c. If the timer is zero, the program branches to step 1322, at which point the proximal pressure is tested to see if it is at a new low. If it is at a new low, the program branches to step 1326, at which point the new low is recorded, and then the program branches to step 1332 in FIG. 46c. If the proximal pressure is not at a new low, the program branches to step 1324, at which the proximal pressure is tested with the previously-recorded high proximal pressure to determine if it is at a new high. If it is not at a new high, the program branches to step 1332 in FIG. 46c. If it is at a new high, the new high proximal pressure is recorded, and the program branches to step 1332.

Figure 46C:
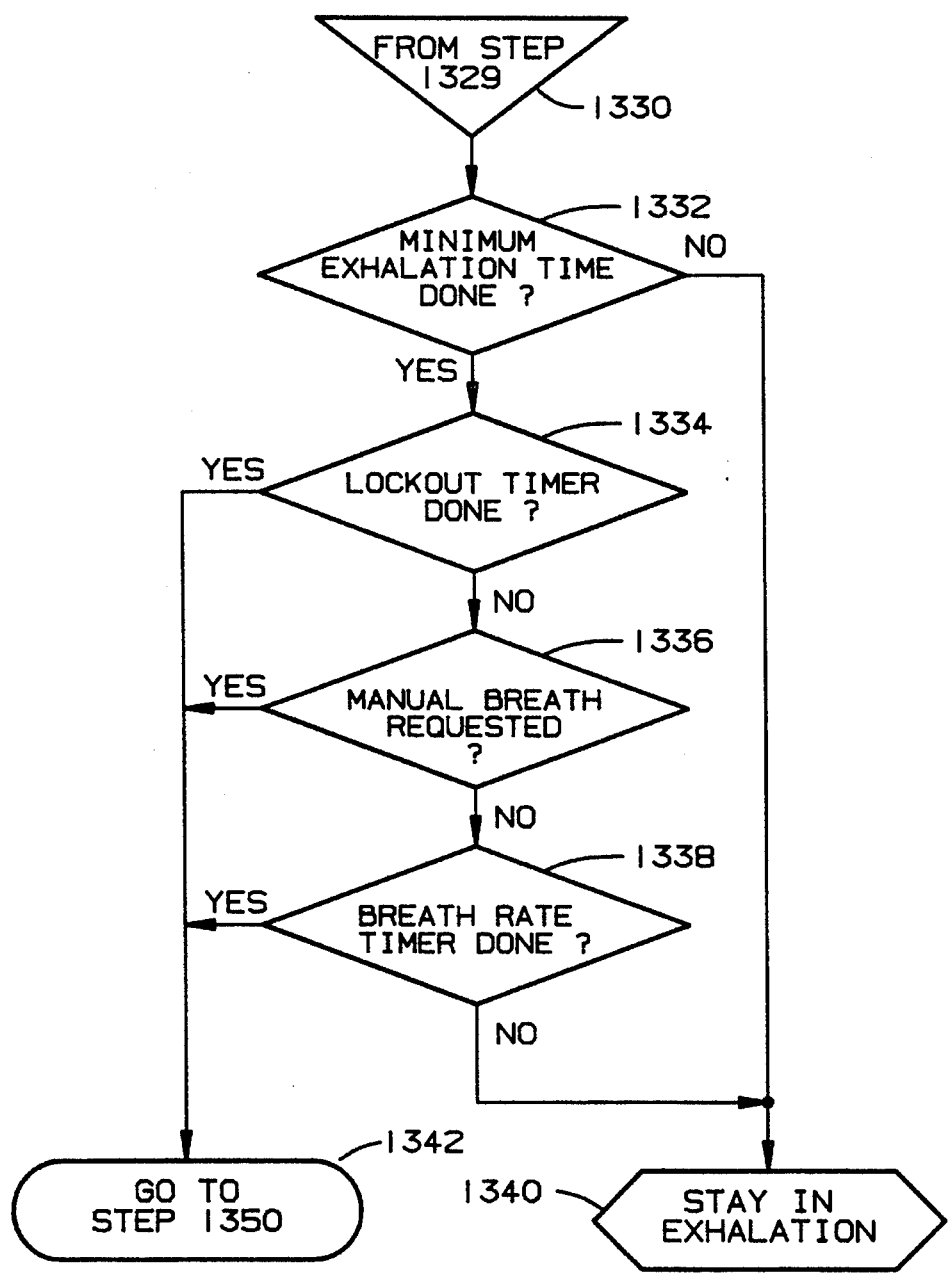
FIG. 46c is a detailed flow chart of a third portion of step 514 of FIG. 22.

A third portion of the exhalation servo routine is set forth in FIG. 46c. Now referring to FIG. 46c, at step 1332, the minimum exhalation timer described above is tested to see if the minimum exhalation time is done. If it is not, the program branches to step 1340 and stays in exhalation. If the minimum exhalation time is done, the program branches to step 1334 to determine whether the lock-out timer that prevents patient-initiated breaths as described above has timed out. If it has, the program branches to step 1342 which causes the program to branch to step 1350 in FIG. 47. If the lock-out timer is not done, the program branches to step 1336, at which point it is determined whether a manual breath is requested. A manual breath may be requested by the ventilator operator by pushing one of the pushbuttons on the ventilator control panel. If a manual breath has been requested, the program branches to step 1342. If not, the program branches to step 1338, at which point the breath rate timer is tested to determine if it has timed out. If it has, the program branches to step 1342; otherwise, the program branches to step 1340 and stays in exhalation. At step 1340, the program branches to step 1282 in FIG. 46a to stay in the servo portion of the exhalation routine.

Figure 47:
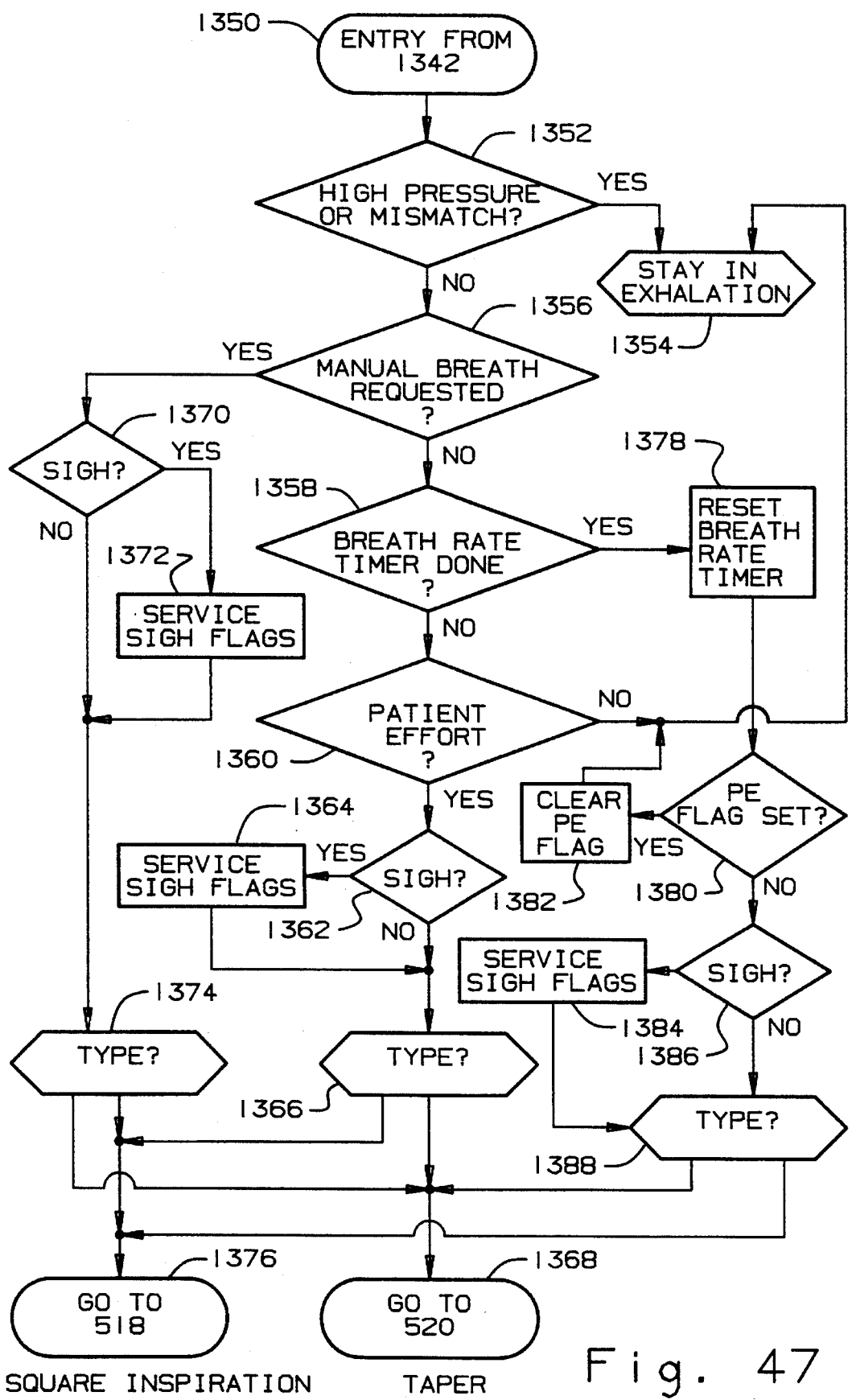
FIG. 47 is a detailed flow chart of step 516 of FIG. 22.

A detailed flow chart of step 514, which is schematically shown in FIG. 22, is set forth in FIG. 47. Now referring to FIG. 47, at step 1352, the proximal pressure is tested to determine if it is above a set alarm limit or it is not within a predetermined limit from the machine pressure. If so, the program branches to step 1354 and stays in exhalation. At step 1354, the program branches to step 1282 shown in FIG. 46a. If not, the program branches to step 1356, at which point the controller determines whether a manual breath has been requested. If it has, the program branches to step 1370, at which point the program determines whether it is a sigh breath. If it is, the program branches to step 1372 in order to service the sigh flags and then branches to step 1374. If it is not a sigh breath, the program branches from step 1370 directly to step 1374. At step 1374 the program determines what type of breath the next breath will be and branches accordingly.

If the program determines that a manual breath is not requested at step 1356, the program branches to step 1358, at which point the breath rate timer is tested to determine whether it has timed out yet. If it has, the program branches to step 1378, at which point the breath rate timer is reset. At step 1380, the program determines whether the PE flag was set. If so, the program branches to step 1382, at which point the PE flag is cleared and then the program returns to step 1354 to stay in exhalation. If the PE flag was not set as determined at step 1380, the program branches to step 1386, at which point the sigh flags are serviced at step 1384 if this is a sigh breath. Finally, at steps 1366, 1374 and 1388, the program determines what type of breath is to be delivered to the patient on the next inspiration cycle, and branches accordingly.

Control of Flow Control Valve

The control of the flow control valve by the motor control processor 190 is described below in connection with FIGS. 48–77, which include detailed flowcharts of a motor control computer program stored in the EPROM associated with the motor control processor 190.

Figure 48:
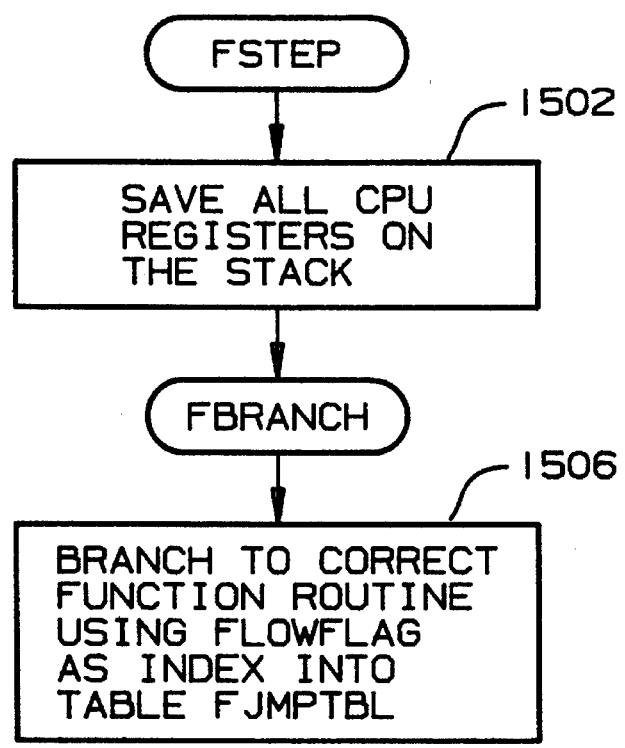
FIGS. 48–77 contain detailed flow charts of the motor control computer program.

Now referring to FIG. 48, an FSTEP routine is shown. Each time the FSTEP routine is executed, the flow control valve stepping motor is driven a single step. The FSTEP routine is executed each time that an interrupt is generated from an interrupt-generating timer. As is described in more detail below, the interrupt-generating timer is repeatedly loaded with the various time delays retrieved from the ramp tables that control the stepping of the motors. Each time the interrupt-generating timer times out, the FSTEP routine is called. When the FSTEP routine is called, at step 1502 the CPU registers of the motor control processor are saved to the stack, and at step 1506, the program branches to one of a number of software routines. Each of these software routines, which are described in detail below, is branched to when the stepping motor being driven is in a certain mode of operation. For example, the FSTEPF6 routine is branched to when the motor is being driven a total of six steps in the forward direction. For purposes of the following explanation, the "forward direction" is that direction that causes the valves to be opened, and the "reverse direction" is that direction that causes the valves to be closed. Also, when a stepping motor is stepped "up," the motor is being stepped in a direction that will cause the respective valve to open, and when the motor is being stepped "down," the motor is being stepped in a direction that will cause the valve to close. Also, unless otherwise indicated, the words "steps" and "half steps" are used interchangeably and both are intended to mean half steps.

The branch that occurs at step 1506 is made based upon the numeric value of a variable FLOWFLAG. The variable FLOWFLAG represents the current mode in which the flow control valve stepping motor is being driven. The various values of FLOWFLAG and the corresponding software routines and stepping motor modes that they represent are reproduced in Table 14 below. For example, if the value of FLOWFLAG is equal to the hexadecimal number 2, the motor is in a mode in which it is being driven four half steps in the reverse direction. In this case, at step 1506 the program would branch to the FSTEPR4 routine set forth in FIG. 75.

TABLE 14

| FLOWFLAG | STATE | BRANCH TO | PERFORM |
|---|---|---|---|
| — | 0 | FINOP0 | Illegal State - Vent Inop |
| FCR2 | 1 | FSTEPR2 | Reverse 2 Half Steps |
| FCR4 | 2 | FSTEPR4 | Reverse 4 Half Steps |
| FCR6 | 3 | FSTEPR6 | Reverse 6 Half Steps |
| FCR8 | 4 | FSTEPR8 | Reverse 8 Half Steps |
| FCR10 | 5 | FSTEPR10 | Reverse 10 Half Steps |
| FCR12 | 6 | FSTEPR12 | Reverse 12 Half Steps |
| FCRA2000 | 7 | FSTEPRA2 | Rev Accel to 2000 hs/ |

TABLE 14-continued

| FLOWFLAG | STATE | BRANCH TO | PERFORM |
|---|---|---|---|
| FCRM2000 | 8 | FSTEPRM2 | Rev Slew at 2000 hs/sec |
| FCRD2000 | 9 | FSTEPRD2 | Rev Decel from 2000 hs/sec |
| FCRA3000 | A | FSTEPRA3 | Rev Accel to 3000 hs/sec |
| FCRM3000 | B | FSTEPRM3 | Rev Slew at 3000 hs/sec |
| FCRD3000 | C | FSTEPRD3 | Rev Decel from 3000 hs/sec |
| — | D | FINOPD | Illegal State - Vent Inop |
| FCH | E | FSTEPH | Hold for ring out delay |
| FCNM | F | FSTEPNM | No motion idle |
| — | 10 | FINOP10 | Illegal State - Vent Inop |
| FCF2 | 11 | FSTEPF2 | Forward 2 Half Steps |
| FCF4 | 12 | FSTEPF4 | Forward 4 Half Steps |
| FCF6 | 13 | FSTEPF6 | Forward 6 Half Steps |
| FCF8 | 14 | FSTEPF8 | Forward 8 Half Steps |
| FCF10 | 15 | FSTEPF10 | Forward 10 Half Steps |
| FCF12 | 16 | FSTEPF12 | Forward 12 Half Steps |
| FCFA2000 | 17 | FSTEPFA2 | Fwd Accel to 2000 hs/sec |
| FCFM2000 | 18 | FSTEPFM2 | Fwd Slew at 2000 hs/sec |
| FCFD2000 | 19 | FSTEPFD2 | Fwd Decel from 2000 hs/sec |
| FCFA3000 | 1A | FSTEPFA3 | Fwd Accel to 3000 hs/sec |
| FCFM3000 | 1B | FSTEPFM3 | Fwd Slew at 3000 hs/sec |
| FCFD3000 | 1C | FSTEPFD3 | Fwd Decel from 3000 hs/sec |
| — | 1D | FINOP1D | Illegal State - Vent Inop |
| FCH | 1E | FSTEPH | Hold for ring out delay |
| FCNM | 1F | FSTEPNM | No motion idle |

Detailed flow charts of the portion of the motor control program that controls the stepping motor that drives the flow control valve are set forth in FIGS. 48–77. Table 14 above sets forth the various states of the variable FLOWFLAG and the various software procedures to which the program branches, depending upon the state of FLOWFLAG. The first column of the Table 14 contains an acronym representing the FLOWFLAG state and the second column contains the actual hexadecimal value of FLOWFLAG that corresponds to this state. The third column of the table includes the name of the software procedure that implements the desired FLOWFLAG state, and the last column in the table describes what the software procedure does. For example, if the value of the FLOWFLAG variable is 4, the FLOWFLAG state is FCR8, the program branches to FSTEPR8, and this FSTEPR8 procedure causes the flow control valve to be driven in its reverse direction by 8 half steps. For purposes of this description, if the stepping motor that drives the flow control valve is driven either forward or upward, it means that the valve is being opened, while if the stepping motor is being driven downward or reverse, it means that the flow control valve is being closed.

Figure 49:
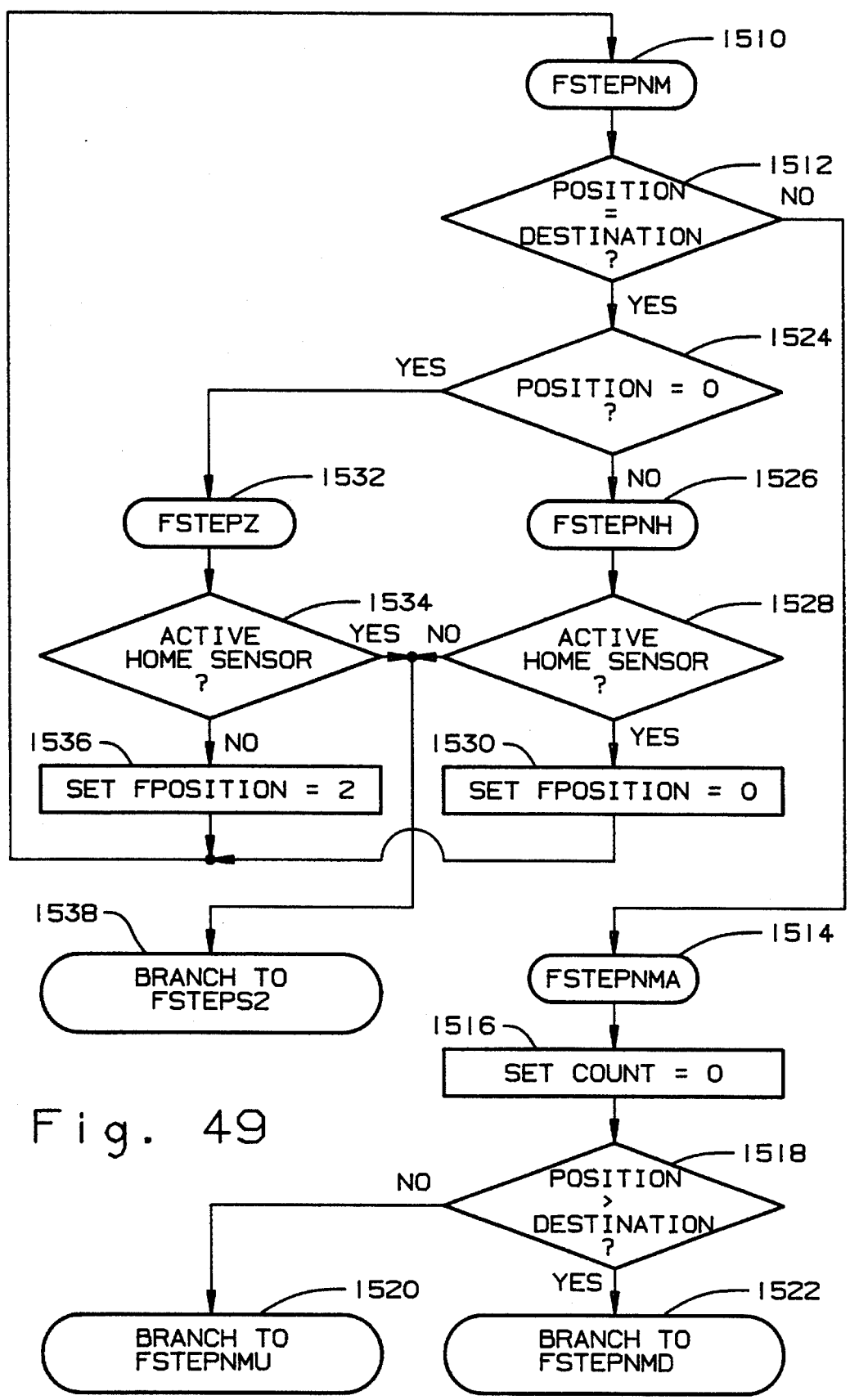

Now referring to FIG. 49, at step 1512, the motor control processor 190 compares the current position of the flow control valve with the destination requested by the main processor 188. As indicated above, the current position of the flow control valve is known to the motor control processor 190 at all times. If the current position of the flow control valve does not equal its requested destination, the flow control valve must be moved, and the program branches to step 1516. At this step, the variable COUNT is set equal to zero, and then the program branches to step 1518, at which point the program determines whether the current position is greater than the requested destination. If it is, the program branches to step 1522 which causes the flow control valve to be stepped down, as indicated by the acronym FSTEPNMD. If the position is not greater than the requested destination, the program branches to step 1520, in which case the flow control valve is moved up. If the position equals the destination as determined at step 1512, the program branches to step 1524, at which point the program determines whether the position of the flow control valve equals zero. If it does, the program branches to step 1534, at which point the home sensor is read by the motor control processor to determine whether it is active. If it is active, the program branches to step 1538. If it is not active, the variable FPOSITION is set equal to the 2. If the position is not equal to zero as determined at step 1524, the program branches to step 1528, at which point the home sensor is read by the processor 190 in order to determine whether it is active. If it is not active, the program branches to step 1538. If it is active, the variable FPOSITION is set equal to zero, and the program branches back to step 1510.

Figure 50A:
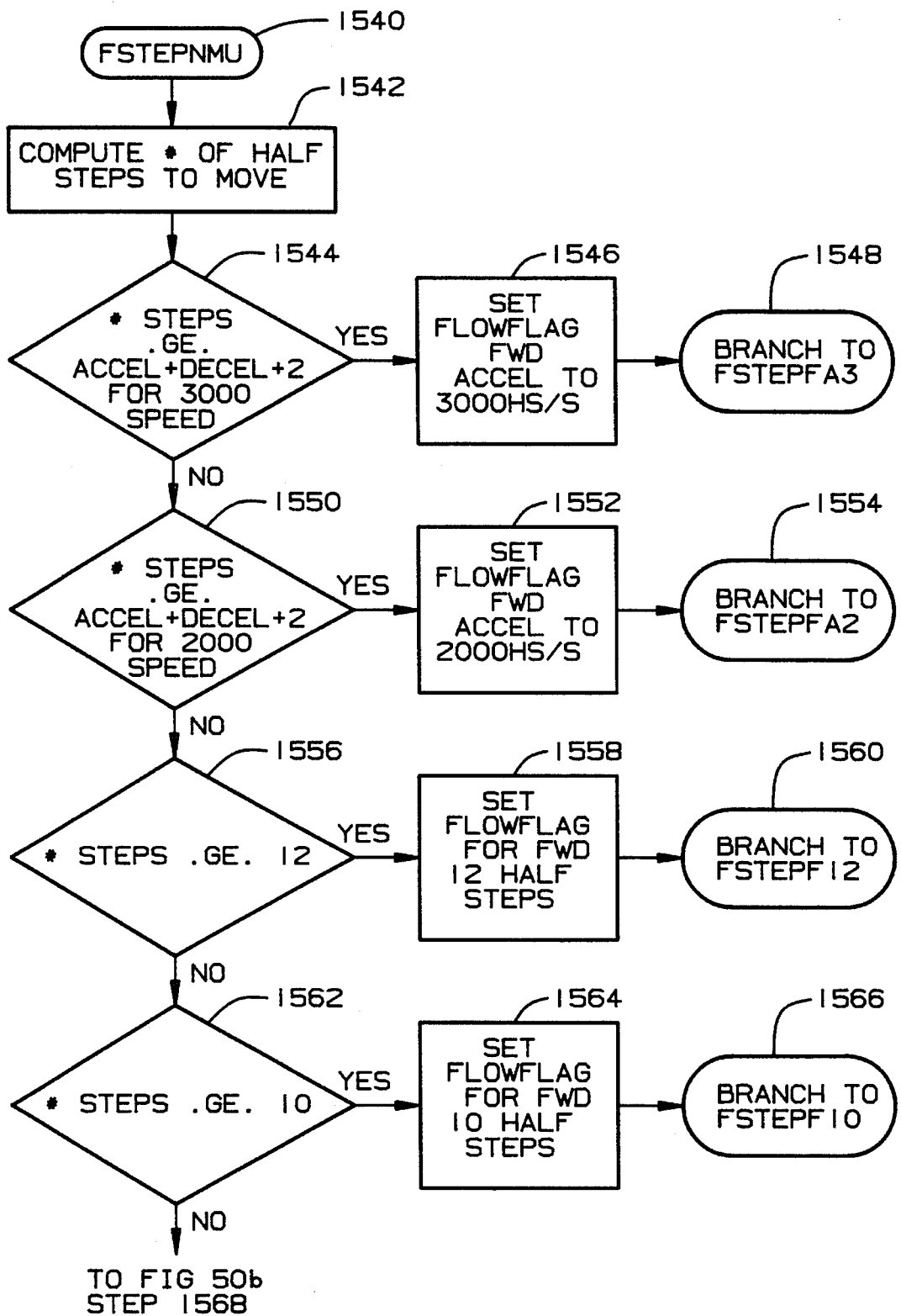
Figure 50B:
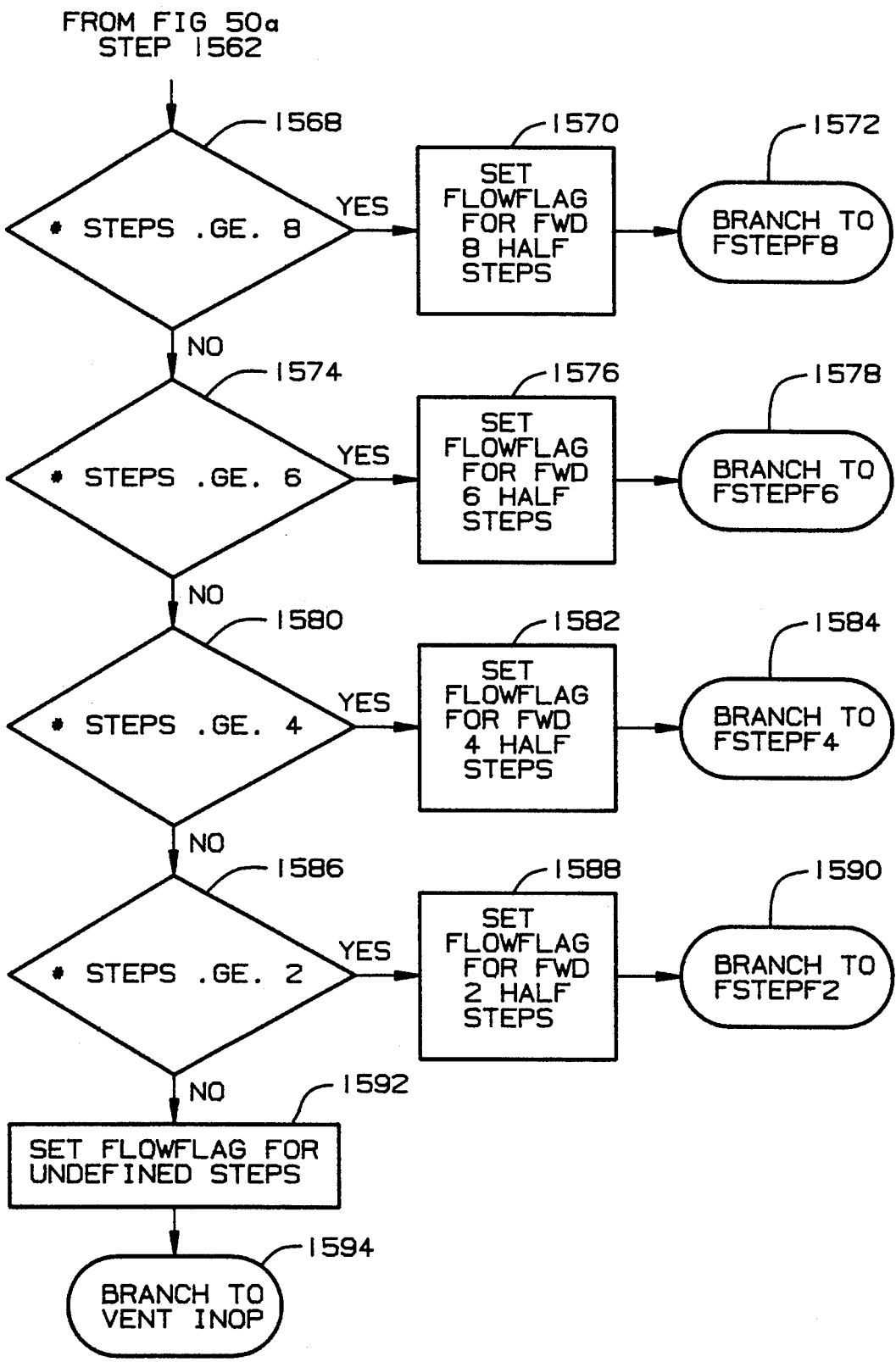

The detailed flow chart in FIG. 50, when executed, causes the variable FLOWFLAG to be set to a hexadecimal number that will cause the flow control valve stepping motor 74 to be opened in accordance with the request from the main processor 188 via the serial interface. At step 1542, the program computes the number of half steps that the flow control valve stepping motor 74 needs to be moved up from the difference between the current position and the requested destination. Using this number, the program branches to step 1544 and tests to see whether the number of steps is greater or equal to a predetermined number of steps that would allow the flow control stepping motor to be accelerated to 3000 half steps per second, decelerated from 3000 half steps per second, and have at least two half steps in between at the peak rate of 3000 half steps per second. If the number of steps the motor needs to be moved is greater than this predetermined number, the program branches to step 1546, at which point it sets the variable FLOWFLAG equal to the hexadecimal number 1A as set forth in Table 14, and the program at step 1548 branches to the procedure FSTEPFA3.

If the number of steps is not greater or equal to the predetermined number in step 1544, the program branches to step 1550, at which point the number of steps determined in step 1542 is compared to determine whether it is greater or equal to a second predetermined number of steps which would allow the flow control valve stepping motor 74 to be accelerated to and decelerated from a rate of 2000 half steps per second, and have at least two half steps in between at that 2000 half-step-per-second speed. If the number of steps that the motor 74 has been requested to move is greater or equal to this predetermined number, the program branches to step 1552, at which point it sets the variable FLOWFLAG to the hexadecimal number 17, and using the Table 14, the program branches to the FSTEPFA2 procedure at step 1554.

If the number of steps in step 1550 is not greater or equal to the second predetermined number, the program branches to step 1556 in order to determine whether the number of half steps that the flow control stepping motor is to be moved is greater or equal to 12. If so, the program branches to step 1558, at which point FLOWFLAG is set so that the program will branch to the procedure which moves the stepping motor forward by 12 half steps at step 1560.

If the number of steps is less than 12, the program branches to step 1562 where the number of steps is compared with 10. If the number of steps is greater or equal to 10, the program branches to step 1564 where FLOWFLAG is accordingly set in order to cause the program to branch to FSTEPF10 at step 1566. At step 1568, if the number of steps is greater or equal to 8, the program branches to step 1570 and then step 1572 An order to move the stepping motor 74 forward 8 half steps. At step 1574, if the number of steps is greater or equal to 6, the program branches to step 1576 and then step 1578 in order to move the stepping motor 74 forward 6 half steps. At step 1580, if the number of steps is greater or equal to 4, the program branches to step 1582 and then step 1584 in order to move the stepping motor 74 forward 4 half steps. At step 1586, if the number of steps is greater or equal to 2, the program branches to step 1588 and then step 1590 in order to move the stepping motor 74 forward 2 half steps.

If the number of steps is not greater or equal to 2, the program branches to step 1592 where FLOWFLAG is set for an undefined number of steps. Since the number of steps is ordinarily expected to be within one of the ranges of the decision-making steps 1544–1586, the program will not branch to 1592 unless there is an error state, and accordingly, at step 1594, the program branches to the VENT INOP state.

Figure 51A:
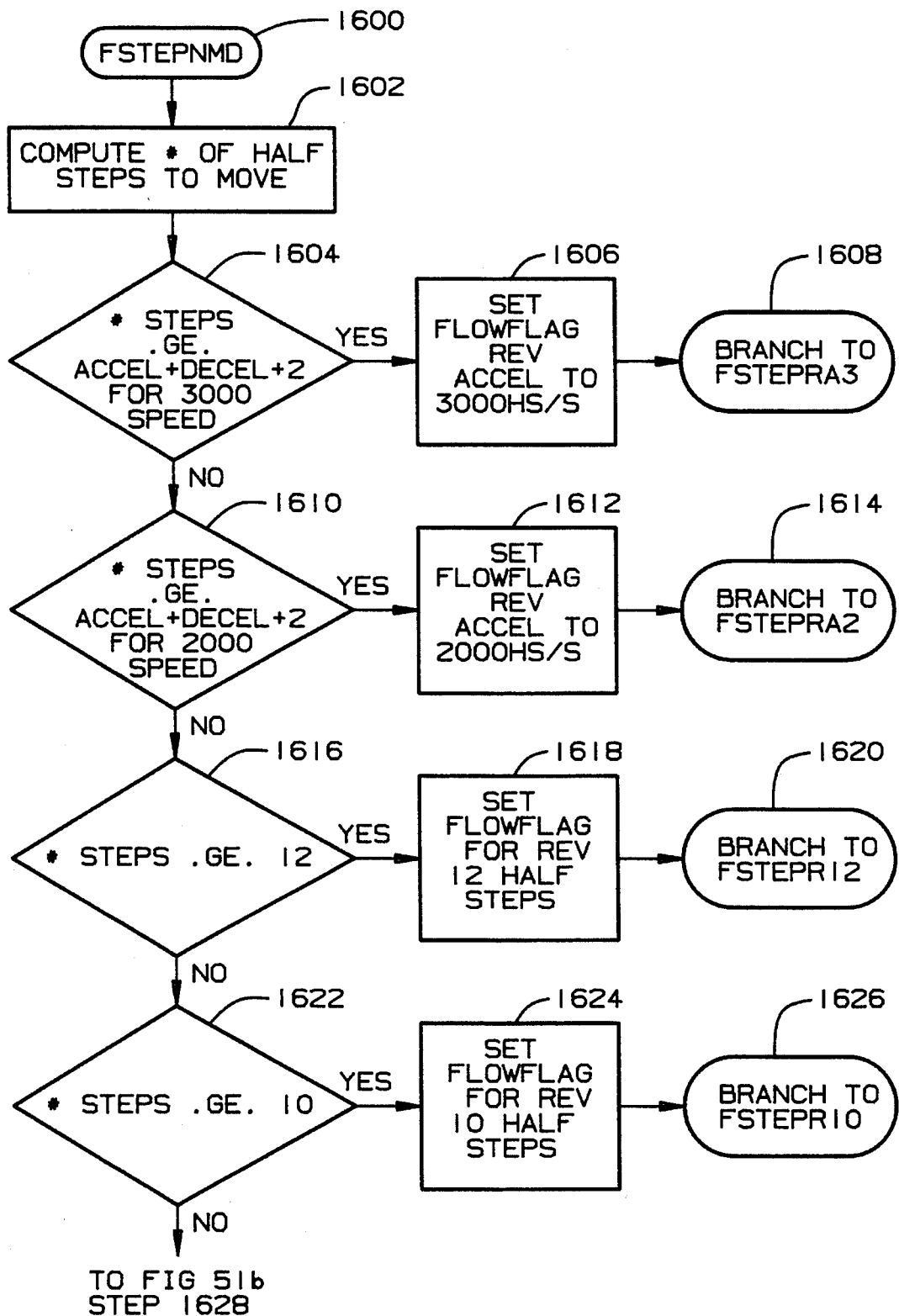
Figure 51B:
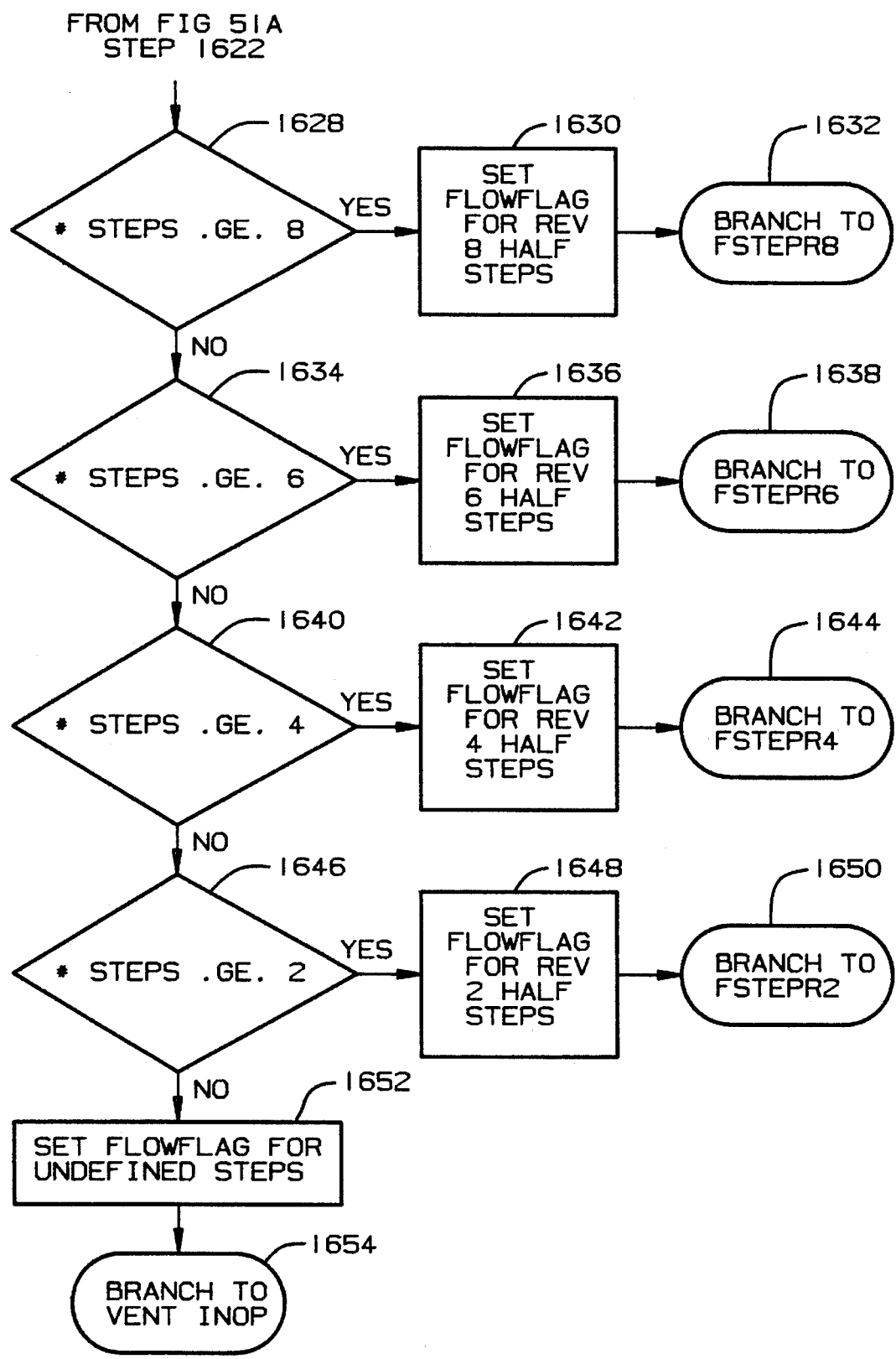

The detailed flow chart in FIG. 51, when executed, causes the variable FLOWFLAG to be set to a hexadecimal number that will cause the flow control valve stepping motor 74 to be driven so that it closes the valve 42 in accordance with the request from the main processor 188 via the serial interface. At step 1602, the program computes the number of half steps that the flow control valve stepping motor 74 needs to be moved up from the difference between the current position and the requested destination. Using this number, the program branches to step 1604 and tests to see whether the number of steps is greater or equal to a predetermined number of steps that would allow the flow control stepping motor to be accelerated to 3000 half steps per second, decelerated from 3000 half steps per second, and have at least two half steps in between at the peak rate of 3000 half steps per second. If the number of steps the motor needs to be moved is greater than this predetermined number, the program branches to step 1606, at which point it sets the variable FLOWFLAG equal to the hexadecimal number 1A as set forth in Table 14, and the program at step 1608 branches to the procedure FSTEPRA3.

If the number of steps is not greater or equal to the predetermined number in step 1604, the program branches to step 1610, at which point the number of steps determined in step 1602 is compared to determine whether it is greater or equal to a second predetermined number of steps which would allow the flow control valve stepping motor 74 to be accelerated to and decelerated from a rate of 2000 half steps per second, and have at least two half steps in between at that 2000 half-step-per-second speed. If the number of steps that the motor 74 has been requested to move is greater or equal to this predetermined number, the program branches to step 1612, at which point it sets the variable FLOWFLAG to the hexadecimal number 7, and using the Table 14, the program branches to the FSTEPRA2 procedure at step 1614.

If the number of steps in step 1610 is not greater or equal to the second predetermined number, the program branches to step 1616 in order to determine whether the number of half steps that the flow control stepping motor is to be moved is greater or equal to 12. If so, the program branches to step 1618, at which point FLOWFLAG is set so that the program will branch to the procedure which moves the stepping motor backwards by 12 half steps at step 1620.

If the number of steps is less than 12, the program branches to step 1622 where the number of steps is compared with 10. If the number of steps is greater or equal to 10, the program branches to step 1624 where FLOWFLAG is accordingly set in order to cause the program to branch to FSTEPR10 at step 1626. At step 1628, if the number of steps is greater or equal to 8, the program branches to step 1630 and then step 1632 in order to move the stepping motor 74 backward 8 half steps. At step 1634, if the number of steps is greater or equal to 6, the program branches to step 1636 and then step 1638 in order to move the stepping motor 74 backward 6 half steps. At step 1640, if the number of steps is greater or equal to 4, the program branches to step 1642 and then step 1644 in order to move the stepping motor 74 backward 4 half steps. At step 1646, if the number of steps is greater or equal to 2, the program branches to step 1648 and then step 1650 in order to move the stepping motor 74 backward 2 half steps.

If the number of steps is not greater or equal to 2, the program branches to step 1652 where FLOWFLAG is set for an undefined number of steps. Since the number of steps is ordinarily expected to be within one of the ranges of the decision-making steps 1604–1646, the program will not branch to 1652 unless there is an error state, and accordingly, at step 1654, the program branches to the VENT INOP state.

Figure 52:
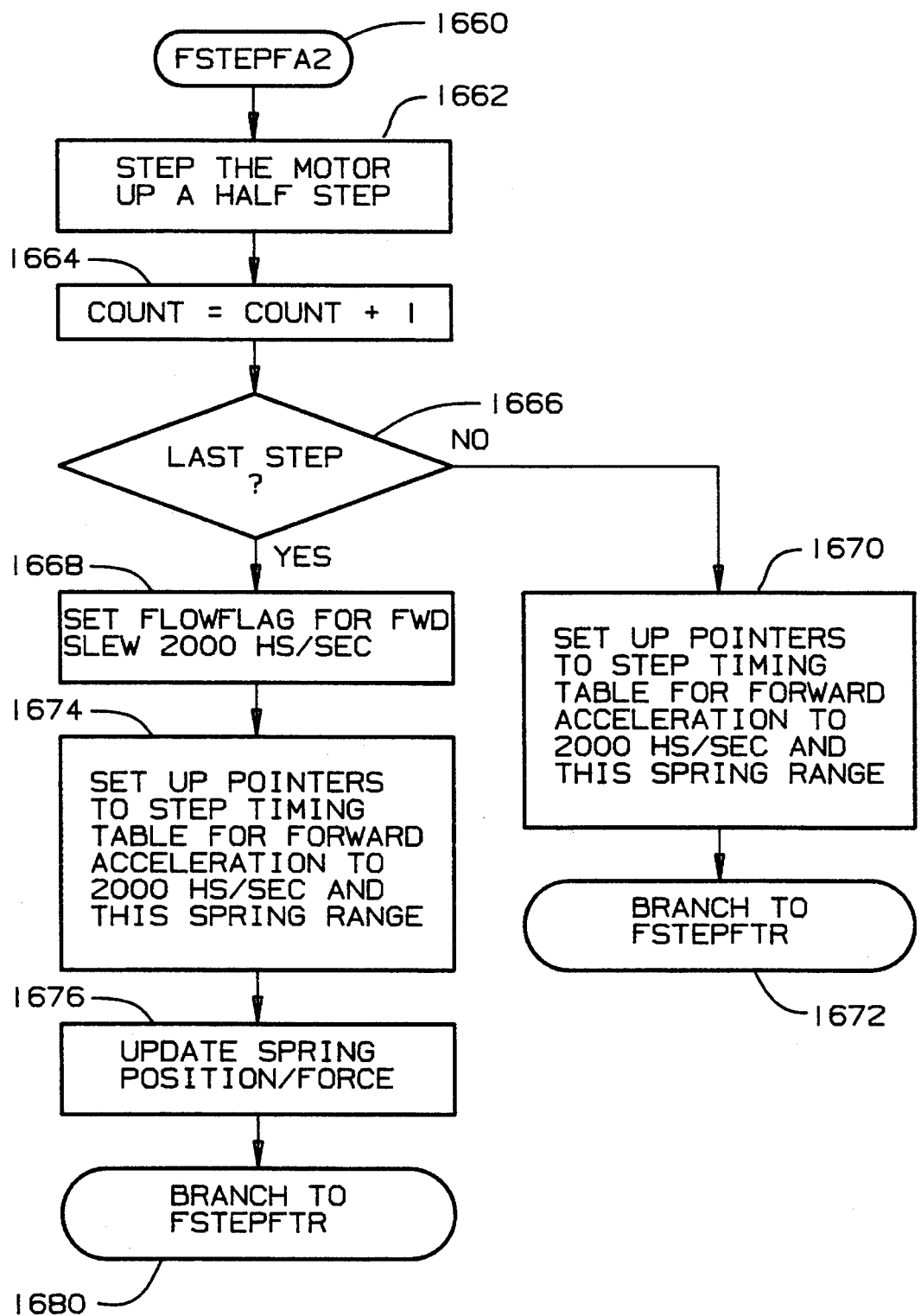

Now referring to FIG. 52, an FSTEPFA2 routine is executed by the program when the flow control valve stepping motor 74 is in a state during which the motor is being accelerated to 2,000 half steps per second. The FSTEPFA2 routine is branched to from step 1506 using the Table 14 based upon the current value of FLOWFLAG. At step 1662, the program steps the motor up a half step. Then at step 1664, the count is incremented to keep track of how many steps the motor has been moved while in this FSTEPFA2 routine. This count number is stored in a variable COUNT. At step 1666, the program determines whether the step just moved is the last step in the forward acceleration sequence by comparing COUNT to the predetermined number of steps in the 2000 step-per-second ramp up profile. If it is not the last step, then the program sets up the table index pointers to retrieve the proper time delay entry from the ramp up table for 2,000 half steps per second and the current spring force range. As described in more detail below, different ramp tables are supplied for different positions of the flow control valve to account for variation in the force exerted by the spring 94. At step 1672, the program branches to the FSTEPFTR routine shown in FIG. 58. If it is the last step in the forward acceleration sequence, the program branches to step 1668 at which FLOWFLAG is set to the hexadecimal number 18 so that the stepping motor will be slewed at 2,000 half steps per second when the next interrupt is generated. At step 1676, the spring position/force range is updated, depending upon the current position of the flow control valve. The program then branches to the FSTEPFTR routine at step 1680.

Figure 53:
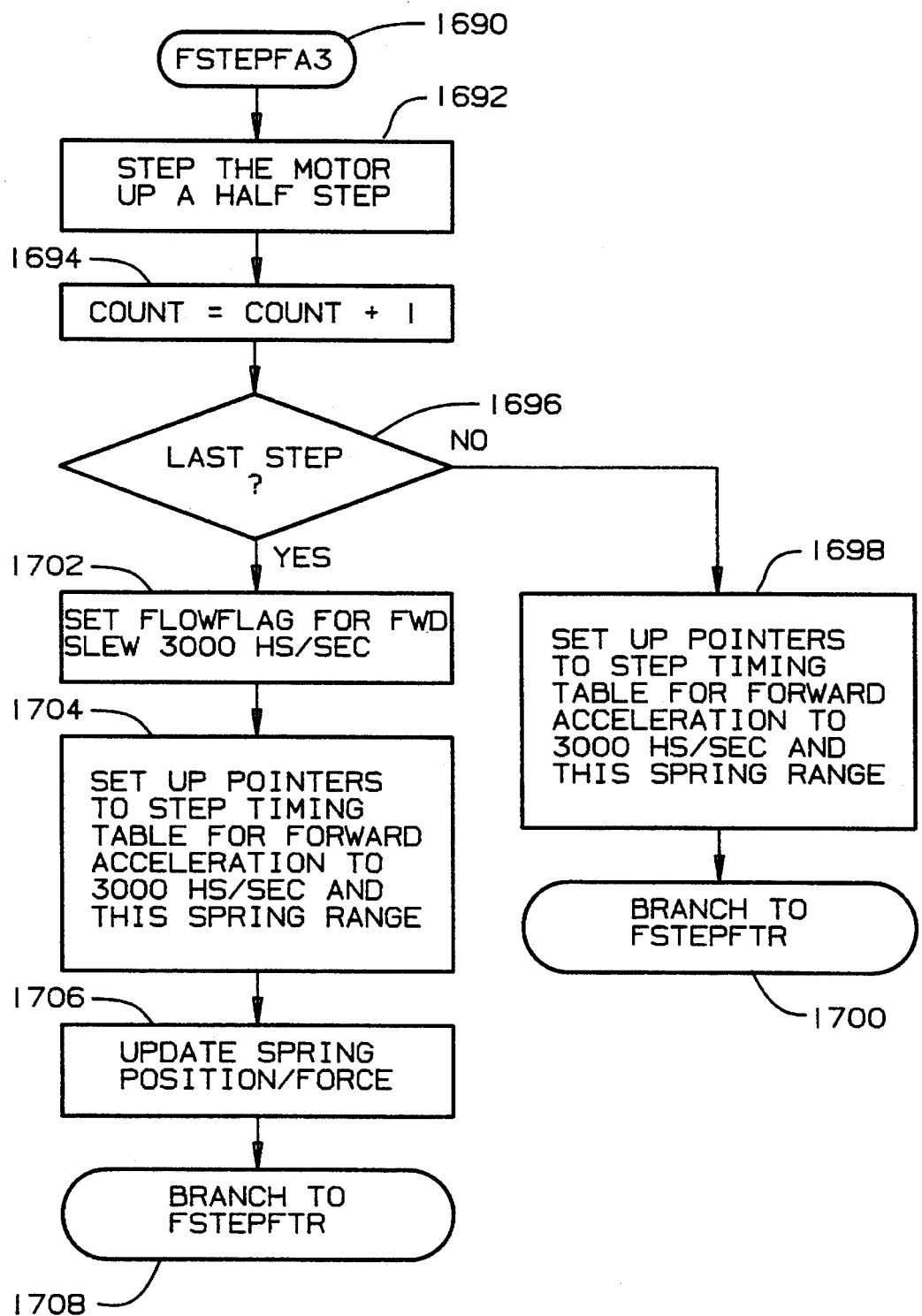

The operation of the program as set forth in FIG. 53 is quite similar to the operation of the program as described in connection with FIG. 52. Now referring to FIG. 53, an FSTEPFA3 routine is executed by the program when the flow control valve stepping motor 74 is in a state during which the motor is being accelerated to 3,000 half steps per second. The FSTEPFA3 routine is branched to from step 1548 using the Table 14 based upon the current value of FLOWFLAG. At step 1692, the program steps the motor up a half step. Then at step 1694, the count is incremented to keep track of how many steps the motor has been moved while in this FSTEPFA3 routine. This count number is stored in a variable COUNT. At step 1696, the program determines whether the step just moved is the last step in the forward acceleration sequence by comparing COUNT to the predetermined number of steps in the 2000 step ramp up profile. If it is not the last step, then at step 1698 the program sets up the table index pointers to retrieve the proper time delay entry from the ramp up table for 3,000 half steps per second and the current spring force range. As described in more detail below, different ramp tables are supplied for different positions of the flow control valve to account for variation in the force exerted by the spring 94. At step 1700, the program branches to the FSTEPFTR routine shown in FIG. 58. If it is the last step in the forward acceleration sequence, the program branches to step 1702 at which FLOWFLAG is set to the hexadecimal number 1B so that the stepping motor will be slewed at 3,000 half steps per second when the next interrupt is generated. At step 1706, the spring position/force range is updated, depending upon the current position of the flow control valve. The program then branches to the FSTEPFTR routine at step 1708.

Figure 54:
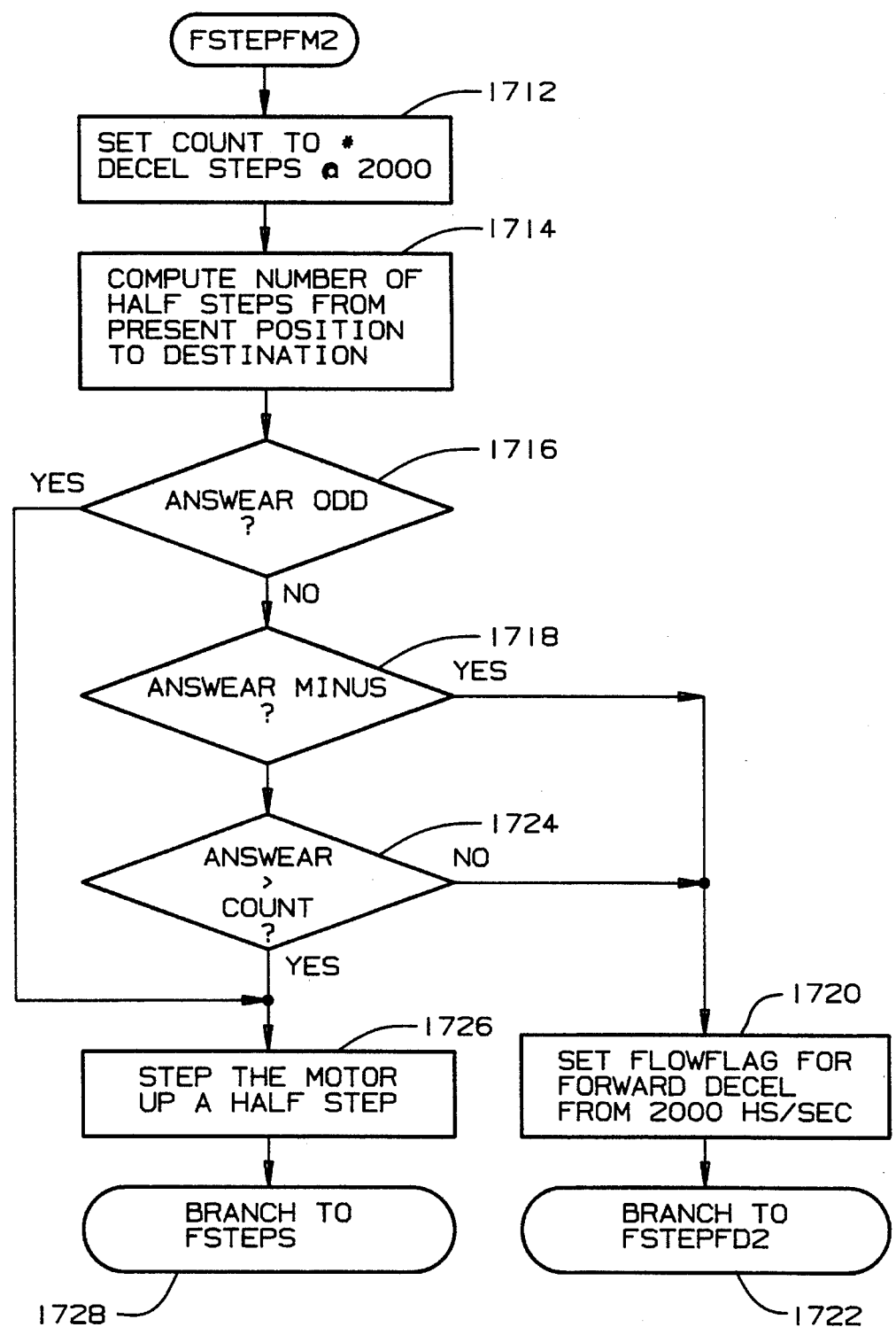

The FSTEPFM2 routine shown in FIG. 54, when executed, causes the flow control valve stepping motor 74 to slew forward at 2,000 half steps per second. At step 1712, the variable COUNT is set to the number of steps that are necessary to decelerate the flow control valve motor 74 from the current 2,000 half steps per second rate. Then, at step 1714, the program computes the number of half steps from the present position to the requested destination. If the answer is odd, at step 1716, the program branches to step 1726 at which point the motor is stepped up a half step. The reason for this is that the deceleration begins from a half step position and not a full step position. If the number of half steps from the present position to the destination is negative as determined at step 1718, the program branches to step 1720 at which point the variable FLOWFLAG is set so that the forward deceleration state is started, since the stepping motor 74 is past its desired destination. At step 1722, the program branches to the FSTEPFD2 routine. If a positive result is achieved at step 1718, the program branches to step 1724 at which point it determines whether the number of half steps from the present position to the requested destination is greater than the number of steps necessary to decelerate as determined at 1712 and stored in the COUNT variable. If the answer is yes, then the program branches to step 1726, at which point it steps the motor up one half step and then branches to the FSTEPS routine at step 1728. If the answer is no, then the program branches to step 1720 at which point it sets FLOWFLAG for the forward deceleration state, and then branches to step 1722.

Figure 55:
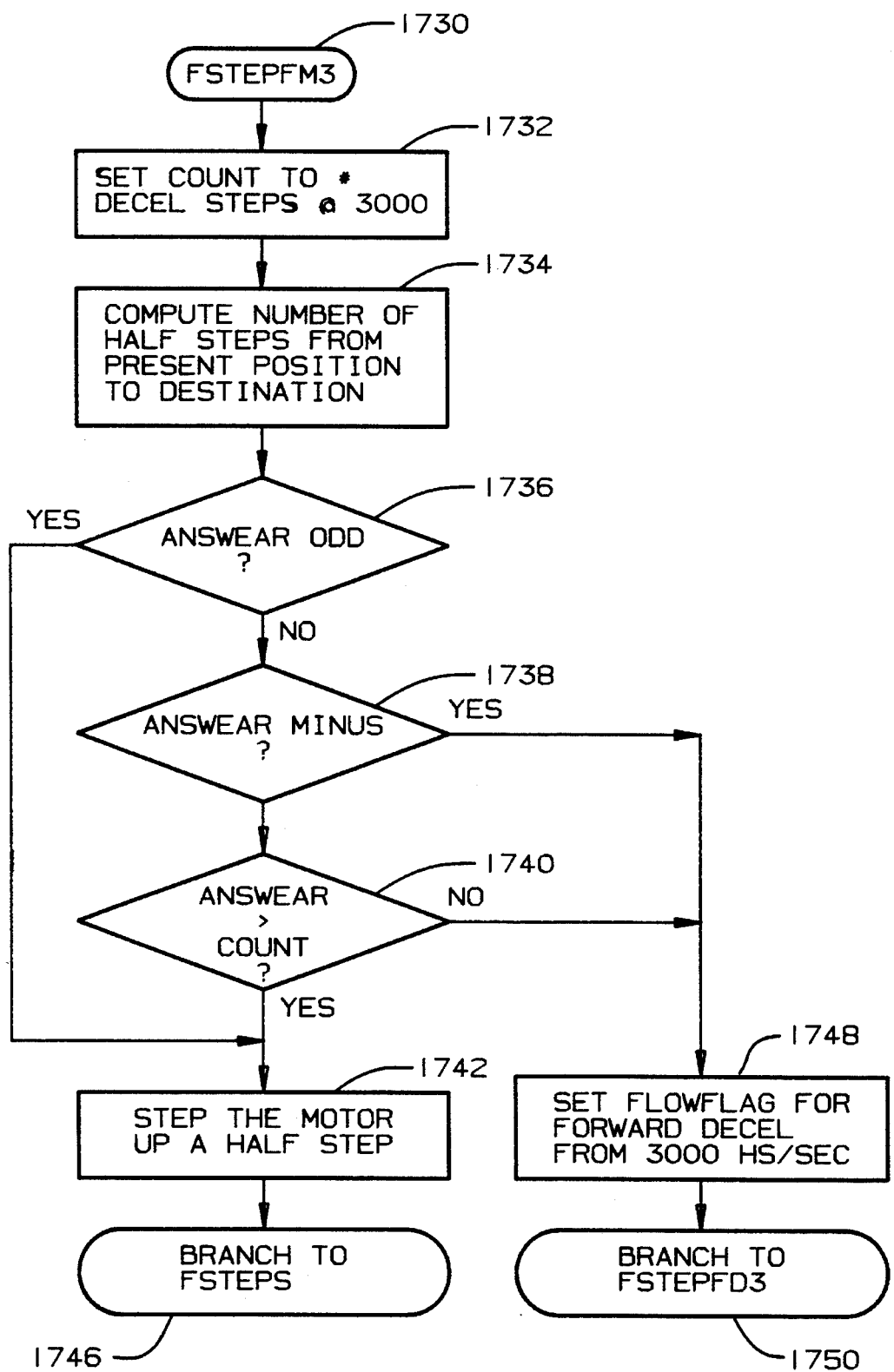

The operation of the program as set forth in FIG. 55 is quite similar to the operation of the program explained in connection with FIG. 54, except that the FSTEPFM3 routine shown in FIG. 55 causes the motor 74 to slew forward at 3000 half steps per second. Now referring to FIG. 55, at step 1732, the variable COUNT is set to the number of steps that are necessary to decelerate the flow control valve motor 74 from the current 3,000 half steps per second rate. Then, at step 1734, the program computes the number of half steps from the present position to the requested destination. If the answer is odd, at step 1736, the program branches to step 1742 at which point the motor is stepped up a half step. If the number of half steps from the present position to the destination is negative as determined at step 1738, the program branches to step 1748 at which point the variable FLOWFLAG is set so that the forward deceleration state is started, since the stepping motor 74 is past its desired destination. At step 1750, the program branches to the FSTEPFD3 routine. If a positive result is achieved at step 1738, the program branches to step 1740 at which point it determines whether the number of half steps from the present position to the requested destination is greater than the number of steps necessary to decelerate as determined at step 1732 and stored in the COUNT variable. If the answer is yes, then the program branches to step 1742, at which point it steps the motor up one half step and then branches to the FSTEPS routine at step 1746. If the answer is no, then the program branches to step 1748 at which point it sets FLOWFLAG for the forward deceleration state, and then branches to step 1750.

Figure 56:
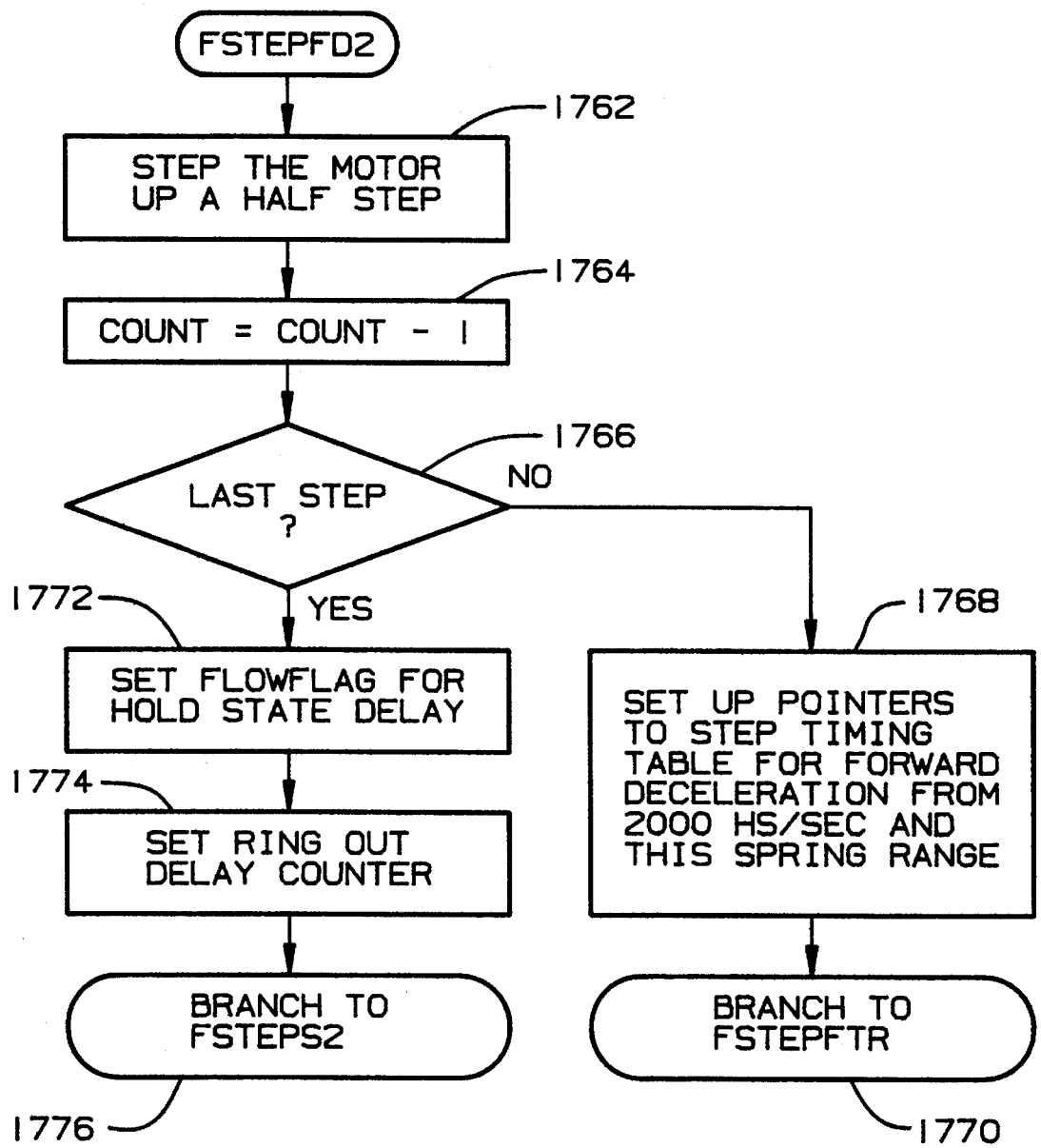

Now referring to FIG. 56, the FSTEPFD2 routine is shown which is a forward deceleration state from 2,000 half steps per second. At step 1762, the stepping motor is stepped up one half step. Then at step 1764, the variable COUNT is decremented since there is one less half step to be moved in this FSTEPFD2 routine. Then at step 1766, the program determines whether it is the last step in the deceleration sequence. If it is, then the FLOWFLAG variable is set for the hold state delay, and at step 1774, the delay ring-out counter is set so that any oscillations of the stepping motor 74 will die out before the motor is attempted to be driven again. If it is not the last step in the deceleration sequence as determined at step 1766, the program branches to step 1768 at which point the program sets up the pointers to the step timing table for the forward deceleration from 2,000 half steps per second and the appropriate spring force range stored in the variable FSPRING. At step 1770, the program branches to the FSTEPFTR routine.

Figure 57:
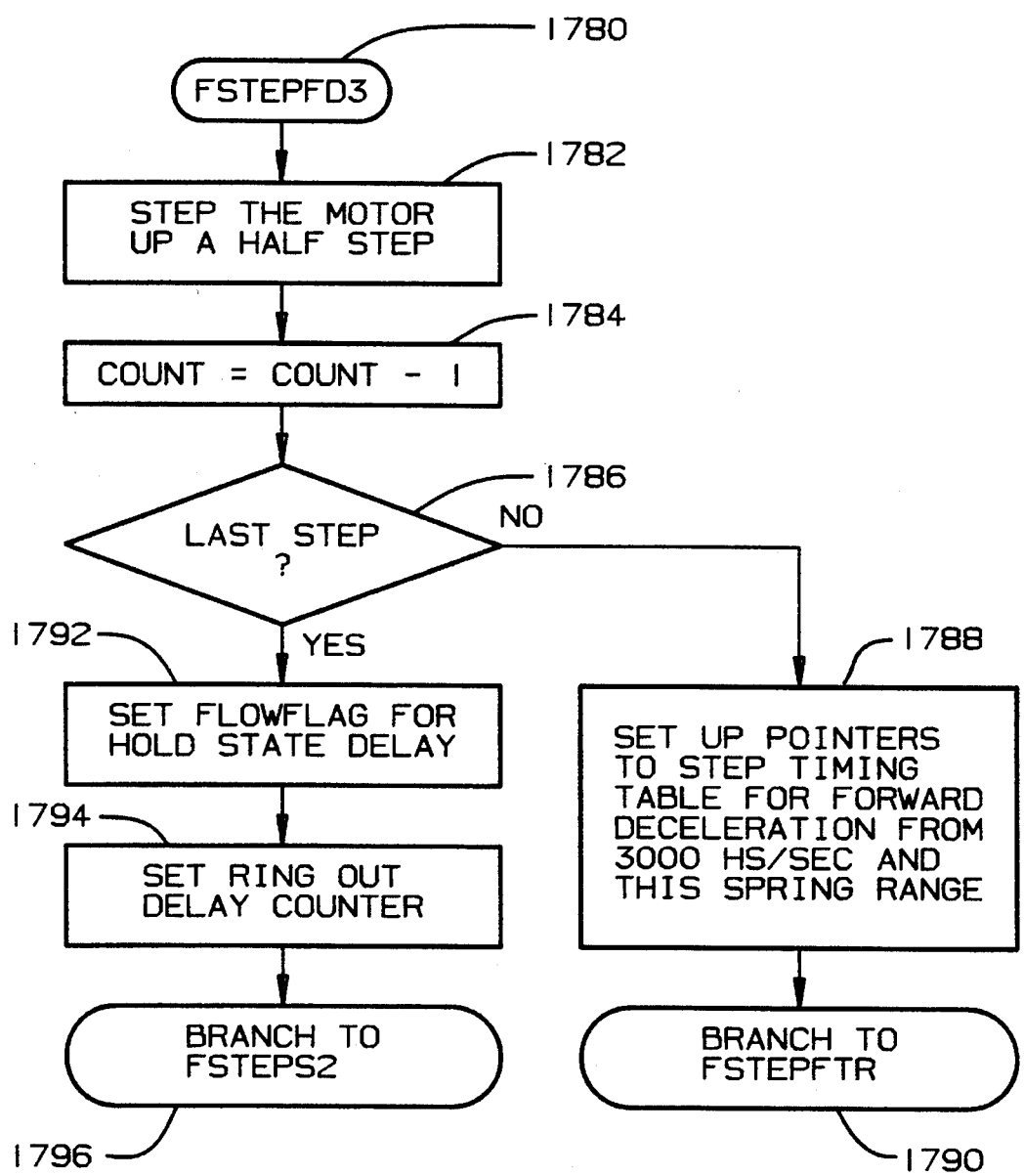

The operation of the program as set forth in FIG. 57 is very similar to the operation as explained in connection with FIG. 56, except that in FIG. 57 the motor is decelerated from 3000 half steps per second. Now referring to FIG. 57, at step 1782, the stepping motor is stepped up one half step. Then at step 1784, the variable COUNT is decremented since there is one less half step to be moved in this FSTEPFD3 routine. Then at step 1786, the program determines whether it is the last step in the deceleration sequence. If it is, then the FLOWFLAG variable is set for the hold state delay at step 1792, and at step 1794, the delay ring-out counter is set so that any oscillations of the stepping motor 74 will die out before the motor is attempted to be driven again. If it is not the last step in the deceleration sequence as determined at step 1786, the program branches to step 1788 at which point the program sets up the pointers to the step timing table for the forward deceleration from 3,000 half steps per second and the appropriate spring force range stored in the variable FSPRING. At step 1790, the program branches to the FSTEPFTR routine.

Figure 58A:
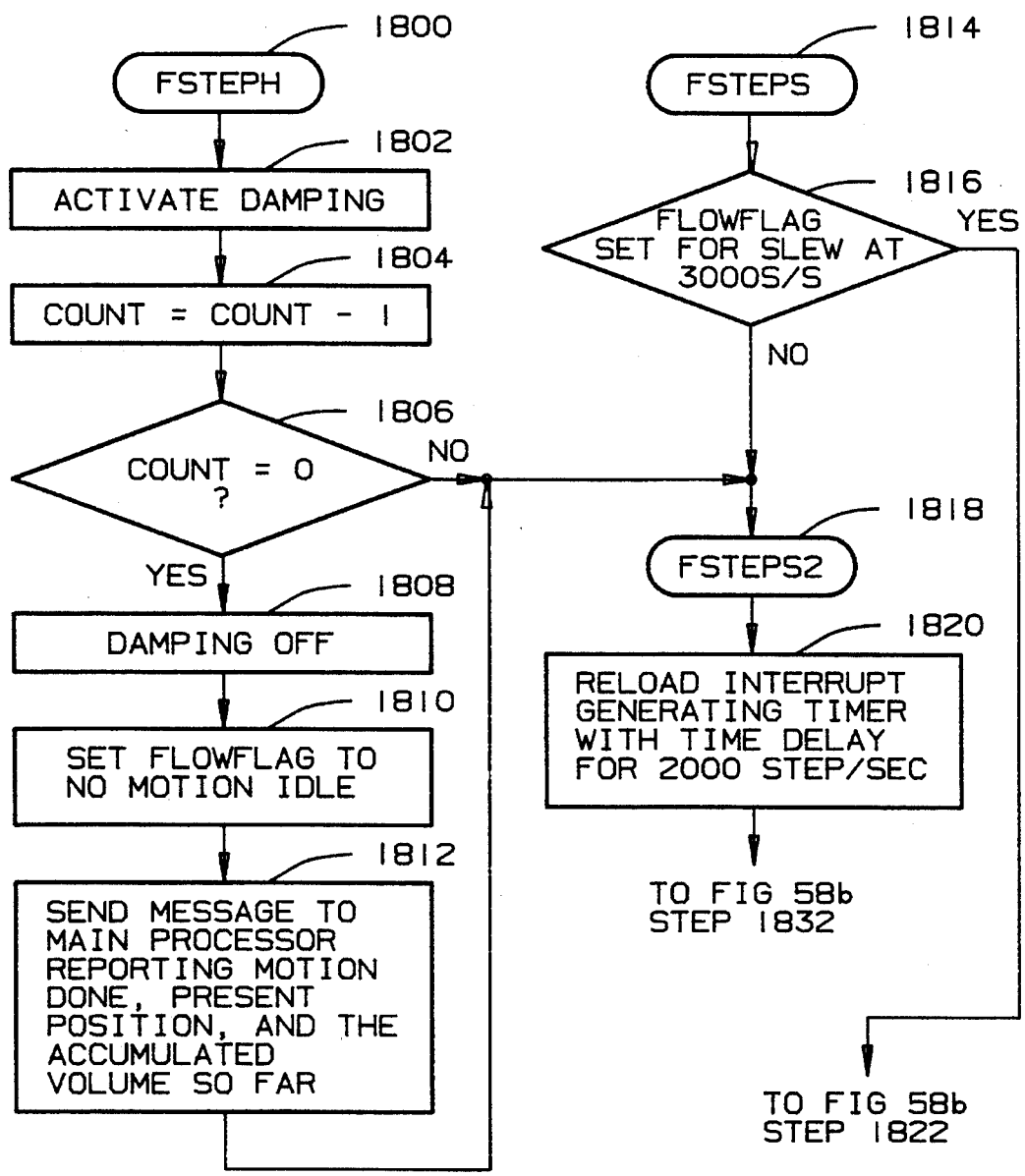
Figure 58B:
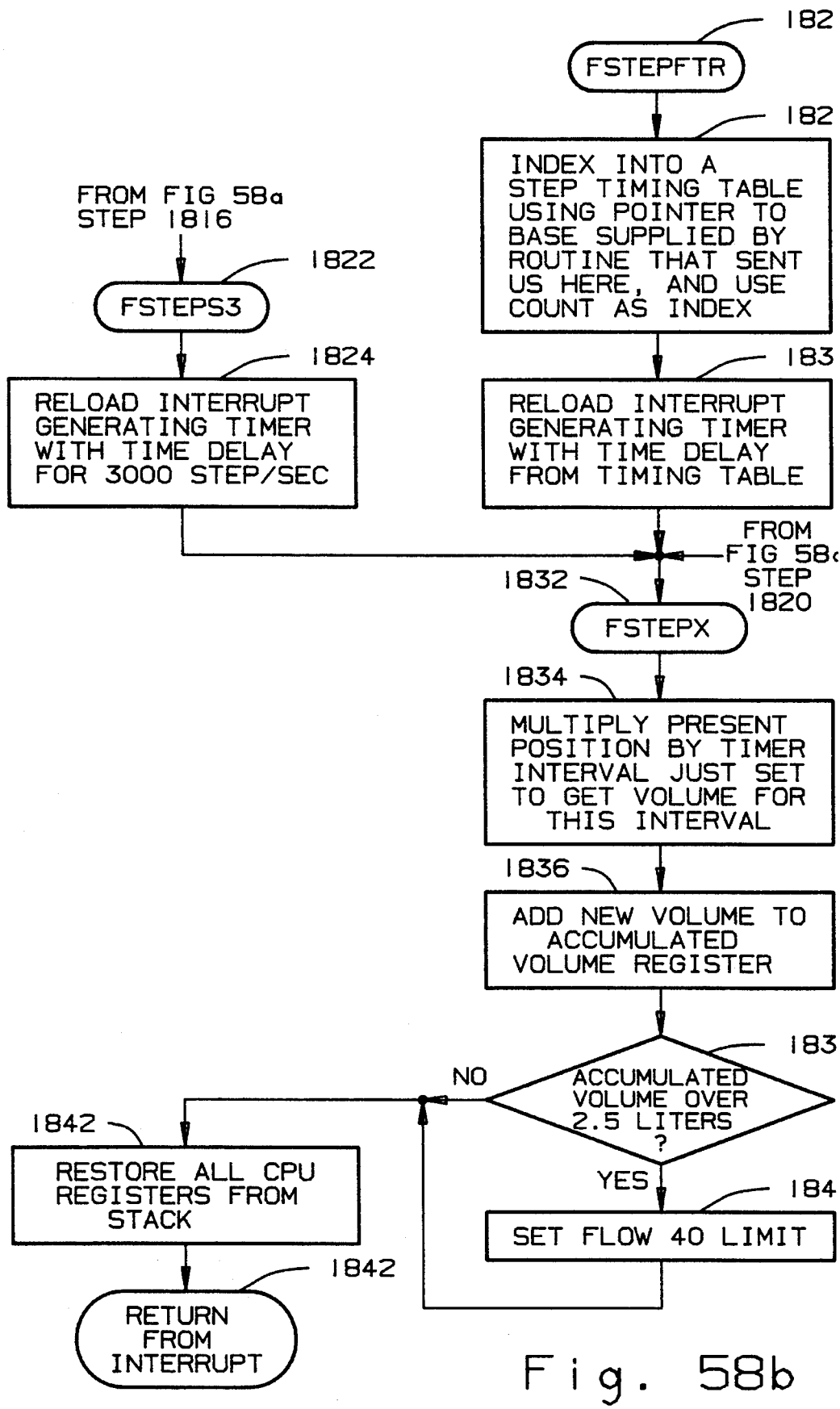

The portion of the program set forth in FIG. 58 performs a number of housekeeping tasks related to the driving of the flow control valve stepping motor. Now referring to FIG. 58, the FSTEPH routine is branched to when the motor is to be held for the ring out delay period. At step 1802, the damping is activated, and then at step 1804 the COUNT variable, which has been previously set to a predetermined number according to the desired ring our delay period, is decremented. Even though the program activates the electronic damping at step 1802, the damping is not used in this embodiment since no damping circuit is attached; however, in the future such a damping circuit could be attached. At step 1806 the COUNT variable is tested to determine if it is zero, indicating that the ring out delay period has elapsed. If it has elapsed, then at step 1808 the electronic damping is turned off and at step 1810 FLOWFLAG is set so that the program will branch to the no motion idle state, in which the stepping motor is not in motion and awaiting another move command from the main processor 188. At step 1812, a message is sent to the main processor indicating that the motor has finished the requested move. The program then branches to step 1820 so that the interrupt-generating timer may be reloaded.

The interrupt-generating timer causes the interrupts during which the motor is moved a single step. By reloading the timer with different numbers, the rate at which the stepping motor is driven is controlled.

The FSTEPS routine shown in FIG. 58 is executed when the stepping motor is in either its 2,000 half steps per second or 3,000 half steps per second slewing mode of operation. At step 1816, the value of FLOWFLAG is compared to determine whether it is set for slewing the motor at 3,000 half steps per second. If so, the program branches to step 1824 at which point the interrupt-generating timer is reloaded with the appropriate time delay to make the motor slew at its 3,000 half steps per second rate. If FLOWFLAG is not set for slewing at 3,000 steps per second as determined at step 1816, the rate must be 2,000 half steps per second, so the program branches to step 1820 at which point the interrupt-generating timer is reloaded with the appropriate time delay to make the motor slew at its 2,000 half steps per second rate. Then from steps 1820 and 1824, the program branches to step 1834 which is explained below.

The FSTEPFTR portion of the program set forth in FIG. 58 is branched to by many of the routines describes above. At step 1828, the FSTEPFTR routine causes the appropriate ramp-up or ramp-down table to be indexed, using the COUNT variable as the index, to retrieve the appropriate time delay for the next step of the motor. At step 1830, the interrupt-generating timer is reloaded with this time delay, and then the program branches to step 1834.

During steps 1834–1840, the accumulated tidal volume is updated. At step 1834, the flow rate corresponding to the present position of the flow control valve is multiplied by the time interval to which the interrupt generating timer has just been set in order to calculate the incremental volume during this step of the motor. At step 1836 this incremental volume is added to the volume already accumulated in the accumulated volume register. At step 1838 the present accumulated volume is tested to determine whether it is over 2.5 liters. If it is, then at step 1840 the flow 40 limit is set, which is the maximum allowable air flow that the ventilator can deliver if a large accumulated volume is present. If the accumulated volume is not over 2.5 liters, then the program branches to step 1842 at which point the contents of the CPU registers are restored from the stack, and the interrupt is terminated at step 1842.

Figure 59:
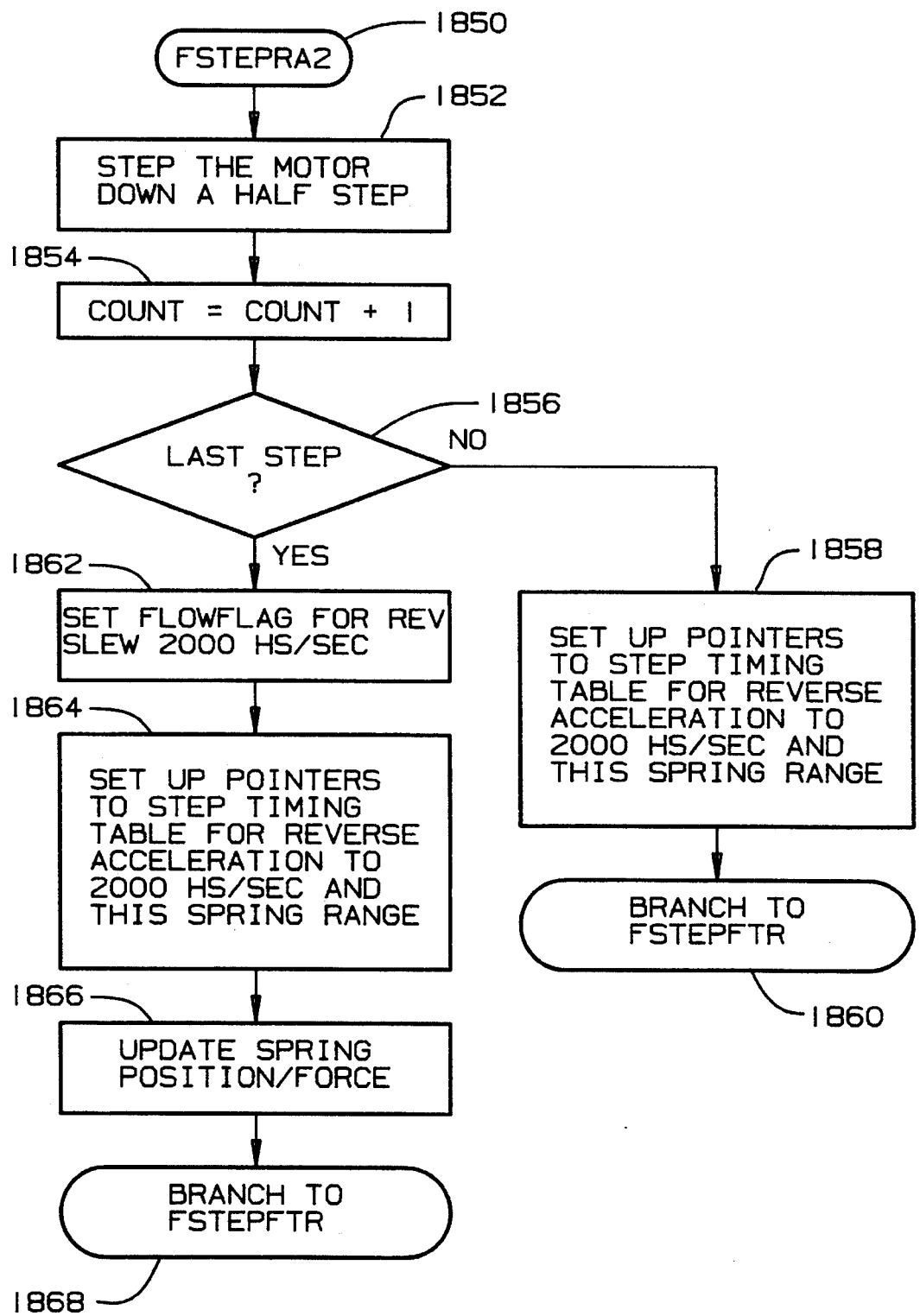

The operation of the program as set forth in FIG. 59 is very similar to the operation as explained in connection with FIG. 52, except that in FIG. 59 the motor is being accelerated to 2000 half steps per second in the reverse direction, which causes the flow control valve 42 to close. Now referring to FIG. 59, at step 1852, the program steps the motor down a half step. Then at step 1854, the count is incremented to keep track of how many steps the motor has been moved while in this FSTEPRA2 routine. This count number is stored in a variable COUNT. At step 1856, the program determines whether the step just moved is the last step in the reverse acceleration sequence by comparing COUNT to the predetermined number of steps in the 2000 step-per-second ramp up profile. If it is not the last step, then at step 1858 the program sets up the table index pointers to retrieve the proper time delay entry from the ramp up table for 2,000 half steps per second and the current spring force range. At step 1860, the program branches to the FSTEPFTR routine shown in FIG. 58. If it is the last step in the reverse acceleration sequence, the program branches to step 1862 at which FLOWFLAG is set to the appropriate hexadecimal number in Table 14 so that the stepping motor will be slewed at 2,000 half steps per second in the reverse direction when the next interrupt is generated. At step 1866, the spring position/force range is updated, depending upon the current position of the flow control valve. The program then branches to the FSTEPFTR routine at step 1868.

Figure 60:
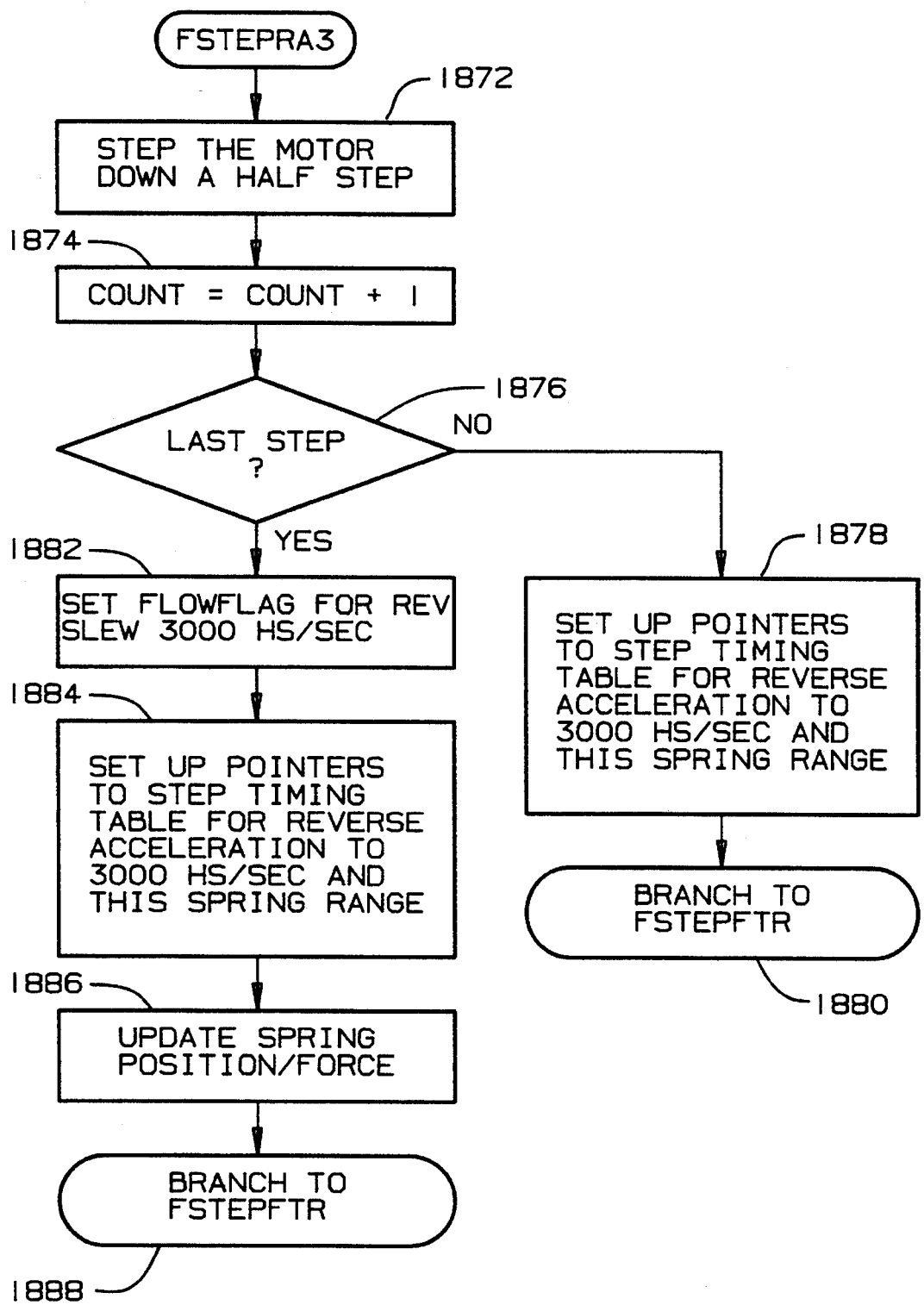

The operation of the program as set forth in FIG. 60 is very similar to the operation as explained in connection with FIG. 59, except that in FIG. 60 the motor is being accelerated to 3000 half steps per second in the reverse direction, which causes the flow control valve 42 to close. Now referring to FIG. 60, at step 1872, the program steps the motor down a half step. Then at step 1874, the count is incremented to keep track of how many steps the motor has been moved while in this FSTEPRA3 routine. This count number is stored in a variable COUNT. At step 1876, the program determines whether the step just moved is the last step in the reverse acceleration sequence by comparing COUNT to the predetermined number of steps in the 3000 step-per-second ramp up profile. If it is not the last step, then at step 1878 the program sets up the table index pointers to retrieve the proper time delay entry from the ramp up table for 3,000 half steps per second and the current spring force range. At step 1880, the program branches to the FSTEPFTR routine shown in FIG. 58. If it is the last step in the reverse acceleration sequence, the program branches to step 1882 at which FLOWFLAG is set to the appropriate hexadecimal number in Table 14 so that the stepping motor will be slewed at 3,000 half steps per second in the reverse direction when the next interrupt is generated. At step 1886, the spring position/force range is updated, depending upon the current position of the flow control valve. The program then branches to the FSTEPFTR routine at step 1888.

Figure 61:
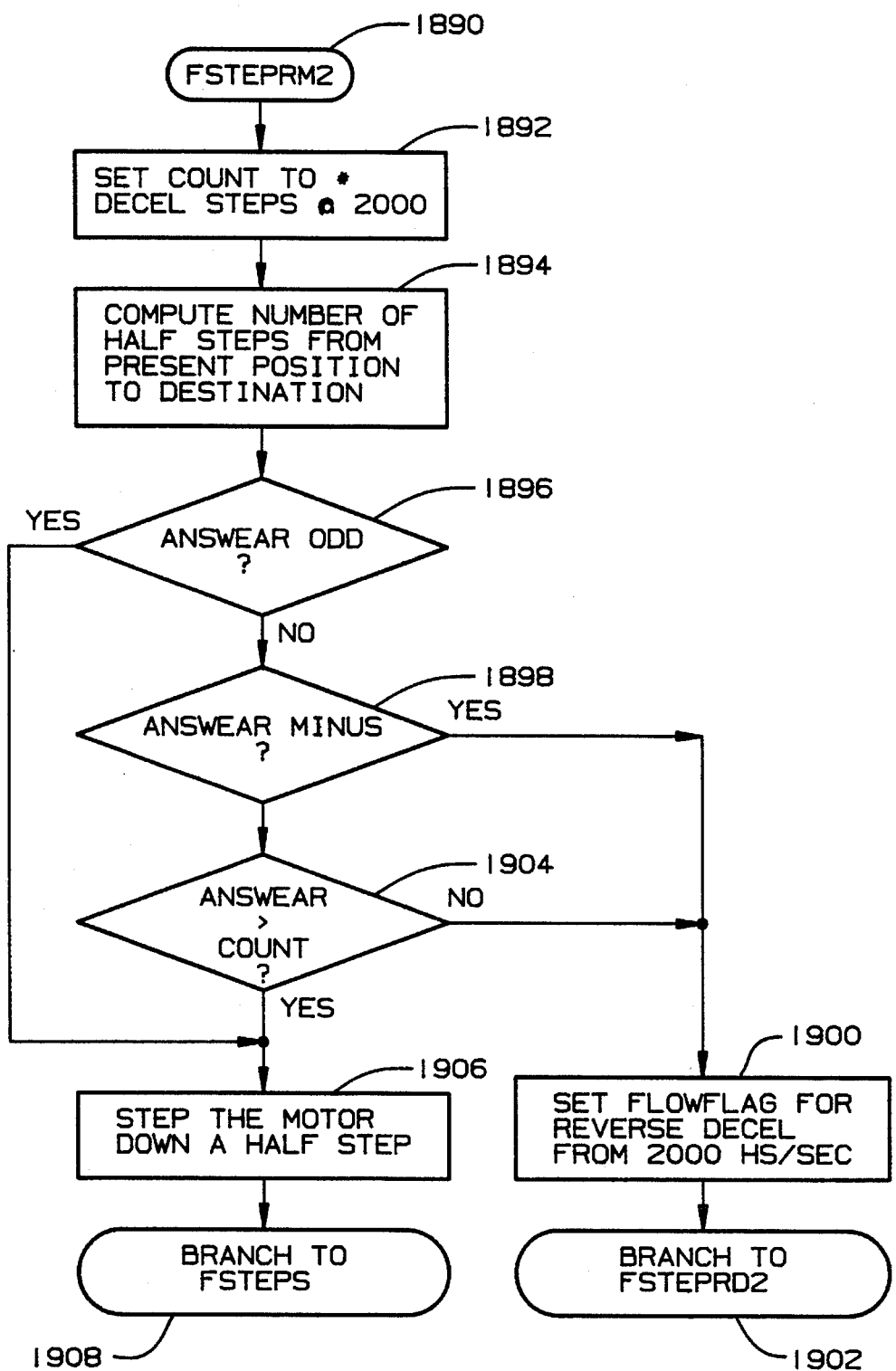

The operation of the FSTEPRM2 routine as set forth in FIG. 61 is very similar to the operation of the FSTEPFM2 routine as explained in connection with FIG. 54, except that in FIG. 61 the motor is slewing at 2000 half steps per second in the reverse direction, which causes the stepping motor 74 to close the flow control valve 42. At step 1892, the variable COUNT is set to the number of steps that are necessary to decelerate the flow control valve motor 74 from the current 2,000 half steps per second rate. Then, at step 1894, the program computes the number of half steps from the present position to the requested destination. If the answer is odd, at step 1896, the program branches to step 1906 at which point the motor is stepped down a half step. If the number of half steps from the present position to the destination is negative as determined at step 1898, the program branches to step 1900 at which point the variable FLOWFLAG is set so that the reverse deceleration state is started, since the stepping motor 74 is past its desired destination. At step 1902, the program branches to the FSTEPRD2 routine. If a positive result is achieved at step 1898, the program branches to step 1904 at which point it determines whether the number of half steps from the present position to the requested destination is greater than the number of steps necessary to decelerate as determined at step 1892 and stored in the COUNT variable. If the answer is yes, then the program branches to step 1906, at which point it steps the motor down one half step and then branches to the FSTEPS routine at step 1908. If the answer is no, then the program branches to step 1900 at which point it sets FLOWFLAG for the reverse deceleration state, and then branches to step 1902.

Figure 62:
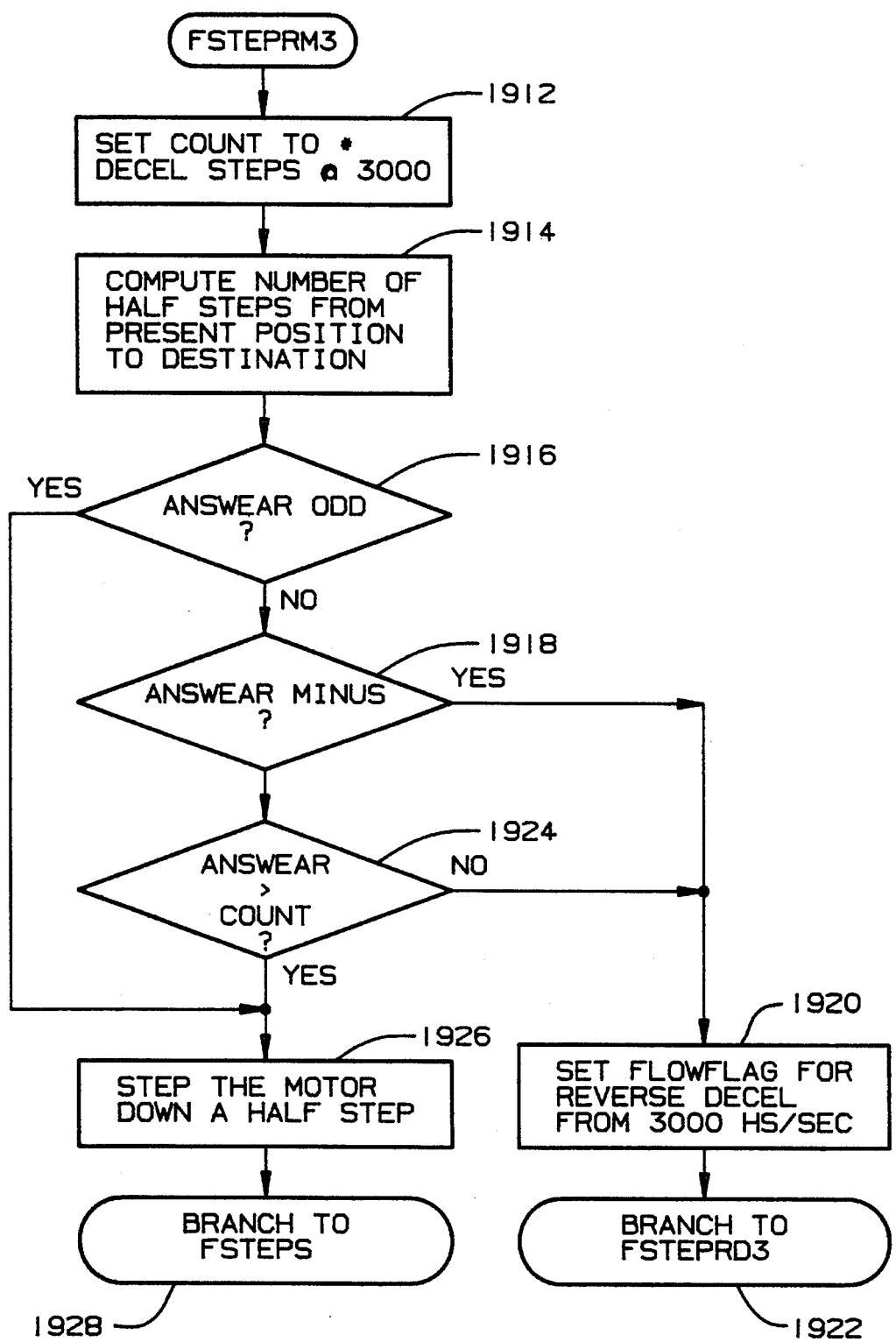

The operation of the FSTEPRM3 routine as set forth in FIG. 62 is very similar to the operation of the FSTEPRM2 routine as explained in connection with FIG. 61, except that in FIG. 62 the motor is being slewed at 3000 half steps per second in the reverse direction. At step 1912, the variable COUNT is set to the number of steps that are necessary to decelerate the flow control valve motor 74 from the current 3,000 half steps per second rate. Then, at step 1914, the program computes the number of half steps from the present position to the requested destination. If the answer is odd, at step 1916, the program branches to step 1926 at which point the motor is stepped down a half step. If the number of half steps from the present position to the destination is negative as determined at step 1918, the program branches to step 1920 at which point the variable FLOWFLAG is set so that the reverse deceleration state is started, since the stepping motor 74 is past its desired destination. At step 1922, the program branches to the FSTEPRD3 routine. If a positive result is achieved at step 1918, the program branches to step 1924 at which point it determines whether the number of half steps from the present position to the requested destination is greater than the number of steps necessary to decelerate as determined at 1912 and stored in the COUNT variable. If the answer is yes, then the program branches to step 1926, at which point it steps the motor down one half step and then branches to the FSTEPS routine at step 1928. If the answer is no, then the program branches to step 1920 at which point it sets FLOWFLAG for the reverse deceleration state, and then branches to step 1922.

Figure 63:
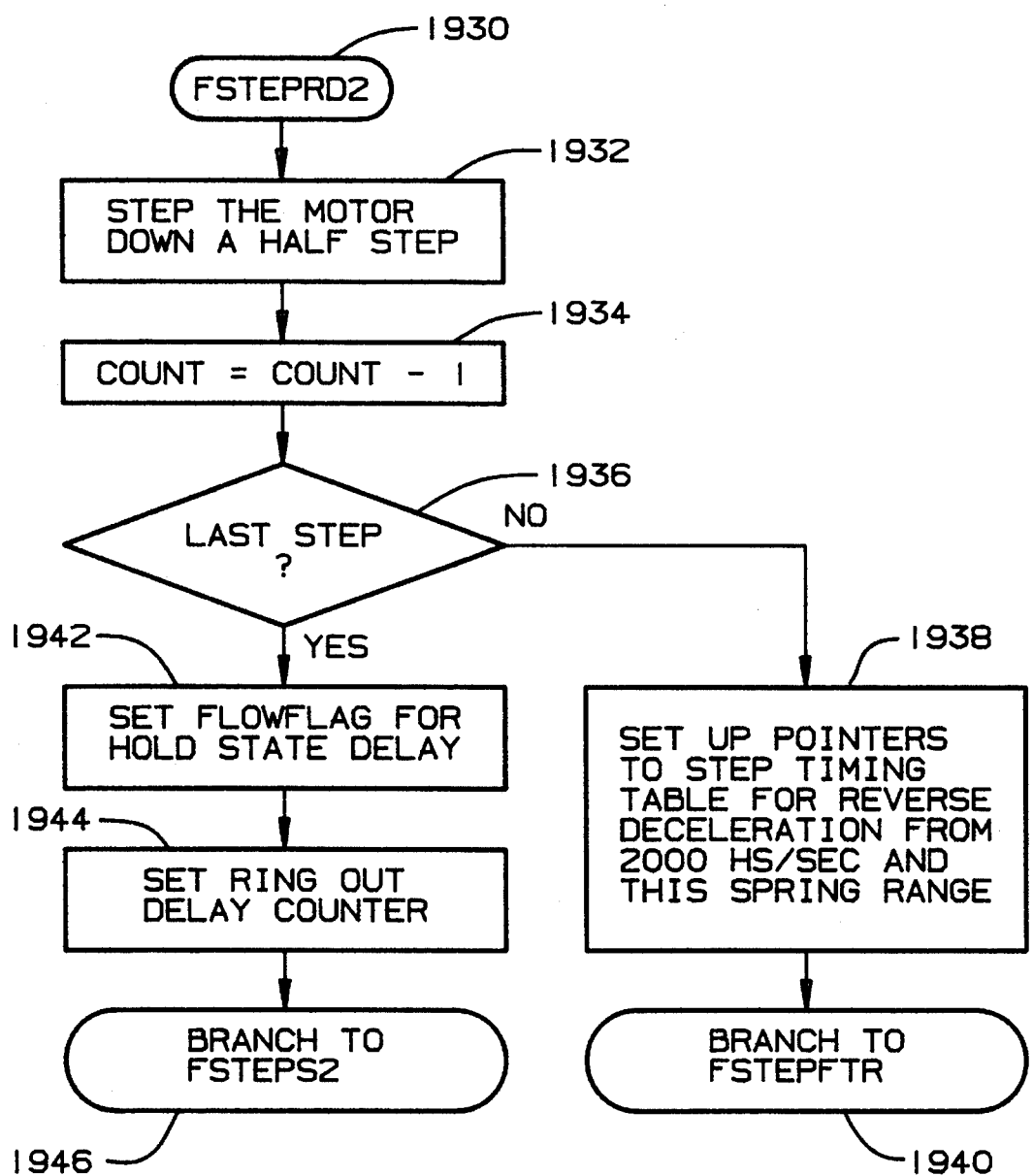

The operation of the FSTEPRD2 routine as set forth in FIG. 63 is very similar to the operation of the FSTEPFD2 as explained in connection with FIG. 56, except that in FIG. 63 the motor is decelerating from 2000 steps per second in the reverse direction, in which case the flow control valve is being closed. At step 1932, the stepping motor is stepped down one half step. Then at step 1934, the variable COUNT is decremented since there is one less half step to be moved in this FSTEPRD2 routine. Then at step 1936, the program determines whether it is the last step in the deceleration sequence. If it is, when the FLOWFLAG variable is set for the hold state delay at step 1942, and at step 1944, the delay ring-out counter is set so that any oscillations of the stepping motor 74 will die out before the motor is attempted to be driven again. If it is not the last step in the deceleration sequence as determined at step 1936, the program branches to step 1938 at which point the program sets up the pointers to the step timing table for the reverse deceleration from 2,000 half steps per second and the appropriate spring force range stored in the variable FSPRING. At step 1940, the program branches to the FSTEPFTR routine.

Figure 64:
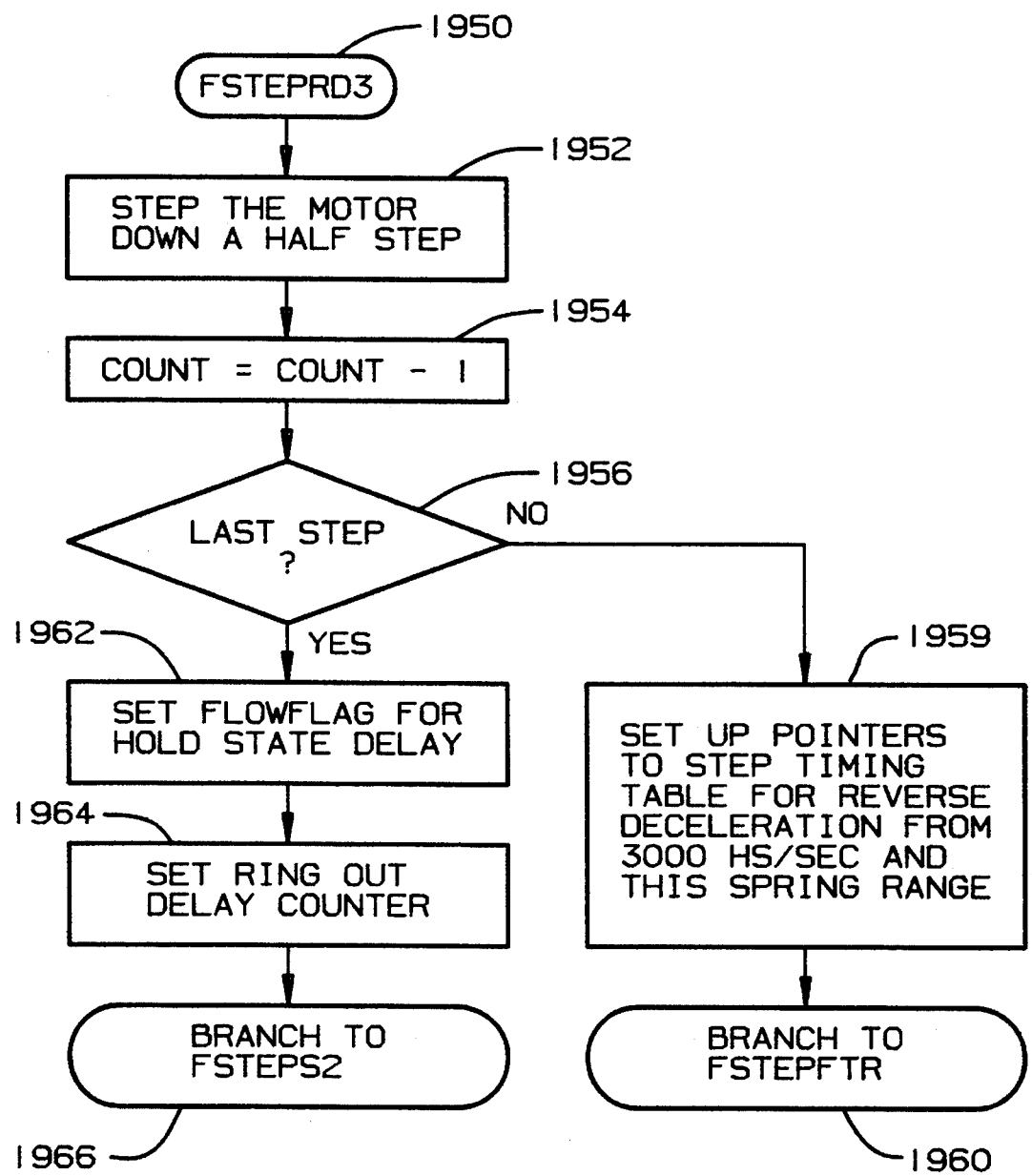

The operation of the FSTEPRD3 routine as set forth in FIG. 64 is very similar to the operation of the FSTEPRD2 routine as explained in connection with FIG. 63, except that in FIG. 64 the motor is decelerating from 3000 half steps per second. At step 1952, the stepping motor is stepped down one half step. Then at step 1954, the variable COUNT is decremented since there is one less half step to be moved in this FSTEPRD3 routine. Then at step 1956, the program determines whether it is the last step in the deceleration sequence. If it is, then the FLOWFLAG variable is set for the hold state delay at step 1962, and at step 1964, the delay ring-out counter is set so that any oscillations of the stepping motor 74 will die out before the motor is attempted to be driven again. If it is not the last step in the deceleration sequence as determined at step 1956, the program branches to step 1959 at which point the program sets up the pointers to the step timing table for the reverse deceleration from 3,000 half steps per second and the appropriate spring force range stored in the variable FSPRING. At step 1960, the program branches to the FSTEPFTR routine.

Figure 65:
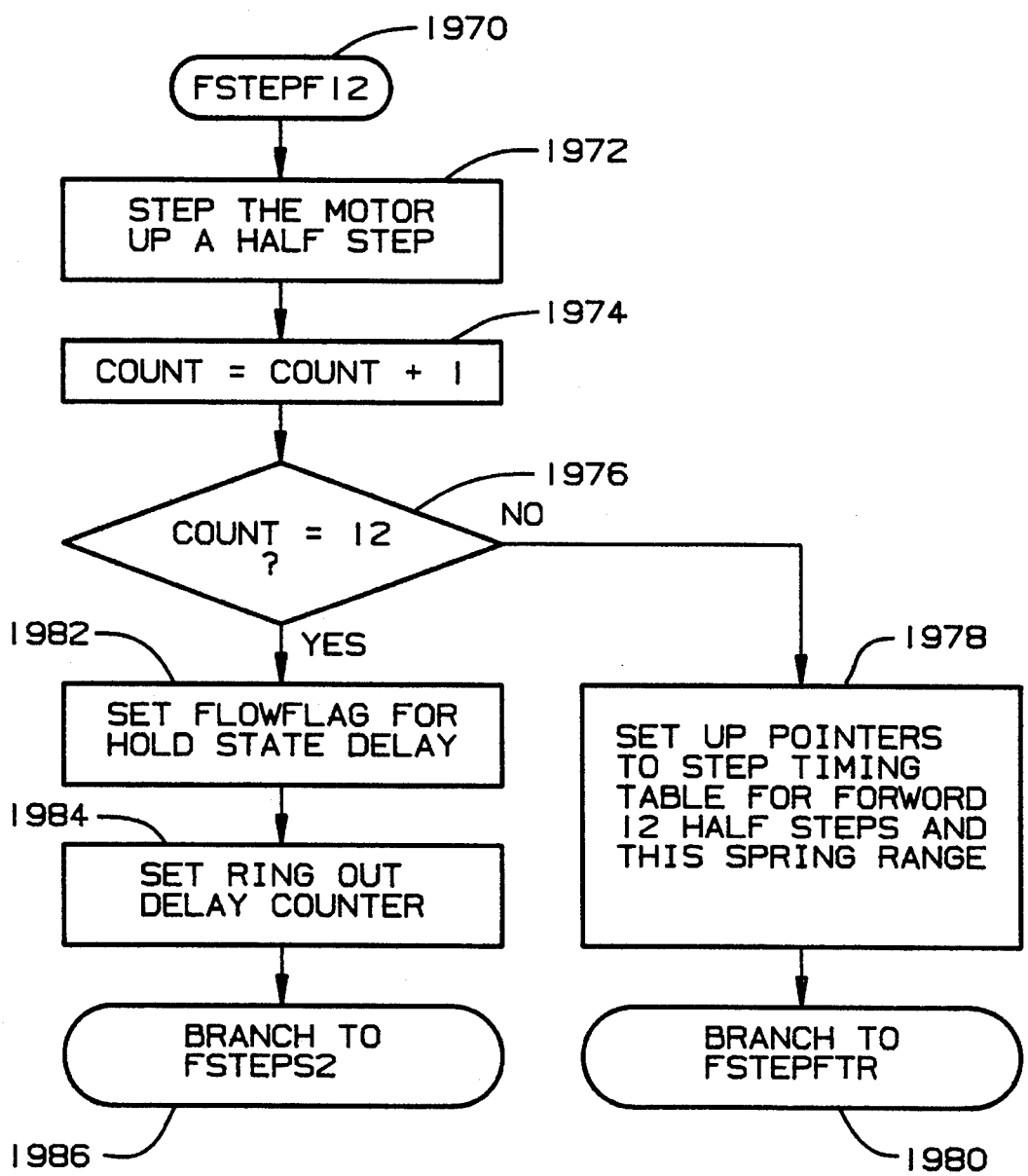

A detailed flow chart of the FSTEPF12 routine is shown in FIG. 65. When executed, this routine causes the flow control valve stepping motor to be driven 12 steps in the forward direction, which causes the flow control valve to be opened by 12 steps. Now referring to FIG. 65, at step 1972 the stepping motor 74 is stepped up one half step. Then, at step 1974 the variable COUNT is incremented since one more of the 12 steps to be moved in this routine has just been moved. At step 1976, the count stored in the COUNT variable is compared with the number 12 to determine whether the motor has been driven 12 steps as has been requested. If the motor has been moved 12 steps, then the program branches to step 1982 at which point the FLOWFLAG variable is set appropriately to cause the program to enter the hold state, which causes the motor to be held in place at its current position. Then at step 1984, the delay ring-out counter is set so that any oscillations of the stepping motor 74 will die out before the motor is attempted to be driven again. At step 1986, the program then branches to the FSTEPS2 routine. If the COUNT variable is not equal to 12, indicating that it is not the last step in the 12-step sequence, as determined at step 1976, the program branches to step 1978 at which point the program sets up the pointers to the step timing table for the 12-forward-half-step sequence and the appropriate spring force range stored in the variable FSPRING. Then, at step 1980 the program branches to the FSTEPFTR routine.

Figure 66:
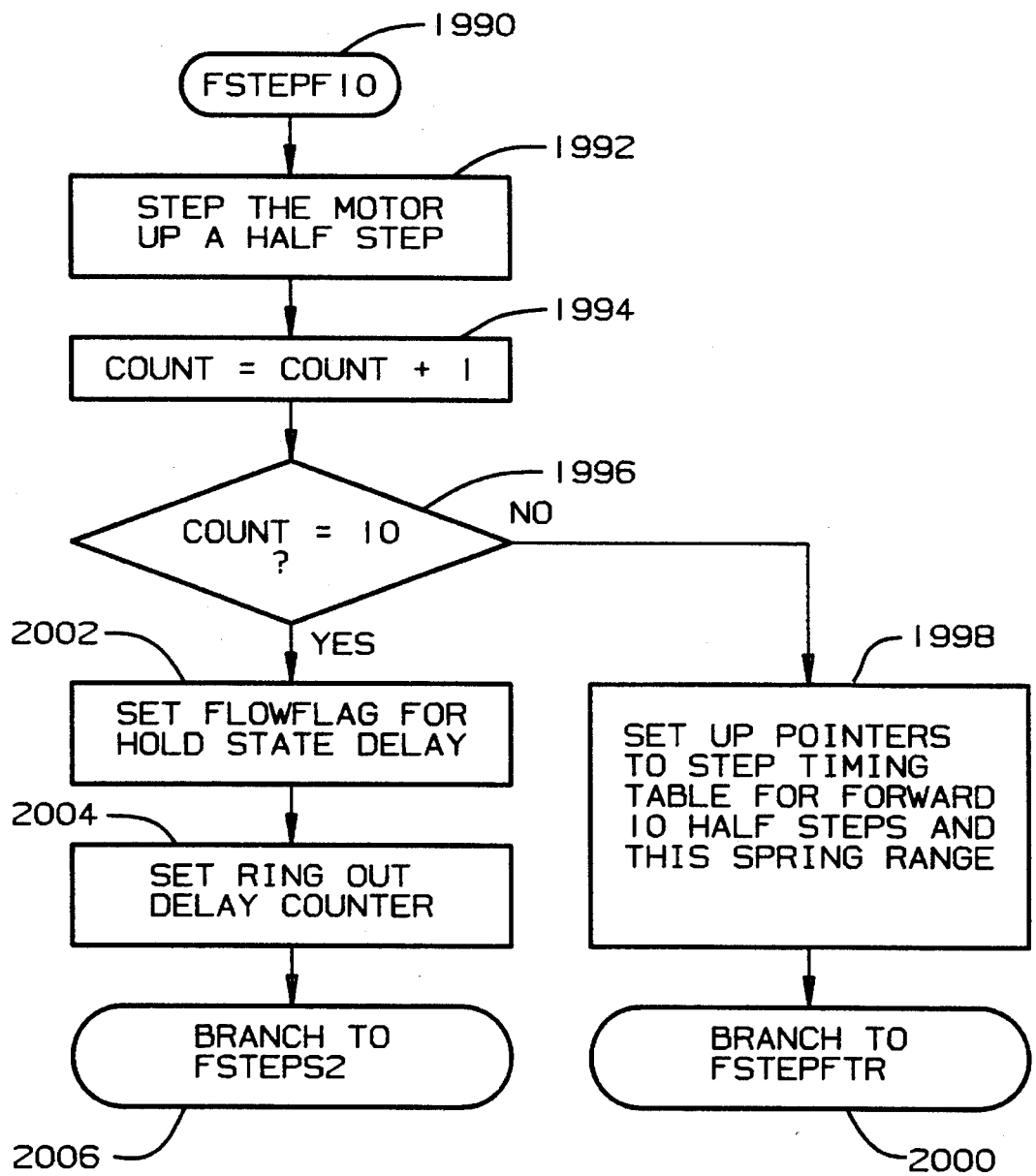

The operation of the FSTEPF10 routine as set forth in FIG. 66 is very similar to the operation of the FSTEPF12 routine explained in connection with FIG. 65, except that in FIG. 66 the motor is being driven a total of 10 steps in the forward direction. Now referring to FIG. 66, at step 1992 the stepping motor 74 is stepped up one half step. Then, at step 1994 the variable COUNT is incremented since one more of the 10 steps to be moved in this routine has just been moved. At step 1996, the count stored in the COUNT variable is compared with the number 10 to determine whether the motor has been driven 10 steps as has been requested. If the motor has been moved 10 steps, then the program branches to step 2002 at which point the FLOWFLAG variable is set appropriately to cause the program to enter the hold state, which causes the motor to be held in place at its current position. Then at step 2004, the delay ring-out counter is set so that any oscillations of the stepping motor 74 will die out before the motor is attempted to be driven again. At step 2006, the program then branches to the FSTEPS2 routine. If the COUNT variable is not equal to 10, indicating that it is not the last step in the 10-step sequence, as determined at step 1996, the program branches to step 1998 at which point the program sets up the pointers to the step timing table for the 10-forward-half-step sequence and the appropriate spring force range stored in the variable FSPRING. Then, at step 2000 the program branches to the FSTEPFTR routine.

Figure 67:
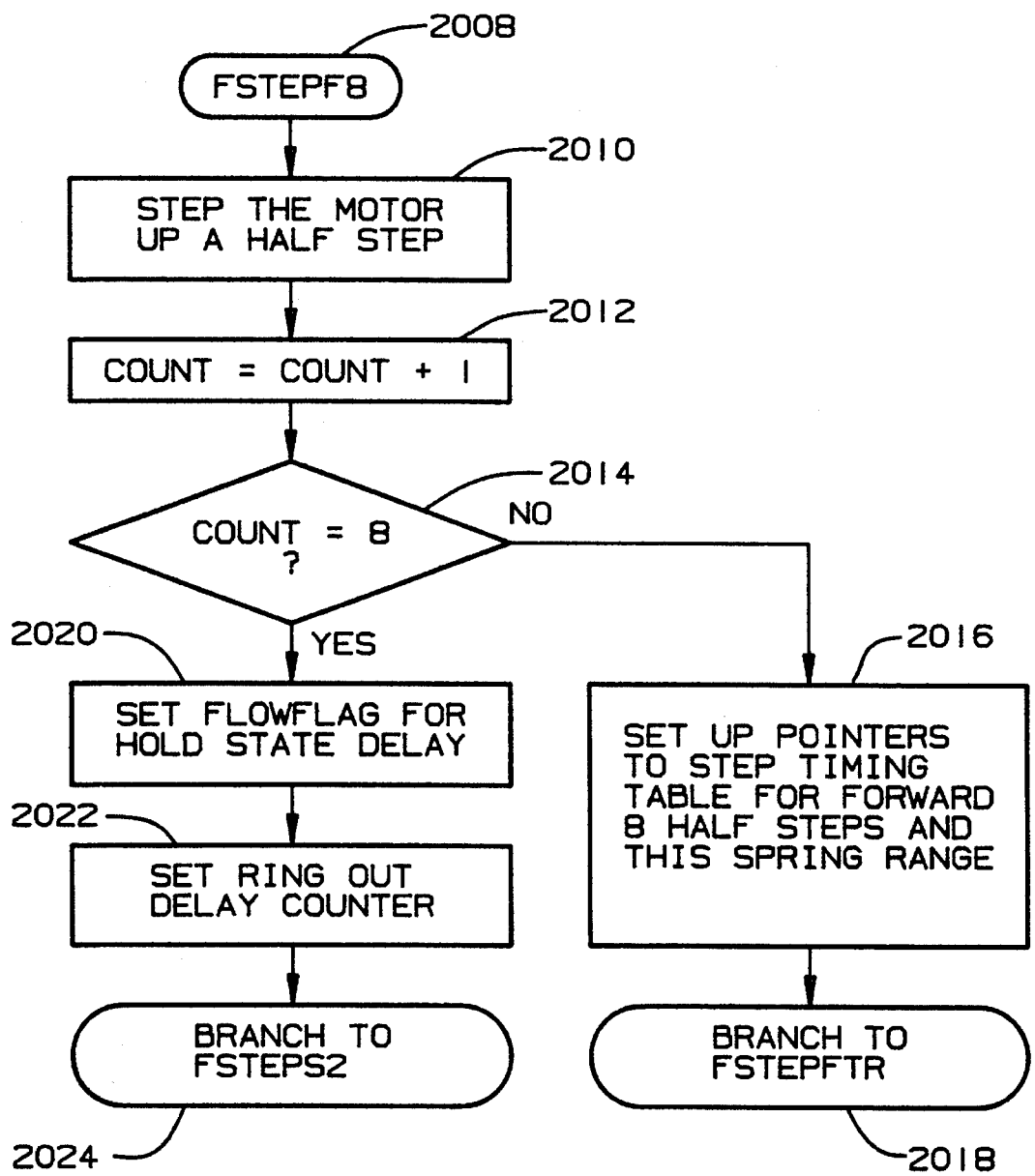

The operation of the FSTEPF8 routine as set forth in FIG. 67 is very similar to the operation of the FSTEPF12 routine explained in connection with FIG. 65, except that in FIG. 67 the motor is being driven a total of 8 steps in the forward direction. A detailed flow chart of the FSTEPF8 routine is shown in FIG. 67. When executed, this routine causes the flow control valve stepping motor to be driven eight steps in the forward direction, which causes the flow control valve to be opened by eight steps. Now referring to FIG. 67, at step 2010 the stepping motor 74 is stepped up one half step. Then, at step 2012 the variable COUNT is incremented since one more of the eight steps to be moved in this routine has just been moved. At step 2014, the count stored in the COUNT variable is compared with the number eight to determine whether the motor has been driven eight steps as has been requested. If the motor has been moved eight steps, then the program branches to step 2020 at which point the FLOWFLAG variable is set appropriately to cause the program to enter the hold state, which causes the motor to be held in place at its current position. Then at step 2022, the delay ring-out counter is set so that any oscillations of the stepping motor 74 will die out before the motor is attempted to be driven again. At step 2024, the program then branches to the FSTEPS2 routine. If the COUNT variable is not equal to eight, indicating that it is not the last step in the 8-step sequence as determined at step 2014, the program branches to step 2016 at which point the program sets up the pointers to the step timing table for the 8-forward-half-step sequence and the appropriate spring force range stored in the variable FSPRING. Then, at step 2018 the program branches to the FSTEPSFTR routine.

Figure 68:
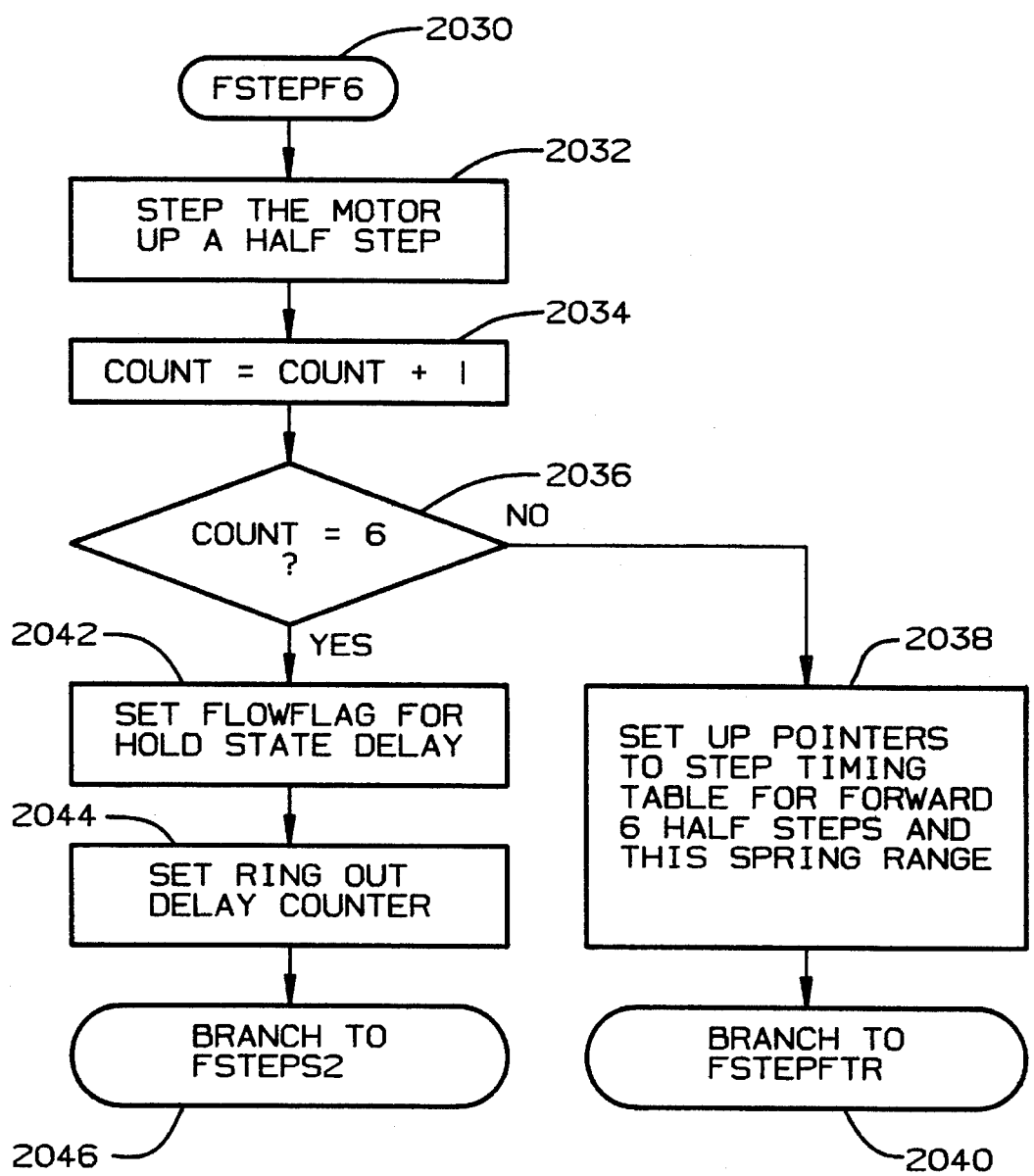

The operation of the FSTEPF6 routine as set forth in FIG. 68 is very similar to the operation of the FSTEPF12 routine explained in connection with FIG. 65, except that in FIG. 68 the motor is being driven a total of six steps in the forward direction. Now referring to FIG. 68, at step 2032 the stepping motor 74 is stepped up one half step. Then, at step 2034 the variable COUNT is incremented since one more of the six steps to be moved in this routine has just been moved. At step 2036, the count stored in the COUNT variable is compared with the number six to determine whether the motor has been driven six steps as has been requested. If the motor has been moved six steps, then the program branches to step 2042 at which point the FLOWFLAG variable is set appropriately to cause the program to enter the hold state, which causes the motor to be held in place at its current position. Then at step 2044, the delay ring-out counter is set so that any oscillations of the stepping motor 74 will die out before the motor is attempted to be driven again. At step 2046, the program then branches to the FSTEPS2 routine. If the COUNT variable is not equal to six, indicating that it is not the last step in the 6-step sequence, as determined at step 2036, the program branches to step 2038 at which point the program sets up the pointers to the step timing table for the 6-forward-half-step sequence and the appropriate spring force range stored in the variable FSPRING. Then, at step 2040 the program branches to the FSTEPFTR routine.

Figure 69:
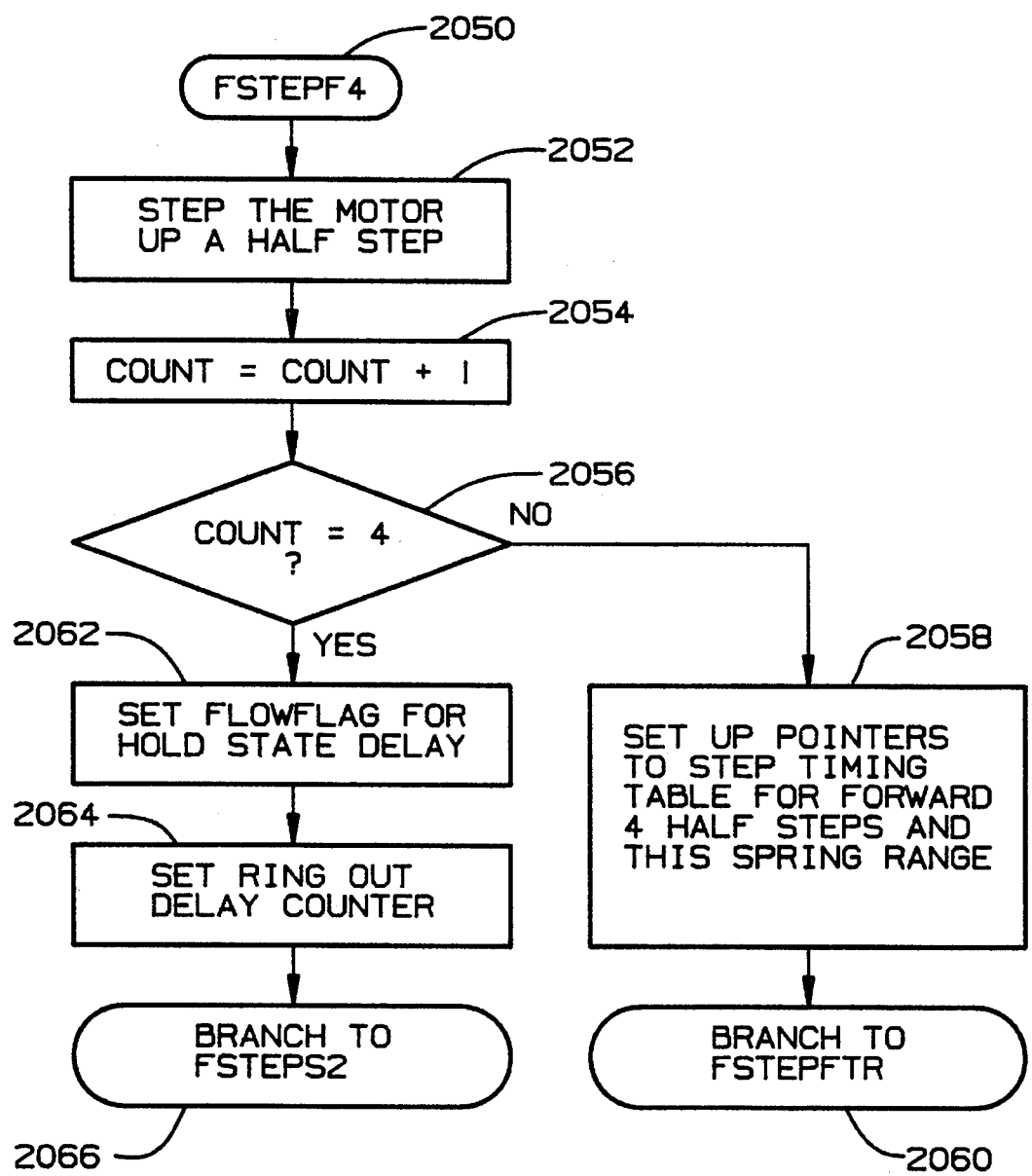

The operation of the FSTEPF4 routine as set forth in FIG. 69 is very similar to the operation of the FSTEPF12 routine explained in connection with FIG. 65, except that in FIG. 69 the motor is being driven a total of four steps in the forward direction. Now referring to FIG. 69, at step 2052 the stepping motor 74 is stepped up one half step. Then, at step 2054 the variable COUNT is incremented since one more of the four steps to be moved in this routine has just been moved. At step 2056, the count stored in the COUNT variable is compared with the number four to determine whether the motor has been driven four steps as has been requested. If the motor has been moved four steps, then the program branches to step 2062 at which point the FLOWFLAG variable is set appropriately to cause the program to enter the hold state, which causes the motor to be held in place at its current position. Then at step 2064, the delay ring-out counter is set so that any oscillations of the stepping motor 74 will die out before the motor is attempted to be driven again. At step 2066, the program then branches to the FSTEPS2 routine. If the COUNT variable is not equal to four, indicating that it is not the last step in the 4-step sequence, as determined at step 2056, the program branches to step 2058 at which point the program sets up the pointers to the step timing table for the 4-forward-half-step sequence and the appropriate spring force range stored in the variable FSPRING. Then, at step 2060 the program branches to the FSTEPFTR routine.

Figure 70:
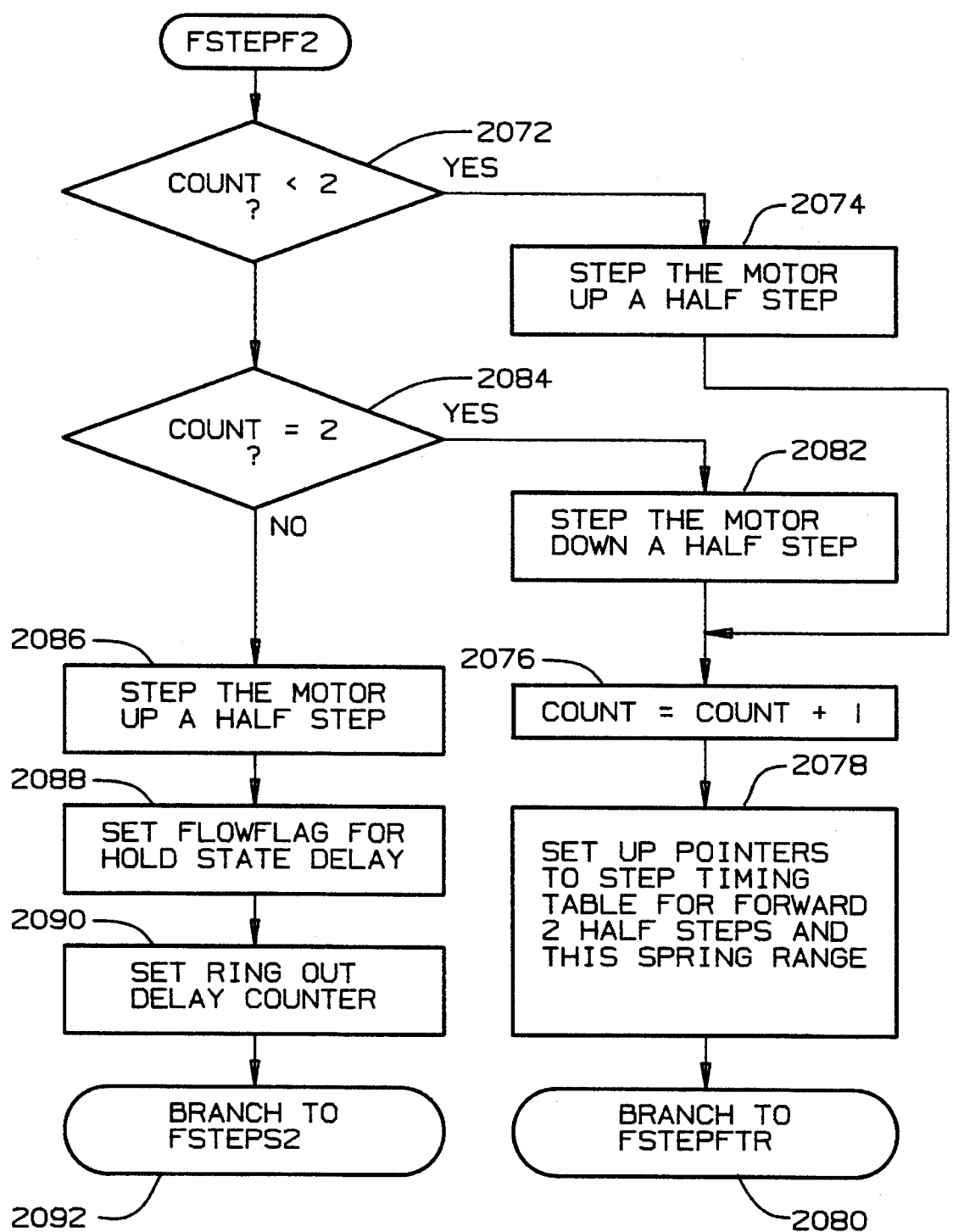

The FSTEPF2 routine, a detailed flow chart of which is shown in FIG. 70, causes the stepping motor for the flow control valve to be moved when the where the motor is to be moved two half steps. At step 2072, the variable COUNT is tested to determine whether it is less than two. If it is, then the program branches to step 2074 at which point the motor is stepped up one half step, and then the program branches to step 2076. If the value of COUNT is not less than two, then the program branches to step 2084 at which point the value of COUNT is tested to determine whether it is equal to two. If it is, then the program branches to step 2082 at which point the motor is given an excitation tending to move the motor down, although the motor does not actually move one half step down. Such a reverse excitation is conventional, and is described in detail in U.S. Pat. No. 4,600,868 to Bryant, the disclosure of which is incorporated herein by reference. If COUNT is not equal to two, then the program branches to step 2086 at which point the motor is stepped up one half step. At step 2088, then value of FLOWFLAG is set to the appropriate value so that the next state will be the hold state. At step 2090, the ring out delay counter is set, and at step 2092 the program branches to the FSTEPS2 routine. If the program branched to step 2076, then at this step COUNT is incremented, and then at step 2078 the pointers to the step timing table for the two half steps forward mode and the appropriate spring force range are set up. Finally, at step 2080, the program branches to the FSTEPFTR routine.

Figure 71:
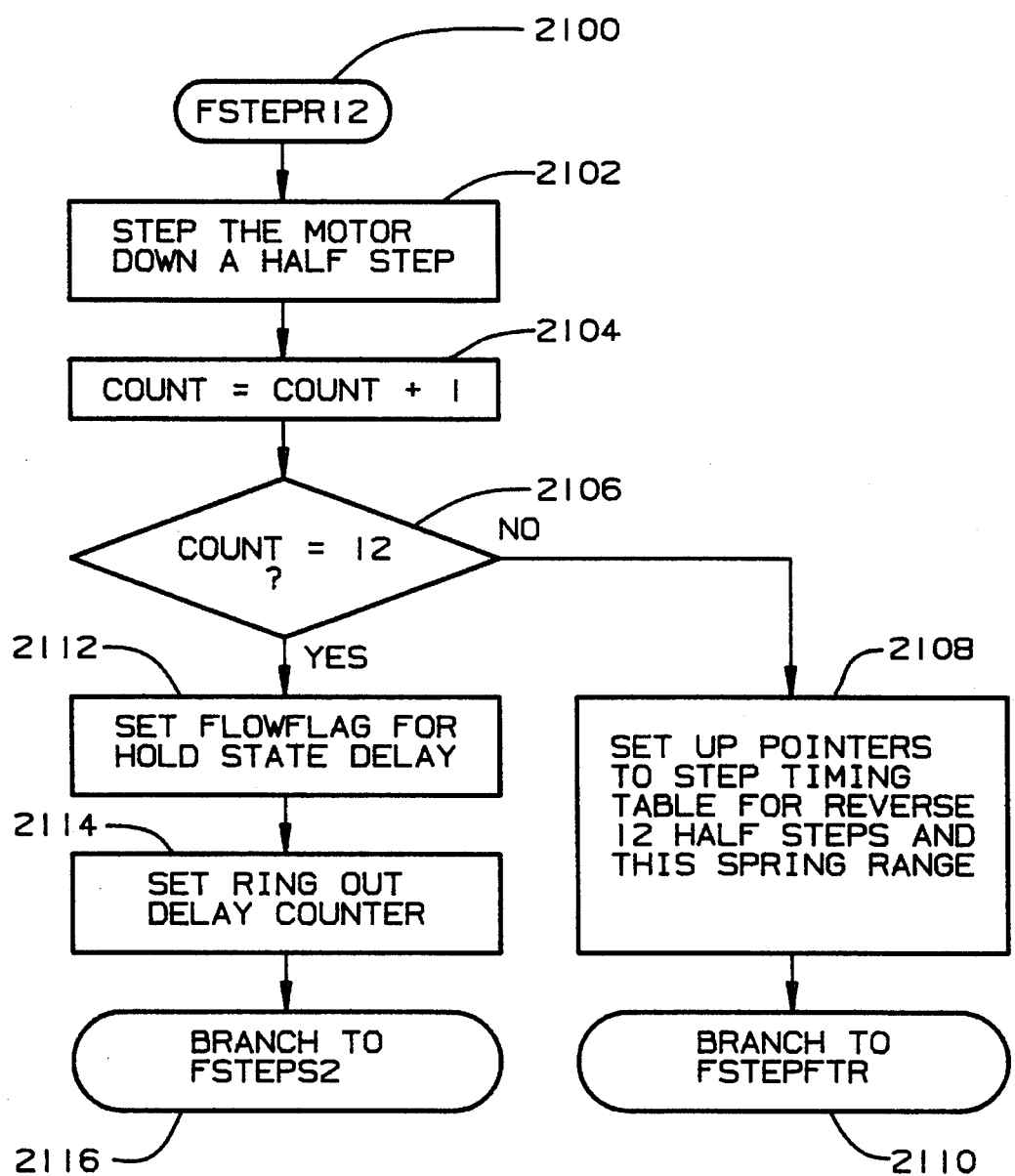

A detailed flow chart of the FSTEPR12 routine is shown in FIG. 71. When executed, this routine causes the flow control valve stepping motor to be driven 12 steps in the reverse direction, which causes the flow control valve to be closed by 12 steps. Now referring to FIG. 71, at step 2102 the stepping motor 74 is stepped down one half step. Then, at step 2104 the variable COUNT is incremented since one more of the 12 steps to be moved in this routine has just been moved. At step 2106, the count stored in the COUNT variable is compared with the number 12 to determine whether the motor has been driven 12 steps as has been requested. If the motor has been moved 12 steps, then the program branches to step 2112 at which point the FLOW-FLAG variable is set appropriately to cause the program to enter the hold state, which causes the motor to be held in place at its current position. Then at step 2114, the delay ring-out counter is set so that any oscillations of the stepping motor 74 will die out before the motor is attempted to be driven again. At step 2116, the program then branches to the FSTEPS2 routine. If the COUNT variable is not equal to 12, indicating that it is not the last step in the 12-step sequence, as determined at step 2106, the program branches to step 2108 at which point the program sets up the pointers to the step timing table for the 12-reverse-half-step sequence and the appropriate spring force range stored in the variable FSPRING. Then, at step 2110 the program branches to the FSTEPFTR routine.

Figure 72:
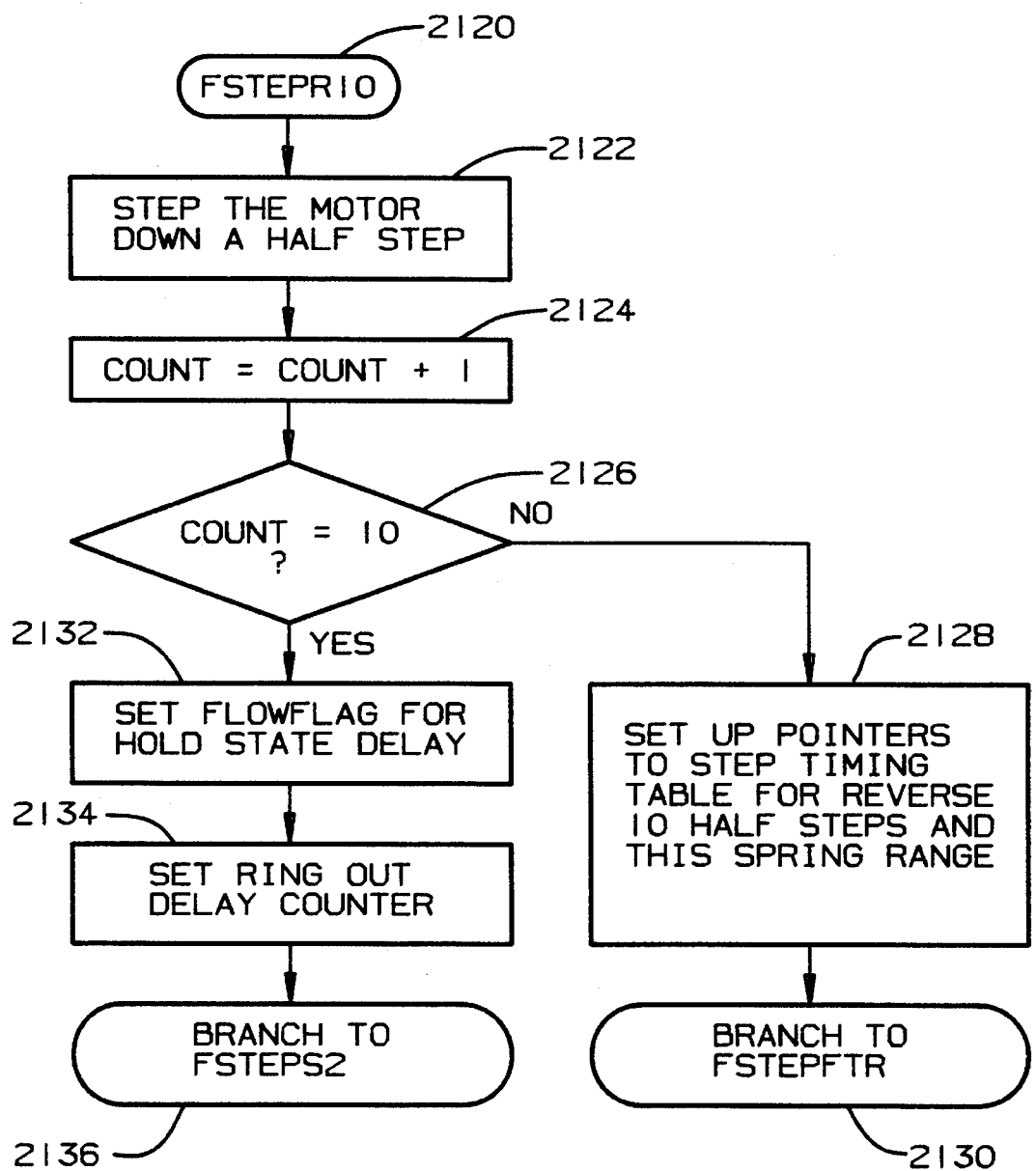

The operation of the FSTEPR10 routine as set forth in FIG. 72 is very similar to the operation of the FSTEPR12 routine explained in connection with FIG. 71, except that in FIG. 72 the motor is being driven a total of ten steps in the reverse direction. Now referring to FIG. 72, at step 2122 the stepping motor 74 is stepped down one half step. Then, at step 2124 the variable COUNT is incremented since one more of the 12 steps to be moved in this routine has just been moved. At step 2126, the count stored in the COUNT variable is compared with the number 10 to determine whether the motor has been driven 10 steps as has been requested. If the motor has been moved 10 steps, then the program branches to step 2132 at which point the FLOW-FLAG variable is set appropriately to cause the program to enter the hold state, which causes the motor to be held in place at its current position. Then at step 2134, the delay ring-out counter is set so that any oscillations of the stepping motor 74 will die out before the motor is attempted to be driven again. At step 2136, the program then branches to the FSTEPS2 routine. If the COUNT variable is not equal to 10, indicating that it is not the last step in the 10-step sequence, as determined at step 2126, the program branches to step 2128 at which point the program sets up the pointers to the step timing table for the 10-reverse-half-step sequence and the appropriate spring force range stored in the variable FSPRING. Then, at step 2130 the program branches to the FSTEPFTR routine.

Figure 73:
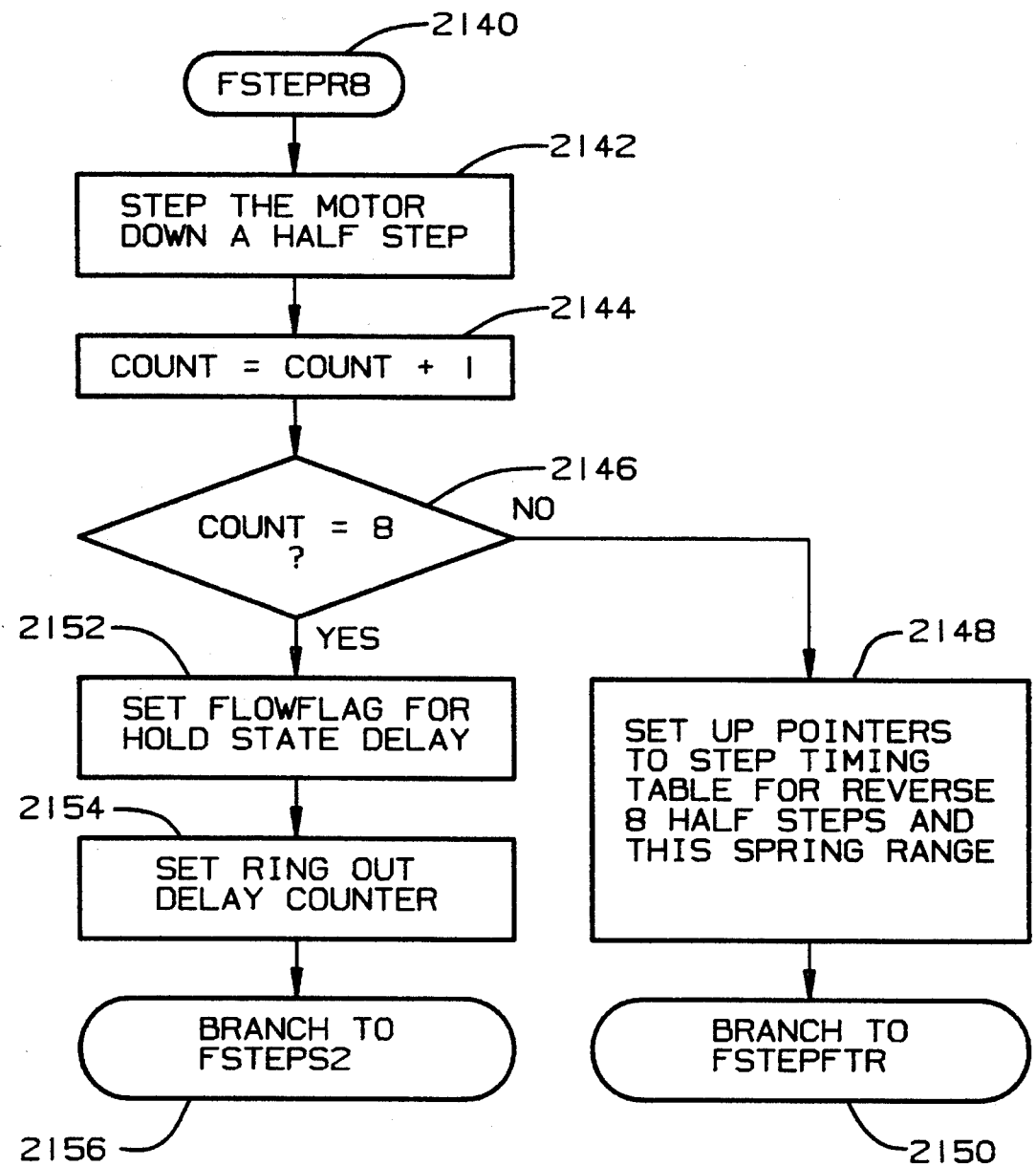

The operation of the FSTEPR8 routine as set forth in FIG. 73 is very similar to the operation of the FSTEPR12 routine explained in connection with FIG. 71, except that in FIG. 73 the motor is being driven a total of eight steps in the reverse direction. Now referring to FIG. 73, at step 2142 the stepping motor 74 is stepped down one half step. Then, at step 2144 the variable COUNT is incremented since one more of the eight steps to be moved in this routine has just been moved. At step 2146, the count stored in the COUNT variable is compared with the number eight to determine whether the motor has been driven eight steps as has been requested. If the motor has been moved eight steps, then the program branches to step 2152 at which point the FLOW-FLAG variable is set appropriately to cause the program to enter the hold state, which causes the motor to be held in place at its current position. Then at step 2154, the delay ring-out counter is set so that any oscillations of the stepping motor 74 will die out before the motor is attempted to be driven again. At step 2156, the program then branches to the FSTEPS2 routine. If the COUNT variable is not equal to eight, indicating that it is not the last step in the 8-step sequence, as determined at step 2146, the program branches to step 2148 at which point the program sets up the pointers to the step timing table for the 8-reverse-half-step sequence and the appropriate spring force range stored in the variable FSPRING. Then, at step 2150 the program branches to the FSTEPFTR routine.

Figure 74:
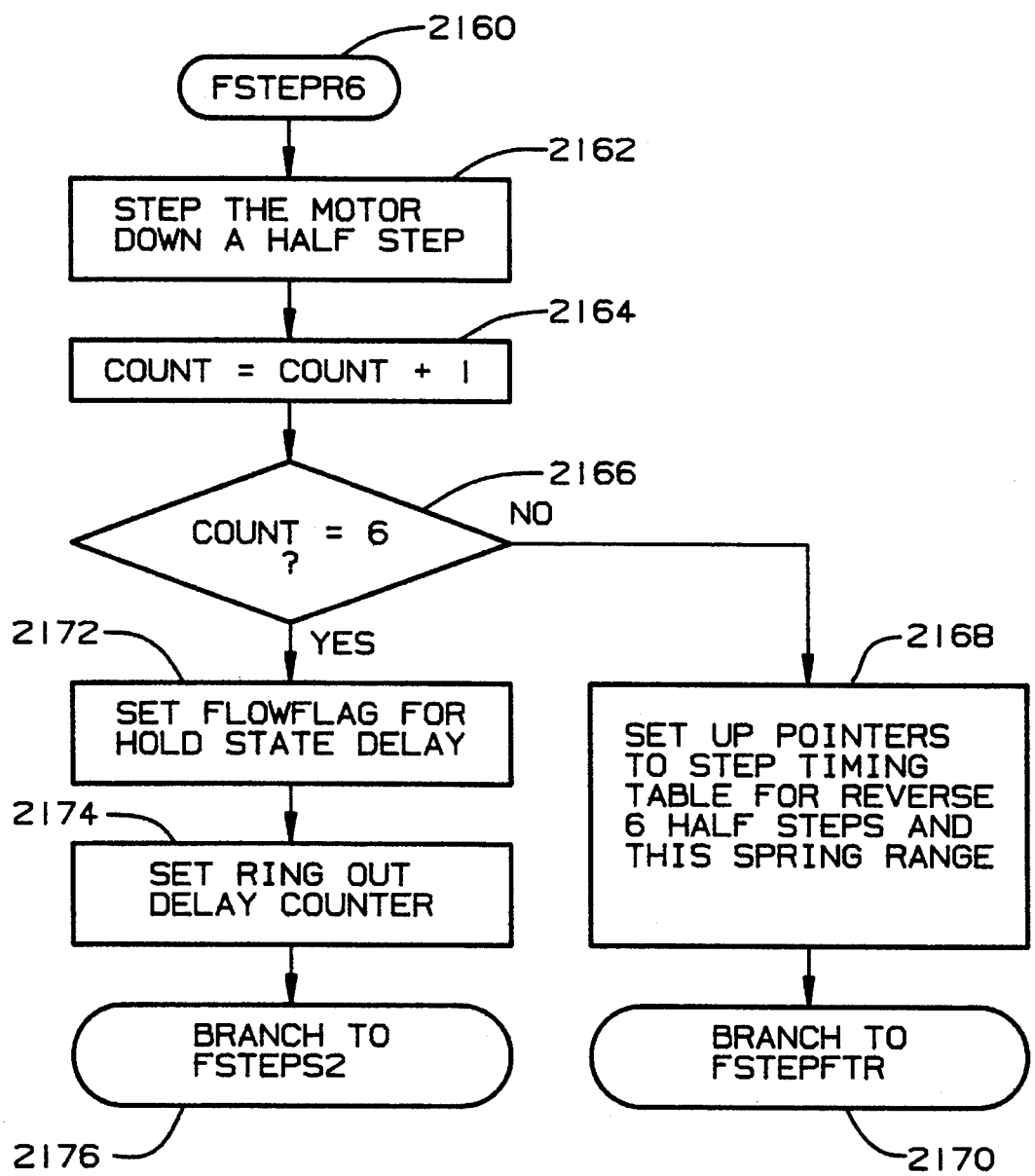

The operation of the FSTEPR6 routine as set forth in FIG. 74 is very similar to the operation of the FSTEPR12 routine explained in connection with FIG. 71, except that in FIG. 74 the motor is being driven a total of six steps in the reverse direction. Now referring to FIG. 74, at step 2162 the stepping motor 74 is stepped down one half step. Then, at step 2164 the variable COUNT is incremented since one more of the six steps to be moved in this routine has just been moved. At step 2166, the count stored in the COUNT variable is compared with the number six to determine whether the motor has been driven six steps as has been requested. If the motor has been moved six steps, then the program branches to step 2172 at which point the FLOW-FLAG variable is set appropriately to cause the program to enter the hold state, which causes the motor to be held in place at its current position. Then at step 2174, the delay ring-out counter is set so that any oscillations of the stepping motor 74 will die out before the motor is attempted to be driven again. At step 2176, the program then branches to the FSTEPS2 routine. If the COUNT variable is not equal to six, indicating that it is not the last step in the 6-step sequence, as determined at step 2166, the program branches to step 2168 at which point the program sets up the pointers to the step timing table for the 6-reverse-half-step sequence and the appropriate spring force range stored in the variable FSPRING. Then, at step 2170 the program branches to the FSTEPFTR routine.

Figure 75:
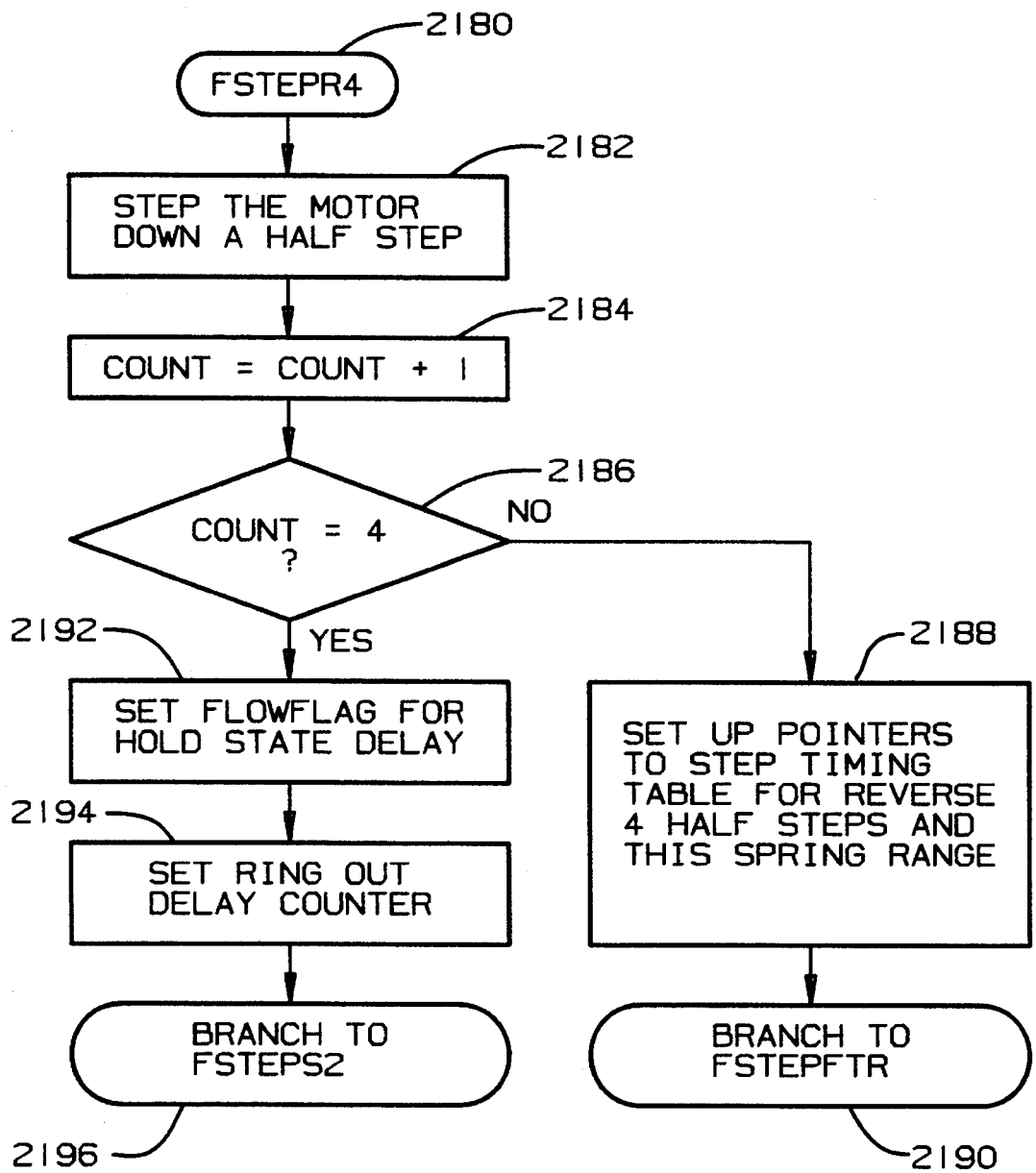

The operation of the FSTEPR4 routine as set forth in FIG. 75 is very similar to the operation of the FSTEPR12 routine explained in connection with FIG. 71, except that in FIG. 75 the motor is being driven a total of four steps in the reverse direction. Now referring to FIG. 75, at step 2182 the stepping motor 74 is stepped down one half step. Then, at step 2184 the variable COUNT is incremented since one more of the four steps to be moved in this routine has just been moved. At step 2186, the count stored in the COUNT variable is compared with the number four to determine whether the motor has been driven four steps as has been requested. If the motor has been moved four steps, then the program branches to step 2192 at which point the FLOW-FLAG variable is set appropriately to cause the program to enter the hold state, which causes the motor to be held in place at its current position. Then at step 2194, the delay ring-out counter is set so that any oscillations of the stepping motor 74 will die out before the motor is attempted to be driven again. At step 2196, the program then branches to the FSTEPS2 routine. If the COUNT variable is not equal to four, indicating that it is not the last step in the 4-step sequence, as determined at step 2186, the program branches to step 2188 at which point the program sets up the pointers to the step timing table for the 4-reverse-half-step sequence and the appropriate spring force range stored in the variable FSPRING. Then, at step 2190 the program branches to the FSTEPFTR routine.

Figure 76:
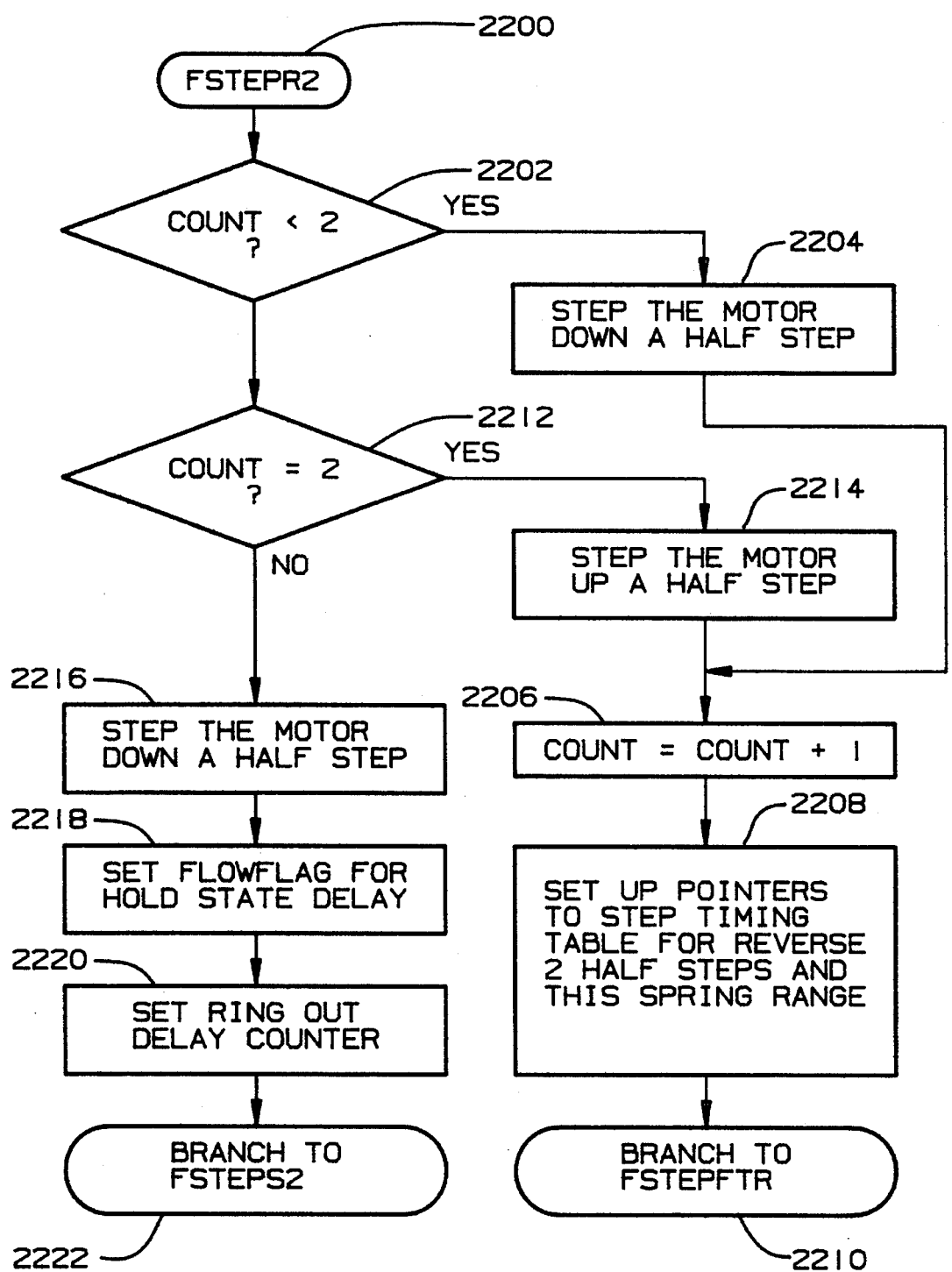

The operation of the FSTEPR2 routine as set forth in FIG. 76 is very similar to the operation of the FSTEPF2 routine explained in connection with FIG. 70, except that in FIG. 76 the motor is being stepped down instead of up. Now referring to FIG. 76, at step 2202, the variable COUNT is tested to determine whether it is less than two. If it is, then the program branches to step 2204 at which point the motor is stepped down one half step, and then the program branches to step 2206. If the value of COUNT is not less than two, then the program branches to step 2212 at which point the value of COUNT is tested to determine whether it is equal to two. If it is, then the program branches to step 2214 at which point the motor is given an excitation that would tend to cause it to step up one half step, although it does not actually do so. As described above, this excitation is for "braking" purposes. If COUNT is not equal to two, then the program branches to step 2216 at which point the motor is stepped down one half step. At step 2218, then value of FLOWFLAG is set to the appropriate value so that the next state will be the hold state. At step 2220, the ring out delay counter is set, and at step 2222 the program branches to the FSTEPS2 routine. If the program branched to step 2206, then at this step COUNT is incremented, and then at step 2208 the pointers to the step timing table for the two half steps reverse mode and the appropriate spring force range are set up. Finally, at step 2080, the program branches to the FSTEPFTR routine.

Figure 77:
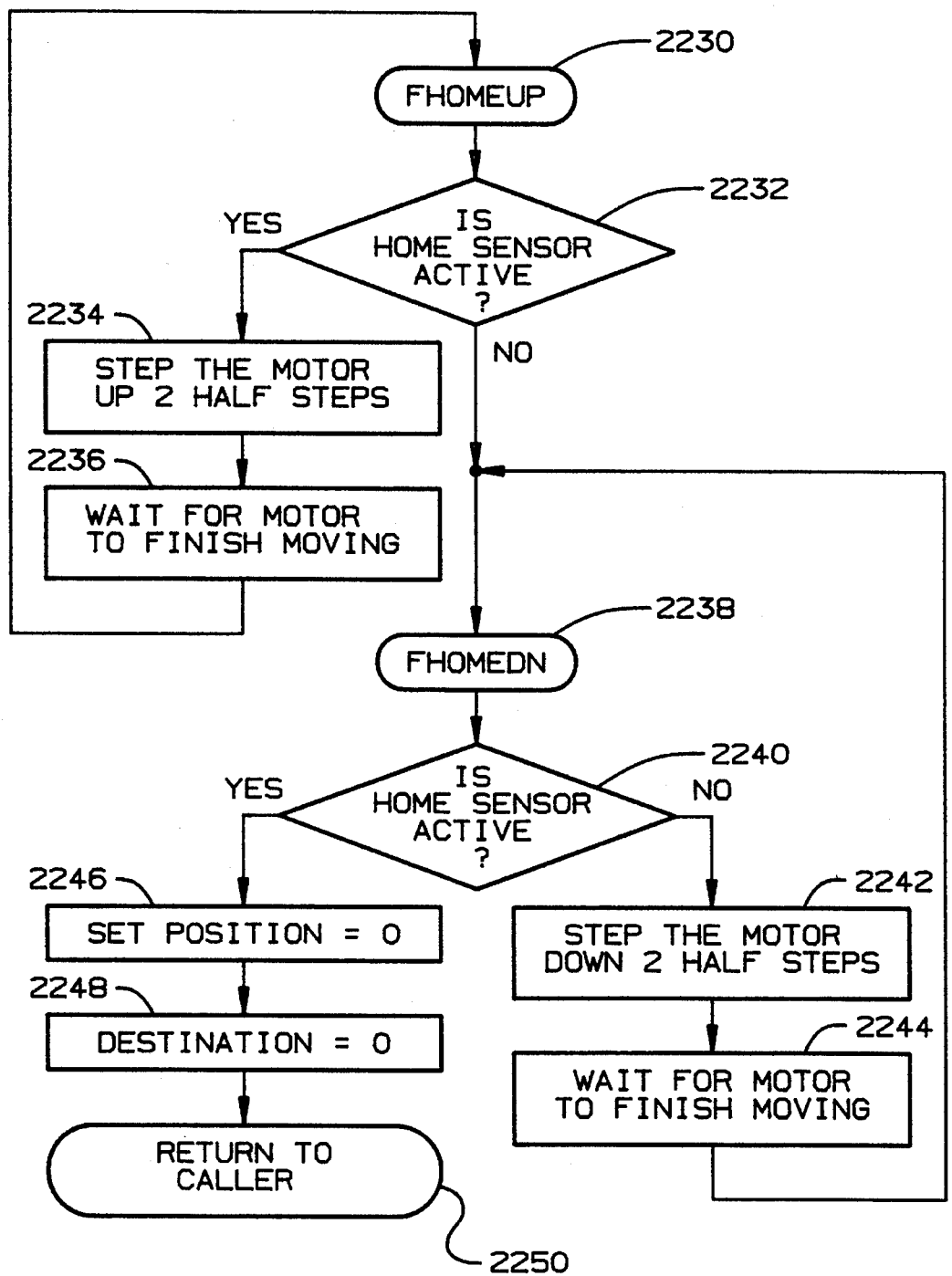

Now referring to FIG. 77, a stepping motor home routine is shown. The purpose of this software routine is to verify the home position of the flow control valve stepping motor. This verification is accomplished by first moving the flow control valve up out of its home position, and then moving the flow control valve towards its home position until the position sensor is activated, at which point the POSITION variable that stores the current position of the flow control valve is set to zero. When Now referring to FIG. 77, at step 2232, the flow control valve position sensor is read and tested to determine whether it is active. If it is active, then the program branches to step 2234 at which point it steps the motor up two half steps, and then at step 2236, waits for the motor to finish moving at which point it branches back to step 2232. The program Continues branching to steps 2234 and 2236 until the home sensor becomes inactive, indicating that the flow control valve is not at home anymore. Then the program branches to step 2240 at which point the position sensor is again tested. If the position sensor is still inactive, the program branches to steps 2242 and 2244 in order to step the motor down two half steps and wait for the motor to finish moving. The program then branches back to step 2240 at which point the position sensor is tested again. If the position sensor is active, then the program branches to step 2246 at which point the variable POSITION, which keeps track of the current position of the flow control valve at all times, is set to zero, and the variable DESTINATION, is also set to zero. At step 2250, the program returns to the calling procedure.

Control of Exhalation Valve

The control of the exhalation valve by the motor control processor 190 is described below in connection with FIGS. 78–83, which include detailed flowcharts of a motor control computer program stored in the EPROM associated with the motor control processor 190. The control of the exhalation valve is substantially the same as the control of the flow control valve as described above. The portion of the motor control processor computer program that controls the operation of the exhalation valve is substantially the same as that portion which is described above in connection with FIGS. 48–77, and is described by a corresponding number of flowcharts that are substantially the same as those set forth in FIGS. 48–77. So that this description of the motor control processor is not unduly complicated, only those flowcharts that are different from the flowcharts set forth in FIGS. 48–77, namely the flowcharts set forth in FIGS. 78–83, are included herein.

The control of the exhalation valve by the motor control processor 190 is described below in connection with FIGS. 78–83, which include detailed flowcharts of a portion of the motor control computer program stored in the EPROM associated with the motor control processor 190.

Figure 78:
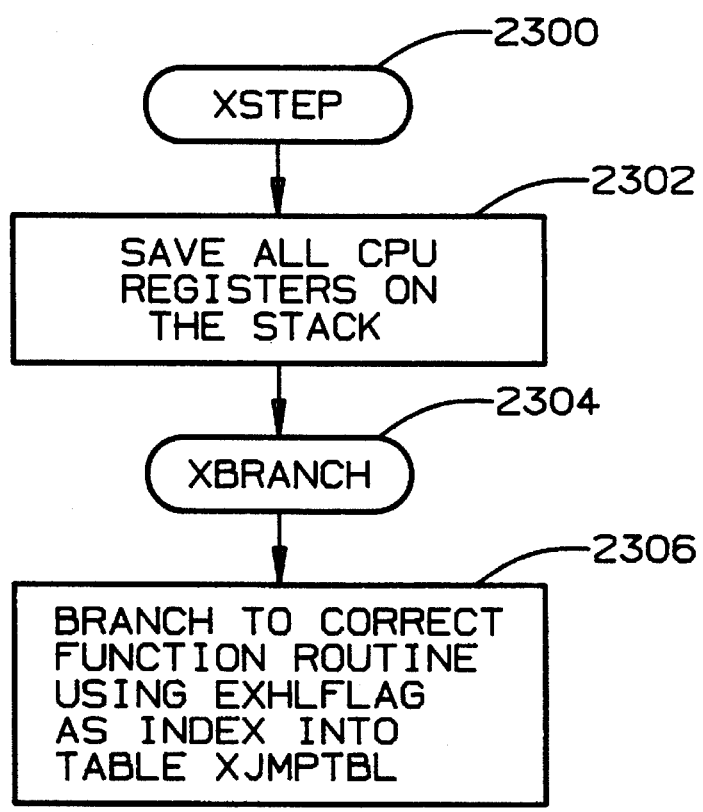
FIGS. 78–83 contain detailed flow charts of a second portion of the motor control computer program.

Now referring to FIG. 78, an XSTEP routine is shown. Each time the XSTEP routine is executed, the exhalation valve stepping motor is driven a single step. The XSTEP routine is executed each time that an interrupt is generated from an interrupt-generating timer. As is described in more detail below, the interrupt-generating timer is repeatedly loaded with the various time delays retrieved from the ramp tables that control the stepping of the exhalation valve motor. Each time the interrupt-generating timer times out, the XSTEP routine is called. When the XSTEP routine is called, at step 1502 the CPU registers of the motor Control processor are saved to the stack, and at step 1506, the program branches to one of a number of software routines. Each of these software routines, which is described in detail either below or above in connection with the flow control valve, is branched to when the stepping motor being driven is in a certain mode of operation. For example, the XSTEPF6 routine is branched to when the motor is being driven a total of six steps in the forward direction. For purposes of the following explanation, the "forward direction" is that direction that causes the valves to be opened, and the "reverse direction" is that direction that causes the valves to be closed. Also, when the stepping motor is stepped "up," the motor is being stepped in a direction that will cause the respective valve to open, and when the motor is being stepped "down," the motor is being stepped in a direction that will cause the valve to close. Also, unless otherwise indicated, the words "steps" and "half steps" are used interchangeably and both are intended to mean half steps.

The branch that occurs at step 1506 is made based upon the numeric value of a variable EXHLFLAG. The variable EXHLFLAG represents the current mode in which the exhalation valve stepping motor is being driven. The various values of EXHLFLAG and the corresponding software routines and stepping motor modes that they represent are reproduced in Table 15 below. For example, if the value of EXHLFLAG is equal to the hexadecimal number 2, the motor is in a mode in which it is being driven four half steps in the reverse direction. In this case, at step 2306 the program would branch to the XSTEPR4 routine, which is not shown but is identical to the FSTEPR4 routine set forth in FIG. 75, except that the name of the routine is XSTEPR4 and not FSTEPR4 and EXHLFLAG is used instead of FLOWFLAG.

TABLE 15

| FLOWFLAG | STATE | BRANCH TO | PERFORM |
|---|---|---|---|
| — | 0 | XINOP0 | Illegal State - Vent Inop |
| XCR2 | 1 | XSTEPR2 | Reverse 2 Half Steps |
| XCR4 | 2 | XSTEPR4 | Reverse 4 Half Steps |
| XCR6 | 3 | XSTEPR6 | Reverse 6 Half Steps |
| XCR8 | 4 | XSTEPR8 | Reverse 8 Half Steps |
| XCR10 | 5 | XSTEPR10 | Reverse 10 Half Steps |
| XCR12 | 6 | XSTEPR12 | Reverse 12 Half Steps |
| XCRA2000 | 7 | XSTEPRA2 | Rev Accel to 2000 hs/sec |
| XCRM2000 | 8 | XSTEPRM2 | Rev Slew at 2000 hs/sec |
| XCRD2000 | 9 | XSTEPRD2 | Rev Decel from 2000 hs/sec |
| XCRA3000 | A | XSTEPRA3 | Rev Accel to 3000 hs/sec |
| XCRM3000 | B | XSTEPRM3 | Rev Slew at 3000 hs/sec |
| XCRD3000 | C | XSTEPRD3 | Rev Decel from 3000 hs/sec |
|  | D | XINOP1D | Illegal State - Vent Inop |
| XCH | E | XSTEPH | Hold for ring out delay |
| XCNM | F | XSTEPNM | No motion idle |
| — | 10 | XINOP10 | Illegal State - Vent Inop |
| XCF2 | 11 | XSTEPF2 | Forward 2 Half Steps |
| XCF4 | 12 | XSTEPF4 | Forward 4 Half Steps |
| XCF6 | 13 | XSTEPF6 | Forward 6 Half Steps |
| XCF8 | 14 | XSTEPFB | Forward 8 Half Steps |
| XCF10 | 15 | XSTEPF10 | Forward 10 Half Steps |
| XCF12 | 16 | XSTEPF12 | Forward 12 Half Steps |
| XCFA2000 | 17 | XSTEPFA2 | Fwd Accel to 2000 hs/sec |

TABLE 15-continued

| FLOWFLAG | STATE | BRANCH TO | PERFORM |
|---|---|---|---|
| XCFM2000 | 18 | XSTEPFM2 | Fwd Slew at 2000 hs/sec |
| XCFD2000 | 19 | XSTEPFD2 | Fwd Decel from 2000 hs/sec |
| XCFA3000 | 1A | XSTEPFA3 | Fwd Accel to 3000 hs/sec |
| XCFM3000 | 1B | XSTEPFM3 | Fwd Accel at 3000 hs/sec |
| XCFD3000 | 1C | XSTEPFD3 | Fwd Decel from 3000 hs/sec |
| — | 1D | XINOP1D | Illegal State - Vent Inop |
| XCH | 1E | XSTEPH | Hold for ring out delay |
| SCNM | 1F | XSTEPNM | No motion idle |

Figure 79:
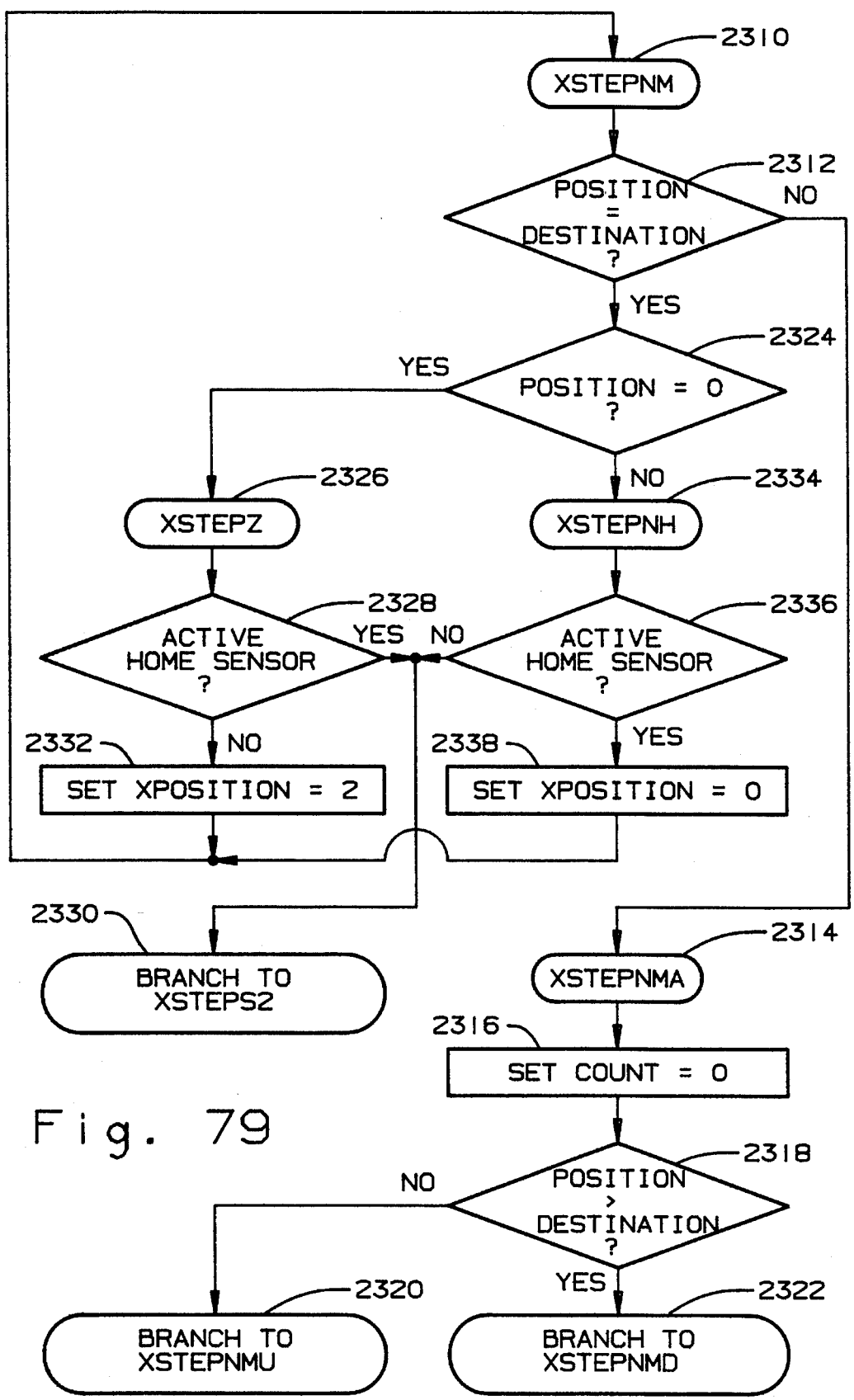

Now referring to FIG. 79, at step 2312, the motor control processor 190 compares the current position of the exhalation valve with the destination requested by the main processor 188. The current position of the exhalation valve is known to the motor control processor 190 at all times. If the current position of the exhalation valve does not equal its requested destination, the exhalation valve must be moved, and the program branches to step 2316. At this step, the variable COUNT is set equal to zero, and then the program branches to step 2318, at which point the program determines whether the current position is greater than the requested destination. If it is, the program branches to step 2322 which causes the exhalation valve to be stepped down, and the program branches to the XSTEPNMD routine. If the position is not greater than the requested destination, the program branches to step 2320, in which case the exhalation valve is moved up. If the position equals the destination as determined at step 2312, the program branches to step 2324, at which point the program determines whether the position of the exhalation valve equals zero. If it does, the program branches to step 2328, at which point the home sensor is read by the motor control processor to determine whether it is active. If it is active, the program branches to step 2330. If it is not active, the variable XPOSITION is set equal to 2. If the position is not equal to zero as determined at step 2324, the program branches to step 2334, at which point the home sensor is read by the processor 190 in order to determine whether it is active. If it is not active, the program branches to step 2330. If it is active, the variable XPOSITION is set equal to zero, and the program branches back to step 2310.

Figure 80A:
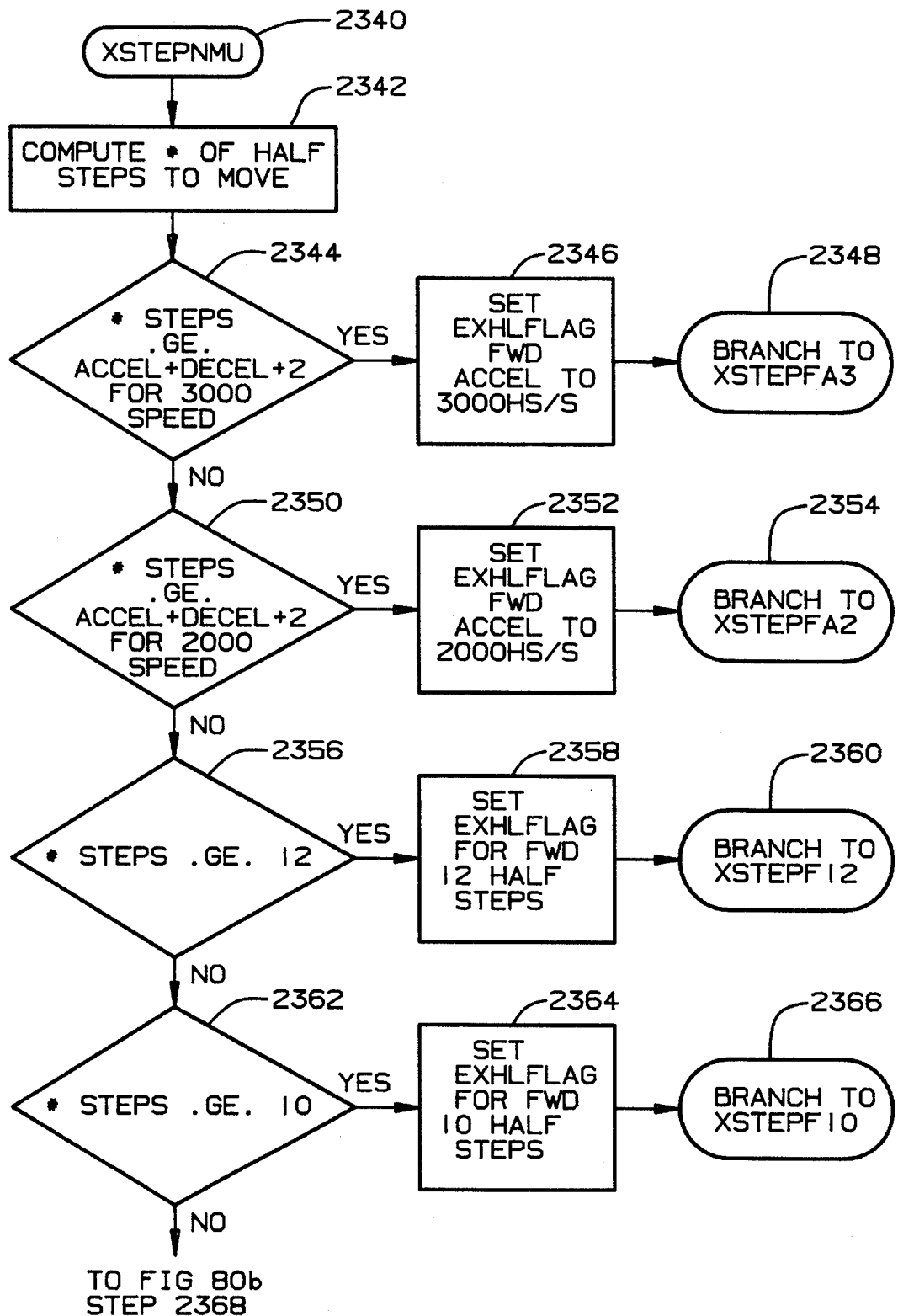
Figure 80B:
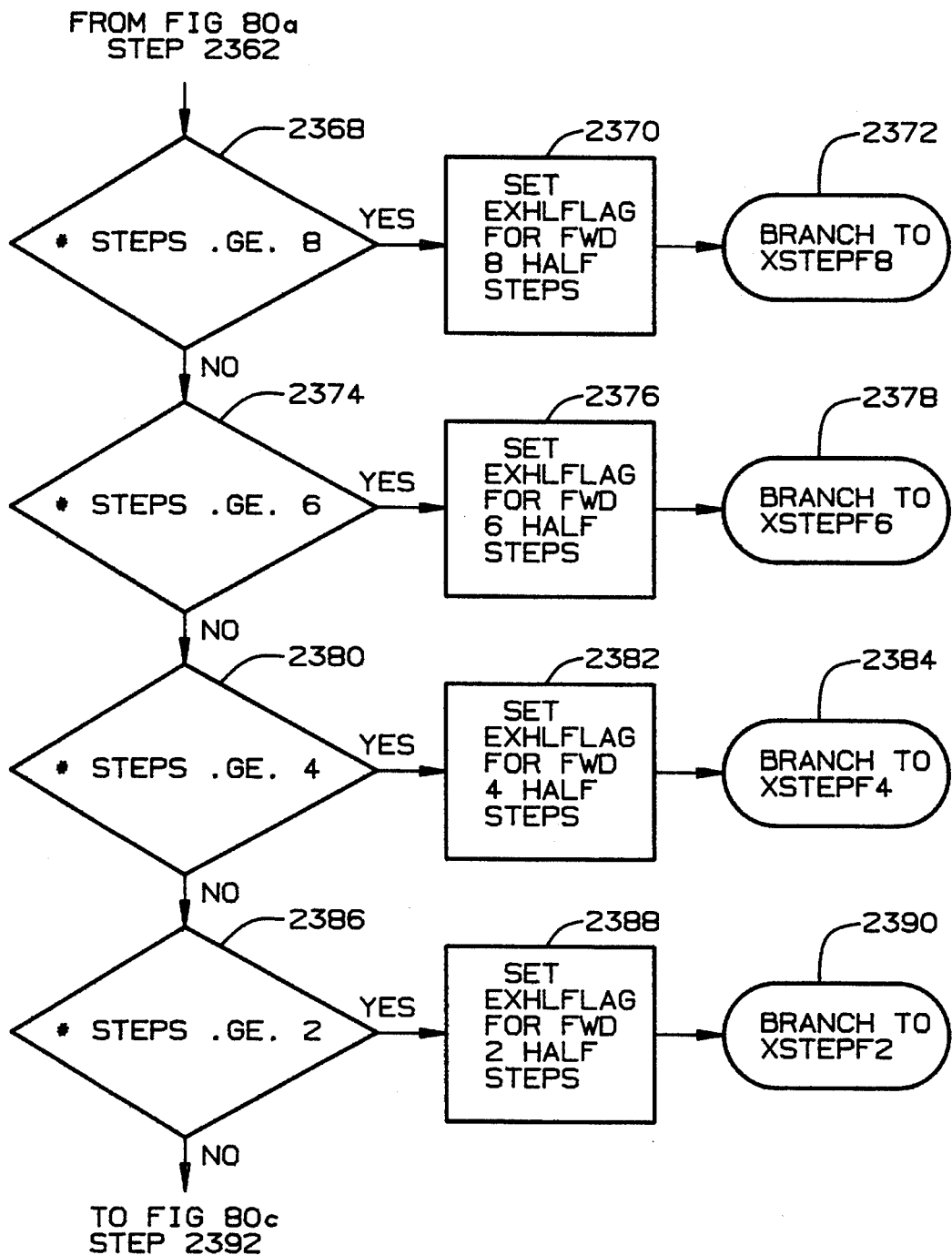
Figure 80C:
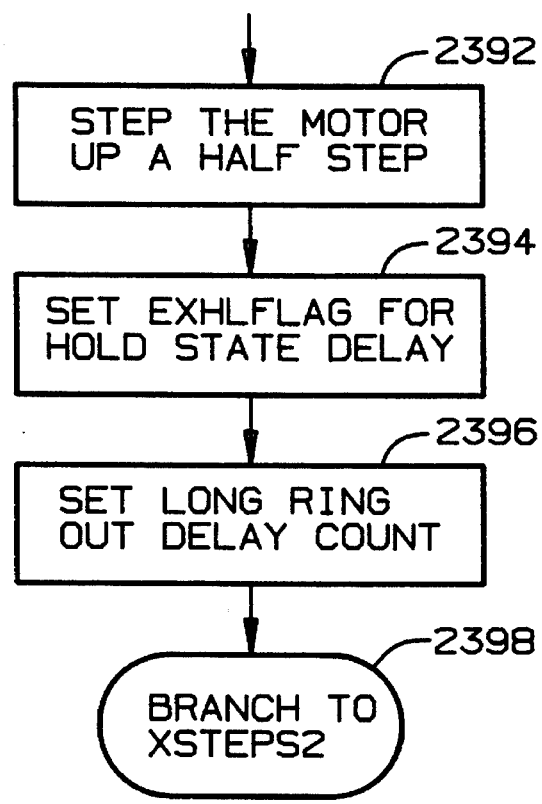

The detailed flow chart in FIG. 80, when executed, causes the variable EXHLFLAG to be set to a hexadecimal number that will cause the exhalation valve stepping motor to be opened in accordance with the request from the main processor 188 via the serial interface. At step 2342, the program computes the number of half steps that the exhalation valve stepping motor needs to be moved up from the difference between the current position and the requested destination. Using this number, the program branches to step 2344 and tests to see whether the number of steps is greater or equal to a predetermined number of steps that would allow the exhalation stepping motor to be accelerated at 3000 half steps per second, decelerated at 3000 half steps per second, and have at least two half steps in between at the peak rate of 3000 half steps per second. If the number of steps the motor needs to be moved is greater than this predetermined number, the program branches to step 2346, at which point it sets the variable EXHLFLAG equal to the hexadecimal number 1A as set forth in Table 15, and the program at step 2348 branches to the procedure XSTEPFA3.

If the number of steps is not greater or equal to the predetermined number in step 2344, the program branches to step 2350, at which point the number of steps determined in step 2342 is compared to determine whether it is greater or equal to a second predetermined number of steps which would allow the exhalation valve stepping motor to be accelerated and decelerated at a rate of 2000 half steps per second, and have at least two half steps in between at that 2000 half-step-per-second speed. If the number of steps that the motor has been requested to move is greater or equal to this predetermined number, the program branches to step 2352, at which point it sets the variable EXHLFLAG to the hexadecimal number 17, and using the Table 15, the program branches to the XSTEPFA2 routine at step 2354.

If the number of steps in step 2350 is not greater or equal to the second predetermined number, the program branches to step 2356 in order to determine whether the number of half steps that the exhalation stepping motor is to be moved is greater or equal to 12. If so, the program branches to step 2358, at which point EXHLFLAG is set so that the program will branch to the procedure which moves the stepping motor forward by 12 half steps at step 2360.

If the number of steps is less than 12, the program branches to step 2362 where the number of steps is compared with 10. If the number of steps is greater or equal to 10, the program branches to step 2364 where EXHLFLAG is accordingly set in order to cause the program to branch to XSTEPF10 at step 2366. At step 2368, if the number of steps is greater or equal to 8, the program branches to step 2570 and then step 2372 in order to move the stepping motor forward 8 half steps. At step 2374, if the number of steps is greater or equal to 6, the program branches to step 2376 and then step 2378 in order to move the stepping motor forward 6 half steps. At step 2380, if the number of steps is greater or equal to 4, the program branches to step 2382 and then step 2384 in order to move the stepping motor forward 4 half steps. At step 2386, if the number of steps is greater or equal to 2, the program branches to step 2388 and then step 2390 in order to move the stepping motor forward 2 half steps.

If the number of steps is not greater or equal to 2, the program branches to step 2392 where EXHLFLAG is set for an undefined number of steps. Since the number of steps is ordinarily expected to be within one of the ranges of the decision-making steps 2344–2386, the program will not branch to 2392 unless there is an error state, and accordingly, at step 2394, the program branches to the VENT INOP state.

Figure 81A:
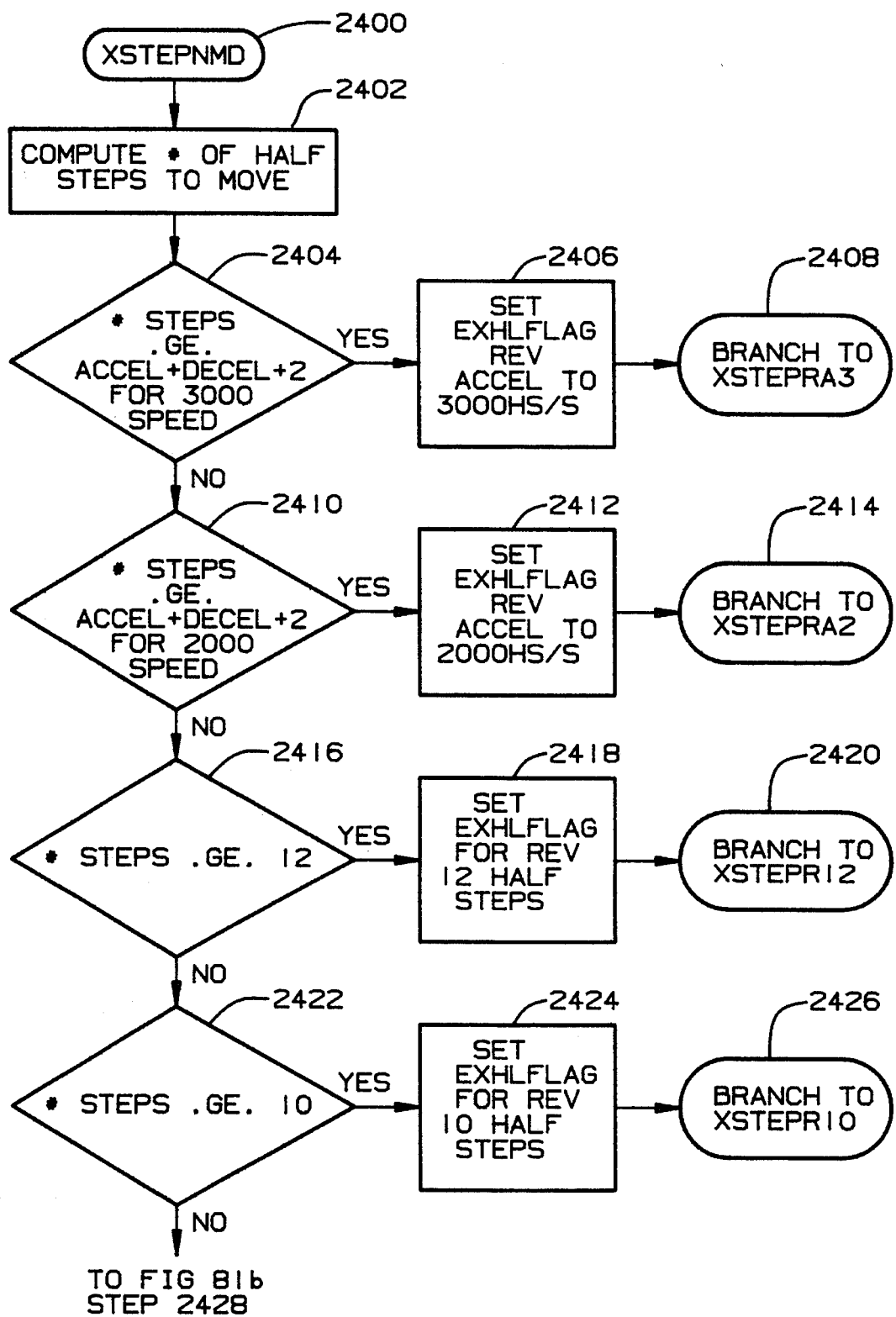
Figure 81B:
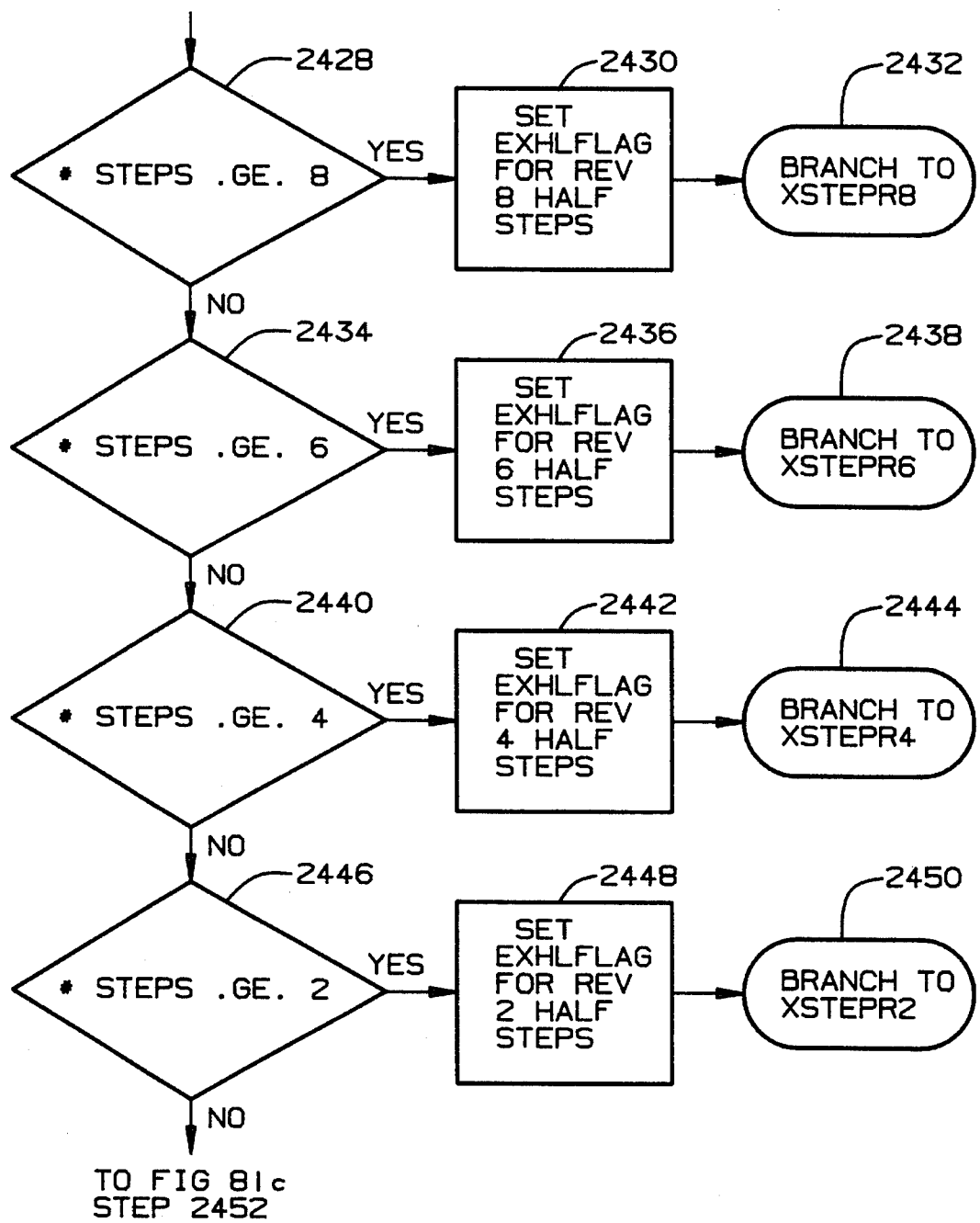
Figure 81C:
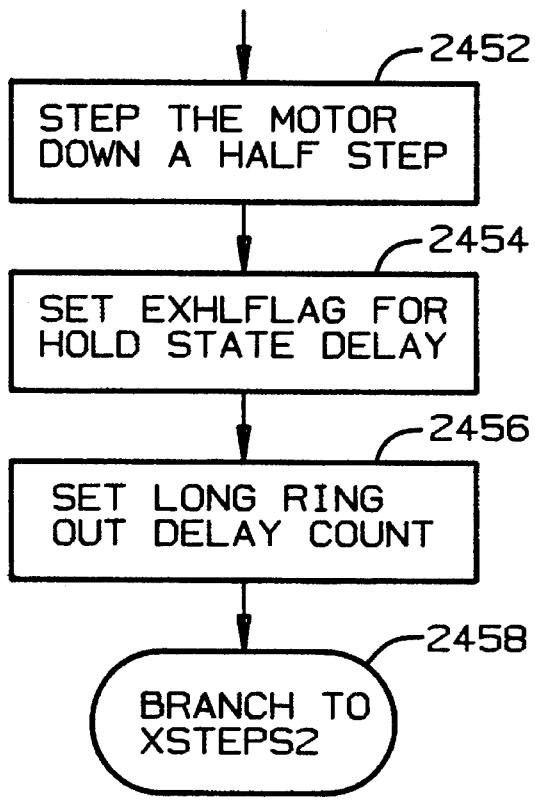

The detailed flow chart in FIG. 81, when executed, causes the variable EXHLFLAG to be set to a hexadecimal number that will cause the exhalation valve stepping motor to be driven so that it closes the valve 48 in accordance with the request from the main processor 188 via the serial interface. At step 2402, the program computes the number of half steps that the exhalation valve stepping motor needs to be moved up from the difference between the current position and the requested destination. Using this number, the program branches to step 2404 and tests to see whether the number of steps is greater or equal to a predetermined number of steps that would allow the exhalation stepping motor to be accelerated at 3000 half steps per second, decelerated at 3000 half steps per second, and have at least two half steps in between at the peak rate of 3000 half steps per second. If the number of steps the motor needs to be moved is greater than this predetermined number, the program branches to step 2406, at which point it sets the variable EXHLFLAG equal to the hexadecimal number 1A as set forth in Table 15, and the program at step 2408 branches to the procedure XSTEPRA3.

If the number of steps is not greater or equal to the predetermined number in step 2404, the program branches to step 2410, at which point the number of steps determined in step 2402 is compared to determine whether it is greater or equal to a second predetermined number of steps which would allow the exhalation valve stepping motor to be accelerated and decelerated at a rate of 2000 half steps per second, and have at least two half steps in between at that 2000 half-step-per-second speed. If the number of steps that the motor has been requested to move is greater or equal to this predetermined number, the program branches to step 2412, at which point it sets the variable EXHLFLAG to the hexadecimal number __, and using the Table 15, the program branches to the XSTEPRA2 procedure at step 2414.

If the number of steps in step 2410 is not greater or equal to the second predetermined number, the program branches to step 2416 in order to determine whether the number of half steps that the exhalation stepping motor is to be moved is greater or equal to 12. If so, the program branches to step 2418, at which point EXHLFLAG is set so that the program will branch to the procedure which moves the stepping motor backwards by 12 half steps at step 2420.

If the number of steps is less than 12, the program branches to step 2422 where the number of steps is compared with 10. If the number of steps is greater or equal to 10, the program branches to step 2424 where EXHLFLAG is accordingly set in order to cause the program to branch to XSTEPR10 at step 2426. At step 2428, if the number of steps is greater or equal to 8, the program branches to step 2430 and then step 2432 in order to move the stepping motor backward 8 half steps. At step 2434, if the number of steps is greater or equal to 6, the program branches to step 2436 and then step 2438 in order to move the stepping motor backward 6 half steps. At step 2440, if the number of steps is greater or equal to 4, the program branches to step 2442 and then step 2444 in order to move the stepping motor backward 4 half steps. At step 2446, if the number of steps is greater or equal to 2, the program branches to step 2448 and then step 2450 in order to move the stepping motor backward 2 half steps.

If the number of steps is not greater or equal to 2, the program branches to step 2452 where the motor is stepped down one half step. At step 2454, EXHLFLAG is set so that the program enters the hold state, and then at step 2456 a long ring out delay count is set to damp the oscillations of the stepping motor.

Figure 82A:
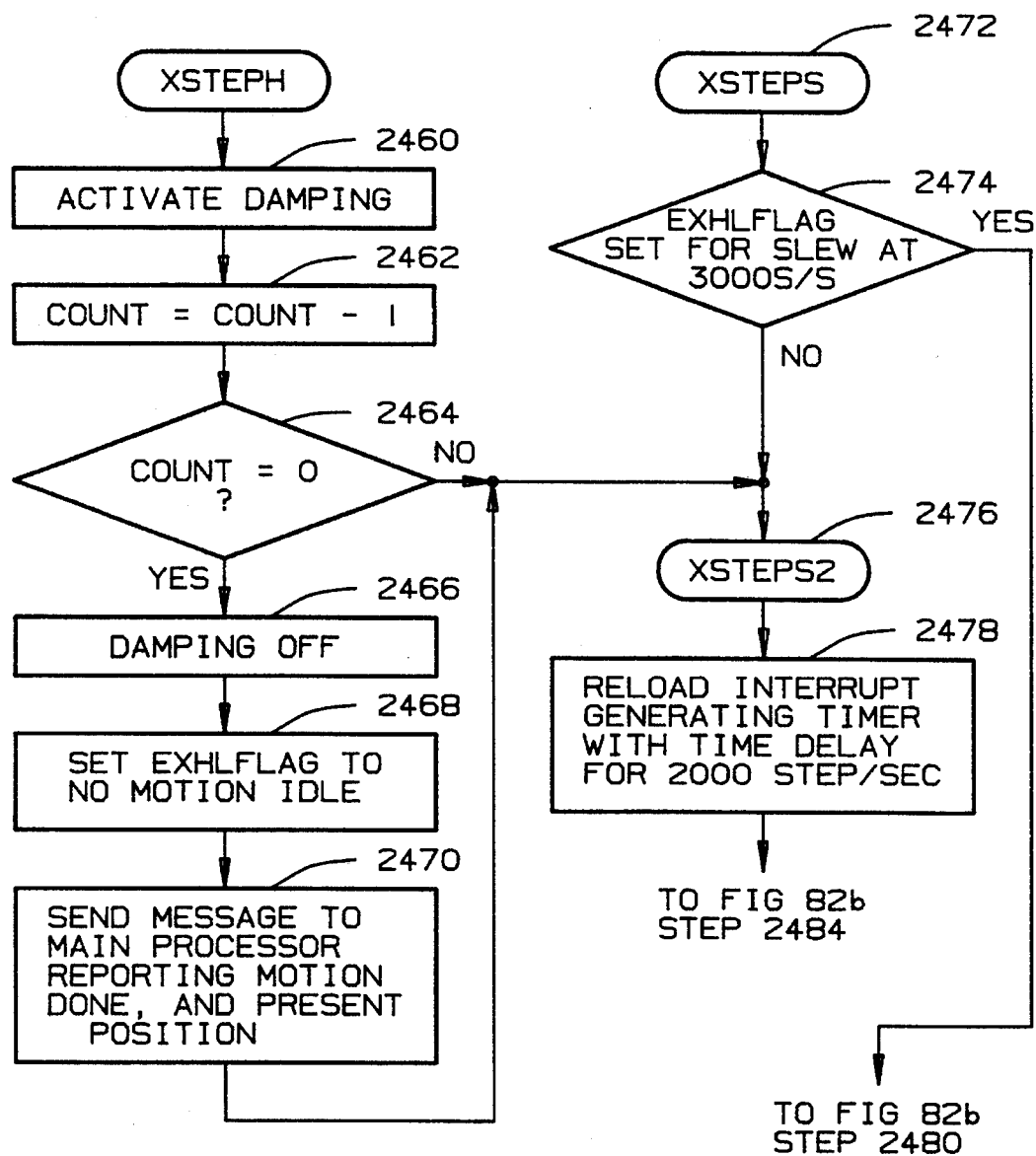
Figure 82B:
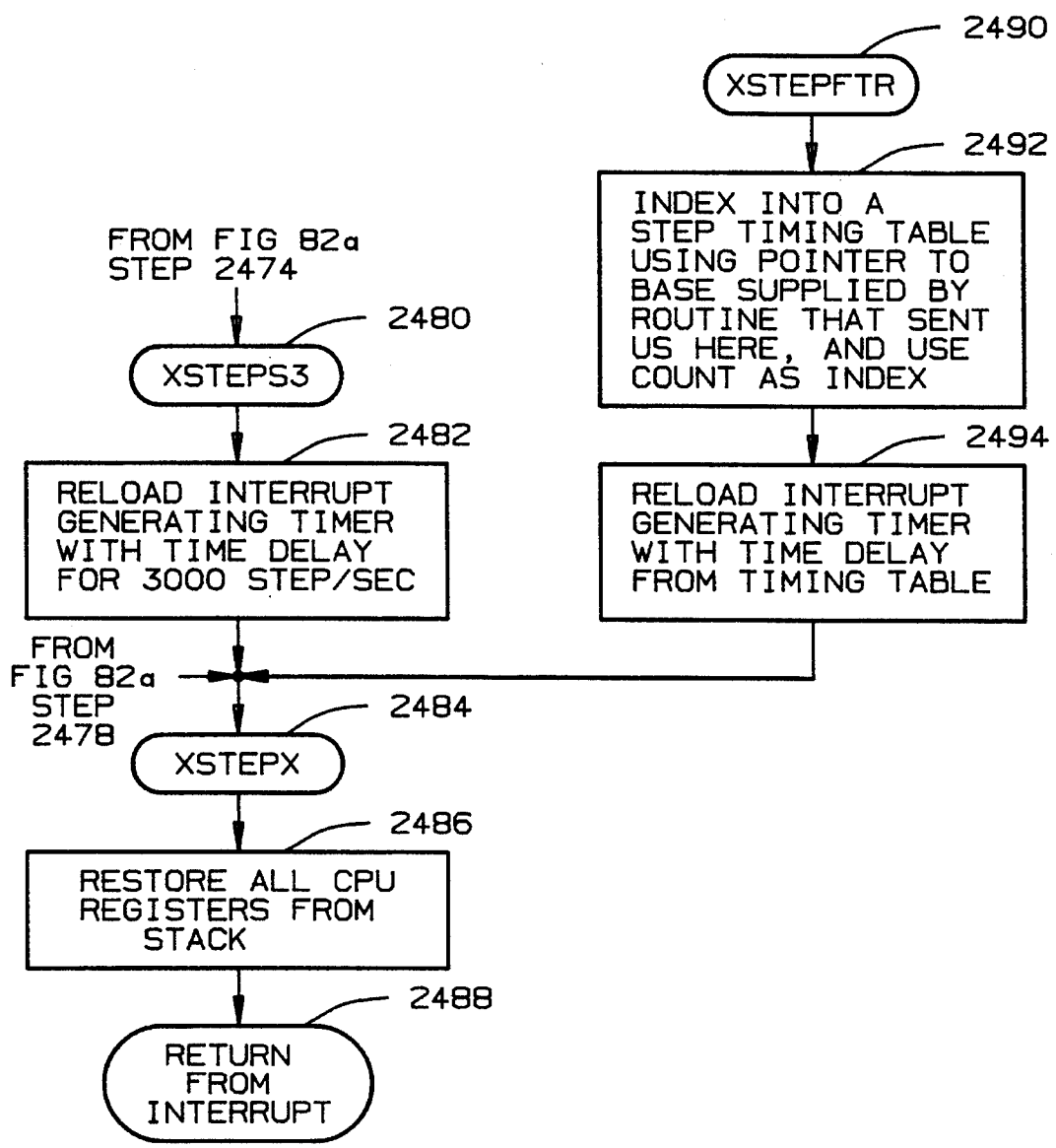

The portion of the program set forth in FIG. 82 performs a number of housekeeping tasks related to the driving of the exhalation valve stepping motor. Now referring to FIG. 82, the XSTEPH routine is branched to when the motor is to be held for the ring out delay period. At step 2460, the damping is activated, and then at step 2462 the COUNT variable, which has been previously set to a predetermined number according to the desired ring our delay period, is decremented. At step 2464 the COUNT variable is tested to determine if it is zero, indicating that the ring out delay period has elapsed. If it has elapsed, then at step 2466 the electronic damping is turned off and at step 2468 EXHLFLAG is set so that the program will branch to the no motion idle state, in which the stepping motor is not in motion and awaiting another move command from the main processor 188. At step 2470, a message is sent to the main processor indicating that the motor has finished the requested move and the present position of the motor. The program then branches to step 2478 so that the interrupt-generating timer may be reloaded.

The XSTEPS routine shown in FIG. 82 is executed when the stepping motor is in either its 2,000 half steps per second or 3,000 half steps per second slewing mode of operation. At step 2474, the value of EXHLFLAG is compared to determine whether it is set for slewing the motor at 3,000 half steps per second. If so, the program branches to step 2480 at which point the interrupt-generating timer is reloaded with the appropriate time delay to make the motor slew at its 3,000 half steps per second rate. If EXHLFLAG is not set for slewing at 3,000 steps per second as determined at step 2474, the rate must be 2,000 half steps per second, so the program branches to step 2478 at which point the interrupt-generating timer is reloaded with the appropriate time delay to make the motor slew at its 2,000 half steps per second rate.

The XSTEPFTR portion of the program set forth in FIG. 82 is branched to by many of the routines describes above. At step 2492, the XSTEPFTR routine causes the appropriate ramp-up or ramp-down table to be indexed, using the COUNT variable as the index, to retrieve the appropriate time delay for the next step of the motor. At step 2494, the interrupt-generating timer is reloaded with this time delay, and then the program branches to step 2486 at which point the CPU registers that were previously saved are restored from the stack.

Figure 83:
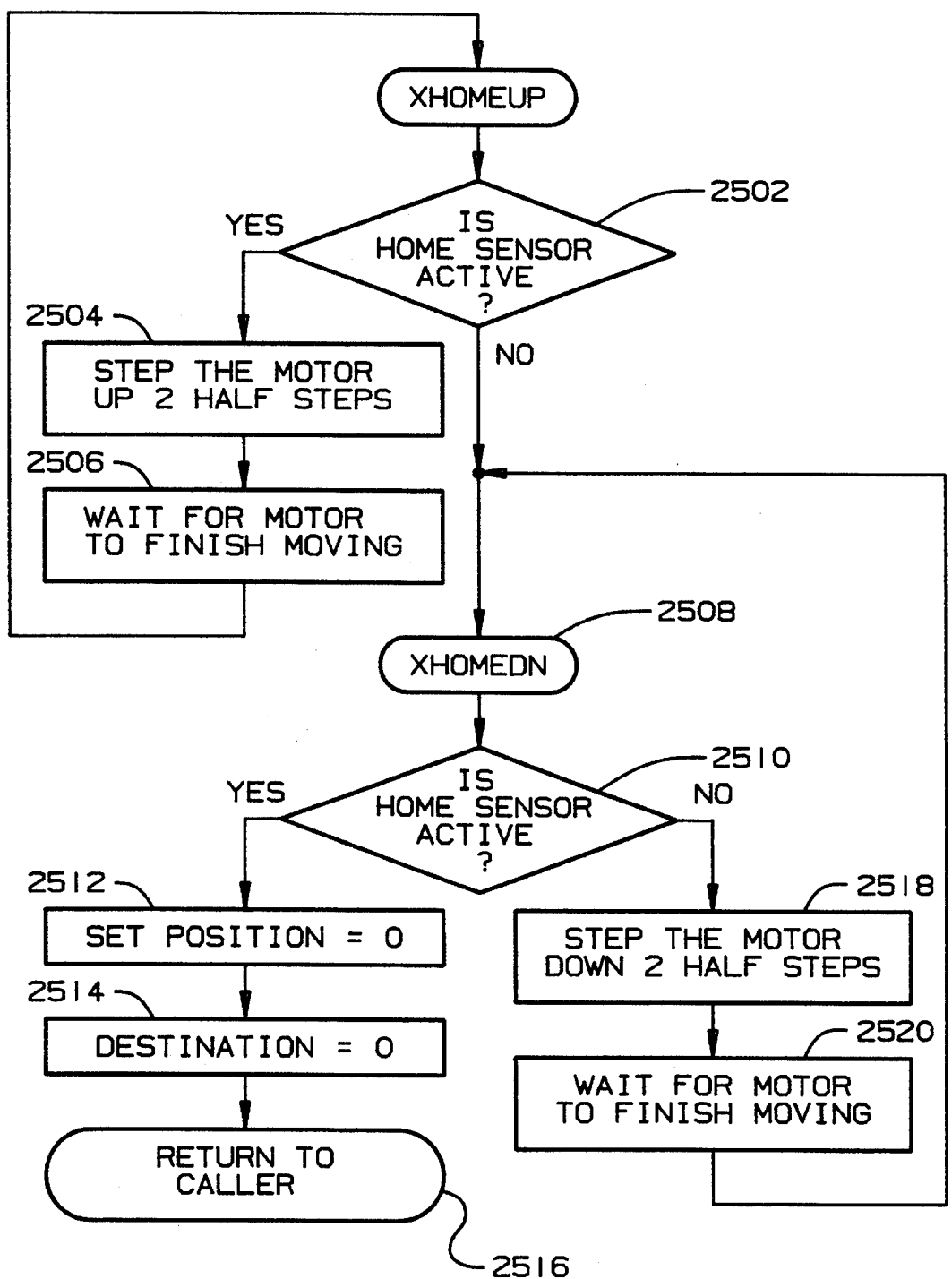

Now referring to FIG. 83, a stepping motor home routine is shown. The purpose of this software routine is to verify the home position of the exhalation valve stepping motor. This verification is accomplished by first moving the exhalation valve up out of its home position, and then moving the exhalation valve towards its home position until the position sensor is activated, at which point the POSITION variable that stores the current position of the exhalation valve is set to zero. Now referring to FIG. 83, at step 2502, the exhalation valve position sensor is read and tested to determine whether it is active. If it is active, then the program branches to step 2504 at which point it steps the motor up two half steps, and then at step 2506, waits for the motor to finish moving at which point it branches back to step 2502. The program continues branching to steps 2504 and 2506 until the home sensor becomes inactive, indicating that the exhalation valve is not at home anymore. Then the program branches to step 2510 at which point the position sensor is again tested. If the position sensor is still inactive, the program branches to steps 2518 and 2520 in order to step the motor down two half steps and wait for the motor to finish moving. The program then branches back to step 2510 at which point the position sensor is tested again. If the position sensor is active, then the program branches to step 2512 at which point the variable POSITION, which keeps track of the current position of the exhalation valve at all times, is set to zero, and the variable DESTINATION, is also set to zero. At step 2516, the program returns to the calling procedure.

Ramp Profiles

As explained above, conventional ramp-up and ramp-down tables are used for the flow control and exhalation valve stepping motors. The ramp-up tables determine the rate at which the motors are accelerated, and the ramp-down tables determine the rate at which the motors are decelerated. Each of the ramp tables comprises a series of time delays which govern the rate at which one of the stepping motors is energized. Different ramp tables are provided for the flow control valve 42 based upon direction because the flow control valve 42 is spring-biased closed, as described above, which affects the rates at which the stepping motor 74 can be accelerated and decelerated. Thus, if the valve 42 is being opened, the stepping motor 74 must be accelerated more slowly since it must overcome the force of the spring 84, while if the valve is being closed, the stepping motor 74 can be accelerated more rapidly. Different ramp tables are provided based on the number of steps in order to minimize the travel time of the stepping motor 74. For example, if the desired valve position is 12 steps away from the current valve position, a particular ramp table is used. If the desired valve position is only 6 steps away, a different ramp table set is used. The ramp tables are developed in a conventional well-known manner, and the particular time delays contained in the ramp tables depend upon the stepping motors used and the mass and friction of the coupling between the stepping motors and the valves 42, 48, in addition to direction and distances as described above.

The motor control processor 190 utilizes many ramp tables in order to drive the stepping motors that control the flow control and exhalation valve. In particular, each of the FSTEPF2, FSTEPF4, FSTEPF6, FSTEPF8, FSTEPF10, FSTEPF12, FSTEPFA2, FSTEPFD2, FSTEPFA3, and FSTEPFD3 routines described above have three ramp tables associated therewith, one ramp table for each of the three spring force ranges. Similarly, the FSTEPR2, FSTEPR4, FSTEPR6, FSTEPR8, FSTEPR10, FSTEPR12, FSTEPRA2, FSTEPRD2, FSTEPRA3, and FSTEPRD3 routines described above also have three ramp tables associated therewith, one ramp table for each of the three spring force ranges. Thus the flow control valve stepping motor has 60 ramp tables that are used to drive it. The exhalation valve also has a set of different ramp profiles used to drive it, since the valve has different physical characteristics. All of these ramp profiles are listed in the microfiche appendix submitted herewith.

An exemplary portion of a ramp table having the same format as those included in the microfiche appendix is listed below in Table 16. The odd-numbered lines (1)–(7) in Table 16 are used in the driving of the stepping motors, and the even-numbered lines (2)–(8) are used in the accumulation of the inspiratory tidal volume as each breath is delivered to the patient, which as described above, is only for the informational purposes of the ventilator operator.

TABLE 16

| FLOW VALVE -- FORWARD ACCELERATION TO 3,000 -- RANGE1 | | |
| --- | --- | --- |
| FCODECOMP - | (1441 * FOSC/12) | (1) |
| | (1441 + 4)/8 | (2) |
| FCODECOMP - | (712 * FOSC/12) | (3) |
| | (712 + 4)/8 | (4) |
| FCODECOMP - | (592 * FOSC/12) | (5) |
| | (592 + 4)/8 | (6) |
| FCODECOMP - | (530 * FOSC/12) | (7) |
| | (530 + 4)/8 | (8) |

Now referring to Table 16, each of the odd-numbered lines used for driving the motor contains a time delay comprising a number multiplied by a variable FOSC and divided by the number 12. Thus, the first time delay in Table 16 is (1441*FOSC/12). This time delay is specified by the number 1441, which represents a predetermined period of time. The factor FOSC/12 which the number 1441 is multiplied by is included as a convenience to account for the clock frequency at which the motor control processor is driven. The FOSC variable contains a constant, which when multiplied by the number 12, causes the interrupt generating timer to be initially loaded with a binary number to effectuate the desired time delay. As a result, if the clock frequency of the motor control processor is changed as a result of an engineering change, FOSC can be initialized to a different number and the whole ramp table will not have to be recalculated.

The time delay just described is subtracted from a FCODECOMP variable. The FCODECOMP variable is set to a predetermined number to account for the processing time of the main processor. As explained above, an interrupt-generating timer is used to store the time delays that control the rate at which the motors are energized. However, the execution of the computer program that loads the timer and responds to the interrupt generated by the timer takes a predetermined period of time which, unless accounted for, would add a predetermined time delay to the activation rate of the stepping motors.

Accordingly, in order to account for this extra overhead period of time, the variable FCODECOMP is set to the extra time delay incurred during the execution of the software. As a result, when the desired time delay is subtracted from the overhead time delay stored in FCODECOMP, the somewhat smaller time delay retrieved from the ramp table will cause the motor to be driven at a rate specified by the desired time delays. The desired time delays are subtracted from FCODECOMP, and not vice versa, since the interrupt-generating counter is initially loaded with a negative number and counts up to zero in order to generate an interrupt.

Each of the odd-numbered rows (1)–(7) represents a time delay occurring between respective excitations of the stepping motor. Thus, in order to ramp the motor up in accordance with Table 16, the motor would be given a first electrical excitation, then the time delay of line (1) would be loaded into the interrupt-generating counter. When the counter timed out, the motor would be given a second electrical excitation, and the timer would be reloaded with the time delay as specified by line (3) of Table 16, and so forth.

As indicated above, the even-numbered lines (2)–(8) are used in the accumulation of the inspiratory tidal volume as each breath is delivered to the patient, which is only for the informational purposes of the ventilator operator. The even-numbered rows contain the actual time delays of the motor to which the number 4 is added, and the resulting sum is divided by the number 8, for example, (1441+4)/8. This quantity, which equals 1441/8+½ and represents the time that the motor is opened to a particular position, is multiplied by the flow that is delivered by the valve when the motor is at that position in order to calculate the incremental volume delivered by the valve at that position. The 8 is used as a scaling factor and the ½ is added to account for the fact that the time delay is truncated when retrieved from the ramp table.

The ramp profiles were generated in accordance with conventional principles, for example, those set forth in the book entitled, "The Art and Practice of Step Motor Control," by Albert C. Leenhouts, published by Intertec Communications, Inc. of Ventura, Calif. in 1987, which is incorporated herein by reference. Appropriate ramp profiles used to drive stepping motors similar to the ramp profiles disclosed herein are commercially available from and developed by Litchfield Engineering Co. of Marwington, Conn., based upon customer-supplied information such as the particular stepping motor used, the mass and inertia of the stepping motor drive system, etc.

What is claimed is:

1. A method of ventilating in which a breath of a predetermined tidal volume is delivered at a variable flow rate to a patient whose breathing ability is impaired, the flow rate rapidly increasing during the initial portion of the breath and rapidly decreasing during the final portion of the breath, the tidal volume of the delivered breath being made substantially equal to a preselected tidal volume by taking into account and compensating for the variability of the flow rate at which the breath is delivered, said method comprising the steps of:

(a) providing a breath delivery period based upon the preselected tidal volume, the undelivered volume that would be lost during the increase of the flow rate during the initial portion of the breath, the extra volume that would be delivered during the decrease of the flow rate during the final portion of the breath, and a peak flow rate, the contribution of the undelivered volume that would be lost increasing the breath delivery period and the contribution of the extra volume that would be delivered decreasing the breath delivery period; and (b) after said providing step, delivering a complete breath at a pre-determined variable flow rate to a patient using the breath delivery period provided in step (a) whereby the actual tidal volume delivered to the patient substantially equals the preselected tidal volume.

2. A method of ventilating as defined in claim 1, wherein the breath delivery period includes the initial portion of the breath during which the flow rate is increasing but excludes the final portion of the breath during which the flow rate is decreasing.

3. A method of ventilating as defined in claim 1, additionally comprising the step of computing an actual peak flow rate based upon a preselected peak flow rate and using said actual peak flow rate in said step (a) to compute the breath delivery period.

4. A method of ventilating as defined in claim 1, wherein said undelivered volume that would be lost is related to the sum of a plurality of time-flow products derived from a ramp-up profile for a stepping motor, and wherein said extra volume that would be delivered is related to the sum of a plurality of time-flow products derived from a ramp-down profile for a stepping motor.

5. A method of ventilating as defined in claim 4, wherein said breath delivery period is increased by substantially one-third to deliver a breath with a tapered breath profile whereby the breath has an actual tidal volume substantially equal to the preselected tidal volume.

6. A method of ventilating in which a breath of a predetermined tidal volume is delivered at a variable flow rate to a patient whose breathing ability is impaired, the flow rate rapidly increasing during the initial portion of the breath and rapidly decreasing to zero during the final portion of the breath, the tidal volume of the delivered breath being made substantially equal to a preselected tidal volume by taking into account and compensating for the variability of the flow rate at which the breath is delivered, said method comprising the steps of:

(a) determining a breath delivery period in accordance with the following equation:

$$BDP = (V_X + VOLUME - V_Y)/FLOW$$

where $V_X$ is the undelivered volume that would be lost during the increase of the flow rate during the initial portion of the breath, $V_Y$ is the extra volume that would be delivered during the decrease of the flow rate to zero during the final portion of the breath, VOLUME is the preselected tidal volume, FLOW is the peak flow rate, and BDP is the breath delivery period;

(b) starting to deliver a breath to a patient at an initial time by increasing the flow rate from zero to a peak flow rate;

(c) continuing to deliver the breath by maintaining a pre-determined non-zero flow rate until a later time, said later time following said initial time by a time period substantially equal to the breath delivery period determined in said step (a); and (d) after said later time, decreasing the flow rate to zero to complete the delivery of the breath.

7. A method of ventilating as defined in claim 6, additionally comprising the step of determining an actual peak flow rate based upon a preselected peak flow rate and using said actual peak flow rate for FLOW in the equation in said step (a) to determine the breath delivery period.

8. A method of ventilating as defined in claim 6, wherein the breath delivery period is increased by substantially one-third to deliver a breath with a tapered breath profile whereby the breath has an actual tidal volume substantially equal to the preselected tidal volume.

9. A method of delivering a plurality of substantially identical breaths to a patient whose breathing ability is impaired by determining what the flow profile of a plurality of breaths will be prior to the delivery of the breaths, said method comprising:

(a) determining what the flow profile of a breath will be prior to the delivery of a plurality of breaths, said flow profile being determined based upon a desired peak flow rate and a desired tidal volume; and (b) delivering a plurality of complete breaths to a patient at a pre-determined variable flow rate, each of each breaths being substantially identical.

10. A method as defined in claim 9, wherein said determining what the flow profile in step (a) will be comprises preparing a ramp-up profile for the initial portion of a breath whereby the breath flow rate increases from zero to a peak flow rate when said ramp-up profile is used to deliver a breath in said step (b).

11. A method as defined in claim 10, wherein said determining what the flow profile will be additionally comprises preparing a ramp-down profile for the final portion of a breath whereby the breath flow rate decreases from a peak flow rate to zero when said ramp-down profile is used to deliver a breath in said step (b).

12. A method as defined in claim 11, wherein said ramp-up profile comprises a plurality of predetermined time delays which control the incremental opening of a flow control valve, and said ramp-down profile comprises a plurality of predetermined time delays which control the incremental closing of a flow control valve.

13. A method as defined in claim 12, wherein said determining what the flow profile will be additionally comprises determining a breath delivery period which determines what the tidal volume of a breath will be.

14. A method of delivering a plurality of substantially identical breaths at a variable flow rate to a patient whose breathing ability is impaired by determining a breath delivery period prior to the delivery of a plurality of breaths, said method comprising:

(a) determining a breath delivery period prior to the delivery of a plurality of breaths, said breath delivery period being determined based upon a desired peak flow rate and a desired tidal volume; and (b) using the breath delivery period determined in said step (a) to deliver a plurality of complete breaths at a predetermined variable flow rate to a patient whereby each of said breaths is substantially identical.

15. A method as defined in claim 14, wherein said breath delivery period includes the initial portion of a breath during which the flow rate is increasing but excludes the final portion of the breath during which the flow rate is decreasing.

16. A method of controlling the position of a valve including a valve member add a valve seat in a ventilator which provides artificial respiration to a patient through the use of a control means so that a predetermined tidal volume of gas is delivered to the patient on each breath, wherein a known relationship exists between the position of said valve member relative said valve seat and the flow rate through the valve, said method comprising the steps of:

inputting the desired tidal volume into said control means;

determining the required positions of the valve member relative said valve seat over time in order to deliver said desired tidal volume;

generating command signals which cause said valve to move to said positions determined in said second step; and delivering a breath to said patient having said desired tidal volume by incrementally varying the displacement of said valve member relative said valve seat in accordance with said command signals.

17. The method of claim 16, wherein said valve is driven by a stepping motor, and said command signals result in a sequence of steps which are carried out by the stepping motor, each step corresponding to a known change in flow rate through the valve.

18. The method of claim 17, wherein said control means causes said breaths to be delivered with a square flow rate versus time waveform, said control means receiving input providing the desired peak flow rate of respiratory gas to the patient, wherein the required positions of the valve are determined by the steps of:

determining the number of steps of the stepping motor required to bring the valve to a position in which the flow rate is substantially equal to the peak flow rate; and determining the length of time that the peak flow rate must be maintained in order to deliver the desired tidal volume.

19. The method of claim 17, further comprising the step of compensating for ramping of the stepping motor as the valve opens and closes in determining the length of time during which the valve is to be held open.

* * * * *